US011465997B2

(12) United States Patent
Nicolaou et al.

(10) Patent No.: US 11,465,997 B2
(45) Date of Patent: Oct. 11, 2022

(54) SYNTHESIS OF DISORAZOLES AND ANALOGS THEREOF AS POTENT ANTICANCER AGENTS

(71) Applicant: WILLIAM MARSH RICE UNIVERSITY, Houston, TX (US)

(72) Inventors: Kyriacos C. Nicolaou, Houston, TX (US); Gabriel Bellavance, Ottawa (CA); Marek Buchman, Houston, TX (US); Kiran Kumar Pulukuri, Houston, TX (US); Stephan Rigol, Houston, TX (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 16/625,667

(22) PCT Filed: Jun. 21, 2018

(86) PCT No.: PCT/US2018/038813
§ 371 (c)(1),
(2) Date: Dec. 20, 2019

(87) PCT Pub. No.: WO2018/237178
PCT Pub. Date: Dec. 27, 2018

(65) Prior Publication Data
US 2021/0155616 A1     May 27, 2021

Related U.S. Application Data

(60) Provisional application No. 62/571,537, filed on Oct. 12, 2017, provisional application No. 62/523,509, filed on Jun. 22, 2017.

(51) Int. Cl.
*C07D 413/14*     (2006.01)
*C07D 417/14*     (2006.01)

(52) U.S. Cl.
CPC ......... *C07D 413/14* (2013.01); *C07D 417/14* (2013.01)

(58) Field of Classification Search
CPC .................. C07D 413/14; C07D 417/14
USPC ........................................................ 514/375
See application file for complete search history.

(56) References Cited

U.S. PATENT DOCUMENTS

2009/0311264 A1   12/2009   Irschik et al.

FOREIGN PATENT DOCUMENTS

EP         1743897        1/2007
EP         1900742        3/2008
WO    WO 2008/028934     3/2008

OTHER PUBLICATIONS

Extended European Search Report issued in European Application No. 18820741.9, dated Jan. 13, 2021.
Cosp et al., "Enantiopure β-methoxy carboxyl derivatives from a chiral titanium enolate and dimethyl acetals," Tetrahedron Letters, 42:4629-4631, 2001.
Dosio et al.,"Advances in Anticancer Antibody-Drug Conjugates and Immunotoxins," Recent Pat. Anti Canc., 9:35-65, 2014.
Elnakady et al., "Disorazol A 1, a Highly Effective Antimitotic Agent Acting on Tubulin Polymerization and Inducing Apoptosis in Mammalian Cells," Biochem. Pharmacol., 67:927-935, 2004.
Wu et al., "Bis-cyclopropane Analog of Disorazole C1 Is a Microtubule-Destabilizing Agent Active in ABCB1-overepressing Human Colon Cancer Cells," Oncotarget, 6:40866-40879, 2015.
Allred and Liebeskind, "Copper-Mediated Cross-Coupling of Organostannanes with Organic Iodides at or below Room Temperature," J. Am. Chem. Soc., 118:2748-2749, 1996.
Chari et al., "Antibody-drug Conjugates: An Emerging Concept in Cancer Therapy," Angew. Chem. Int. Ed., 53:3796-3827, 2014.
Cosp et al., "Enantiopure β-methoxy carboxyl derivatives from a chiral titanium enolate and dimethyl acetals," Tetrahedron Letters, 42:4629-4631, 2001.
de Carné-Carnaval et al., "Copper-free Sonogashira Coupling of Cyclopropyl Iodides With Terminal Alkynes," Org. Lett., 13:956-959, 2011.
Dosio et al.,"Advances in Anticancer Antibody-Drug Conjugates and Immunotoxins," Recent Pat. Anti Canc., 9:35-65, 2014.

(Continued)

*Primary Examiner* — Kahsay Habte
(74) *Attorney, Agent, or Firm* — Parker Highlander PLLC

(57) ABSTRACT

In one aspect, the present disclosure provides disorazole analogs of the formula: Formula (I) wherein the variables are as defined herein. In another aspect, the present disclosure also provides methods of preparing the compounds disclosed herein. In another aspect, the present disclosure also provides pharmaceutical compositions and methods of use of the compounds disclosed herein. Additionally, drug conjugates with cell targeting moieties of the compounds are also provided.

19 Claims, 4 Drawing Sheets

(56) References Cited

OTHER PUBLICATIONS

Elnakady et al., "Disorazol A1, a Highly Effective Antimitotic Agent Acting on Tubulin Polymerization and Inducing Apoptosis in Mammalian Cells," Biochem. Pharmacol., 67:927-935, 2004.
Fürstner et al."Toward the Total Synthesis of Spirastrellolide A. Part 2: Conquest of the Northern Hemisphere,", Angew. Chem. Int. Ed., 45:5510-5515, 2006.
Gerber et al.,"The Antibody-Drug Conjugate: An Enabling Modality for Natural Product-Based Cancer Therapeutics," Nat. Prod. Rep., 30:625-639, 2013.
Ghanem and Aboul-Enein, "Application of Lipases in Kinetic Resolution of Racemates," Chirality, 17:1-15, 2005.
Hartung et al., "Toward the Total Synthesis of Disorazole A1: Asymmetric Synthesis of the MaskedNorthern Half," Synthesis, 12:1844-1850, 2003.
Höfle, "Chemistry of bioactive compounds from microorganisms," In Wissenschaftlicher Ergebnisbericht, Druckerei und Verlag GmbH: Braunschweig-Stöckheim, Germany, p. 101-104, 1999/2000.
Hopkins et al., "Isolation, biology and chemistry of the disorazoles: new anticancer 26 Macrodiolides," Nat Prod Rep., 26(5):585-601, 2009.
Hopkins et al., "Total synthesis of (−)-CP2-disorazole C1," Org Lett., 13(15):4088-4091, 2011.
Irschik et al., "Disorazol A, an Efficient Inhibitor of Eukaryotic Organisms Isolated From Myxobacteria," J. Antibiot., 48 31-35, 1995.
Jansen et al., "Antibiotics from Gliding Bacteria, LIX. Disorazoles, Highly Cytotoxic Metabolites from the Sorangicin—Producing Bacterium Sorangium Cellulosum, Strain So ce12," Liebigs Ann. Chem., 759-773, 1994.
López et al., "First Stereoselective Syntheses of (−)-Siphonodiol and (−)-Tetrahydrosiphonodiol, Bioactive Polyacetylenes From Marine Sponges," J. Org. Chem., 70:6346-6352, 2005.
Nagao et al., "New C-4-chiral 1,3-thiazolidine-2-thiones: excellent chiral auxiliaries for highly diastereo-controlled aldol-type reactions of acetic acid and .alpha.,.beta.-unsaturated aldehydes," J. Org. Chem., 51:2391-2393, 1986.
Nicolaou et al., "A Mild and Selective Method for the Hydrolysis of Esters With Trimethyltin Hydroxide," Angew. Chem. Int. Ed., 44:1378-1382, 2005.
Nicolaou, "The Chemistry-Biology-Medicine Continuum and the Drug Discovery and Development Process in Academia," Chem. Biol., 21:1039-1045, 2014.
PCT International Preliminary Report on Patentability issued in International Application No. PCT/US2018/038813, dated Dec. 24, 2019.
PCT International Search Report and Written Opinion issued in International Application No. PCT/US2018/038813, dated Sep. 18, 2018.
Phillips et al., "Synthesis of Functionalized Oxazolines and Oxazoles With DAST and Deoxo-Fluor," Org. Lett., 2:1165-1168, 2000.
Pulukuri "Formal Synthesis of Actin Binding Macrolide Rhizopodin," et al., Org. Lett., 16:2284 2287, 2014.
Sapra & Shor, "Monoclonal Antibody-Based Therapies in Cancer: Advances and Challenges," Pharmacol. Ther., 138:452-469, 2013.
Schackel et al., "The Synthesis of Novel Disorazoles," Angew. Chem. Int. Ed., 49:1619-1622, 2010.
Sievers & Senter, "Antibody-drug Conjugates in Cancer Therapy," Annu. Rev. Med., 64:15-29, 2013.
Speed et al., "Catalytic Z-selective Cross-Metathesis in Complex Molecule Synthesis: A Convergent Stereoselective Route to Disorazole C1," J. Am. Chem. Soc., 136:16136-16139, 2014.
Wang and Lin, "Stille cross-coupling reactions of alkenylstannanes with alkenyl iodides mediated by copper (I) thiophene-2-carboxylate: a density functional study," Organometallic, 29:3077-3084, 2010.
Wipf & Graham, "Synthesis and hetero-Michael Addition Reactions of 2-alkynyl Oxazoles and Oxazolines," Org. Biomol. Chem., 3:31-35, 2005.
Wu et al., "Bis-cyclopropane Analog of "Disorazole Cl Is a Microtubule-Destabilizing Agent Active in ABCB1-overepressing Human Colon Cancer Cells, Oncotarget, 6:40866-40879, 2015.

84: bis-cp-disorazole B$_1$

85: cp-(bis-thiazolyl)-disorazole A$_1$

86: bis-(cp-thiazolyl)-disorazole B$_1$ a: Yamaguchi esterification
c: Yamaguchi macrolactonization
b: Cu/Pd-catalyzed cross-coupling
d: Cu-catalyzed cross-coupling

SYNTHESIS OF DISORAZOLES AND ANALOGS THEREOF AS POTENT ANTICANCER AGENTS

This application is a national phase application under 35 U.S.C. § 371 of International Application No. PCT/US2018/038813 filed Jun. 21, 2018 and claims the benefit of U.S. Provisional Application No. 62/523,509, filed on Jun. 22, 2017 and U.S. Provisional Application No. 62/571,537, filed on Oct. 12, 2017, the entire contents of both are hereby incorporated by reference.

BACKGROUND

The development of this disclosure was funded in part by the Cancer Prevention and Research Institute of Texas (CPRIT) under Grant No. R1226 and the Welch Foundation under Grant No. C-1819.

1. Field

This disclosure relates to the fields of medicine, pharmacology, chemistry, and oncology. In particular, new compounds, compositions, methods of treatment, and methods of synthesis relating to analogs of disorazoles are disclosed.

2. Related Art

Antibody-drug conjugates (ADCs) constitute a powerful new paradigm for targeted chemotherapy (e.g. Kadcyla® and Adcetris®) (Chari et al., 2014; Dosio et al., 2014, Gerber et al., 2013, Sapra & Shor, 2013, Sievers & Senter, 2013 and Nicolaou 2014). These new targeted anticancer drugs are molecular constructs containing a specific antibody targeting a particular type of cancer cells and a potent cytotoxic agent (the payload) joined together by a chemical linker which is able to undergo decomposition in vivo. Numerous cancer targeting antibodies have been developed for different cancer types, but available payloads are significantly limited. The potential payloads which do exist are often too scarce to be harvested from their natural sources in sufficient quantities for biological studies, much less use as a clinical candidate.

Generally, these payloads are potent cytotoxic compounds, often with $IC_{50}$ values in the low picomolar range that can affect cell death once the compound is released from the antibody-drug conjugate within the targeted cell. One important advantage of higher potency payloads means that fewer of the payload molecules per antibody molecule will be required to kill the malignant cell. Typically, one to four payload molecules are preferred by researchers for clinical development because a larger number may interfere with the recognition ability of the antibody. Additionally, not all of the bound antibody molecules are drawn into the targeted cell. Another problem that often exists is the lack of synthetic routes to obtain these compounds for potential clinical development.

The disorazoles are a growing class of highly potent antitumor agents possessing cytotoxic properties in the picomolar range against tumor cells and exerting their activities by interfering with microtubule dynamics (Irschik et al., 1995, Jansen et al., 1994 and Hopkins & Wipf, 2009). Disorazole $A_1$ (1, FIG. 1) is one of the most potent members of this class of compounds, exhibiting single digit picomolar $IC_{50}$ values against lung ($IC_{50}$=2.3 pM), ovarian ($IC_{50}$=4.9 pM) and prostate ($IC_{50}$=7.1 pM) cancer cell lines (Jansen et al., 1994 and Elnakady et al., 2004). This compound, 1, acts by inhibiting polymerization of microtubulins (Elnakady et al., 2004). While this compound has been attached to other cell-binding molecules, such as peptides, no antibody-drug conjugates have been synthesized utilizing disorazoles as the payload (WO2008028934 A1). The scarcity and relatively high chemical reactivity of disorazole $A_1$, however, constitute liabilities in that these factors pose serious challenges of supply and stability, hindering their application and development as payloads for ADCs particularly in a clinical setting. Therefore, there remains a need for additional disorazole analogs which can be used in the development of payloads for antibody-drug conjugates.

SUMMARY

In some aspects, the present disclosure provides analogs of disorazoles which may be used as payloads in an antibody-drug conjugate. In some embodiments, the compounds are further defined by the formula:

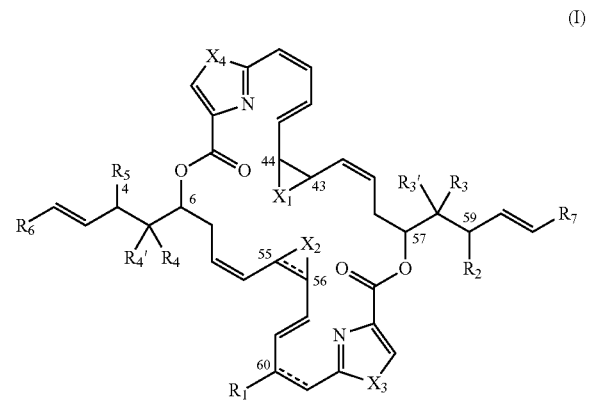

(I)

wherein:
$X_1$ is —O—, —S—, —NR$_a$—, or —CR$_b$R$_c$—; wherein:
  R$_a$ is hydrogen, alkyl$_{(C≤8)}$, substituted alkyl$_{(C≤8)}$, acyl$_{(C≤8)}$, substituted acyl$_{(C≤8)}$, or a monovalent amino protecting group, or —C(O)R$_a$', wherein:
    R$_a$' is amino, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤8)}$, or substituted dialkylamino$_{(C≤8)}$; and
  R$_b$ and R$_c$ are each independently hydrogen, amino, cyano, halo, hydroxy, or mercapto, or alkyl$_{(C≤8)}$, cycloalkyl$_{(C≤8)}$, alkenyl$_{(C≤8)}$, alkynyl$_{(C≤8)}$, aryl$_{(C≤8)}$, aralkyl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, alkylamino$_{(C≤8)}$, dialkylamino$_{(C≤8)}$, or a substituted version of any of the last fourteen groups;
$X_2$ is absent, —O—, —S—, —NR$_d$—, or —CR$_e$R$_f$—; wherein:
  R$_d$ is hydrogen, alkyl$_{(C≤8)}$, substituted alkyl$_{(C≤8)}$, acyl$_{(C≤8)}$, substituted acyl$_{(C≤8)}$, or a monovalent amino protecting group, or —C(O)R$_d$', wherein:
    R$_d$' is amino, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤8)}$, or substituted dialkylamino$_{(C≤8)}$; and
  R$_e$ and R$_f$ are each independently hydrogen, amino, cyano, halo, hydroxy, or mercapto, or alkyl$_{(C≤8)}$, cycloalkyl$_{(C≤8)}$, alkenyl$_{(C≤8)}$, alkynyl$_{(C≤8)}$, aryl$_{(C≤8)}$, aralkyl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, alkylamino$_{(C≤8)}$, dialkylamino$_{(C≤8)}$, or a substituted version of any of the last fourteen groups; and provided that $X_2$ is absent, then the bond between carbon atoms 55 and 56 is a double bond; and provided that when the bond between carbon atoms 55 and 56 is a double bond, then $X_2$ is absent;

$X_3$ and $X_4$ are each independently O, NR$_h$, or S; wherein:
R$_h$ is hydrogen, alkyl$_{(C≤8)}$, substituted alkyl$_{(C≤8)}$, or a monovalent amino protecting group;

R$_1$ is hydrogen, hydroxy, alkoxy$_{(C≤8)}$, substituted alkoxy$_{(C≤8)}$, acyloxy$_{(C≤8)}$, substituted acyloxy$_{(C≤8)}$, or —OR$_g$, wherein R$_g$ is a hydroxy protecting group;

$R_2$ and $R_5$ are hydroxy, oxo, alkoxy$_{(C≤8)}$, or substituted alkoxy$_{(C≤8)}$;

$R_3$, $R_3$', $R_4$, and $R_4$' are each independently alkyl$_{(C≤8)}$, acyl$_{(C≤8)}$, or a substituted version of either group; and $R_6$ and $R_7$ are each independently alkyl$_{(C≤8)}$ or substituted alkyl$_{(C≤8)}$;

provided that $X_1$ is not —O—, when $X_2$ is absent, the bond between carbon atom 55 and carbon atom 56 is a double bond, $X_3$ and $X_4$ are both —O—, $R_1$ is hydrogen or methoxy, $R_2$ and $R_5$ is hydroxy, and $R_3$, $R_3$', $R_4$, $R_4$', $R_6$, and $R_7$ are all methyl, or provided that that $X_1$ and $X_2$ are not both —O—, when $X_3$ and $X_4$ are both —O—, $R_c$, is hydrogen or methoxy, $R_2$ and $R_5$ is hydroxy, and $R_3$, $R_3$', $R_4$, $R_4$', $R_6$, and $R_7$ are all methyl;

or a pharmaceutically acceptable salt thereof. In some embodiments, the compound is further defined as:

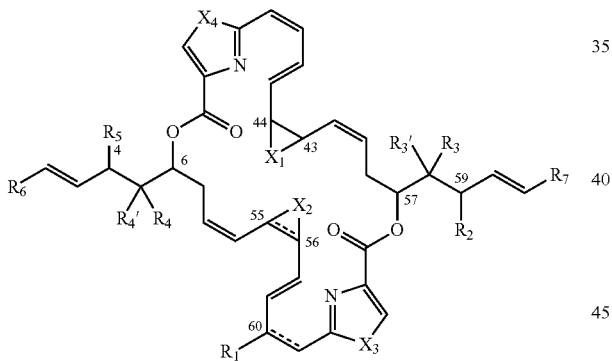

(I)

wherein:
$X_1$ is —O—, —S—, —NR$_a$—, or —CR$_b$R$_c$—; wherein:
R$_a$ is hydrogen, alkyl$_{(C≤8)}$, substituted alkyl$_{(C≤8)}$, or a monovalent amino protecting group; and R$_b$ and R$_c$ are each independently hydrogen, amino, cyano, halo, hydroxy, or mercapto, or alkyl$_{(C≤8)}$, cycloalkyl$_{(C≤8)}$, alkenyl$_{(C≤8)}$, alkynyl$_{(C≤8)}$, aryl$_{(C≤8)}$, aralkyl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, alkylamino$_{(C≤8)}$, dialkylamino$_{(C≤8)}$, or a substituted version of any of the last fourteen groups;

$X_2$ is absent, —NR$_d$—, or —CR$_e$R$_f$—; wherein:
R$_d$ is hydrogen, alkyl$_{(C≤8)}$, substituted alkyl$_{(C≤8)}$, or a monovalent amino protecting group;

R$_e$ and R$_f$ are each independently hydrogen, amino, cyano, halo, hydroxy, or mercapto, or alkyl$_{(C≤8)}$, cycloalkyl$_{(C≤8)}$, alkenyl$_{(C≤8)}$, alkynyl$_{(C≤8)}$, aryl$_{(C≤8)}$, aralkyl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, alkylamino$_{(C≤8)}$, dialkylamino$_{(C≤8)}$, or a substituted version of any of the last fourteen groups; and provided that $X_2$ is absent, then the bond between carbon atoms 55 and 56 is a double bond; and provided that when the bond between carbon atoms 55 and 56 is a double bond, then $X_2$ is absent;

$X_3$ and $X_4$ are each independently O, NR$_h$, or S; wherein:
R$_h$ is hydrogen, alkyl$_{(C≤8)}$, substituted alkyl$_{(C≤8)}$, or a monovalent amino protecting group;

R$_1$ is hydrogen, hydroxy, alkoxy$_{(C≤8)}$, substituted alkoxy$_{(C≤8)}$, acyloxy$_{(C≤8)}$, substituted acyloxy$_{(C≤8)}$, or —OR$_g$, wherein R$_g$ is a hydroxy protecting group;

$R_2$ and $R_5$ are hydroxy, oxo, alkoxy$_{(C≤8)}$, or substituted alkoxy$_{(C≤8)}$;

$R_3$, $R_3$', $R_4$, and $R_4$' are each independently alkyl$_{(C≤8)}$, acyl$_{(C≤8)}$, or a substituted version of either group; and $R_6$ and $R_7$ are each independently alkyl$_{(C≤8)}$ or substituted alkyl$_{(C≤8)}$;

provided that $X_1$ is not —O—, when $X_2$ is absent, the bond between carbon atom 55 and carbon atom 56 is a double bond, $X_3$ and $X_4$ are both —O—, $R_1$ is hydrogen or methoxy, $R_2$ and $R_5$ is hydroxy, and $R_3$, $R_3$', $R_4$, $R_4$', $R_6$, and $R_7$ are all methyl;

or a pharmaceutically acceptable salt thereof. In some embodiments, the compounds are further defined as:

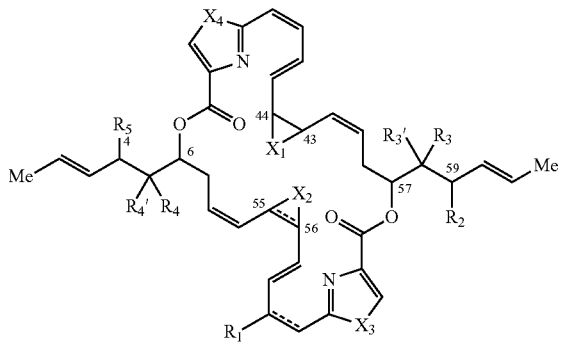

(II)

wherein:
$X_1$ is —O—, —S—, —NR$_a$—, or —CR$_b$R$_c$—; wherein:
R$_a$ is hydrogen, alkyl$_{(C≤8)}$, substituted alkyl$_{(C≤8)}$, or a monovalent amino protecting group; and R$_b$ and R$_c$ are each independently hydrogen, amino, cyano, halo, hydroxy, or mercapto, or alkyl$_{(C≤8)}$, cycloalkyl$_{(C≤8)}$, alkenyl$_{(C≤8)}$, alkynyl$_{(C≤8)}$, aryl$_{(C≤8)}$, aralkyl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, alkylamino$_{(C≤8)}$, dialkylamino$_{(C≤8)}$, or a substituted version of any of the last fourteen groups;

$X_2$ is absent, —NR$_d$—, or —CR$_e$R$_f$—; wherein:
R$_d$ is hydrogen, alkyl$_{(C≤8)}$, substituted alkyl$_{(C≤8)}$, or a monovalent amino protecting group;

R$_e$ and R$_f$ are each independently hydrogen, amino, cyano, halo, hydroxy, or mercapto, or alkyl$_{(C≤8)}$, cycloalkyl$_{(C≤8)}$, alkenyl$_{(C≤8)}$, alkynyl$_{(C≤8)}$, aryl$_{(C≤8)}$, aralkyl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, alkylamino$_{(C≤8)}$, dialkylamino$_{(C≤8)}$, or a substituted version of any of the last fourteen groups; and provided that $X_2$ is absent, then the bond between carbon atoms 55 and 56 is a double bond; and provided that when the bond between carbon atoms 55 and 56 is a double bond, then $X_2$ is absent;

$X_3$ and $X_4$ are each independently O, NRs, or S; wherein:
$R_h$ is hydrogen, alkyl$_{(C\leq8)}$, substituted alkyl$_{(C\leq8)}$, or a monovalent amino protecting group;

$R_1$ is hydrogen, hydroxy, alkoxy$_{(C\leq8)}$, substituted alkoxy$_{(C\leq8)}$, acyloxy$_{(C\leq8)}$, substituted acyloxy$_{(C\leq8)}$, or —OR$_g$, wherein R$_g$ is a hydroxy protecting group;

$R_2$ and $R_5$ are hydroxy, oxo, alkoxy$_{(C\leq8)}$, or substituted alkoxy$_{(C\leq8)}$; and $R_3$, $R_3'$, $R_4$, and $R_4'$ are each independently alkyl$_{(C\leq8)}$, acyl$_{(C\leq8)}$, or a substituted version of either group;

or a pharmaceutically acceptable salt thereof. In some embodiments, the compounds are further defined as:

(III)

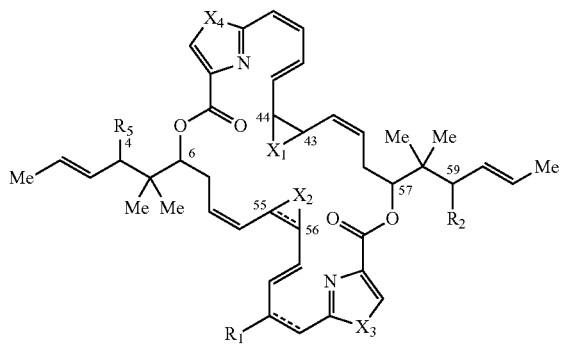

wherein:
$X_1$ is —O—, —S—, —NR$_a$—, or —CR$_b$R$_c$—; wherein:
$R_a$ is hydrogen, alkyl$_{(C\leq8)}$, substituted alkyl$_{(C\leq8)}$, or a monovalent amino protecting group; and $R_b$ and $R_c$ are each independently hydrogen, amino, cyano, halo, hydroxy, or mercapto, or alkyl$_{(C\leq8)}$, cycloalkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\leq8)}$, acyl$_{(C\leq8)}$, amido$_{(C\leq8)}$, alkoxy$_{(C\leq8)}$, acyloxy$_{(C\leq8)}$, alkylamino$_{(C\leq8)}$, dialkylamino$_{(C\leq8)}$, or a substituted version of any of the last fourteen groups;

$X_2$ is absent, —NR$_d$—, or —CR$_e$R$_f$—; wherein:
$R_d$ is hydrogen, alkyl$_{(C\leq8)}$, substituted alkyl$_{(C\leq8)}$, or a monovalent amino protecting group;

$R_e$ and $R_f$ are each independently hydrogen, amino, cyano, halo, hydroxy, or mercapto, or alkyl$_{(C\leq8)}$, cycloalkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\leq8)}$, acyl$_{(C\leq8)}$, amido$_{(C\leq8)}$, alkoxy$_{(C\leq8)}$, acyloxy$_{(C\leq8)}$, alkylamino$_{(C\leq8)}$, dialkylamino$_{(C\leq8)}$, or a substituted version of any of the last fourteen groups; and provided that $X_2$ is absent, then the bond between carbon atoms 55 and 56 is a double bond; and provided that when the bond between carbon atoms 55 and 56 is a double bond, then $X_2$ is absent;

$X_3$ and $X_4$ are each independently O, NR$_h$, or S; wherein:
$R_h$ is hydrogen, alkyl$_{(C\leq8)}$, substituted alkyl$_{(C\leq8)}$, or a monovalent amino protecting group; and $R_1$ is hydrogen, hydroxy, alkoxy$_{(C\leq8)}$, substituted alkoxy$_{(C\leq8)}$, acyloxy$_{(C\leq8)}$, substituted acyloxy$_{(C\leq8)}$, or —OR$_g$, wherein R$_g$ is a hydroxy protecting group;

$R_2$ and $R_5$ are hydroxy, oxo, alkoxy$_{(C\leq8)}$, or substituted alkoxy$_{(C\leq8)}$;

or a pharmaceutically acceptable salt thereof. In some embodiments, the compounds are further defined as:

(IV)

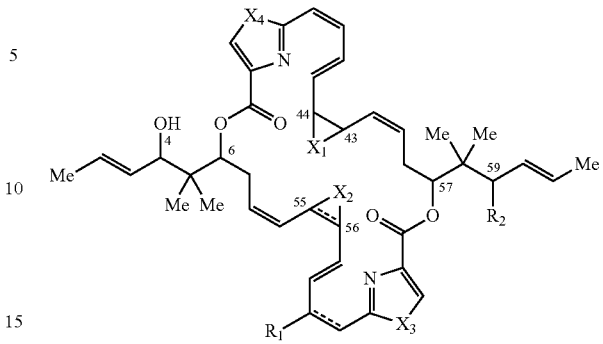

wherein:
$X_1$ is —O—, —S—, —NR$_a$—, or —CR$_b$R$_c$—; wherein:
$R_a$ is hydrogen, alkyl$_{(C\leq8)}$, substituted alkyl$_{(C\leq8)}$, or a monovalent amino protecting group; and $R_b$ and $R_c$ are each independently hydrogen, amino, cyano, halo, hydroxy, or mercapto, or alkyl$_{(C\leq8)}$, cycloalkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\leq8)}$, acyl$_{(C\leq8)}$, amido$_{(C\leq8)}$, alkoxy$_{(C\leq8)}$, acyloxy$_{(C\leq8)}$, alkylamino$_{(C\leq8)}$, dialkylamino$_{(C\leq8)}$, or a substituted version of any of the last fourteen groups;

$X_2$ is absent, —NR$_d$—, or —CR$_e$R$_f$—; wherein:
$R_d$ is hydrogen, alkyl$_{(C\leq8)}$, substituted alkyl$_{(C\leq8)}$, or a monovalent amino protecting group;

$R_e$ and $R_f$ are each independently hydrogen, amino, cyano, halo, hydroxy, or mercapto, or alkyl$_{(C\leq8)}$, cycloalkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\leq8)}$, acyl$_{(C\leq8)}$, amido$_{(C\leq8)}$, alkoxy$_{(C\leq8)}$, acyloxy$_{(C\leq8)}$, alkylamino$_{(C\leq8)}$, dialkylamino$_{(C\leq8)}$, or a substituted version of any of the last fourteen groups; and provided that $X_2$ is absent, then the bond between carbon atoms 55 and 56 is a double bond; and provided that when the bond between carbon atoms 55 and 56 is a double bond, then $X_2$ is absent;

$X_3$ and $X_4$ are each independently O, NR$_h$, or S; wherein:
$R_h$ is hydrogen, alkyl$_{(C\leq8)}$, substituted alkyl$_{(C\leq8)}$, or a monovalent amino protecting group; and $R_1$ is hydrogen, hydroxy, alkoxy$_{(C\leq8)}$, substituted alkoxy$_{(C\leq8)}$, acyloxy$_{(C\leq8)}$, substituted acyloxy$_{(C\leq8)}$, or —OR$_g$, wherein R$_g$ is a hydroxy protecting group;

or a pharmaceutically acceptable salt thereof.

In some embodiments, $R_6$ is alkyl$_{(C\leq8)}$ such as methyl. In other embodiments, $R_6$ is substituted alkyl$_{(C\leq8)}$ such as 2-aminoethyl or 2-hydroxyethyl. In some embodiments, $R_7$ is alkyl$_{(C\leq8)}$ such as methyl. In other embodiments, $R_7$ is substituted alkyl$_{(C\leq8)}$ such as 2-aminoethyl or 2-hydroxyethyl. In some embodiments, $R_3$ is alkyl$_{(C\leq8)}$ such as methyl. In some embodiments, $R_3'$ is alkyl$_{(C\leq8)}$ such as methyl. In some embodiments, $R_3$ and $R_3'$ are the same. In some embodiments, $R_4$ is alkyl$_{(C\leq8)}$ such as methyl. In some embodiments, $R_4'$ is alkyl$_{(C\leq8)}$ such as methyl. In some embodiments, $R_4$ and $R_4'$ are the same.

In some embodiments, $R_2$ is hydroxy. In some embodiments, $R_5$ is hydroxy. In some embodiments, $X_1$ is —O—. In other embodiments, $X_1$ is —CR$_b$R$_c$—; wherein: R$_b$ and R$_c$ are each independently hydrogen, amino, cyano, halo, hydroxy, or mercapto, or alkyl$_{(C\leq8)}$, cycloalkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\leq8)}$, acyl$_{(C\leq8)}$, amido$_{(C\leq8)}$, alkoxy$_{(C\leq8)}$, acyloxy$_{(C\leq8)}$, alkylamino$_{(C\leq8)}$, dialkylamino$_{(C\leq8)}$, or a substituted version of any of the last fourteen groups. In some embodiments, $R_b$ is hydrogen. In some embodiments, $R_c$ is hydrogen. In some embodiments, $X_1$ is —CH$_2$—. In other embodiments, $X_1$ is —NR$_a$—; wherein: $R_a$ is hydrogen, alkyl$_{(C\leq8)}$, substituted alkyl$_{(C\leq8)}$, or a monovalent amino protecting group. In some embodiments, $R_a$ is hydrogen. In some embodiments, $X_1$ is —NH—.

In some embodiments, $X_2$ is —NR$_d$—; wherein: $R_d$ is hydrogen, alkyl$_{(C\leq8)}$, substituted alkyl$_{(C\leq8)}$, or a monovalent amino protecting group. In some embodiments, $R_d$ is hydrogen. In other embodiments, $X_2$ is —CR$_e$R$_f$—; wherein: $R_e$ and $R_f$ are each independently hydrogen, amino, cyano, halo, hydroxy, or mercapto, or alkyl$_{(C\leq8)}$, cycloalkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\leq8)}$, acyl$_{(C\leq8)}$, amido$_{(C\leq8)}$, alkoxy$_{(C\leq8)}$, acyloxy$_{(C\leq8)}$, alkylamino$_{(C\leq8)}$, dialkylamino$_{(C\leq8)}$, or a substituted version of any of the last fourteen groups. In some embodiments, $R_e$ is hydrogen. In some embodiments, $R_f$ is hydrogen. In some embodiments, $X_2$ is —CH$_2$—. In other embodiments, $X_2$ is —NR$_d$—; wherein: $R_d$ is hydrogen, alkyl$_{(C\leq8)}$, substituted alkyl$_{(C\leq8)}$, or a monovalent amino protecting group. In some embodiments, $R_d$ is hydrogen. In some embodiments, $X_2$ is —NH—.

In some embodiments, $X_3$ is O. In other embodiments, $X_3$ is NR$_h$; wherein: $R_h$ is hydrogen, alkyl$_{(C\leq8)}$, substituted alkyl$_{(C\leq8)}$, or a monovalent amino protecting group. In still other embodiments, $X_3$ is S. In some embodiments, $X_4$ is O. In other embodiments, $X_4$ is NR$_h$; wherein: $R_h$ is hydrogen, alkyl$_{(C\leq8)}$, substituted alkyl$_{(C\leq8)}$, or a monovalent amino protecting group. In still other embodiments, $X_4$ is S.

In some embodiments, carbon atom 4 is in the (S) configuration. In some embodiments, carbon atom 6 is in the (S) configuration. In some embodiments, carbon atom 43 is in the (R) configuration. In some embodiments, carbon atom 44 is in the (S) configuration. In some embodiments, carbon atom 57 is in the (S) configuration. In some embodiments, carbon atom 59 is in the (S) configuration. In some embodiments, carbon atom 60 is in the (R) configuration. In some embodiments, carbon atom 55 is in the (R) configuration. In some embodiments, carbon atom 56 is in the S configuration.

In some embodiments, the compound is further defined as:

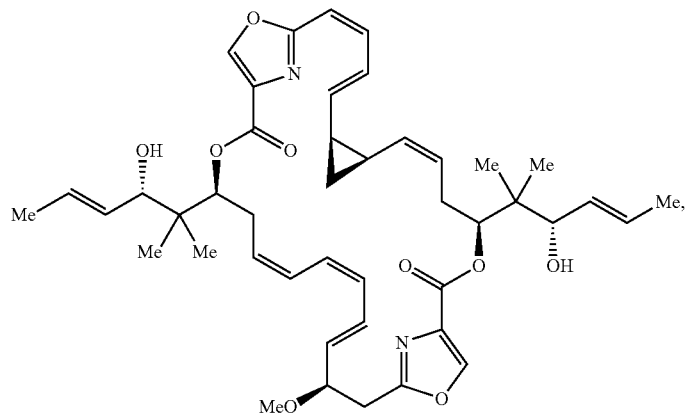

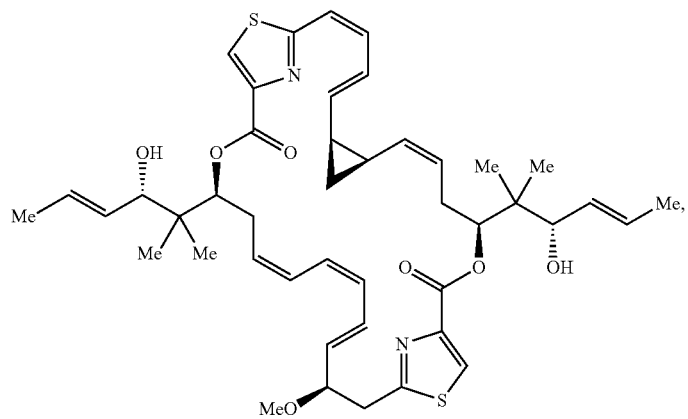

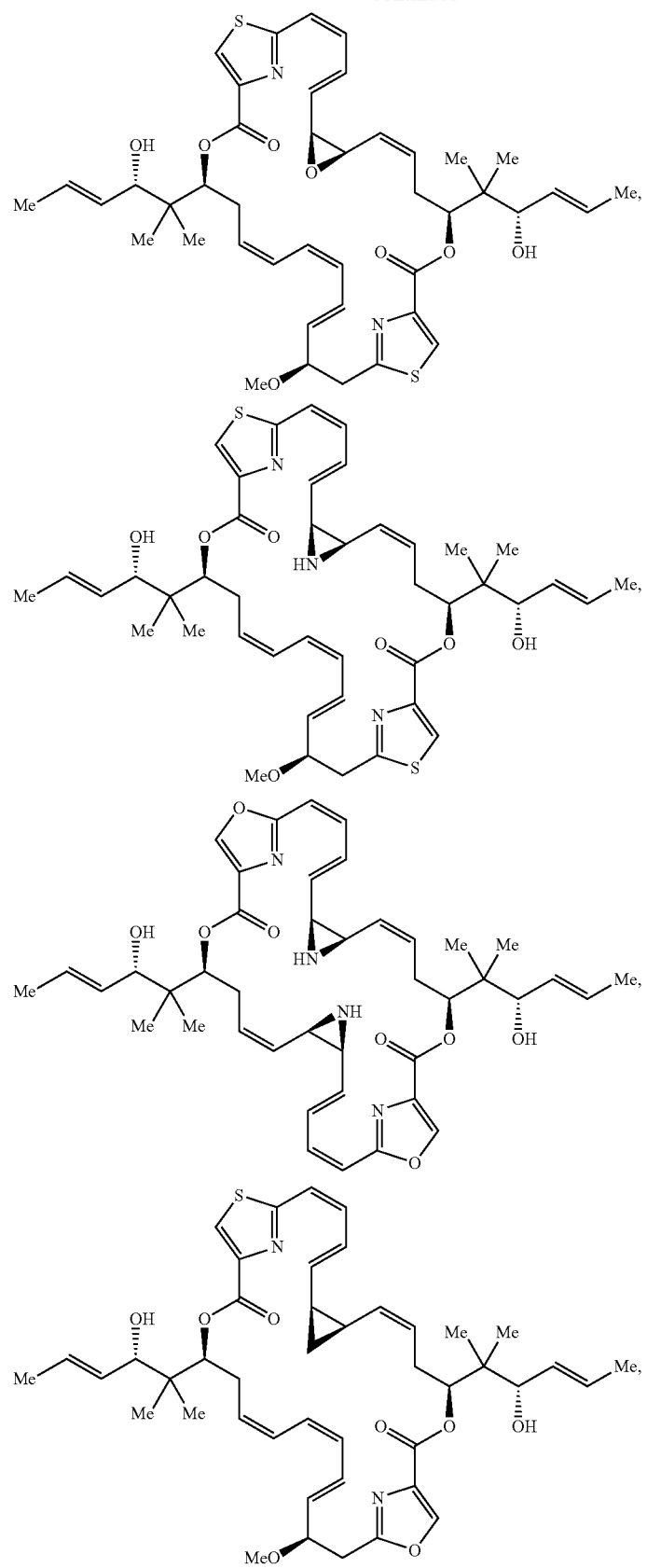

-continued
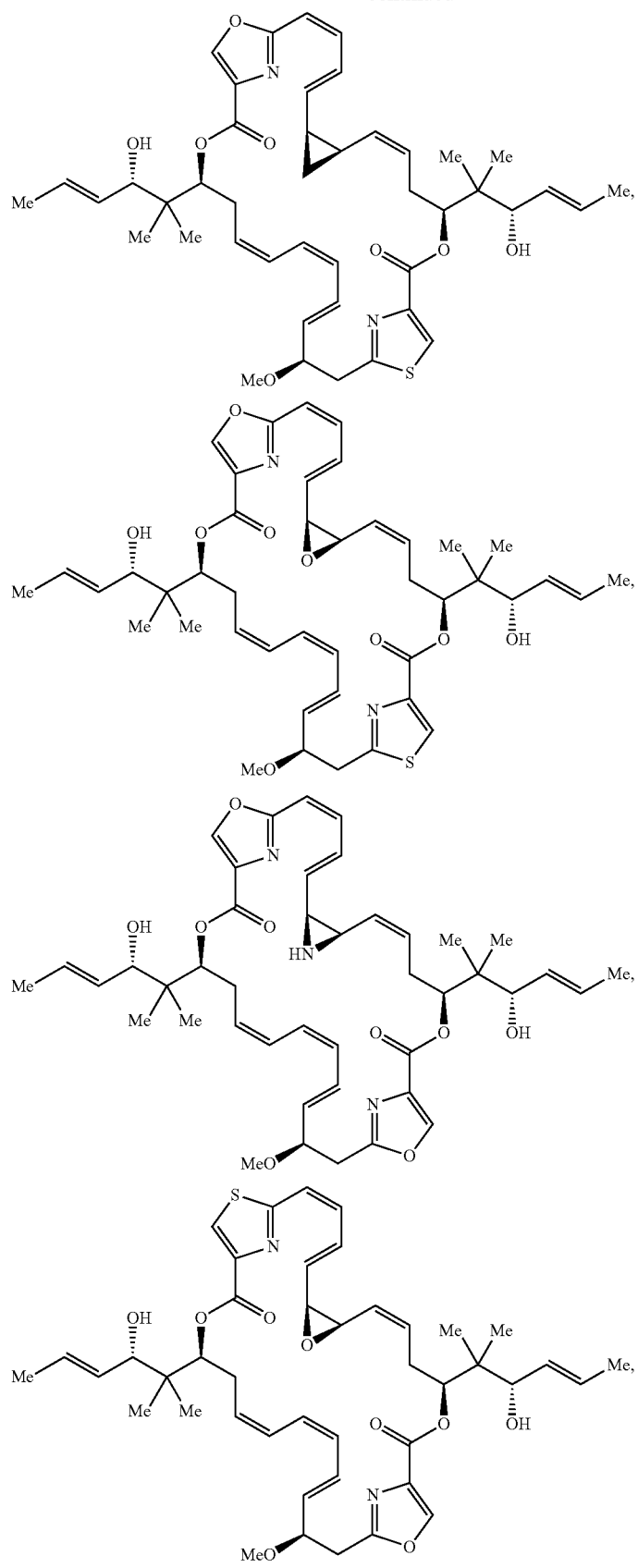

-continued
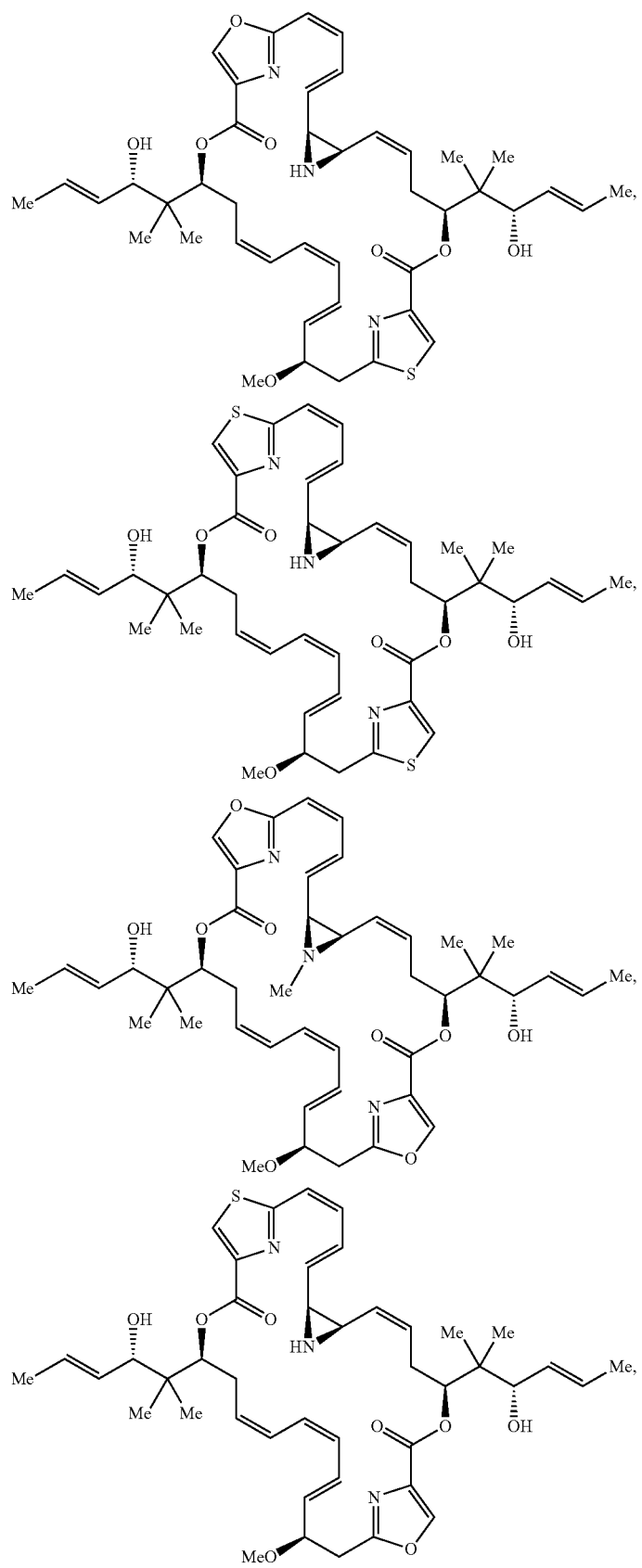

-continued
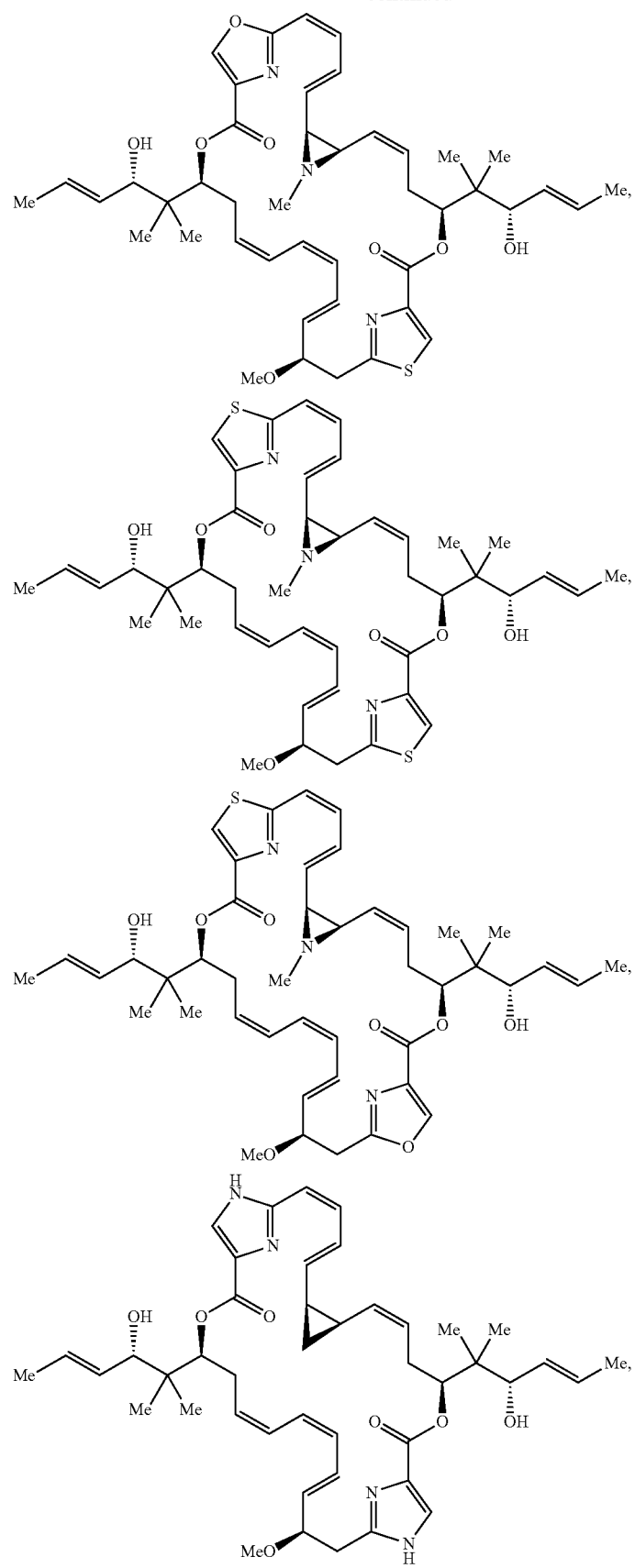

-continued
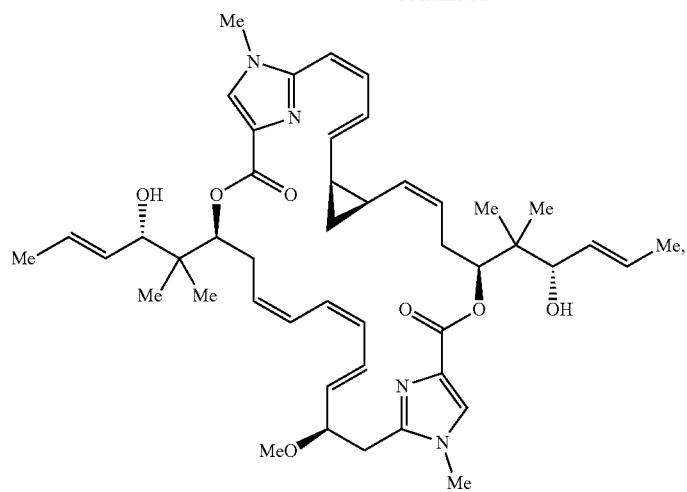
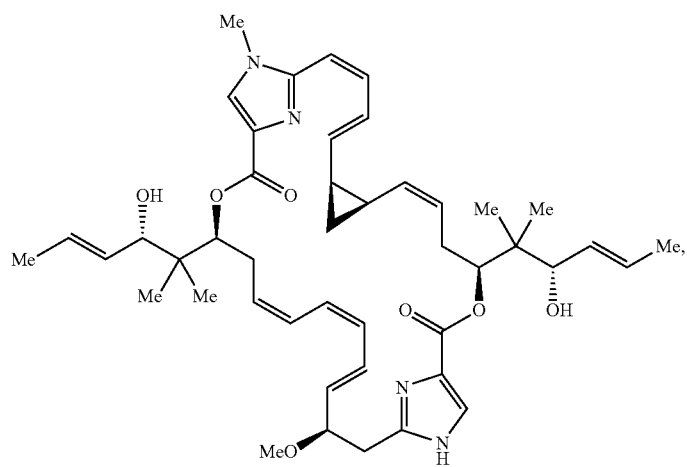
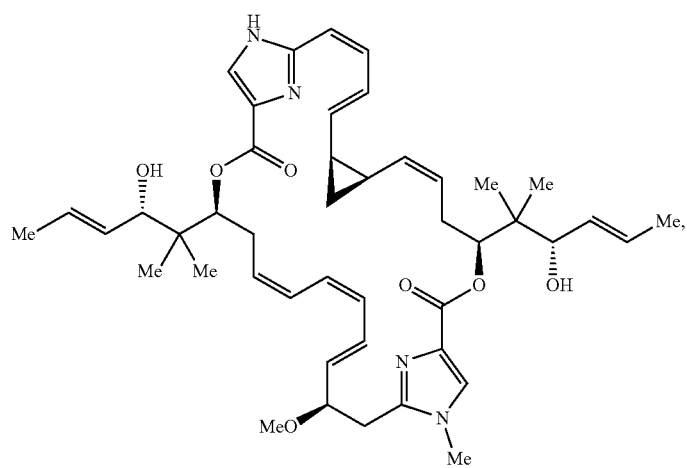

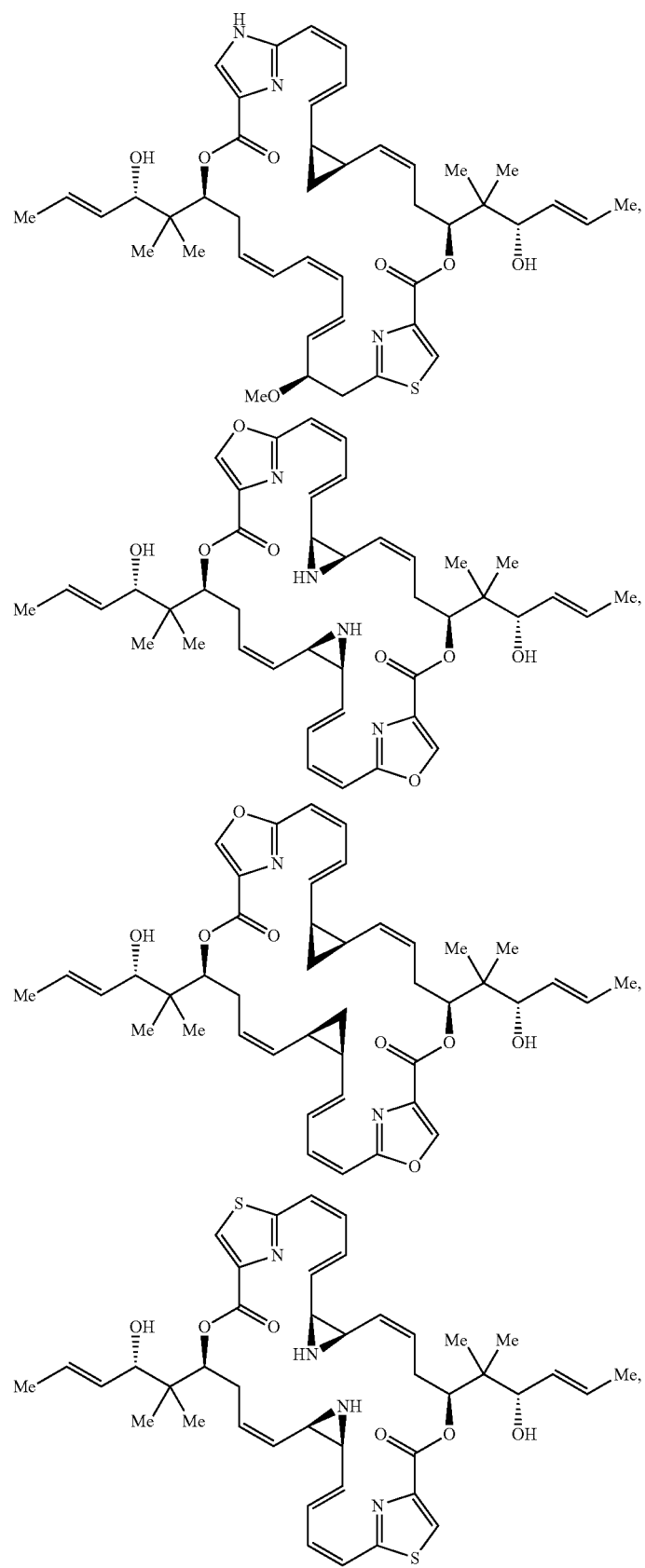

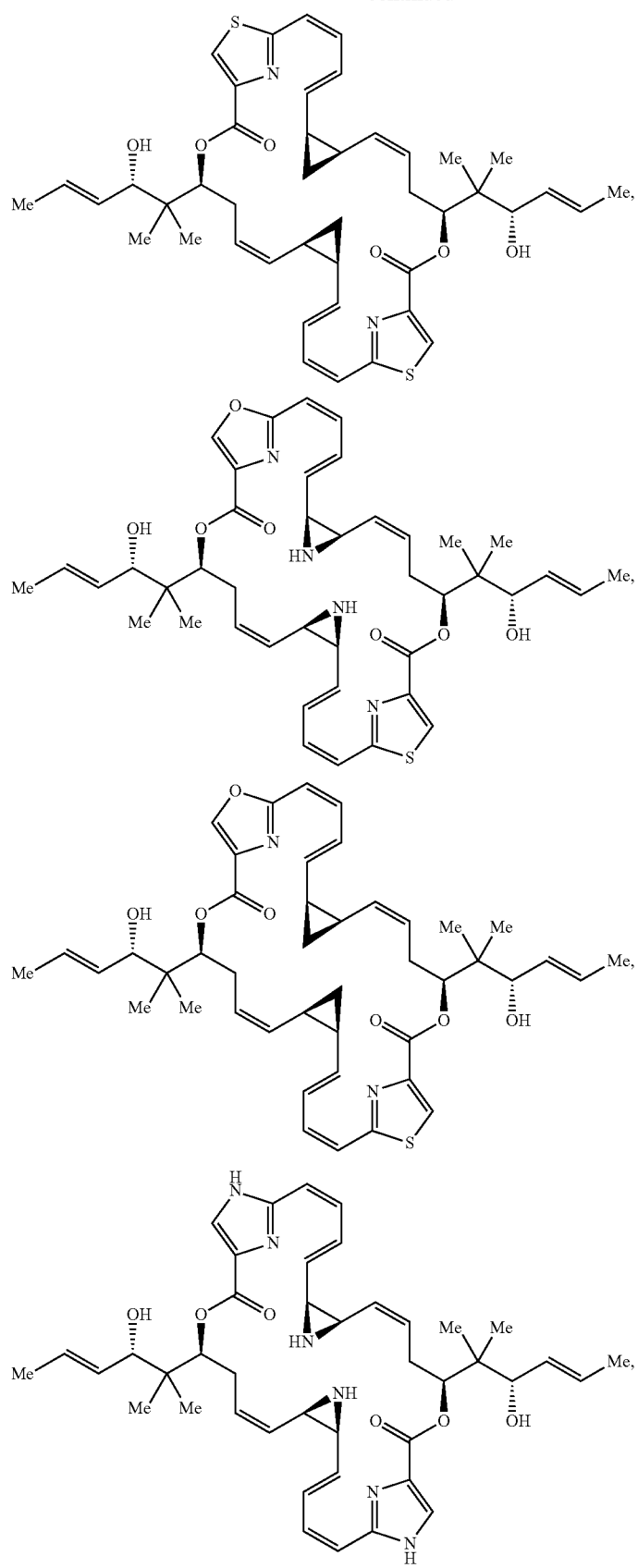

-continued
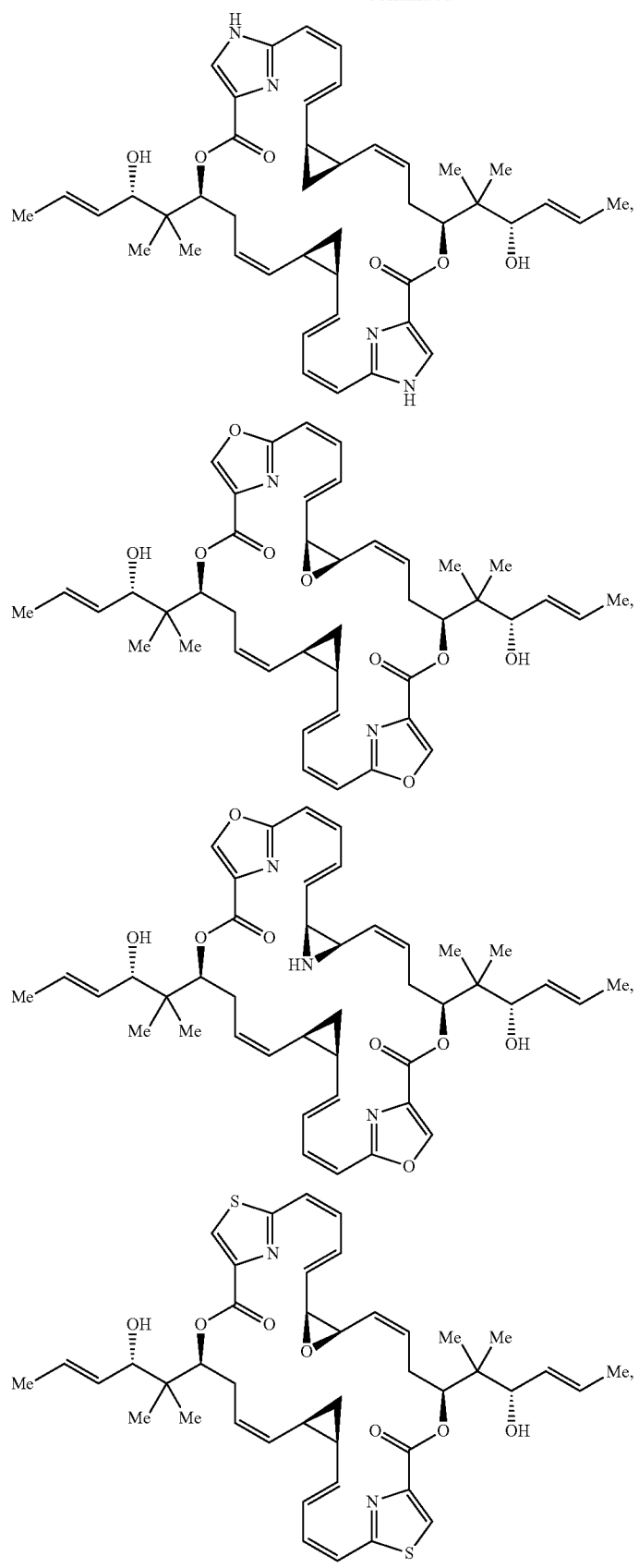

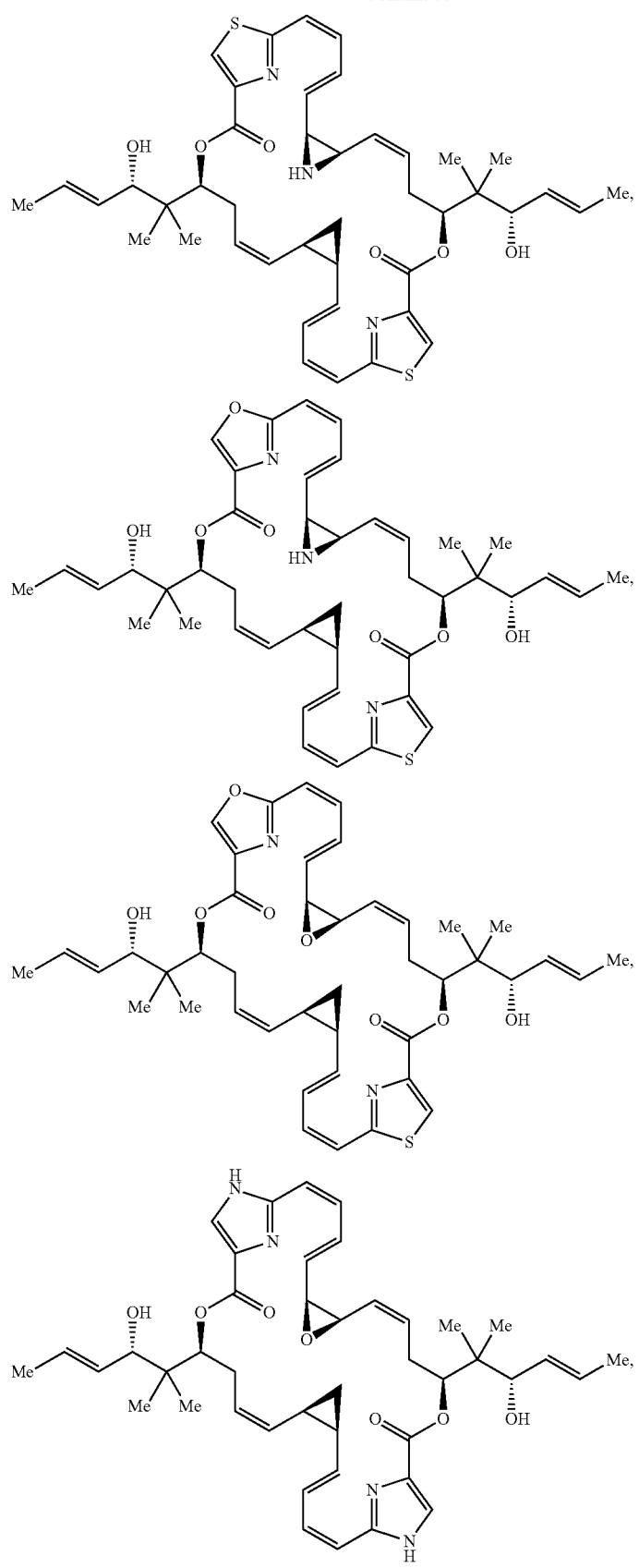

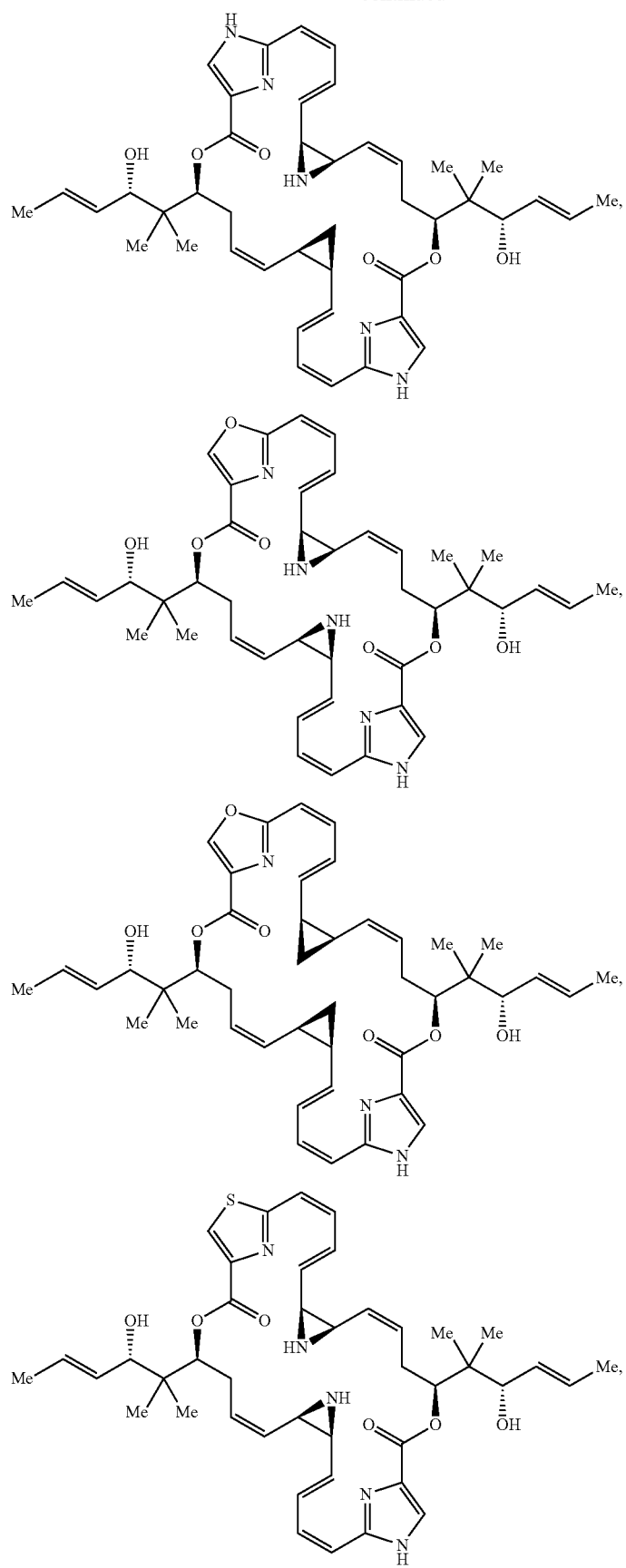

-continued
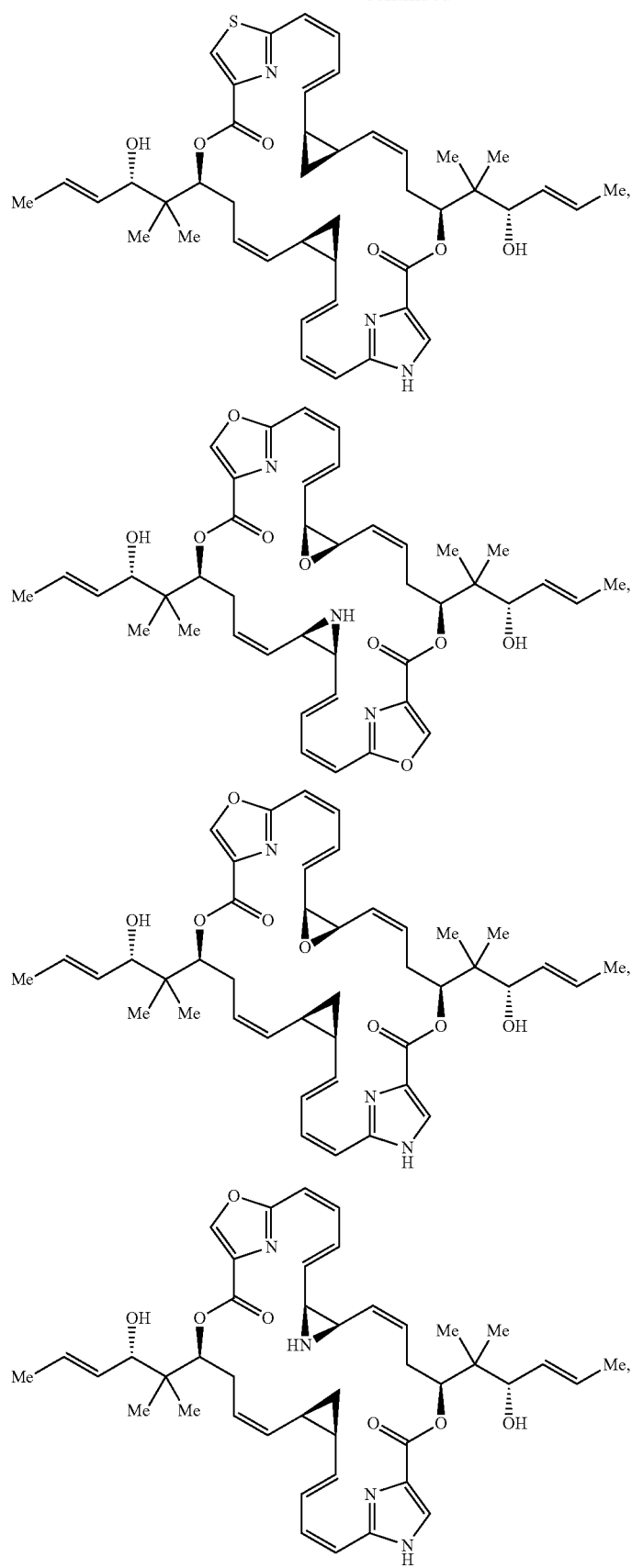

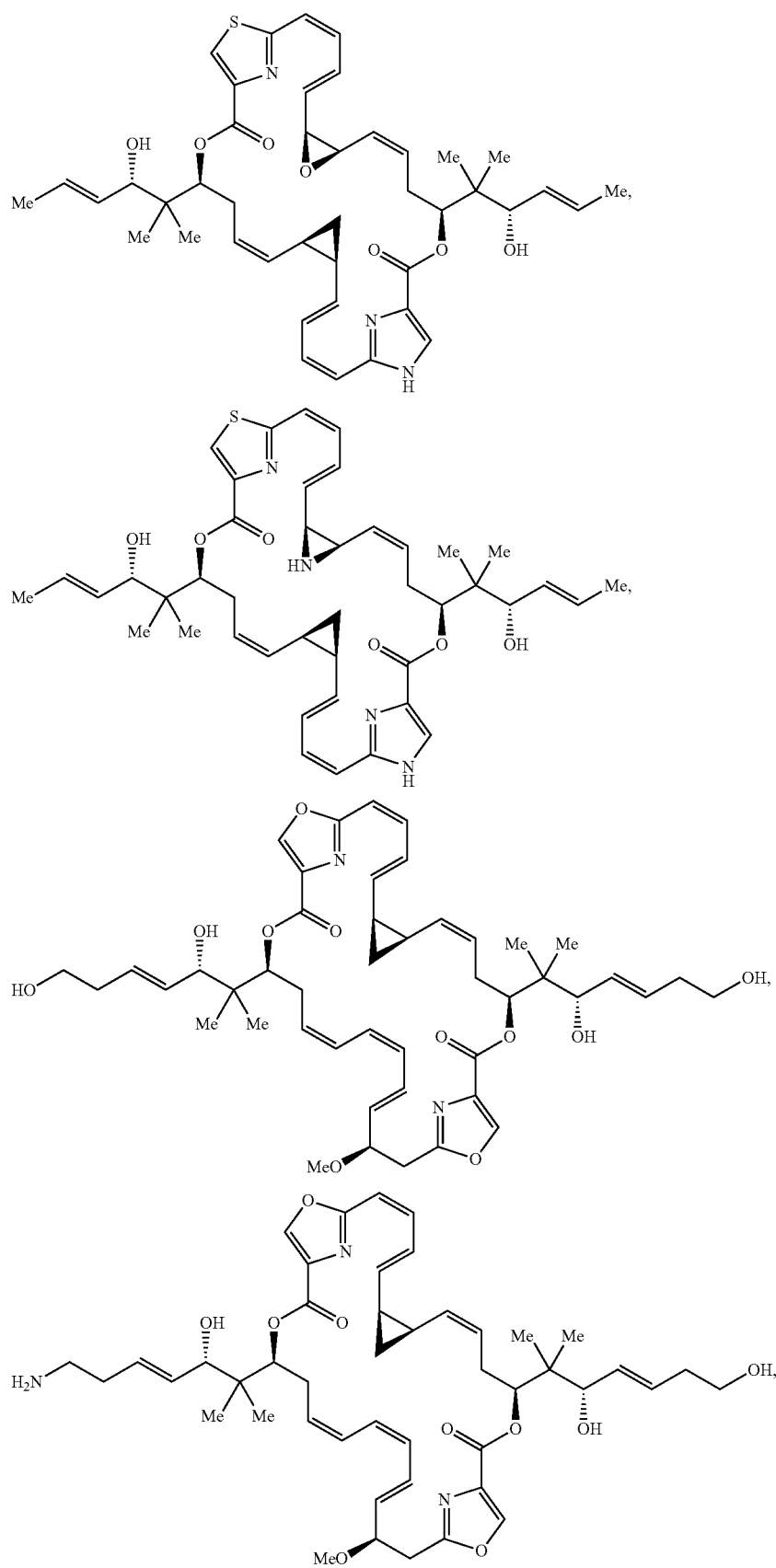

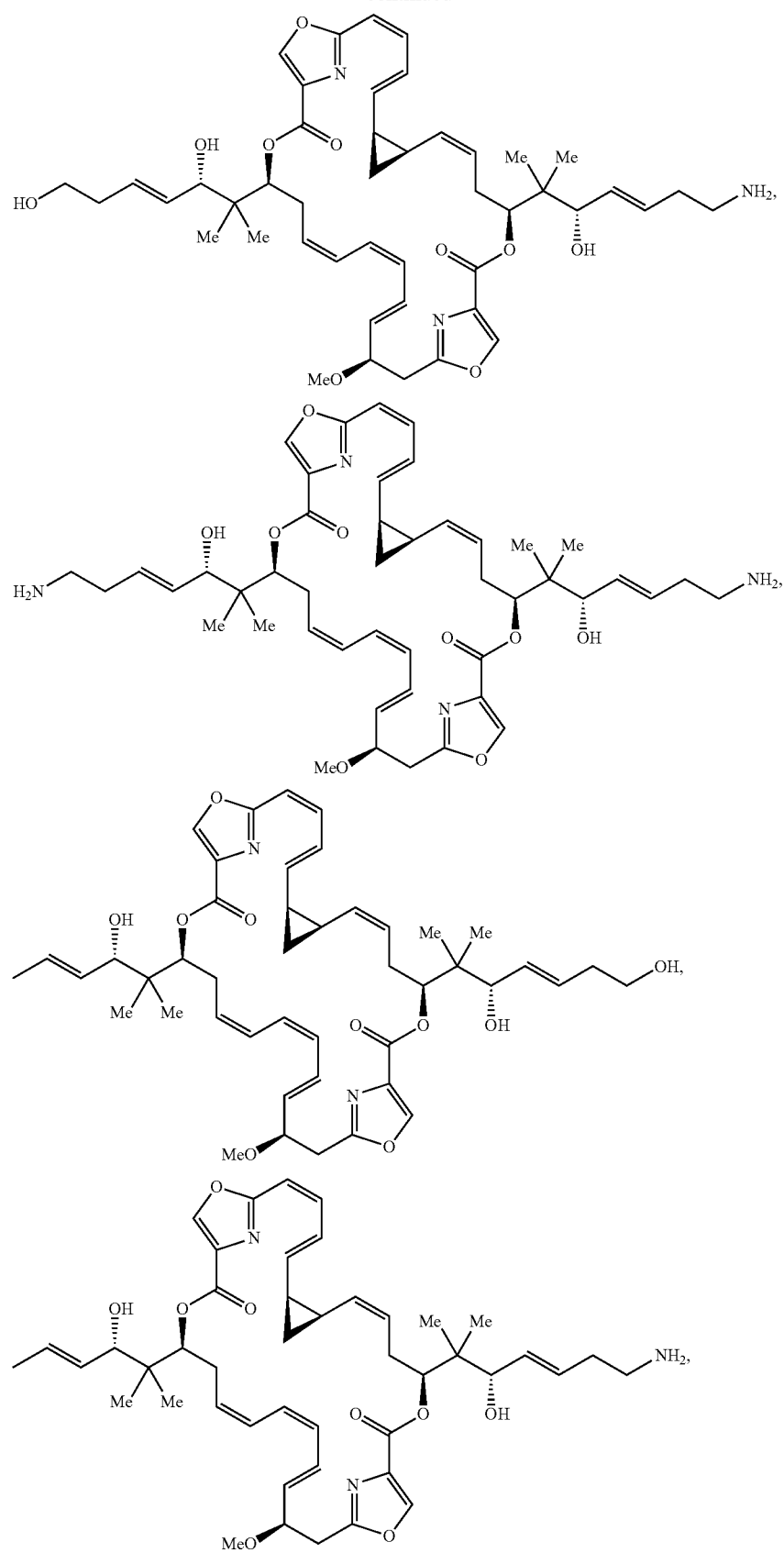

-continued
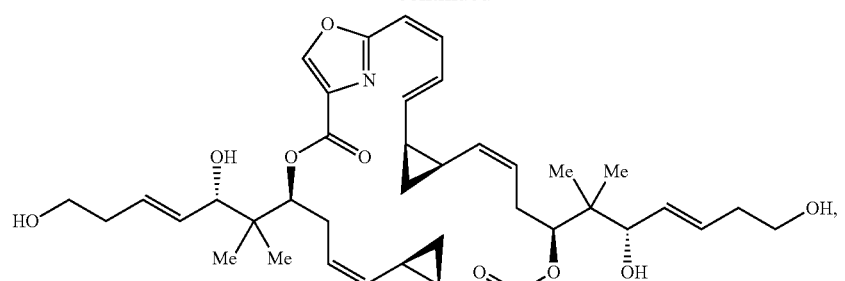
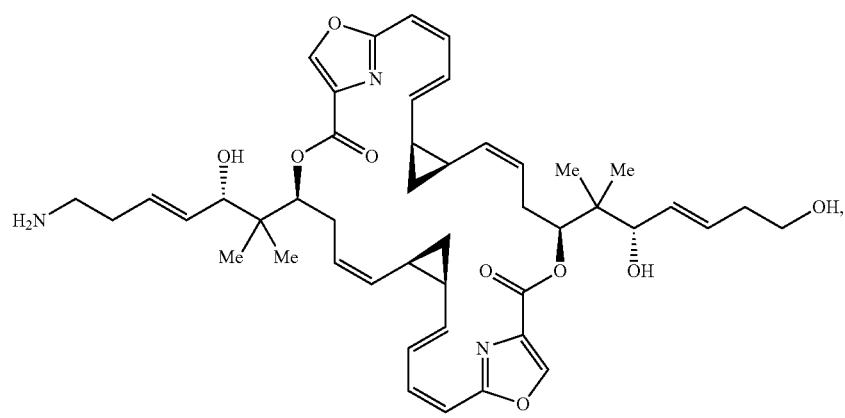
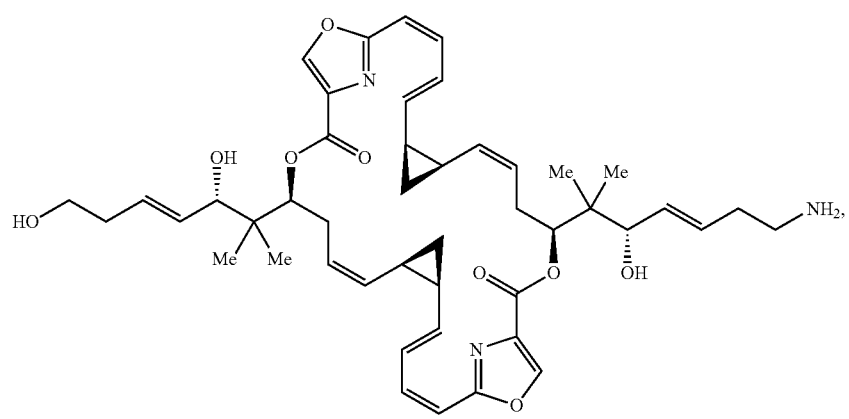
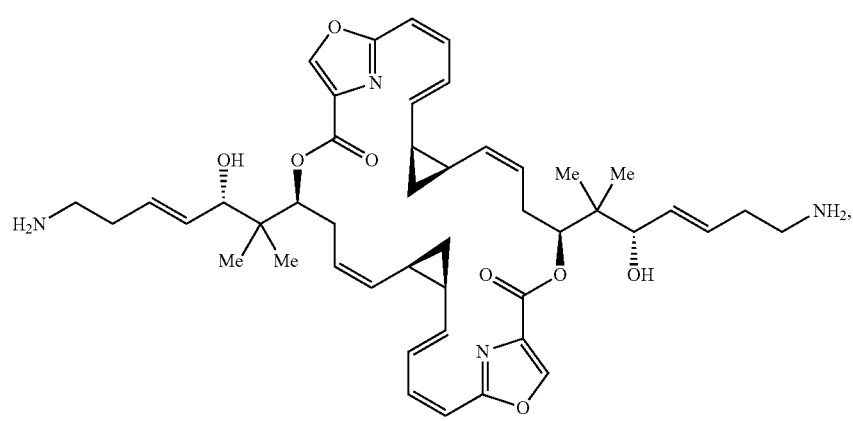

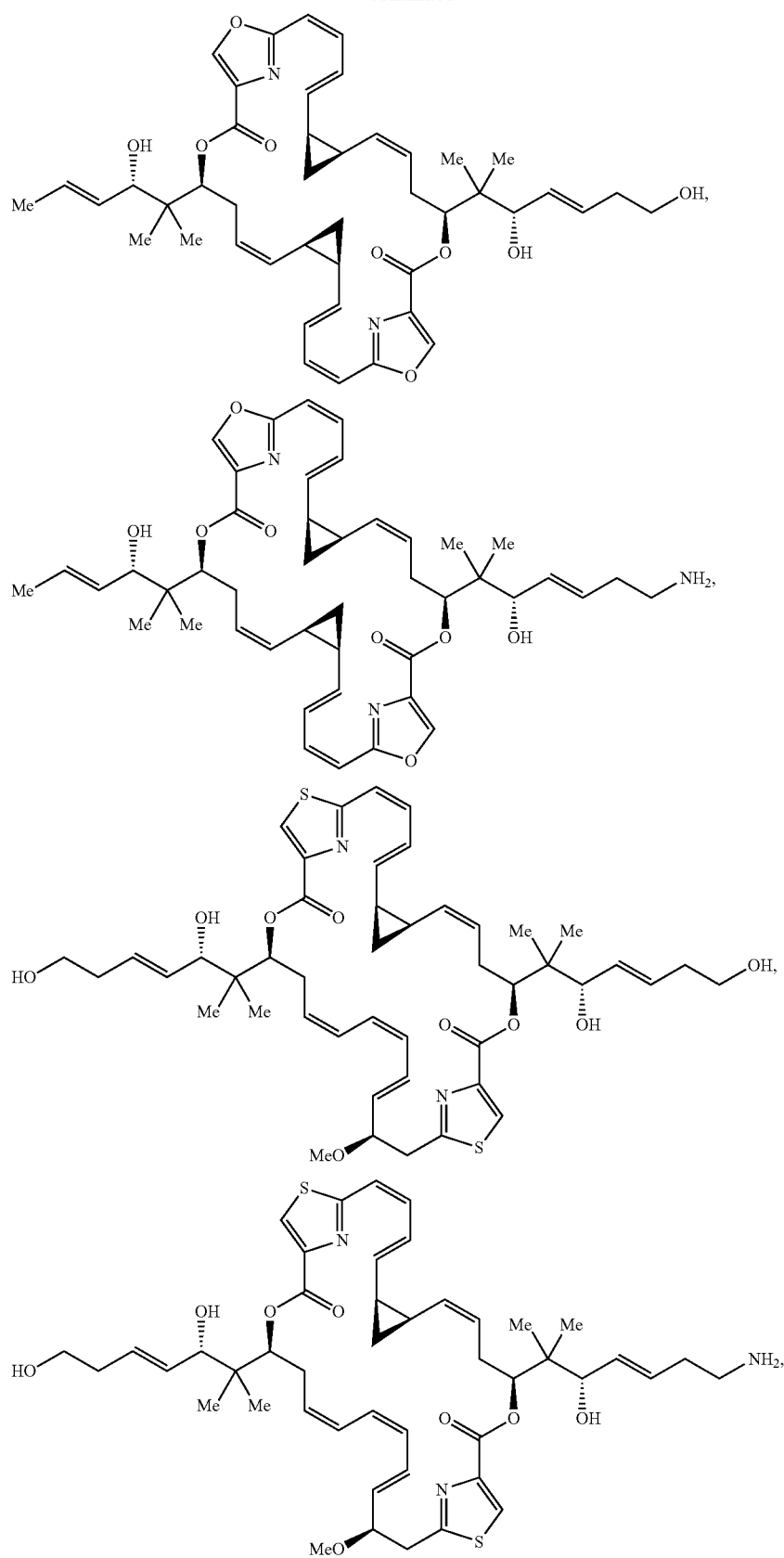

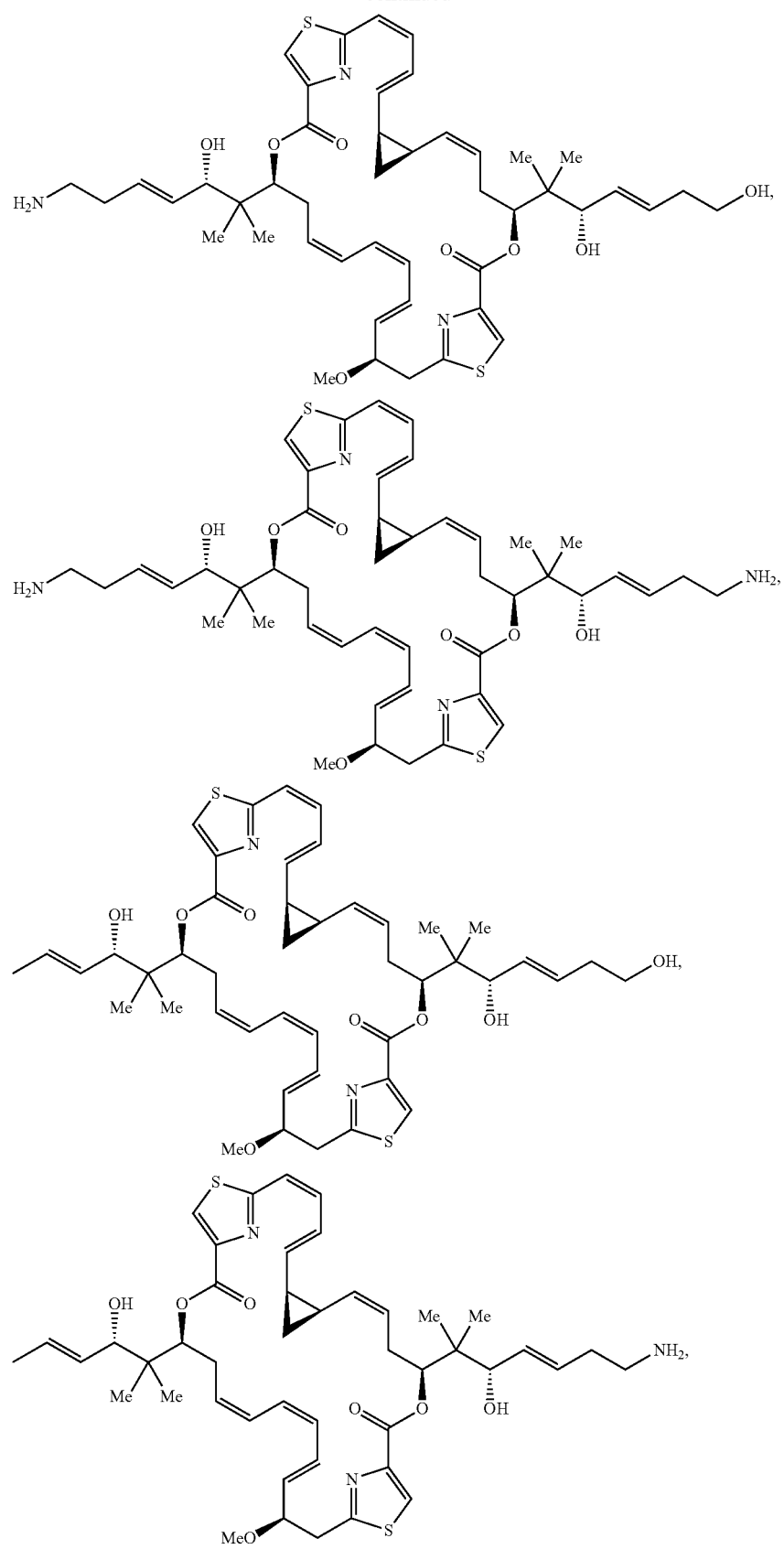

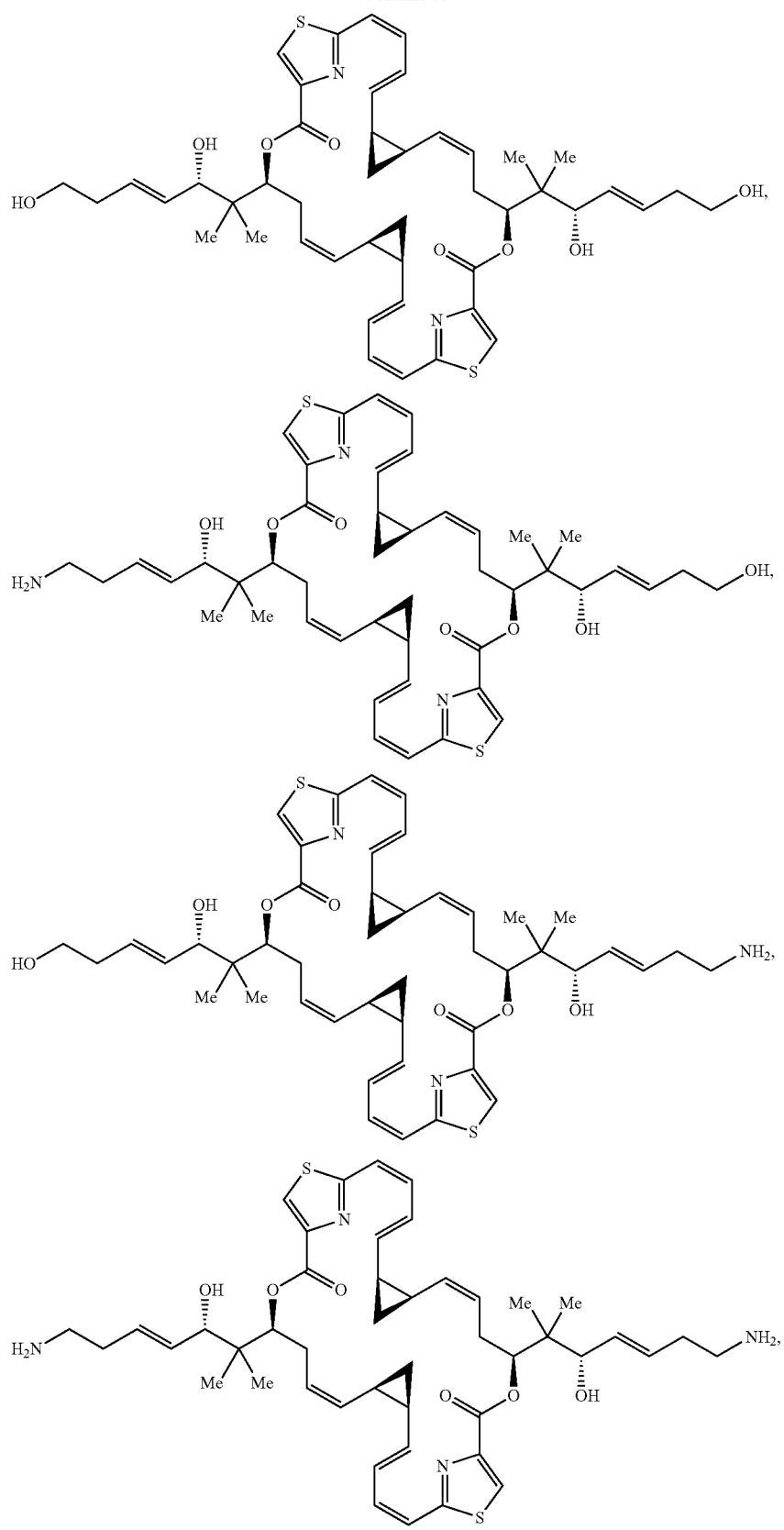

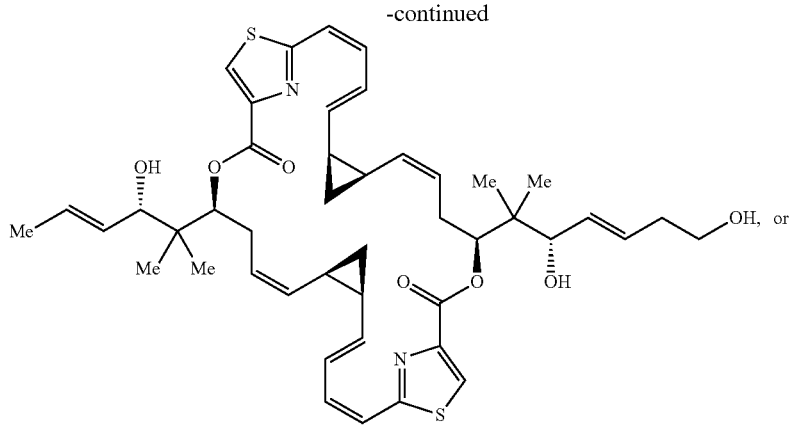

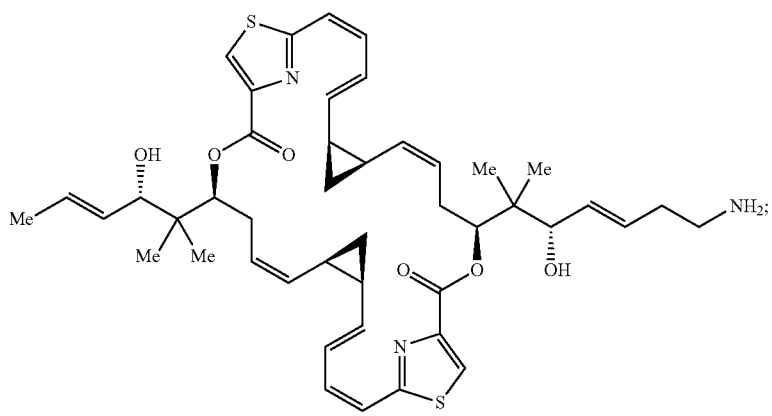

or a pharmaceutically acceptable salt thereof.

In some aspects, the present disclosure provides pharmaceutical compositions comprising:

(A) a compound described herein; and
(B) an excipient.

In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularly, intravitreally, liposomally, locally, mucosally, parenterally, rectally, subconjunctivally, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. In some embodiments, the pharmaceutical composition is formulated as a unit dose.

In still yet another aspect, the present disclosure provides methods of treating a disease or disorder in a patient comprising administering to the patient in need thereof a therapeutically effective amount of a compound or composition described herein. In some embodiments, the disease or disorder is cancer. In some embodiments, the cancer is a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the methods further comprise a second cancer therapy. In some embodiments, the second cancer therapy is surgery, a second chemotherapeutic agent, a radiotherapy, or an immunotherapy. In some embodiments, the patient is a mammal such as a human. In some embodiments, the methods comprise administering the compound once. In other embodiments, the methods comprise administering the compound two or more times.

In still another aspect, the present disclosure provides antibody-drug conjugate comprising:

(A) an antibody; and
(B) a compound described herein.

In some embodiments, the antibody and the compound are connected through a linker. In some embodiments, the antibody comprises two or more compounds conjugated to the antibody. In some embodiments, the linker is an enzymatically degradable linker.

In still yet another aspect, the present disclosure provides methods of preparing a compound of the formula:

(V)

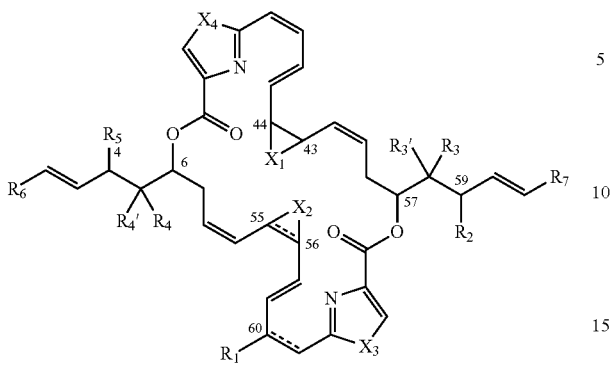

wherein:
  X$_1$ is —O—, —S—, —NR$_a$—, or —CR$_b$R$_c$—; wherein:
    R$_a$ is hydrogen, alkyl$_{(C\leq 8)}$, substituted alkyl$_{(C\leq 8)}$, acyl$_{(C\leq 8)}$, substituted acyl$_{(C\leq 8)}$, or a monovalent amino protecting group, or —C(O)R$_a$'; wherein:
      R$_a$' is amino, hydroxy, alkoxy$_{(C\leq 8)}$, substituted alkoxy$_{(C\leq 8)}$, alkylamino$_{(C\leq 8)}$, substituted alkylamino$_{(C\leq 8)}$, dialkylamino$_{(C\leq 8)}$, or substituted dialkylamino$_{(C\leq 8)}$; and
    R$_b$ and R$_c$ are each independently hydrogen, amino, cyano, halo, hydroxy, or mercapto, or alkyl$_{(C\leq 8)}$, cycloalkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heterocycloalkyl$_{(C\leq 8)}$, acyl$_{(C\leq 8)}$, amido$_{(C\leq 8)}$, alkoxy$_{(C\leq 8)}$, acyloxy$_{(C\leq 8)}$, alkylamino$_{(C\leq 8)}$, dialkylamino$_{(C\leq 8)}$, or a substituted version of any of the last fourteen groups;
  X$_2$ is absent, —NR$_d$—, or —CR$_e$R$_f$—; wherein:
    R$_d$ is hydrogen, alkyl$_{(C\leq 8)}$, substituted alkyl$_{(C\leq 8)}$, acyl$_{(C\leq 8)}$, substituted acyl$_{(C\leq 8)}$, or a monovalent amino protecting group, or —C(O)R$_d$'; wherein:
      R$_d$' is amino, hydroxy, alkoxy$_{(C\leq 8)}$, substituted alkoxy$_{(C\leq 8)}$, alkylamino$_{(C\leq 8)}$, substituted alkylamino$_{(C\leq 8)}$, dialkylamino$_{(C\leq 8)}$, or substituted dialkylamino$_{(C\leq 8)}$; and
    R$_e$ and R$_f$ are each independently hydrogen, amino, cyano, halo, hydroxy, or mercapto, or alkyl$_{(C\leq 8)}$, cycloalkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heterocycloalkyl$_{(C\leq 8)}$, acyl$_{(C\leq 8)}$, amido$_{(C\leq 8)}$, alkoxy$_{(C\leq 8)}$, acyloxy$_{(C\leq 8)}$, alkylamino$_{(C\leq 8)}$, dialkylamino$_{(C\leq 8)}$, or a substituted version of any of the last fourteen groups; and
  provided that X$_2$ is absent, then the bond between carbon atoms 55 and 56 is a double bond; and provided that when the bond between carbon atoms 55 and 56 is a double bond, then X$_2$ is absent;
  X$_3$ and X$_4$ are each independently O, NR$_h$, or S; wherein:
    R$_h$ is hydrogen, alkyl$_{(C\leq 8)}$, substituted alkyl$_{(C\leq 8)}$, or a monovalent amino protecting group; and
  R$_1$ is hydrogen, hydroxy, alkoxy$_{(C\leq 8)}$, substituted alkoxy$_{(C\leq 8)}$, acyloxy$_{(C\leq 8)}$, substituted acyloxy$_{(C\leq 8)}$, or —OR$_g$, wherein R$_g$ is a hydroxy protecting group;
  R$_2$ and R$_5$ are hydroxy, oxo, alkoxy$_{(C\leq 8)}$, substituted alkoxy$_{(C\leq 8)}$, or —OR$_h$, wherein R$_h$ is a hydroxy protecting group;
  R$_3$, R$_3$', R$_4$, and R$_4$' are each independently alkyl$_{(C\leq 8)}$, acyl$_{(C\leq 8)}$, or a substituted version of either group;
  R$_6$ and R$_7$ are each independently alkyl$_{(C\leq 8)}$ or substituted alkyl$_{(C\leq 8)}$; and X$_5$ is —O—, —S—, or —NR$_i$—; wherein:
  R$_i$ is hydrogen, alkyl$_{(C\leq 8)}$, substituted alkyl$_{(C\leq 8)}$, or a monovalent amino protecting group;
comprising reacting a compound of the formula:

(VI)

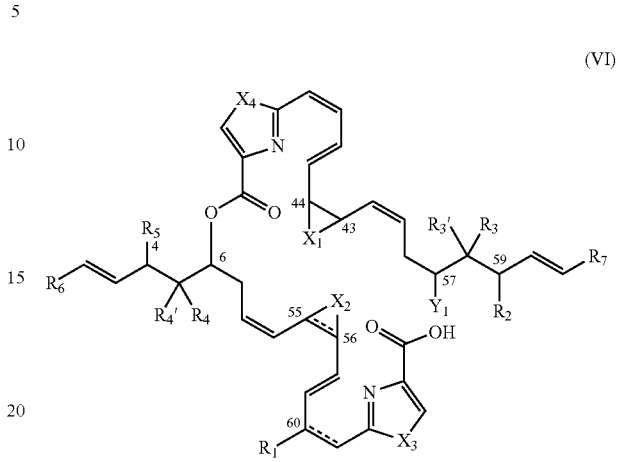

wherein:
  Y$_1$ is amino, hydroxy, mercapto, alkylamino$_{(C\leq 8)}$, or substituted alkylamino$_{(C\leq 8)}$; and
  X$_1$, X$_2$, X$_3$, X$_4$, R$_1$, R$_2$, R$_3$, R$_3$', R$_4$, R$_4$', R$_5$, R$_6$, and R$_7$ are as defined above;
in the presence of a carboxylic acid activating agent and a base.

In some embodiments, the carboxylic acid activating agent is a reagent useful for covering the free carboxylic acid into an anhydride. In some embodiments, the carboxylic acid activating agent is a compound of the formula:

(VII)

or

(VIII)

wherein:
  Y$_2$, Y$_2$', and Y$_3$ are aryl$_{(C\leq 8)}$ or substituted aryl$_{(C\leq 8)}$; and
  X$_6$ is halo.

In some embodiments, the carboxylic acid activating agent is:

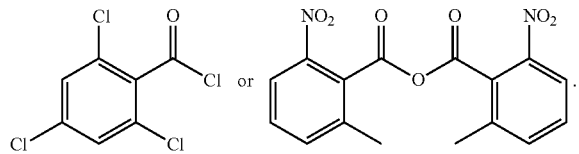

In some embodiments, the methods further comprise two bases. In some embodiments, the two bases are both nitrogenous bases. In some embodiments, the first base is dimethylaminopyridine. In some embodiments, the second base is triethylamine. In some embodiments, the methods further comprise adding from about 1 equivalent to about 20 equivalents of the carboxylic acid activating agent relative to the compound of formula VI. In some embodiments, from about 5 equivalents to about 15 equivalents of the carboxylic acid activating agent are added. In some embodiments, the methods further comprise adding from about 0.05 equivalents to about 5 equivalents of the first base relative to the compound of formula VI. In some embodiments, from about 0.5 equivalents to about 6 equivalents of the first base are added. In some embodiments, the methods further comprise adding from about 1 equivalent to about 20 equivalents of the second base relative to the compound of formula VI. In some embodiments, from about 5 equivalents to about 15 equivalents of the second base are added.

In some embodiments, the methods further comprise reacting the reaction to a temperature from about 10° C. to about 75° C. In some embodiments, the temperature is from about 25° C. to about 50° C. In some embodiments, the method further comprises an organic solvent. In some embodiments, the organic solvent is an arene$_{(C \leq 12)}$ or substituted arene$_{(C \leq 12)}$ such as toluene. In some embodiments, the methods further comprise reacting the compound of formula VI with the carboxylic acid activating agent and the base for a time period from about 1 h to about 48 h. In some embodiments, the time period is from about 4 h to about 36 h.

In still yet another aspect, the present disclosure provides methods of preparing a compound of the formula:

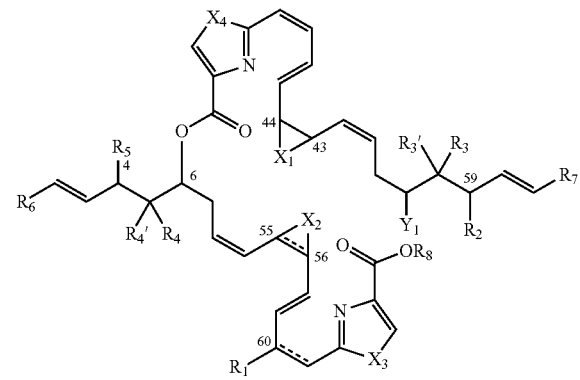

(VI)

wherein:
X$_1$ is —O—, —S—, —NR$_a$—, or —CR$_b$R$_c$—; wherein:
R$_a$ is hydrogen, alkyl$_{(C \leq 8)}$, substituted alkyl$_{(C \leq 8)}$, acyl$_{(C \leq 8)}$, substituted acyl$_{(C \leq 8)}$, or a monovalent amino protecting group, or —C(O)R$_a$', wherein:
R$_a$' is amino, hydroxy, alkoxy$_{(C \leq 8)}$, substituted alkoxy$_{(C \leq 8)}$, alkylamino$_{(C \leq 8)}$, substituted alkylamino$_{(C \leq 8)}$, dialkylamino$_{(C \leq 8)}$, or substituted dialkylamino$_{(C \leq 8)}$; and
R$_b$ and R$_c$ are each independently hydrogen, amino, cyano, halo, hydroxy, or mercapto, or alkyl$_{(C \leq 8)}$, cycloalkyl$_{(C \leq 8)}$, alkenyl$_{(C \leq 8)}$, alkynyl$_{(C \leq 8)}$, aryl$_{(C \leq 8)}$, aralkyl$_{(C \leq 8)}$, heteroaryl$_{(C \leq 8)}$, heterocycloalkyl$_{(C \leq 8)}$, acyl$_{(C \leq 8)}$, amido$_{(C \leq 8)}$, alkoxy$_{(C \leq 8)}$, acyloxy$_{(C \leq 8)}$, alkylamino$_{(C \leq 8)}$, dialkylamino$_{(C \leq 8)}$, or a substituted version of any of the last fourteen groups;
X$_2$ is absent, —O—, —S—, —NR$_d$—, or —CR$_e$R$_f$—; wherein:
R$_d$ is hydrogen, alkyl$_{(C \leq 8)}$, substituted alkyl$_{(C \leq 8)}$, acyl$_{(C \leq 8)}$, substituted acyl$_{(C \leq 8)}$, or a monovalent amino protecting group, or —C(O)R$_d$', wherein:
R$_d$' is amino, hydroxy, alkoxy$_{(C \leq 8)}$, substituted alkoxy$_{(C \leq 8)}$, alkylamino$_{(C \leq 8)}$, substituted alkylamino$_{(C \leq 8)}$, dialkylamino$_{(C \leq 8)}$, or substituted dialkylamino$_{(C \leq 8)}$; and
R$_e$ and R$_f$ are each independently hydrogen, amino, cyano, halo, hydroxy, or mercapto, or alkyl$_{(C \leq 8)}$, cycloalkyl$_{(C \leq 8)}$, alkenyl$_{(C \leq 8)}$, alkynyl$_{(C \leq 8)}$, aryl$_{(C \leq 8)}$, aralkyl$_{(C \leq 8)}$, heteroaryl$_{(C \leq 8)}$, heterocycloalkyl$_{(C \leq 8)}$, acyl$_{(C \leq 8)}$, amido$_{(C \leq 8)}$, alkoxy$_{(C \leq 8)}$, acyloxy$_{(C \leq 8)}$, alkylamino$_{(C \leq 8)}$, dialkylamino$_{(C \leq 8)}$, or a substituted version of any of the last fourteen groups; and
provided that X$_2$ is absent, then the bond between carbon atoms 55 and 56 is a double bond; and provided that when the bond between carbon atoms 55 and 56 is a double bond, then X$_2$ is absent;
X$_3$ and X$_4$ are each independently O, NR$_h$, or S; wherein:
R$_h$ is hydrogen, alkyl$_{(C \leq 8)}$, substituted alkyl$_{(C \leq 8)}$, or a monovalent amino protecting group; and
R$_1$ is hydrogen, hydroxy, alkoxy$_{(C \leq 8)}$, substituted alkoxy$_{(C \leq 8)}$, acyloxy$_{(C \leq 8)}$, substituted acyloxy$_{(C \leq 8)}$, or —OR$_g$, wherein R$_g$ is a hydroxy protecting group;
R$_2$ and R$_5$ are hydroxy, oxo, alkoxy$_{(C \leq 8)}$, substituted alkoxy$_{(C \leq 8)}$, or —OR$_h$, wherein R$_h$ is a hydroxy protecting group;
R$_3$, R$_3$', R$_4$, and R$_4$' are each independently alkyl$_{(C \leq 8)}$, acyl$_{(C \leq 8)}$, or a substituted version of either group;
R$_6$ and R$_7$ are each independently alkyl$_{(C \leq 8)}$ or substituted alkyl$_{(C \leq 8)}$; and
R$_8$ is hydrogen, alkyl$_{(C \leq 8)}$, or substituted alkyl$_{(C \leq 8)}$;
comprising reacting a compound of the formula:

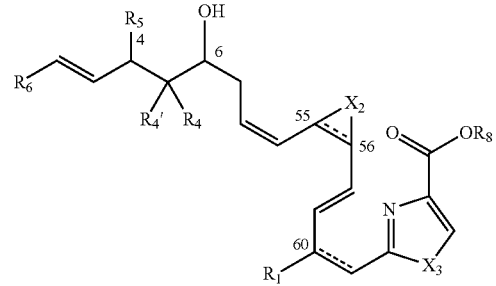

(IX)

wherein:
X$_2$, X$_3$, R$_1$, R$_4$, R$_4$', R$_5$, R$_6$, and R$_8$ are as defined above;
with a compound of the formula:

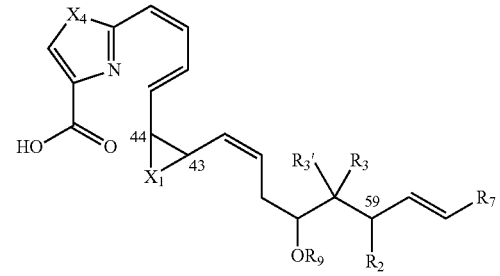

(X)

wherein:
R$_9$ is hydrogen or a hydroxy protecting group; and
X$_1$, X$_4$, R$_1$, R$_2$, R$_3$, R$_3$', and R$_7$ are as defined above;

in the presence of an carboxylic acid activating agent and a base.

In some embodiments, the carboxylic acid activating agent is a reagent useful for covering the free carboxylic acid into an anhydride. In some embodiments, the carboxylic acid activating agent is a compound of the formula:

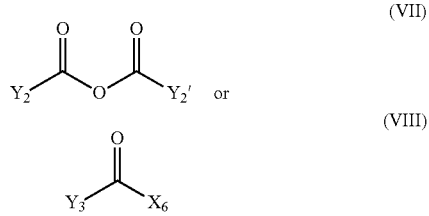

(VII)

(VIII)

wherein:
$Y_2$, $Y_2'$, and $Y_3$ are $aryl_{(C≤12)}$ or substituted $aryl_{(C≤12)}$; and $X_6$ is halo.

In some embodiments, the carboxylic acid activating agent is:

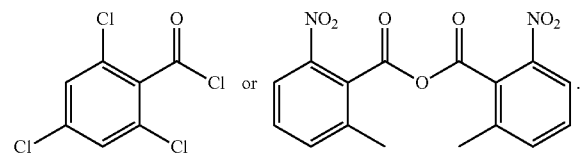 [SMILES: O=C(Cl)c1c(Cl)cc(Cl)cc1Cl ; Cc1cccc([N+](=O)[O-])c1C(=O)OC(=O)c1c(C)cccc1[N+](=O)[O-]]

In some embodiments, the methods further comprise two bases. In some embodiments, the two bases are both nitrogenous bases. In some embodiments, the first base is dimethylaminopyridine. In some embodiments, the second base is triethylamine. In some embodiments, the methods further comprise adding from about 1 equivalent to about 20 equivalents of the carboxylic acid activating agent relative to the compound of formula IX. In some embodiments, from about 1 equivalents to about 5 equivalents of the carboxylic acid activating agent are added. In some embodiments, the methods further comprise adding from about 0.5 equivalent to about 5 equivalents of the compound of formula X relative to the compound of formula IX. In some embodiments, from about 1 equivalents to about 3 equivalents of the compound of formula X are added. In some embodiments, the methods further comprise adding from about 2 equivalents to about 20 equivalents of the first base relative to the compound of formula IX. In some embodiments, from about 5 equivalents to about 10 equivalents of the first base are added. In some embodiments, the methods further comprise adding from about 1 equivalent to about 20 equivalents of the second base relative to the compound of formula IX. In some embodiments, from about 5 equivalents to about 15 equivalents of the second base are added.

In some embodiments, the methods further comprise reacting the reaction to a temperature from about 0° C. to about 50° C. In some embodiments, the temperature is from about 10° C. to about 40° C. In some embodiments, the method further comprises an organic solvent. In some embodiments, the organic solvent is an $arene_{(C≤12)}$ or substituted $arene_{(C≤12)}$ such as toluene. In some embodiments, the methods further comprise reacting the compound of formula IX and the compound of formula X with the carboxylic acid activating agent and the base for a time period from about 0.25 h to about 12 h. In some embodiments, the time period is from about 0.5 h to about 4 h.

It is contemplated that any method or composition described herein can be implemented with respect to any other method or composition described herein. For example, a compound synthesized by one method may be used in the preparation of a final compound according to a different method.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed description.

DESCRIPTION OF ILLUSTRATIVE EMBODIMENTS

Figure 1:
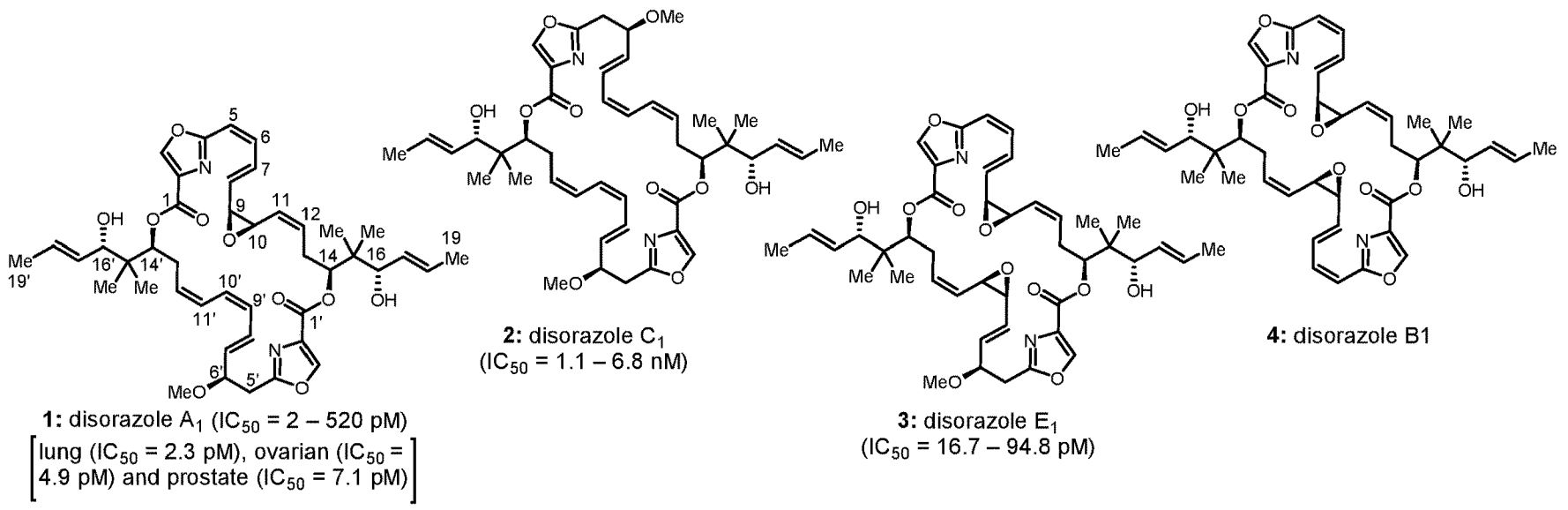
FIG. 1 shows the structure of disorazole $A_1$, $B_1$, $C_1$, and $E_1$.
Figure 2A:
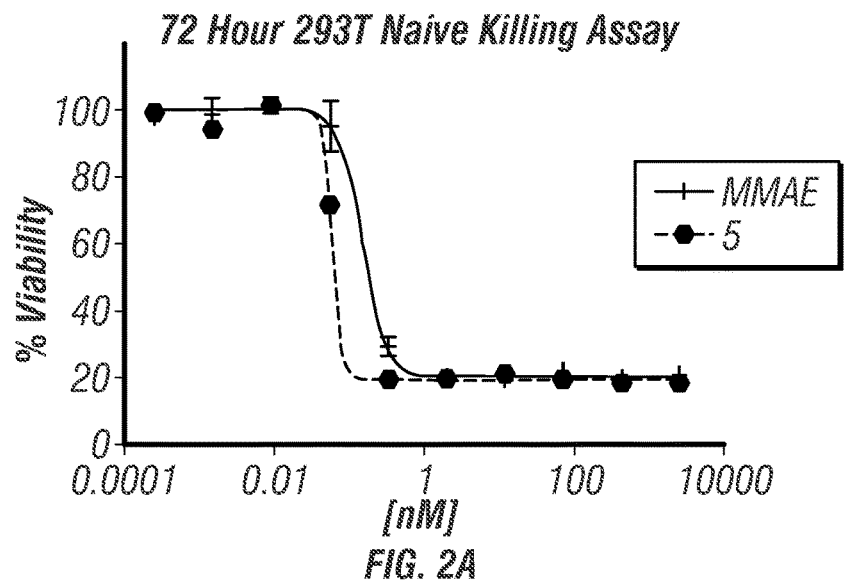
FIGS. 2A-2C show the 72 h killing assay for 5 and known antibody-drug conjugate payload, MMAE for 293T (FIG. 2A), MES SA (FIG. 2B), and MES SA DX (FIG. 2C).
Figure 2B:
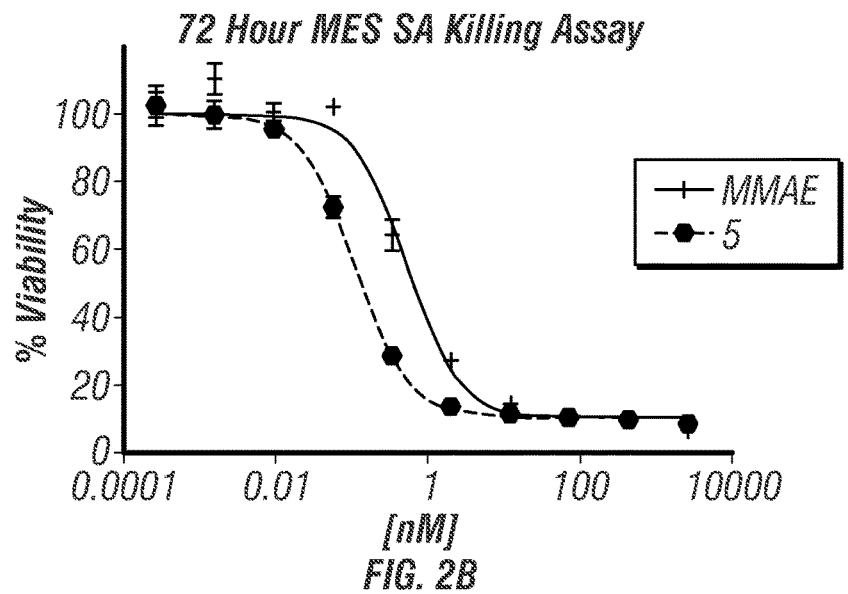
Figure 2C:
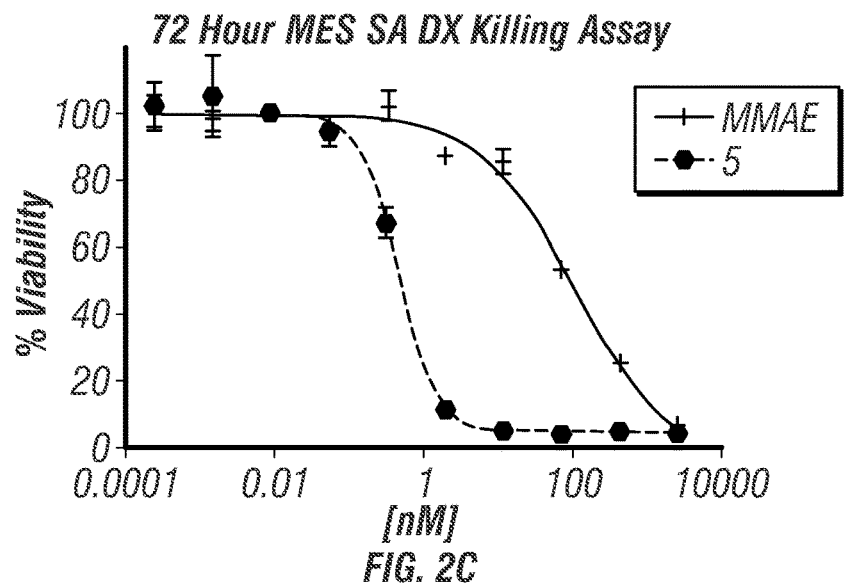

The present disclosure provides derivatives of disorazoles which may be used in antibody-drug conjugates. In some aspects, these compounds may contain modifications which increase the activity, chemical stability, or both. Also, provided herein are methods of using these compounds, antibody-drug conjugates thereof, and methods of preparing these compounds.

I. COMPOUNDS AND FORMULATIONS THEREOF

A. Compounds

The compounds provided by the present disclosure are shown, for example, above in the summary section and in the examples and claims below. They may be made using the methods outlined in the Examples section. The disorazole analogs described herein can be synthesized according to the methods described, for example, in the Examples section below. These methods can be further modified and optimized using the principles and techniques of organic chemistry as applied by a person skilled in the art. Such principles and techniques are taught, for example, in March's *Advanced Organic Chemistry: Reactions, Mechanisms, and Structure* (2007), which is incorporated by reference herein.

The disorazole analogs described herein may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the (S) or the (R) configuration.

Chemical formulas used to represent the disorazole analogs described herein will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

The disorazole analogs described herein may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the disorazole analogs described herein are intended to include all isotopic forms of such atoms. Isotopes, as used herein, include those atoms having the same atomic number but different mass numbers. By way of general example and without limitation, isotopes of hydrogen include tritium and deuterium. and isotopes of carbon include $^{13}C$ and $^{14}C$.

The disorazole analogs described herein may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the disorazole analogs described herein may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Those skilled in the art of organic chemistry will appreciate that many organic compounds can form complexes with solvents in which they are reacted or from which they are precipitated or crystallized. These complexes are known as "solvates". For example, a complex with water is known as a "hydrate." Solvates of the disorazole analogs described herein are within the scope of the disclosure. It will also be appreciated by those skilled in organic chemistry that many organic compounds can exist in more than one crystalline form. For example, crystalline form may vary from solvate to solvate. Thus, all crystalline forms of the disorazole analogs described herein are within the scope of the present disclosure.

B. Formulations

In some embodiments of the present disclosure, the disorazole analogs are included a pharmaceutical formulation. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Formulations for oral use include tablets containing the active ingredient(s) (e.g., the disorazole analogs described herein) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate. zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

II. CANCER AND OTHER HYPERPROLIFERATIVE DISEASES

While hyperproliferative diseases can be associated with any disease which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In this disclosure, the disorazole analogs described herein may be used to lead to decreased cell counts and as such can potentially be used to treat a variety of types of cancer lines. In some aspects, it is anticipated that the disorazole analogs described herein may be used to treat virtually any malignancy.

Cancer cells that may be treated with the compounds of the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

III. CELL TARGETING MOIETIES

In some aspects, the present disclosure provides compounds conjugated directly or through linkers to a cell targeting moiety. In some embodiments, the conjugation of the compound to a cell targeting moiety increases the efficacy of the compound in treating a disease or disorder. Cell targeting moieties according to the embodiments may be, for example, an antibody, a growth factor, a hormone, a peptide, an aptamer, a small molecule such as a hormone, an imaging agent, or cofactor, or a cytokine. For instance, a cell targeting moiety according the embodiments may bind to a liver cancer cell such as a Hep3B cell. It has been demonstrated that the gp240 antigen is expressed in a variety of melanomas but not in normal tissues. Thus, in some embodiments, the compounds of the present disclosure may be used in conjugates with an antibody for a specific antigen that is expressed by a cancer cell but not in normal tissues.

In certain additional embodiments, it is envisioned that cancer cell targeting moieties bind to multiple types of cancer cells. For example, the 8H9 monoclonal antibody and the single chain antibodies derived therefrom bind to a glycoprotein that is expressed on breast cancers, sarcomas and neuroblastomas (Onda, et al., 2004). Another example is the cell targeting agents described in U.S. Patent Publication No. 2004/005647 and in Winthrop, et al. (2003) that bind to MUC-1, an antigen that is expressed on a variety cancer types. Thus, it will be understood that in certain embodiments, cell targeting constructs according the embodiments may be targeted against a plurality of cancer or tumor types.

Additionally, certain cell surface molecules are highly expressed in tumor cells, including hormone receptors such as human chorionic gonadotropin receptor and gonadotropin releasing hormone receptor (Nechushtan et al., 1997). Therefore, the corresponding hormones may be used as the cell-specific targeting moieties in cancer therapy. Additionally, the cell targeting moiety that may be used include a cofactor, a sugar, a drug molecule, an imaging agent, or a fluorescent dye. Many cancerous cells are known to over express folate receptors and thus folic acid or other folate derivatives may be used as conjugates to trigger cell-specific interaction between the conjugates of the present disclosure and a cell (Campbell, et al., 1991; Weitman, et al., 1992).

Since a large number of cell surface receptors have been identified in hematopoietic cells of various lineages, ligands or antibodies specific for these receptors may be used as cell-specific targeting moieties. IL-2 may also be used as a cell-specific targeting moiety in a chimeric protein to target IL-2R+ cells. Alternatively, other molecules such as B7-1, B7-2 and CD40 may be used to specifically target activated T cells (The Leucocyte Antigen Facts Book, 1993, Barclay, et al. (eds.), Academic Press). Furthermore, B cells express CD19, CD40 and IL-4 receptor and may be targeted by moieties that bind these receptors, such as CD40 ligand, IL-4, IL-5, IL-6 and CD28. The elimination of immune cells such as T cells and B cells is particularly useful in the treatment of lymphoid tumors.

Other cytokines that may be used to target specific cell subsets include the interleukins (IL-1 through IL-15), granulocyte-colony stimulating factor, macrophage-colony stimulating factor, granulocyte-macrophage colony stimulating factor, leukemia inhibitory factor, tumor necrosis factor, transforming growth factor, epidermal growth factor, insulin-like growth factors, and/or fibroblast growth factor (Thompson (ed.), 1994, The Cytokine Handbook. Academic Press, San Diego). In some aspects, the targeting polypeptide is a cytokine that binds to the Fn14 receptor, such as TWEAK (see, e.g., Winkles, 2008; Zhou, et al., 2011 and Burkly, et al., 2007, incorporated herein by reference).

A skilled artisan recognizes that there are a variety of known cytokines, including hematopoictins (four-helix bundles) (such as EPO (erythropoietin), IL-2 (T-cell growth factor), IL-3 (multicolony CSF), IL-4 (BCGF-1, BSF-1), IL-5 (BCGF-2), IL-6 IL-4 (IFN-$\beta$2, BSF-2, BCDF), IL-7, IL-8, IL-9, IL-11, IL-13 (P600), G-CSF, IL-15 (T-cell growth factor), GM-CSF (granulocyte macrophage colony stimulating factor), OSM (OM, oncostatin M), and LIF (leukemia inhibitory factor)); interferons (such as IFN-$\gamma$, IFN-$\alpha$, and IFN-$\beta$); immunoglobin superfamily (such as B7.1 (CD80), and B7.2 (B70, CD86)); TNF family (such as TNF-$\alpha$ (cachectin), TNF-$\beta$ (lymphotoxin, LT, LT-$\alpha$), LT-$\beta$, CD40 ligand (CD40L), Fas ligand (FasL), CD27 ligand (CD27L), CD30 ligand (CD30L), and 4-1BBL)); and those unassigned to a particular family (such as TGF-$\beta$, IL 1$\alpha$, IL-1$\beta$, IL-1 RA, IL-10 (cytokine synthesis inhibitor F), IL-12 (NK cell stimulatory factor), MIF, IL-16, IL-17 (mCTLA-8), and/or IL-18 (IGIF, interferon-$\gamma$ inducing factor)). Furthermore, the Fc portion of the heavy chain of an antibody may be used to target Fc receptor-expressing cells such as the use of the Fc portion of an IgE antibody to target mast cells and basophils.

Furthermore, in some aspects, the cell-targeting moiety may be a peptide sequence or a cyclic peptide. Examples, cell- and tissue-targeting peptides that may be used according to the embodiments are provided, for instance, in U.S. Pat. Nos. 6,232,287; 6,528,481; 7,452,964; 7,671,010; 7,781,565; 8,507,445; and 8,450,278, each of which is incorporated herein by reference.

Thus, in some embodiments, cell targeting moieties are antibodies or avimers. Antibodies and avimers can be generated against virtually any cell surface marker thus, providing a method for targeted to delivery of GrB to virtually any cell population of interest. Methods for generating antibodies that may be used as cell targeting moieties are detailed below. Methods for generating avimers that bind to a given cell surface marker are detailed in U.S. Patent Publications Nos. 2006/0234299 and 2006/0223114, each incorporated herein by reference.

Additionally, it is contemplated that the compounds described herein may be conjugated to a nanoparticle or other nanomaterial. Some non-limiting examples of nanoparticles include metal nanoparticles such as gold or silver nanoparticles or polymeric nanoparticles such as poly-L-lactic acid or poly(ethylene) glycol polymers. Nanoparticles and nanomaterials which may be conjugated to the instant compounds include those described in U.S. Patent Publications Nos. 2006/0034925, 2006/0115537, 2007/0148095, 2012/0141550, 2013/0138032, and 2014/0024610 and PCT Publication No. 2008/121949, 2011/053435, and 2014/087413, each incorporated herein by reference.

IV. THERAPIES

A. Pharmaceutical Formulations and Routes of Administration

Where clinical applications are contemplated, it will be necessary to prepare pharmaceutical compositions in a form appropriate for the intended application. In some embodiments, such formulation with the disorazole analogs of the present disclosure is contemplated. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present disclosure comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the disorazole analogs described herein may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 mL of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the appropriate regulatory agencies for the safety of pharmaceutical agents.

B. Methods of Treatment

In particular, the compositions that may be used in treating cancer in a subject (e.g., a human subject) are disclosed herein. The compositions described above are preferably administered to a mammal (e.g., rodent, human, non-human primates, canine, bovine, ovine, equine, feline, etc.) in an effective amount, that is, an amount capable of producing a desirable result in a treated subject (e.g., causing apoptosis of cancerous cells). Toxicity and therapeutic efficacy of the compositions utilized in methods of the disclosure can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the infection or cancer and other drugs being administered concurrently. A composition as described herein is typically administered at a dosage that induces death of cancerous cells (e.g., induces apoptosis of a cancer cell), as assayed by identifying a reduction in hematological parameters (complete blood count—CBC), or cancer cell growth or proliferation. In some embodiments, amounts of the disorazole analogs used to induce apoptosis of the cancer cells is calculated to be from about 0.01 mg to about 10,000 mg/day. In some embodiments, the amount is from about 1 mg to about 1,000 mg/day. In some embodiments, these dosings may be reduced or increased based upon the biological factors of a particular patient such as increased or decreased metabolic breakdown of the drug or decreased uptake by the digestive tract if administered orally. Additionally, the disorazole analogs may be more efficacious and thus a smaller dose is required to achieve a similar effect. Such a dose is typically administered once a day for a few weeks or until sufficient reducing in cancer cells has been achieved.

The therapeutic methods of the disclosure (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

In one embodiment, the disclosure provides a method of monitoring treatment progress. The method includes the step of determining a level of changes in hematological parameters and/or cancer stem cell (CSC) analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer in which the subject has been administered a therapeutic amount of a composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

C. Combination Therapies

It is envisioned that the disorazole analogs described herein may be used in combination therapies with one or more cancer therapies or a compound which mitigates one or more of the side effects experienced by the patient. It is common in the field of cancer therapy to combine therapeutic modalities. The following is a general discussion of therapies that may be used in conjunction with the therapies of the present disclosure.

To treat cancers using the methods and compositions of the present disclosure, one would generally contact a tumor cell or subject with a compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the disorazole analogs described herein may precede or follow the other treatment by intervals ranging from minutes to weeks. One would generally ensure that a significant period of time did not expire between the times of each delivery, such that the therapies would still be able to exert an advantageously combined effect on the cell/subject. In such instances, it is contemplated that one would contact the cell with both modalities within about 12-24 h of each other, within about 6-12 h of each other, or with a delay time of only about 1-2 h. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where a compound of the present disclosure is "A," and the other therapy is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are also contemplated. The following is a general discussion of cancer therapies that may be used combination with the compounds of the present disclosure.

1. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin $\gamma_1$ and calicheamicin $\omega_1$; dynemicin, including dynemicin A; uncialamycin and derivatives thereof; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine. doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, or zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2''-trichloro-triethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present disclosure may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 12.9 to 51.6 mC/kg for prolonged periods of time (3 to 4 wk), to single doses of 0.516 to 1.55 C/kg. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739, 169; Hui and Hashimoto, 1998; Christodoulides, et al., 1998), cytokine therapy, e.g., interferons α, β, and γ; IL-1, GM-CSF and TNF (Bukowski, et al., 1998; Davidson, et al., 1998; Hellstrand, et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras, et al., 1998; Hanibuchi, et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton, et al., 1992; Mitchell, et al., 1990; Mitchell, et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg, et al., 1988; 1989).

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mobs' surgery). It is further contemplated that the present disclosure may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believe to be particularly efficacious in reducing the reoccurance of the tumor. Additionally, the compounds of the present disclosure can also be used in a neoadjuvant setting.

5. Other Agents

It is contemplated that other agents may be used with the present disclosure. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present disclosure by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents may be used in combination with the present disclosure to improve the anti-hyerproliferative efficacy of the treatments. Inhibitors of cell adhesion are contemplated to improve the efficacy of the present disclosure. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present disclosure to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 41.1° C.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the appropriate pharmaceutical agent regulatory agencies.

It also should be pointed out that any of the foregoing therapies may prove useful by themselves in treating cancer.

V. SYNTHETIC METHODS

In some aspects, the disorazole analogs of this disclosure can be synthesized using the methods of organic chemistry as described in this application. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

A. Process Scale-Up

The synthetic methods described herein can be further modified and optimized for preparative, pilot- or large-scale production, either batch of continuous, using the principles and techniques of process chemistry as applied by a person skilled in the art. Such principles and techniques are taught, for example, in *Practical Process Research & Development* (2000), which is incorporated by reference herein. The synthetic method described herein may be used to produce preparative scale amounts of the disorazole analogs described herein.

B. Chemical Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; "hydrazine" means —NHNH$_2$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "hydroxysulfonyl" means —SO$_3$H, "sulfonyl" means —S(O)$_2$-; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "" represents a single bond or a double bond. Thus, the formula

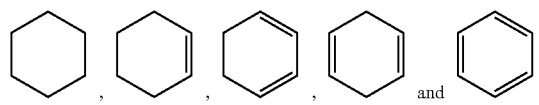

covers, for example,

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "⌇", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "◁||||" means a single bond where the group attached to the thick end of the wedge is "into the page". The symbol "⌇" mean a single bond where the geometry around a double bond [e.g., either (E) or (Z)] is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

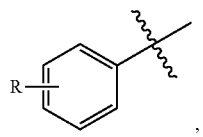

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

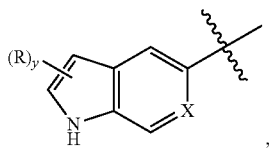

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom(s) in the moiety replacing a hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$. —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e., —F, —Cl, —Br, or —I) such that no other atoms aside from carbon, hydrogen and halogen are present. The group, —CH₂Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH₂F, —CF₃, and —CH₂CF₃ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH₂)₂ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

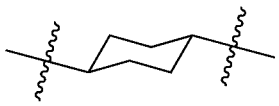 [SMILES: *C1CCC(*)CC1]

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH═CH₂ (vinyl), —CH═CHCH₃, —CH═CHCH₂CH₃, —CH₂CH═CH₂ (allyl), —CH₂CH═CHCH₃, and —CH═CHCH═CH₂. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH═CH—, —CH═C(CH₃)CH₂—, —CH═CHCH₂—, and —CH₂CH═CHCH₂— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. The groups —CH═CHF, —CH═CHCl and —CH═CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH₃, and —CH₂C≡CCH₃ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "aryl" when used without the "substituted" modifier refers to a monovalent unsaturated aromatic group with an aromatic carbon atom as the point of attachment, said carbon atom forming part of a one or more aromatic ring structure, wherein the ring atoms are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and a monovalent group derived from biphenyl (e.g., 4-phenylphenyl). The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

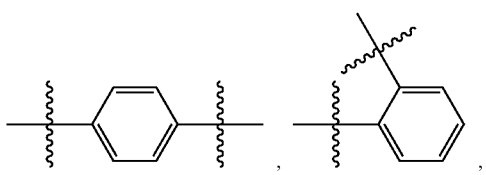

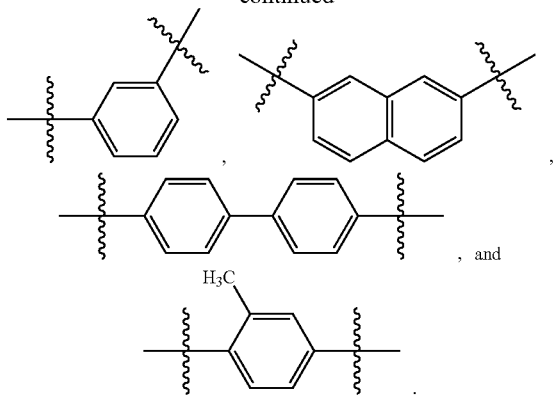

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, the aromatic ring structures being one, two, three, or four ring structures each containing from three to nine ring atoms, and wherein the heteroaryl group consists of no atoms other than carbon, hydrogen, aromatic nitrogen, aromatic oxygen and aromatic sulfur. If more than one ring is present, the rings may be fused or unfused. Unfused rings are connected with a covalent bond. As used herein, the term heteroaryl does not preclude the presence of one or more alkyl or aryl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, the non-aromatic ring structures being one, two, three, or four ring structures each containing from three to nine ring atoms, and wherein the heterocycloalkyl group consists of no atoms other than carbon, hydrogen, nitrogen, oxygen and sulfur. If more than one ring is present the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), or —OC(CH$_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "amido" (acylamino), when used without the "substituted" modifier, refers to the group —NHR. in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

As indicated above in some aspects the cell-targeting moiety is an antibody. As used herein, the term "antibody" is intended to include immunoglobulins and fragments thereof which are specifically reactive to the designated protein or peptide, or fragments thereof. Suitable antibodies include, but are not limited to, human antibodies, primatized antibodies, de-immunized antibodies, chimeric antibodies, bi-specific antibodies, humanized antibodies, conjugated antibodies (i.e., antibodies conjugated or fused to other proteins, radiolabels, cytotoxins). Small Modular Immunopharmaceuticals ("SMIPs™"), single chain antibodies, cameloid antibodies, antibody-like molecules (e.g., anticalins), and antibody fragments. As used herein, the term "antibodies" also includes intact monoclonal antibodies, polyclonal antibodies, single domain antibodies (e.g., shark single domain antibodies (e.g., IgNAR or fragments thereof)), multispecific antibodies (e.g., bi-specific antibodies) formed from at least two intact antibodies, and antibody fragments so long as they exhibit the desired biological activity. Antibody polypeptides for use herein may be of any type (e.g., IgG, IgM, IgA, IgD and IgE). Generally, IgG and/or IgM are preferred because they are the most common antibodies in the physiological situation and because they are most easily made in a laboratory setting. As used herein the term antibody also encompasses an antibody fragment such as a portion of an intact antibody, such as, for example, the antigen-binding or variable region of an antibody. Examples of antibody fragments include Fab, Fab', F(ab')2, Fc and Fv fragments; triabodies; tetrabodies; linear antibodies; single-chain antibody molecules; and multi specific antibodies formed from antibody fragments. The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. An oxygen linked antibody is an antibody which has a chemical function group such that the linkage between the antibody and the linker or compound is joined via an oxygen atom. Similarly, a nitrogen linked antibody is an antibody which has a chemical function group such that the linkage between the antibody and the linker or compound is joined via a nitrogen atom.

A "linker" in the context of this application is divalent chemical group which may be used to join one or more molecules to the compound of the instant disclosure. Linkers may also be an amino acid chain wherein the carboxy and amino terminus serve as the points of attachment for the linker. In some embodiments, the linker contains a reactive functional group, such as a carboxyl, an amide, an amine, a hydroxy, a mercapto, an aldehyde, or a ketone on each end that be used to join one or more molecules to the compounds of the instant disclosure. In some non-limiting examples, —CH$_2$CH$_2$CH$_2$CH$_2$—, —C(O)CH$_2$CH$_2$CH$_2$—, —OCH$_2$CH$_2$NH—, —NHCH$_2$CH$_2$NH—, and —(OCH$_2$CH$_2$)$_n$—, wherein n is between 1-1000, are linkers.

An "amine protecting group" is well understood in the art. An amine protecting group is a group which prevents the reactivity of the amine group during a reaction which modifies some other portion of the molecule and can be easily removed to generate the desired amine. Amine protecting groups can be found at least in Greene and Wuts, 1999, which is incorporated herein by reference. Some non-limiting examples of amino protecting groups include formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxy-benzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Additionally, the "amine protecting group" can be a divalent protecting group such that both hydrogen atoms on a primary amine are replaced with a single protecting group. In such a situation the amine protecting group can be phthalimide (phth) or a substituted derivative thereof wherein the term "substituted" is as defined above. In some embodiments, the halogenated phthalimide derivative may be tetrachlorophthalimide (TCphth). When used herein, a "protected amino group", is a group of the formula $PG_{MA}NH$— or $PG_{DA}N$— wherein $PG_{MA}$ is a monovalent amine protecting group, which may also be described as a "monvalently protected amino group" and $PG_{DA}$ is a divalent amine protecting group as described above, which may also be described as a "divalently protected amino group".

A "hydroxyl protecting group" is well understood in the art. A hydroxyl protecting group is a group which prevents the reactivity of the hydroxyl group during a reaction which modifies some other portion of the molecule and can be easily removed to generate the desired hydroxyl. Hydroxyl protecting groups can be found at least in Greene and Wuts, 1999, which is incorporated herein by reference. Some non-limiting examples of hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. When used herein, a protected hydroxy group is a group of the formula $PG_HO$— wherein $PG_H$ is a hydroxyl protecting group as described above.

A "thiol protecting group" is well understood in the art. A thiol protecting group is a group which prevents the reactivity of the mercapto group during a reaction which modifies some other portion of the molecule and can be easily removed to generate the desired mercapto group. Thiol protecting groups can be found at least in Greene and Wuts, 1999, which is incorporated herein by reference. Some non-limiting examples of thiol protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxy-carbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. When used herein, a protected thiol group is a group of the formula $PG_TS$— wherein $PG_T$ is a thiol protecting group as described above.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedrally substituted carbon centers), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its (R) form, (S) form, or as a mixture of the (R) and (S) forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

VI. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Synthesis of Disorazole $A_1$, $B_1$, and Analogs Thereof

A. Synthesis of Derivatives of Disorazoles $A_1$ and $B_1$

The synthesis of analogue 5 is described in Schemes 1-6 included below. The synthesis of the "south western" fragment boronic acid 20 from crotonaldehyde (12) and vinyl ether 13 are described in Scheme 1. Treatment of crotonaldehyde (12) and vinyl ether 13 in the presence of BF3.Et₂O and N-Ts-D-valine yielded alcohol 14 (79% yield, 98% ee). The TBS moiety was intramolecularly transferred within 14 through the action of NaHMDS to yield aldehyde 15 (83% yield). Addition of auxiliary 22 to aldehyde 15 in the presence of $TiCl_4$ and $iPr_2EtN$ yielded alcohol 16 (89% yield) obtained as a mixture of diastereoisomers (ca. 12:1 dr). Compound 16 was silylated with TMSOTf and imidazole to yield bis-silylated adduct 17, which was reduced immediately with DIBAL-H at −78° C. to give aldehyde 18 (80% yield from 16). The Wittig reaction of the ylide generated from phosphonium salt 21 and NaHMDS with aldehyde 18 afforded (Z)-vinyl iodide 19 in 73% yield. Treatment of vinyl iodide 19 with n-BuLi in the presence of B(Oi-Pr)₃ and subsequent exposure to TBAF provided boronic acid 20 (77% yield) as shown in Scheme 1.

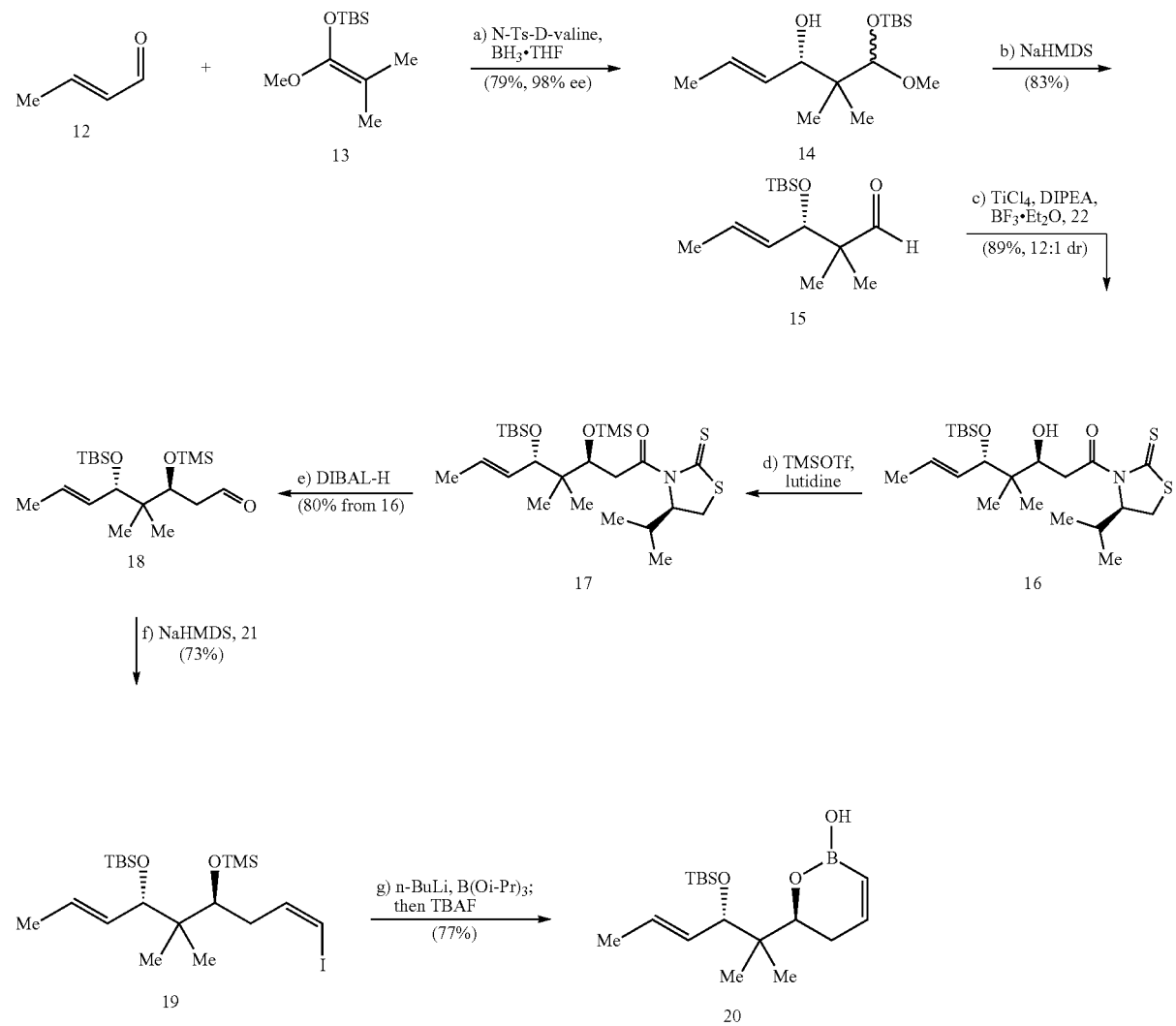

Scheme 1: Synthesis of the "south western" fragment boronic acid 20.

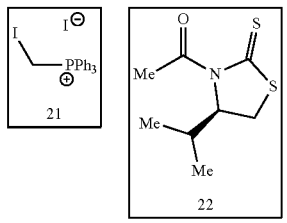

Reagents and conditions: a) N-Ts-D-valine (1.1 equiv), BH₃·THF (1.05 equiv), CH₂Cl₂, 0° C., 30 min; then 23° C., 1 h; then -78° C., 12 (1.0 equiv), 13 (1.15 equiv.), 3 h, 79%, 98% ee; b) NaHMDS (1 equiv), THF, -78° C., 30 min. 83%; c) 22 (1.0 equiv), TiCl₄ (1.5 equiv), CH₂Cl₂, 0° C., 5 min; then -78° C., iPr₂EtN (1.1 equiv), 30 min: then -50° C., 2 h; then -78° C., 15 (1.0 equiv), 1 h, 89%, 12:1 dr; d) 2,6-lutidine (3.0 equiv), TMSOTf (2.0 equiv), CH₂Cl₂, 0° C.; e) DIBAL-H (2.5 equiv), Et₂O, -78° C., 2 h, 80% from 16: f) 21 (1.5 equiv), NaHMDS (1.5 equiv), THF, 0° C. to 23° C., 5 min; then -78° C., DMPU (7.5 equiv), 18 (1.0 equiv), 1 h; then 23° C., 30 min, 73%; g) 19 (1.0 equiv), B(Oi-Pr)₃ (1.1 equiv), n-BuLi (1.15 equiv), -78° C., 30 min; then TBAF (1.4 equiv), 23° C., 48 h, 77%. Abbreviations: N-Ts-D-valine = N-[(4-methylphenyl)sulfonyl]-D-valine, NaHMDS = sodium bis(trimethylsilyl)amide, TMSOTf = trimethylsilyl trifluoromethanesulfonate, DIBAL-H = diisobutylaluminium hydride, DMPU = 1,3-dimethyl-3,4,5,6-tetrahydro-2(1H)-pyrimidinone, TBAF = tetra-n-butylammonium fluoride.

Scheme 2 summarizes the synthesis of the cyclopropyl-aldehyde 32 from ethyl propiolate (23). Thus, treatment of ethyl propiolate (23) with NaI in AcOH yielded (Z)-vinyl iodide 24 (92% yield). Subsequent treatment with DIBAL-H gave alcohol 25 (90% yield) and Simmons-Smith cyclopropanation (Et₂Zn, ClCH₂I) yielded cyclopropane 26 (77% yield). Sonogashira coupling with alkyne 33 provided alcohol 27 (95% yield), which was oxidized to the carboxylic acid 29 by successive oxidation with DMP (92% yield) and Pinnick oxidation (95% yield). The racemic carboxylic acid 29 was kinetically resolved with (R)-BINOL and DCC to give optically pure cyclopropane 30 (39% yield). Then, reduction with DIBAL-H gave alcohol 31 (94% yield) that was finally oxidized with DMP to furnish aldehyde 32 (92% yield) as shown in Scheme 2.

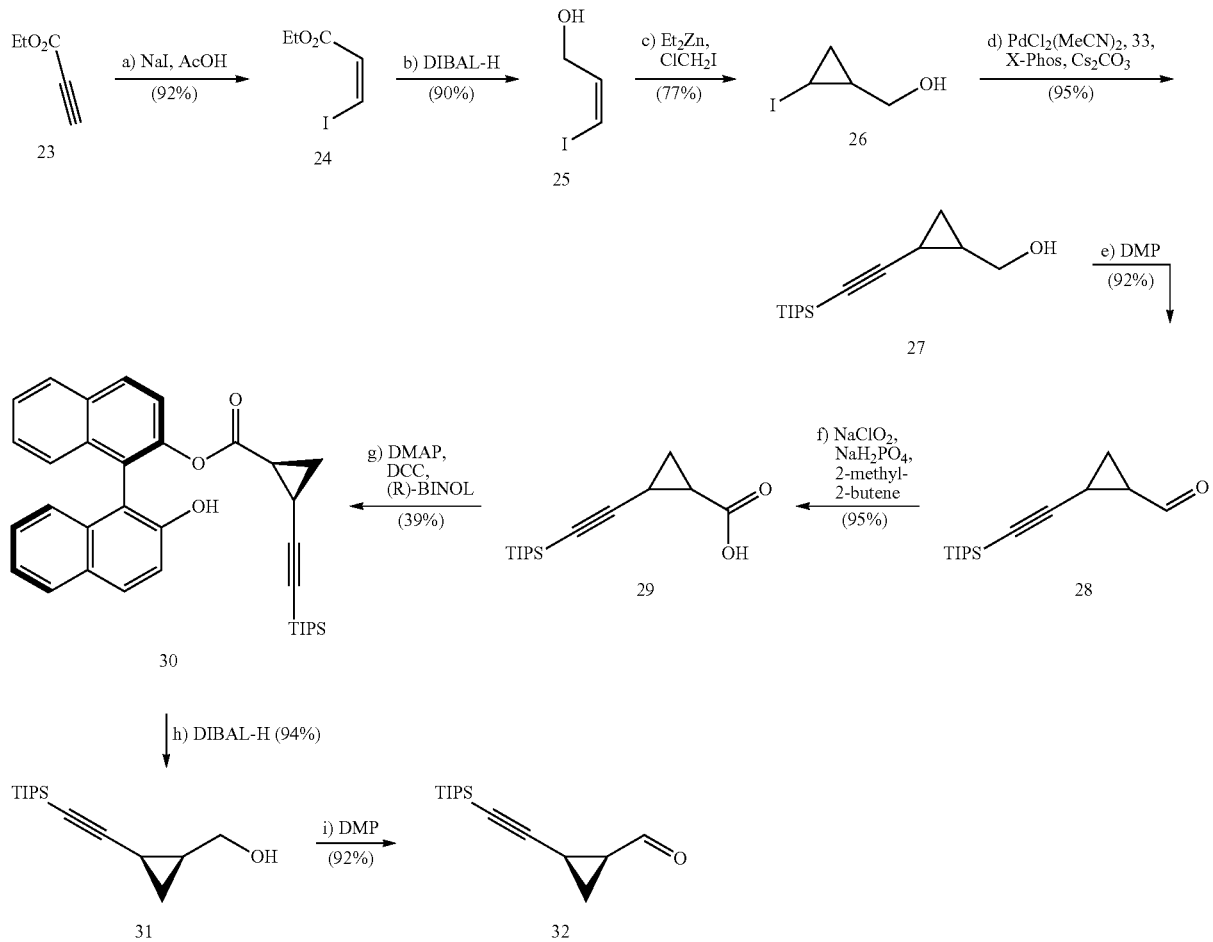

Scheme 2: Synthesis cyclopropyl-aldehyde 32.

-continued

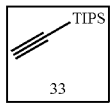
33

Reagents and conditions: a) 23 (1.0 equiv), NaI (1.02 equiv), AcOH (9.0 equiv), 70° C., 16 h, 92%; b) DIBAL-H (2.2 equiv), Et$_2$O, -78° C. to 23° C., 2 h, 90%; c) Et$_2$Zn (2.0 equiv), ClCH$_2$I (4.0 equiv), CH$_2$Cl$_2$, 0° C., 10 min; then 25 (1.0 equiv), 1.5 h, 77%; d) Cs$_2$CO$_3$ (2.5 equiv), X-Phos (0.06 equiv), PdCl$_2$(MeCN)$_2$ (0.02 equiv), 26 (1 equiv), 33 (1.5 equiv), THF, 60° C., 20 h, 95%; e) DMP (1.1 equiv), CH$_2$Cl$_2$, 1 h, 92%; f) NaClO$_2$ (4.0 equiv), NaH$_2$PO$_4$ (8.0 equiv), 2-methyl-2-butene (20 equiv), 3:3:1 t-BuOH:THF:H$_2$O, 23° C., 95%; g) DMAP (0.8 equiv), (R)-BINOL (3.0 equiv.), DCC (1.1 equiv), 0° C. to 23° C., 16 h, 39%; h) DIBAL-H (3.2 equiv), Et$_2$O, -78° C. to 23° C. 3 h, 94%; i) DMP (1.1 equiv), CH$_2$Cl$_2$, 1 h, 92%. Abbreviations: X-Phos = 2-dicyclohexylphosphino-2′,4′,6′-triisopropylbiphenyl, DMP = Dess-Martin periodinane, DMAP = N,N-dimethylpyridin-4-amine, (R)-BINOL = (R)-[1,1′-binaphthalene]-2,2′-diol, DCC = N,N′-dicyclohexylcarbodiimide.

Scheme 3 summarizes the synthesis of the "north eastern" fragment vinyl stannane 40 from amide 17. Treatment of amide 17 with DIBAL-H at 23° C. provided alcohol 34 (71% yield from 16) and submission thereof to the Appel reaction conditions (PPh$_3$, imidazole, I$_2$) yielded iodide 35 (77% yield). The ylide of 35 generated from the corresponding phosphonium salt (formed by reaction with PPh$_3$ in the presence of iPr$_2$EtN) through the action of NaHMDS was reacted with aldehyde 32 to afford cyclopropane 36 in 83% yield. The selective deprotection of the TMS group was orchestrated by stirring 36 for 16 h in a biphasic mixture of Et$_2$O and 4 N aq. HCl to give 37 (quant. yield). The TIPS moiety from the latter compound was removed with AgF to give alcohol 38 (85% yield). Treatment of alkyne 38 with NBS and AgNO$_3$ furnished alkynyl bromide 39 (84% yield) and subsequent hydrostannylation of the latter at low temperature provided vinyl stannane 40 (80% yield).

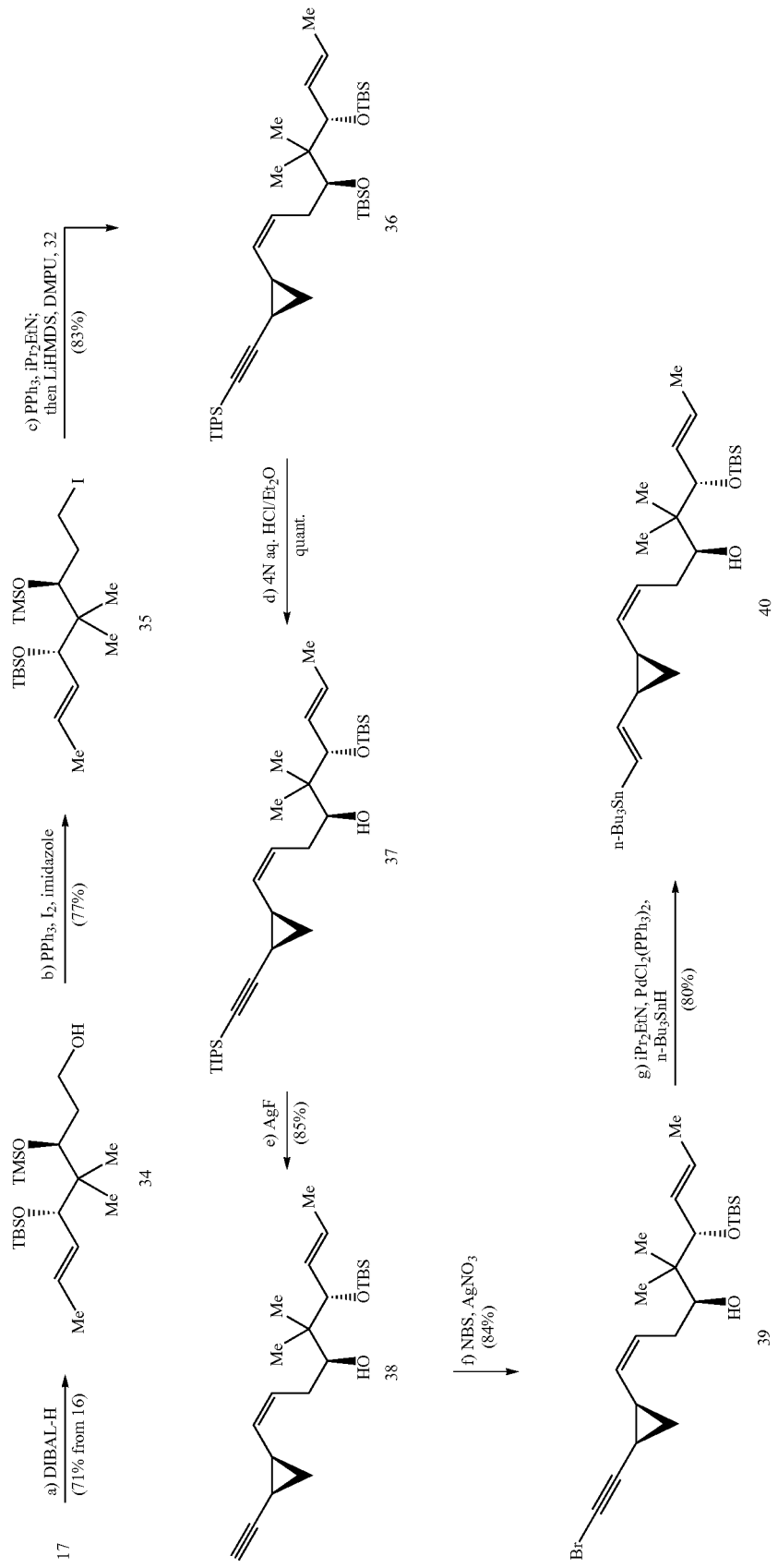

Scheme 4 depicts the synthesis of the "south western" fragment diene 49 from alkyne 33. Thus, treatment of alkyne 33 with AgNO$_3$ and NIS yielded alkynyl iodide 41 (98% yield). (Z)-selective reduction of 33 to vinyl iodide 42 (53% yield) was accomplished with 2-nitrobenzenesulfonylhydrazide (51) in the presence of Et$_3$N. Sonogashira coupling of 42 with alkyne 52 [Pd(PhCN)$_2$Cl$_2$ cat., CuI cat., PPh$_3$ cat., iPr$_2$EtN] led to acetal 43 (90% yield). Exposure of the latter Thiazolidinethione 46 was then transposed by serine methyl ester 50 to amide 47 (92% yield). Cyclization of 47 initiated with Deoxo-Fluor and subsequent oxidation with BrCCl$_3$ in the presence of DBU gave oxazole 48 (91% yield from 47). Finally, the TIPS group within 48 was exchanged for a bromide through action of Ag$_2$CO$_3$ and NBS leading to diene 49 in 91% yield.

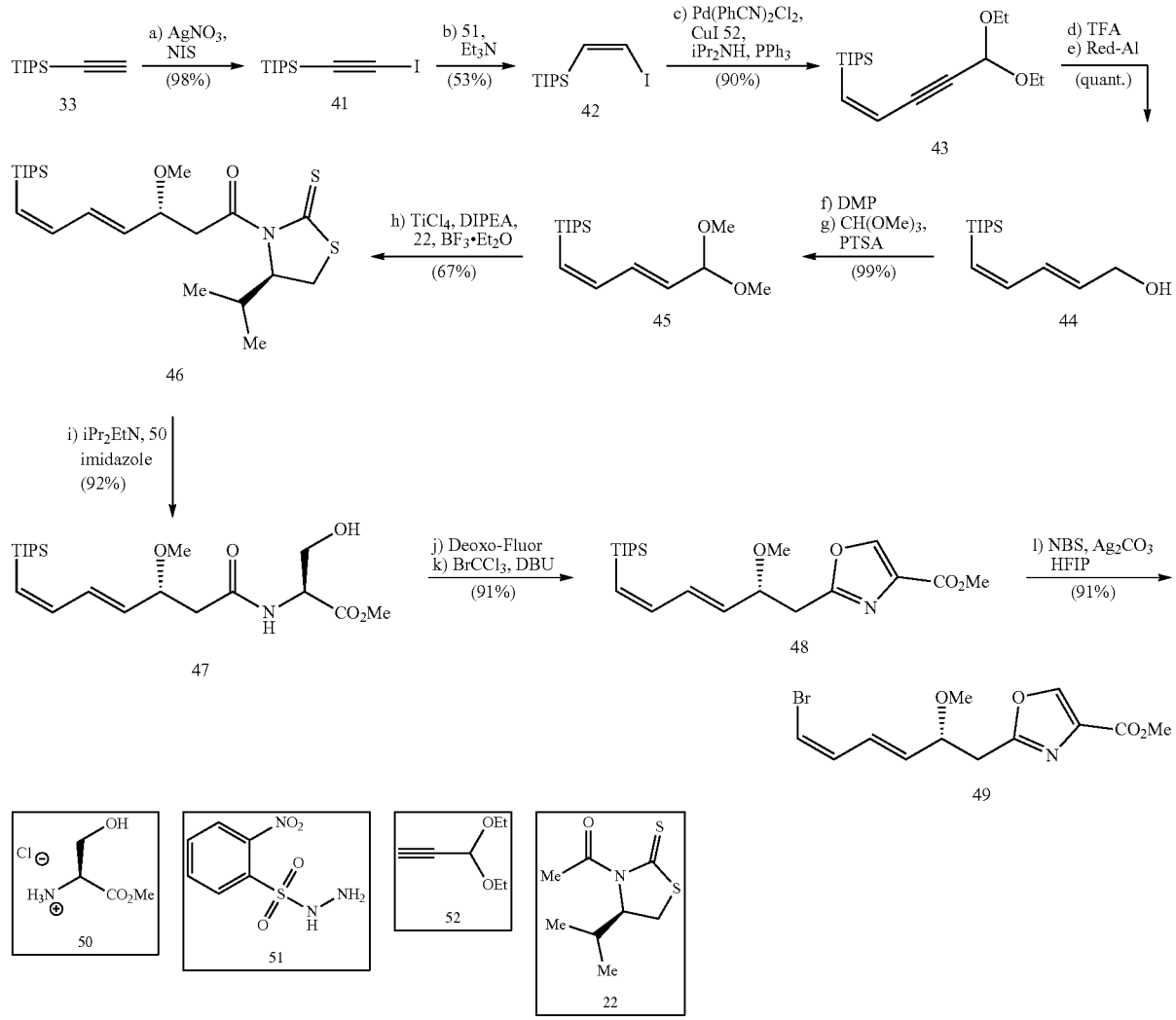

Scheme 4: Synthesis of the "south western" fragment diene 49.

Reagents and conditions: a) AgNO$_3$ (0.1 equiv), NIS (1.2 equiv), acetone, 23° C., 10 min, 98% ; b) NBSH (0.9 equiv), 5:2 THF:i-PrOH, 23° C., 16 h, 53%; c) Pd(PhCN)$_2$Cl$_2$ (0.05 equiv) PPh$_3$ (0.1 equiv), CuI (0.07 equiv), 52 (1.5 equiv), DIPA, 1 h, 23° C., 90%; d) 50% TFA (10 equiv), 23° C., 30 min; e) Red-Al (2.05 equiv), 0° C. to 23° C., Et$_2$O, quant. from 43; f) DMP (2.0 equiv), CH$_2$Cl$_2$, 0° C. to 23° C., 2 h; g) CH(OMe)$_3$ (1.0 equiv), pTsOH (0.01 equiv), CH$_2$Cl$_2$, 23° C., 1 h, 99% from 44; h) 22 (1.0 equiv), TiCl$_4$ (1.1 equiv), CH$_2$Cl$_2$, 0° C., 5 min; then -78° C., iPr$_2$EtN (1.1 equiv), 30 min; then -50° C., 2 h; then -78° C., BF$_3$•Et$_2$O (1.0 equiv), 45 (1.0 equiv), 1 h, 67%, 3:1 dr; i) 50 (1.5 equiv), iPr$_2$EtN (2.0 equiv), THF, 23° C., 10 min; then 47 (1.0 equiv), imidazole (3.0 equiv), 16 h, 92%; j) Deoxo-Fluor (1.2 equiv), CH$_2$Cl$_2$, -20° C., 30 min; k) BrCCl$_3$ (4.0 equiv), DBU (4.0 equiv), CH$_2$Cl$_2$, 0° C. to 23° C., 16 h, 91% from 47; l) AgCO$_3$ (1.0 equiv), NBS (1.25 equiv), HFIP, 0° C., 2 h, 91%. Abbreviations: NBSH = 2-nitrobenzenesulfonylhydrazide, DIPA = diisopropylamine, Red-Al = sodium bis(2-methoxyethoxy)aluminum, pTsOH = p-toluenesulfonic acid, HFIP = hexafluoro-2-propanol.

to TFA furnished the corresponding aldehyde, which was reduced with Red-Al to afford alcohol 44 in quantitative overall yield. Oxidation of the aforementioned alcohol with DMP and acetalization with trimethyl orthoformate in the presence of catalytic amounts of p-TsOH provided dimethyl acetal 45 (99% yield). Attachment of auxiliary 22 to acetal 45 in presence of TiCl$_4$, iPr$_2$EtN and BF$_3$.Et$_2$O yielded amide 46 (67% yield) as a 3:1 mixture of diastereoisomers.

Scheme 5 summarizes the synthesis of the "north western" fragment oxazole 58 from oxazole 53. The transposition of the amino group of 53 for an iodide proceeded with NaNO$_2$ and KI to give 54 (36% yield). Sonogashira coupling [Pd(PPh$_3$)$_4$, CuI, Et$_3$N] with acetylene 33 and iodide 34 provided alkyne 55 in 75% yield. Subsequent removal of the TIPS group from the latter was accomplished with TBAF and AcOH furnishing alkyne 56 (91% yield). Saponification of the ethyl ester in 56 afforded carboxylic acid 57 (96% yield) while treatment of the later with LiBr, LiOAc in AcOH led to vinyl bromide 58 (91% yield).

Scheme 5: Synthesis of the "north western" fragment oxazole 58.

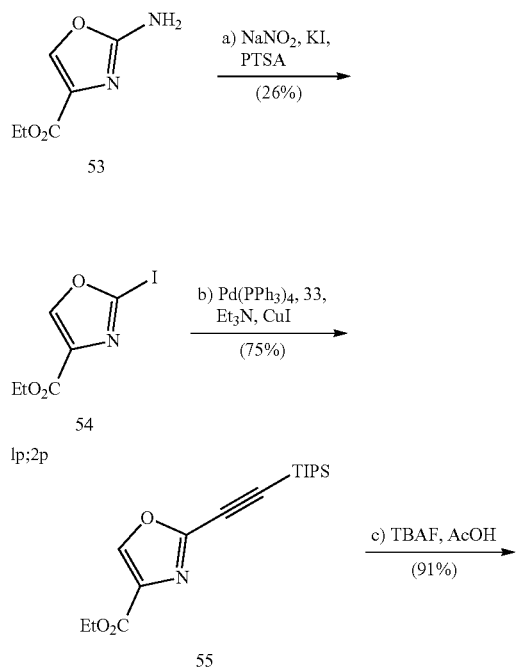

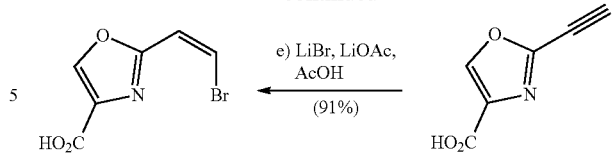

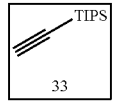

Reagents and conditions:
a) pTsOH (3.0 equiv), CuI (0.10 equiv), NaNO$_2$ (2.0 equvi), KI (2.7 equiv), MeCN:H$_2$O (6.4:1 v/v), 10° C. to 23° C., 26%; b) 33 (5.0 equiv), Pd(PPh$_3$)$_3$ (0.02 equiv), CuI (0.05 equiv), 60° C., 16 h, 75%; c) AcOH (4.0 equiv), TBAF (2.0 equiv), THF, 23° C., 1 h, 91%; d) LiOH (1.5 equiv), H$_2$O:THF (4:3 v/v), 23° C., 1.5 h, 96%; e) LiBr (1.5 equiv), LiOAc (4.5 equiv), AcOH, 70° C., 16 h.

Scheme 6 summarizes the final steps leading to cp-disorazole analogue 5 from fragments 20 and 49. Thus, Suzuki coupling of boronic acid 20 with oxazole vinyl bromide 49 was carried out through the action of catalytic amounts of PdCl$_2$(dppf) in the presence of Tl$_2$CO$_3$ to afford fragment 59 (76% yield). Ester formation between alcohol 59 and carboxylic acid 58 under Yamaguchi conditions [1,3,5-trichlorobenzoyl chloride (64), DMAP, Et$_3$N] then furnished intermediate 60. The latter was subjected to a Stille coupling with vinyl stannane 40 [Pd$_2$(dba)$_3$ cat., AsPh$_3$, CuI] to give hydroxyl ester 61 (36% yield), whose saponification with Ba(OH)$_2$ and macrolactonization under Yamaguchi conditions [1,3,5-trichlorobenzoyl chloride (64), DMAP, Et$_3$N] furnished precursor 62 (28% overall yield for the two steps from 61). Finally, desilylation of 62 with H$_2$SiF$_6$ in MeOH led to the coveted cyclopropyl disorazole A$_1$ analogue 5 (45% yield).

Scheme 6: Synthesis of cp-disorazole A$_1$ (5).

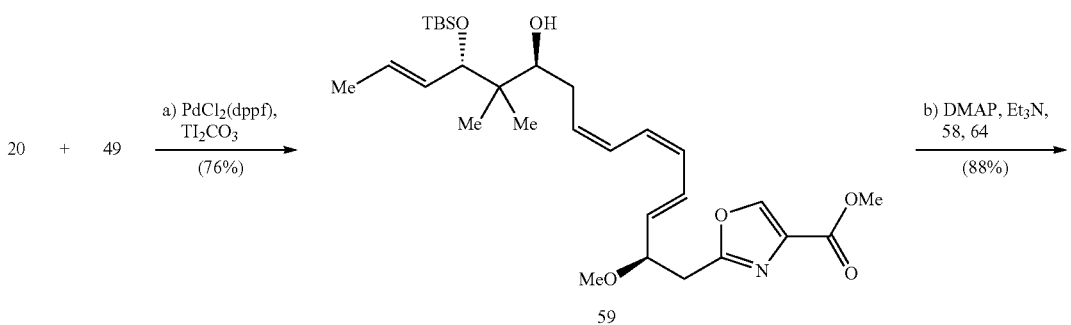

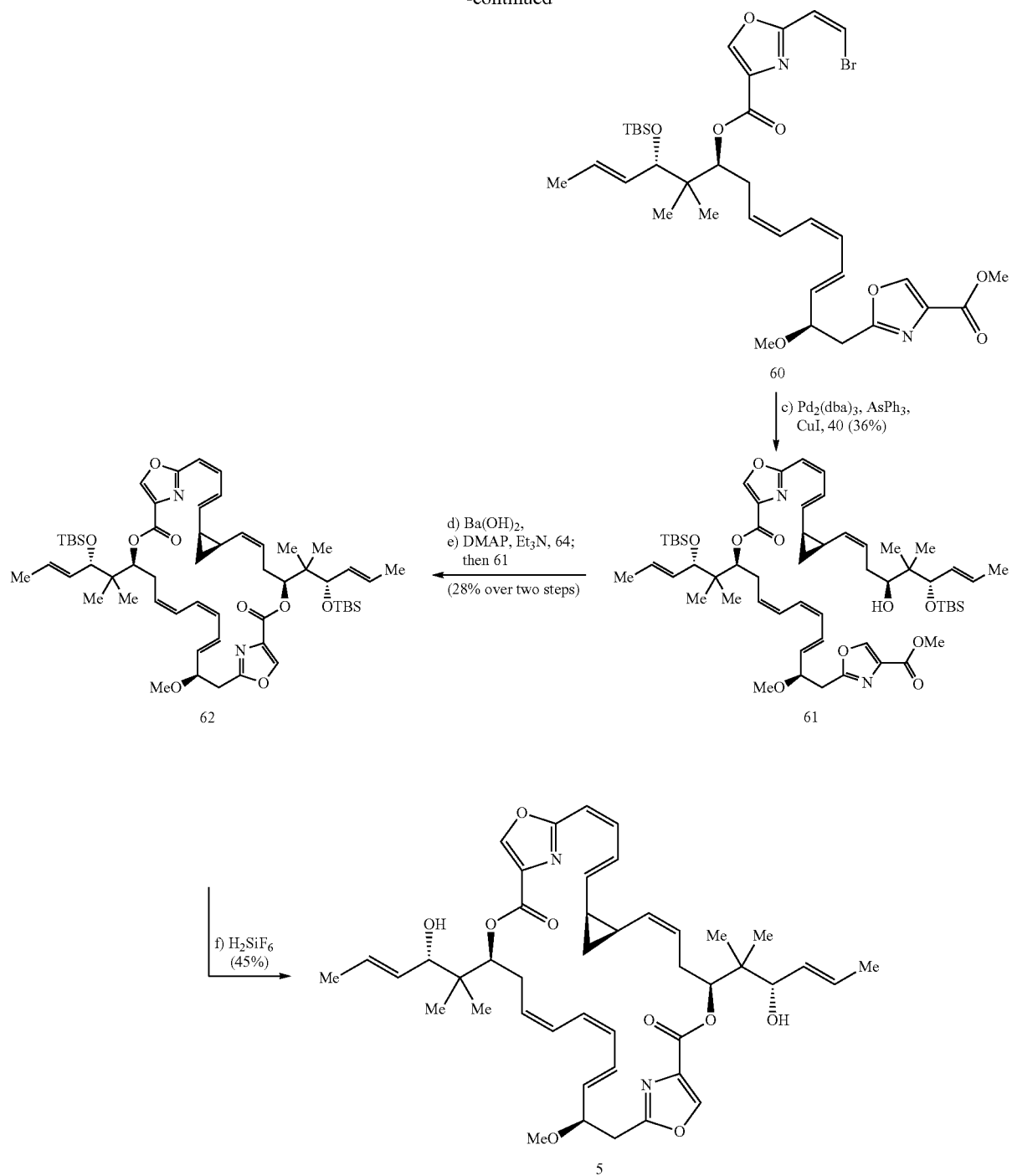
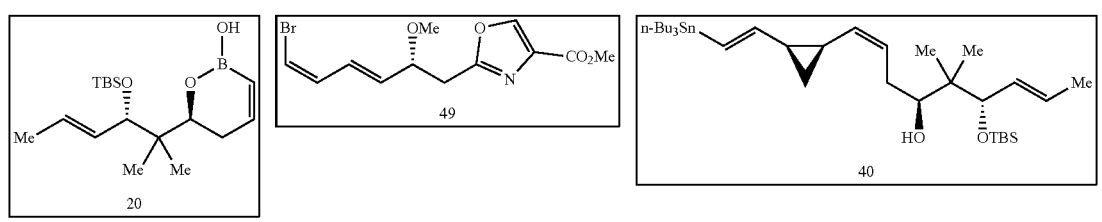

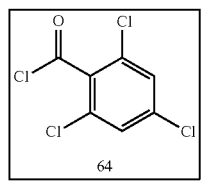

Reagents and conditions: a) 20 (1.4 equiv), 49 (1.0 equiv), Tl$_2$CO$_3$ (5.0 equiv), Pd(dppf)Cl$_2$ (0.1 equiv), THF:H$_2$O (3:1 v/v), 23° C., 16 h, 76%; b) 58 (1.2 equiv), Et$_3$N (6 equiv), DMAP (8.0 equiv), 64, toluene, 0° C. to 23° C., 3 h, 88%; c) 40 (1.3 equiv), Pd$_2$(dba)$_3$ (0.5 equiv), AsPh$_3$ (2.0 equiv), CuI (4.0 equiv), DMF, 23° C., 3 h, 36%; d) Ba(OH)$_2$ (30 equiv) in MeOH/H$_2$O (3:2 v/v), THF, 0° C. to 23° C., 3 h; e) 64 (10 equiv), Et$_3$N (11 equiv), toluene, 23° C., 1 h; then DMAP (4.0 equiv); 40° C., 24 h, 28% from 61; f) H$_2$SiF$_6$ (65 equiv), MeOH, 4° C., 120 h; then 23° C., 24 h, 45%.

B. Synthesis of Natural Product Disorazoles A$_1$ and B$_1$

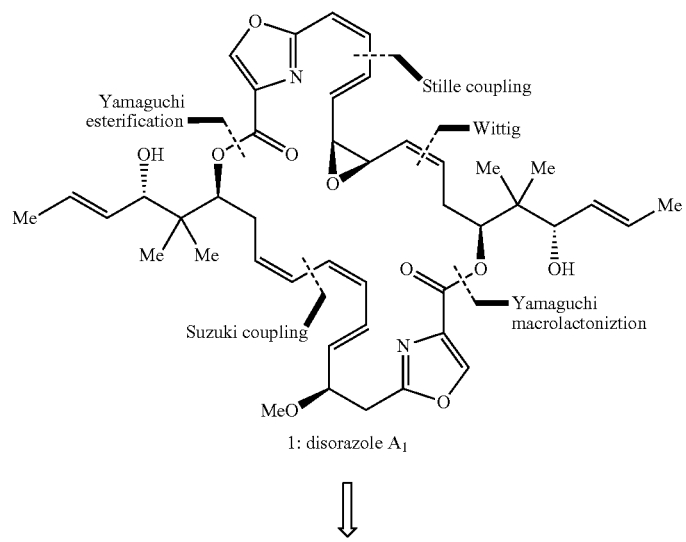

Scheme 7. Retrosynthetic Analysis of Disorazole

1: disorazole A$_1$

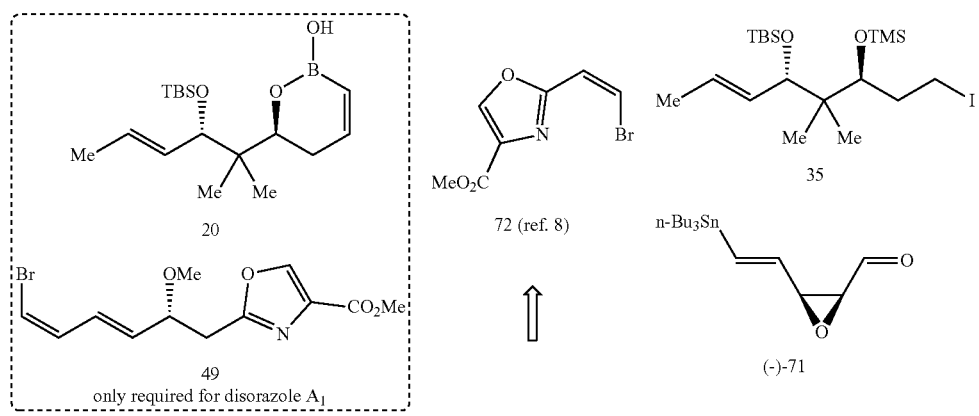

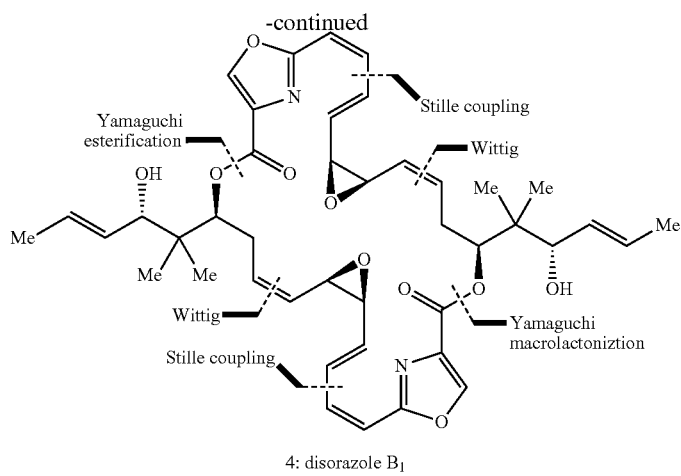

4: disorazole B₁

Scheme 7 summarizes the retrosynthetic analysis of disorazoles A₁ (1) and B₁ (4). Thus, disorazole A₁ was traced back to key building blocks 72, (−)-71, 20, 35, and 49 through the strategic bond disconnections indicated on structure 1 (Wittig reaction, Stille coupling, Suzuki coupling, Yamaguchi esterification, and Yamaguchi macrolactonization). By virtue of its symmetrical nature, disorazole B, (4) required only building blocks 35, 72 (Wipf and Graham, 2005) and (−)-71, revealed through a simpler disconnection pattern requiring two identical Wittig and Stille couplings, a Yamaguchi esterification, and a Yamaguchi macrolactonization as shown in structure 4 (Scheme 7).

Scheme 8 depicts the asymmetric synthesis of intermediates 20 and 35 starting with building blocks 15 (Schäckel et al., 2010) and 22. Thus, reaction of 15 with Nagao auxiliary 22 (Nagao et al., 1986) (TiCl₄; then i-Pr₂NEt) led stereoselectively to alcohol 16 (89% yield, ca. 12:1 dr). Protection of the latter (TMSOTf, 2,6-lut.) gave TMS ether 17, whose reduction with 2.5 equiv of DIBAL-H afforded aldehyde 18 in 80% yield from 16. Reaction of 18 with the ylide generated from iodophosphonium iodide 21 (NaHMDS; then DMPU) gave selectively (Z)-vinyl iodide 19 in 73% yield. Conversion of 19 to the desired boronic acid (20) required sequential treatment with n-BuLi, B(OiPr)₃, and TBAF (77% yield). Iodide 35 was obtained from common intermediate 17 (Scheme 8) through a two-step sequence involving reduction of the latter to the corresponding primary alcohol (5.0 equiv of DIBAL-H, 71% yield from 16) followed by an Appel reaction [I₂, PPh₃, imidazole (77% yield)].

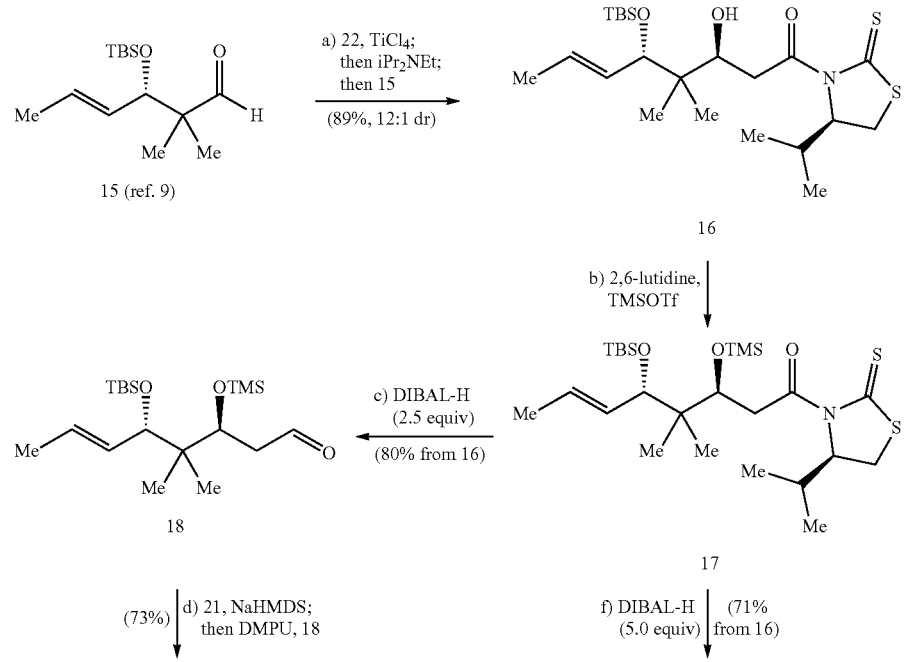

Scheme 8. Synthesis of Iodide 4 and Vinyl Boronic Acid 5ᵃ

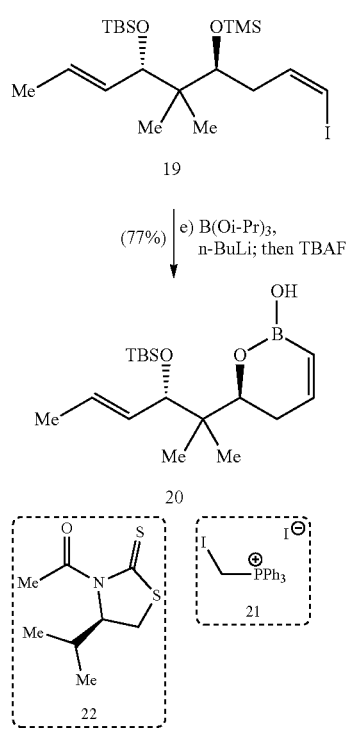
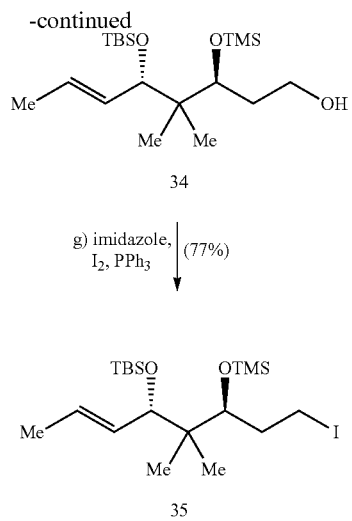

*a*Reagents and conditions: (a) 22 (1.0 equiv), TiCl$_4$ (1.5 equiv), CH$_2$Cl$_2$, 0° C., 5 min; then -78° C., i-Pr$_2$NEt (1.1 equiv), 30 min; then -50° C., 2 h then -78° C., 15 (Schäckel et al, 2010) (1.0 equiv), 1 h, 89%, 12:1 dr; (b) 2,6-lutidine (3.0 equiv), TMSOTf (2.0 equiv), CH$_2$Cl$_2$, 0° C.; (c) DIBAL-H (2.5 equiv), Et$_2$O, -78° C., 2 h, 80% from 16; (d) 21 (1.5 equiv), NaHMDS (1.5 equiv), THF, 0 to 23° C., 5 min; then -78° C., DMPU (7.5 equiv), 18 (1.0 equiv), 1 h; then 23° C., 30 min. 73%; (e) 19 (1.0 equiv), B(Oi-Pr)$_3$ (1.1 equiv), n-BuLi (1.15 equiv), -78° C., 30 min; then TBAF (1.4 equiv), 23° C., 48 h, 77%; (f) DIBAL-H (5.0 equiv), Et$_2$O, -78 to 23° C., 2 h, 71% from 16; (g) imidazole (1.5 equiv), I$_2$ (1.35 equiv), PPh$_3$ (1.2 equiv), 23° C., 1 h, 77%. TMSOTf = trimethylsilyl trifluoromethanesulfonate, DIBAL-H = diisobutylaluminium hydride, NaHMDS = sodium bis(trimethylsilyl)amide, DMPU = 1,3-dimethyl-3,4,5,6-tetrahydro-2(1H)-pyrimidinone, TBAF = tetra-n-butylammonium fluoride.

Intermediate 49 was synthesized asymmetrically from TIPS-acetylene (33) as shown in Scheme 9. Thus, 33 was converted to iodide 41 (NIS, AgNO$_3$, 98% yield) and then to (Z)-vinyl iodide 42 through the action of hydrazine 51 (53% yield, 89% brsm). Coupling of 42 with acetylene 52 [Pd(PhCN)$_2$Cl$_2$, PPh$_3$, CuI, i-Pr$_2$NH, 90% yield] furnished enyne diethoxy ketal 43, whose sequential treatment with TFA and Red-Al® led to hydroxy TIPS diene 44 in quantitative yield. Oxidation (DMP) of the latter, followed by exposure of the resulting aldehyde to CH(OMe)$_3$ and p-TsOH (cat.) furnished diene dimethoxy ketal 45 in 99% overall yield. Sequential treatment of 45 with Nagao auxiliary 22 (Nagao et al., 1986) and TiCl$_4$, i-Pr$_2$NEt and BF$_3$.Et$_2$O afforded intermediate 46 (Cosp et al., 2001), whose reaction with ammonium salt 50 in the presence of i-Pr$_2$NEt and imidazole afforded hydroxy amide 47 in 92% yield (Pulukuri et al., 2014). Conversion of 47 to oxazole intermediate 48 was achieved through sequential exposure of the latter to Deoxo-Fluor® and BrCCl$_3$/DBU (91% overall yield) (Phillips et al., 2000). Finally, the targeted intermediate 49 was generated from 48 through the action of NBS in the presence of Ag$_2$CO$_3$ (91% yield).

The asymmetric synthesis of advanced intermediate 75 started from propargyl alcohol (65) and proceeded as shown in Scheme 10. Thus, AIBN facilitated addition of n-Bu$_3$SnH to 65, followed by buffered DMP oxidation of the resulting alcohol, led to the formation of vinyl tin aldehyde 66 in 42% overall yield. Still-Gennari reaction of the latter with the anion generated from phosphonate ester 67 (KHMDS, 18-crown-6) followed by DIBAL-H reduction of the resulting methyl ester furnished alcohol 68 in 85% overall yield. Sharpless asymmetric epoxidation of 68 [t-BuOOH, Ti(Oi-Pr)$_4$, (−)-DET] gave epoxide 69 (61% yield), albeit in low enantiomeric excess (43% ee). This unsatisfactory result was remedied through kinetic resolution of 69. Thus, acetylation of hydroxy epoxide 69 with vinyl acetate in the presence of Amano lipase PS (Ghanem and Aboul-Enein, 2005) furnished enantiomerically enriched hydroxy epoxide (+)-70 (71% yield, >95% ee) and enantiomerically enriched acetoxy epoxide (−)-70 (25% yield, >95% ee). The absolute configuration assignments of (+)-70 and (−)-70 were made tentatively based on the use of (−)-DET that was expected to afford (+)-70 as the major enantiomer. These assignments were confirmed by the successful synthesis of disorazole A$_1$ (1), whose absolute configuration was known (Höfle, 1999/2000). This resolution presented the opportunity to synthesize enantioselectively disorazole A$_1$ (1) and the two diastereoisomers (2 and 3. FIG. 1) of disorazole B$_1$ (whose relative configuration and absolute structure were not known) (Jansen et al., 1994; Höfle, 1999/2000). Based on biosynthetic considerations, it was believed that the likelihood of both disorazoles featuring the same configuration at their epoxide sites was higher than being antipodal. The synthesis of disorazole B$_1$ (2), rather than its diastereoisomer (3), was carried out first for this reason. To this end, hydroxy epoxide (+)-70 was oxidized to aldehyde (−)-71 (DMP, 81% yield), and then reacted with the ylide generated from iodide 35 (PPh$_3$, i-Pr$_2$NEt; LiHMDS, DMPU) to afford selectively (Z)-olefin vinyl tin triene epoxide 73 in 76% yield. Coupling of vinyl stannane 73 with bromide 72 (Wipf and Graham, 2005) under palladium-free conditions (thus evading potential side reactions caused by the multiple olefinic bonds present in the two substrates) (Allred et al., 1996; Wang and Lin, 2010) then led to key intermediate 75.

Scheme 9. Synthesis of Vinyl Bromide 6[a]

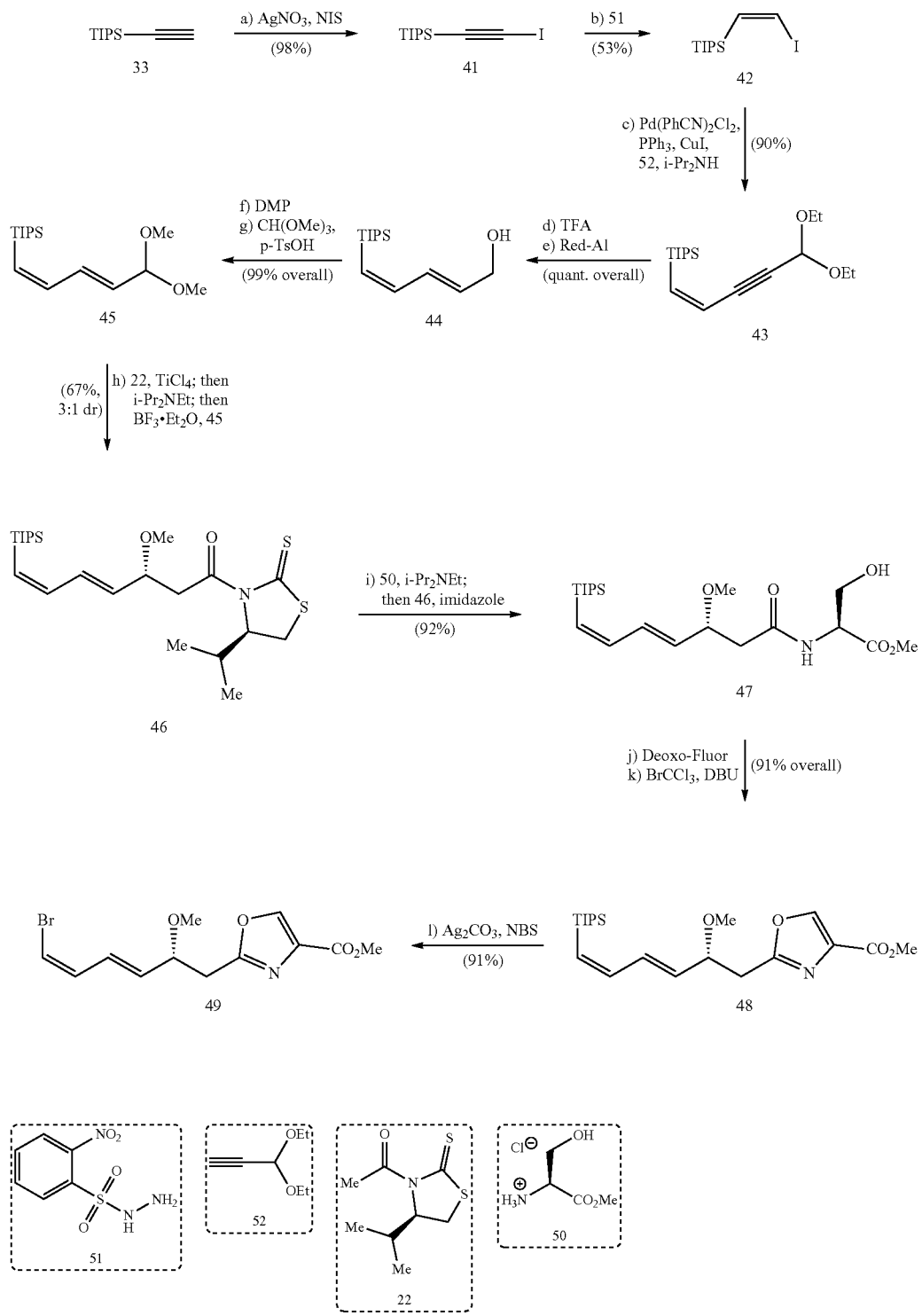

[a]Reagents and conditions: (a) AgNO₃ (0.1 equiv), NIS (1.2 equiv), acetone, 23° C., 10 min, 98%; (b) 51 (0.9 equiv), 5:2 THF:i-PrOH, 23° C., 16 h, 53%, 98% brsm; (c) Pd(PhCN)₂Cl₂ (0.05 equiv), PPh₃ (0.1 equiv), CuI (0.07 equiv), 52 (1.5 equiv), i-Pr₂NH, 23° C., 1 h, 90%; (d) 50% aq. TFA (10 equiv), 23° C., 30 min; (e) Red-Al® (2.05 equiv), 0 to 23° C., 0.5 h, Et₂O, quant. from 43; (f) DMP (2.0 equiv), CH₂Cl₂, 0 to 23° C., 2 h; (g) CH(OMe)₃ (1.0 equiv), p-TsOH (0.01 equiv), CH₂Cl₂, 23° C., 1 h, 99% from 44; (h) 22 (1.0 equiv), TiCl₄ (1.1 equiv), CH₂Cl₂, 0° C., 5 min; then -78° C., i-Pr₂NEt (1.1 equiv), 30 min; then -50° C., 2 h; then -78° C., BF₃•Et₂O (1.0 equiv), 45 (1.0 equiv), 1 h, 67%, ca 3:1 dr; (i) 50 (1.5 equiv), i-Pr₂NEt (2.0 equiv), THF, 23° C., 10 min; then 46 (1.0 equiv), imidazole (3.0 equiv), 23° C., 16 h, 92%; (j) Deoxo-Fluor® (1.2 equiv), CH₂Cl₂, -20° C., 30 min; (k) BrCCl₃ (4.0 equiv), DBU (4.0 equiv), CH₂Cl₂, 0 to 23° C., 16 h, 91% from 47; (l) Ag₂CO₃ (1.0 equiv), NBS (1.25 equiv), HFIP, 0° C., 2 h, 91 %. NBSH = 2-nitrobenzenesulfonylhydrazide, Red-Al® = sodium bis(2-methoxyethoxy)aluminum, p-TsOH = p-toluenesulfonic acid, HFIP = hexafluoro-2-propanol.

Scheme 10. Enantioselective Preparation of Epoxide Fragment 37[a]

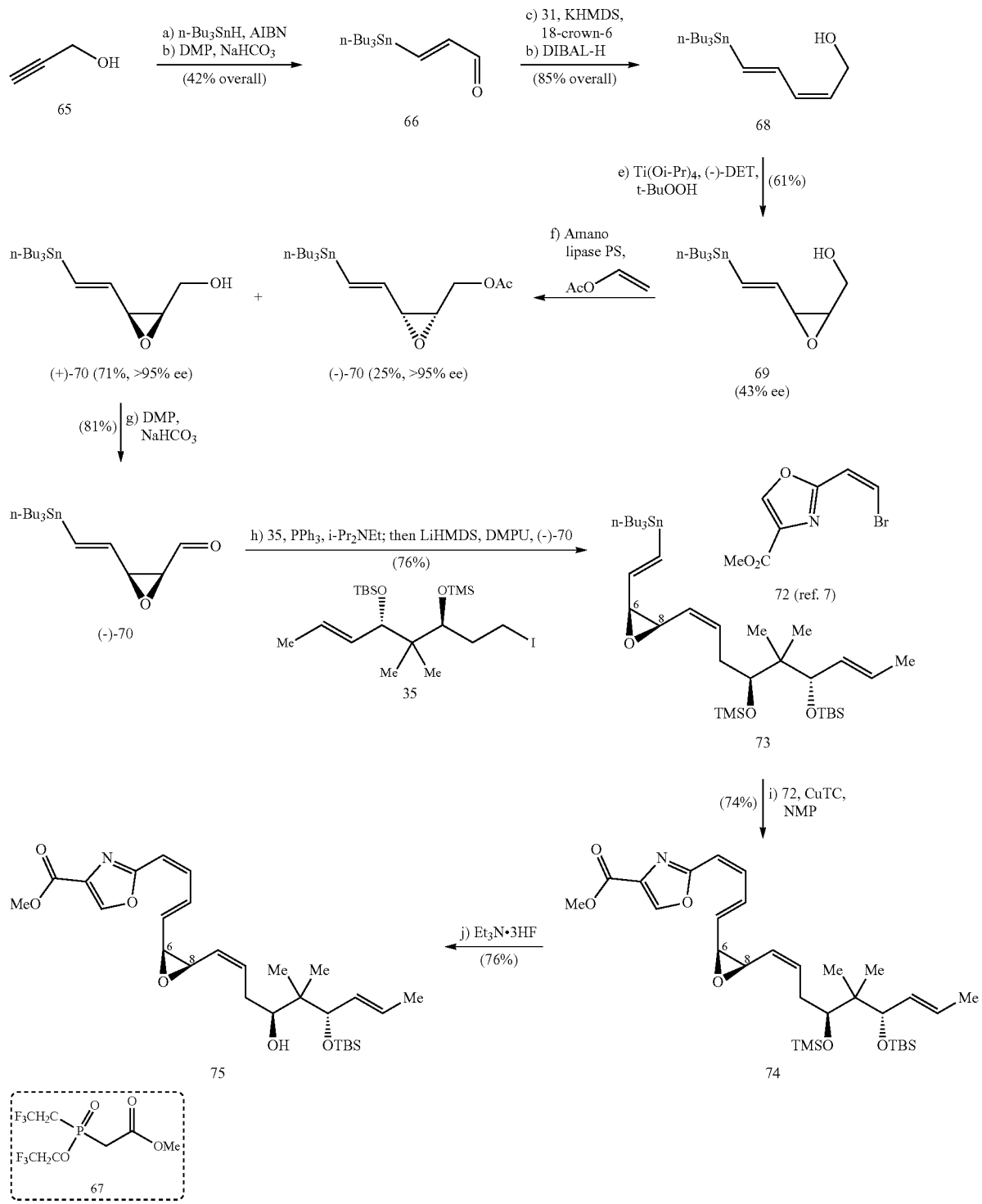

[a]Reagents and conditions: (a) n-Bu₃SnH (1.3 equiv), AIBN (0.08 equiv), 80° C., 2.5 h, 49%; (b) DMP (1.2 equiv), NaHCO₃ (1.2 equiv), CH₂Cl₂, 23° C., 1 h, 86%; (c) 18-crown-6 (4.0 equiv), 67 (1.3 equiv), KHMDS (1.2 equiv), THP, -78° C., 0.5 h, 92%; (d) DIBAL-H (2.5 equiv), Et₂O, -78° C., 1 h, 92%; (e) Ti(Oi-Pr)₄ (1.0 equiv), (-)-DET (1.4 equiv), t-BuOOH (3.0 equiv), CH₂Cl₂, -20° C., 16 h, 61%, 43% ee; (f) Amano lipase PS from *Burkholderia cepacia* (100%, w/w), vinyl acetate (2.0 equiv), CH₂Cl₂, 23° C., 48 h, 71%, >95% ee for (+)-70, 25%, >95% ee for (-)-70; (g) DMP (1.3 equiv), NaHCO₃ (1.3 equiv), CH₂Cl₂, 23° C., 1 h, 81%; (h) 35 (1.05 equiv), PPh₃ (1.75 equiv), i-Pr₂NEt (7.0 equiv), 90° C., 16 h; then -78° C., LiHMDS (1.05 equiv), DMPU (0.6 equiv), (-)-70 (1.0 equiv), THF, 15 min; then 23° C., 1 h, 76%; (i) 72 (1.0 equiv), CuTc (1.5 equiv), NMP, 23° C., 1 h, 74%; (j) Et₃N•3HF (3.0 equiv), THF, 23° C., 1 h, 76%. AIBN = 2,2′-azobis(2-methylpropionitrile), DMP = Dess-Martin periodinane, KHMDS = potassium bis(trimethylsilyl)amide, LiHMDS = lithium bis(trimethylsilyl)amide, CuTc = copper(I) thiophene-2-carboxylate.

Scheme 11 summarizes the completion of the total synthesis of disorazole A₁. Thus, Suzuki coupling of boronic acid 20 with vinyl bromide 49 [Pd(dppf)Cl₂ cat., Tl₂CO₃] furnished conjugated hydroxy triene 76 (84% yield), which was reacted with carboxylic acid 77 (obtained from methyl ester 74 through the action of Me₃SnOH (Nicolaou et al., 2005), Scheme 4) under Yamaguchi conditions to afford diester 78 in 99% overall yield from 74. The more labile TMS silyl ether was cleaved from 78 (Et₃N.3HF) leading to hydroxy methyl ester 79 (99% yield). The methyl ester of the latter was selectively hydrolyzed using Me₃SnOH (Nicolaou et al., 2005), and the resulting hydroxy acid was cyclized under Yamaguchi conditions to afford macrolactone 80 in 48% overall yield. Finally, the TBS groups were cleaved by treatment with TASF (Scheidt et al., 1998) (17% yield), furnishing disorazole A₁ (1). Synthetic disorazole A₁ exhibited identical $^1$H— and $^{13}$C-NMR spectroscopic data and comparable specific rotation $\{[\alpha]_D^{25}=-85$ (c=0.08, MeOH); Lit.$^1$ $[\alpha]_D^{22}=-77$ (c=0.75, MeOH)$\}$ with the natural product. Without wishing to be bound by any theory, it is believed that the relatively low yield of the deprotection step is due the chemical lability of the final product may arise from the epoxide moiety and its surrounding olefin bonds, and the resistance of the TBS silyl ethers to cleavage due to steric crowding, a predicament that should be improvable upon further experimentation.

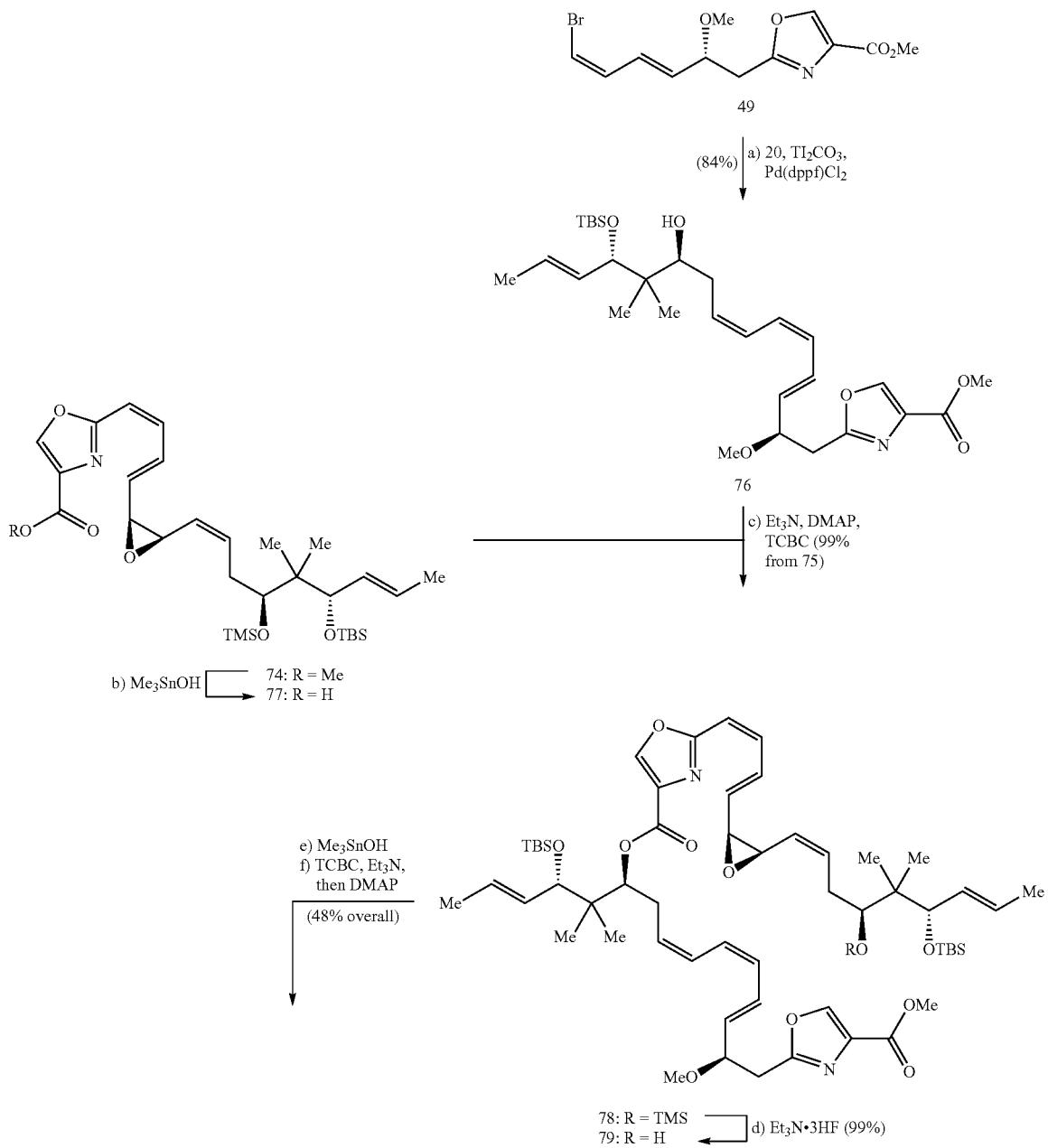

Scheme11: Completion of the Total Synthesis of Disorazole A1 (1)$^a$

-continued

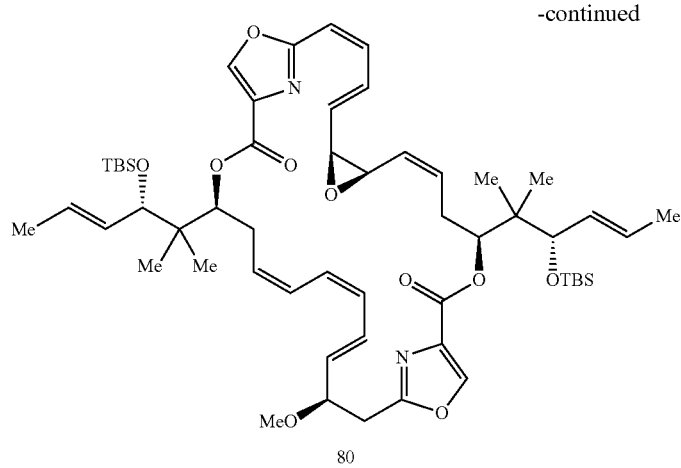
80

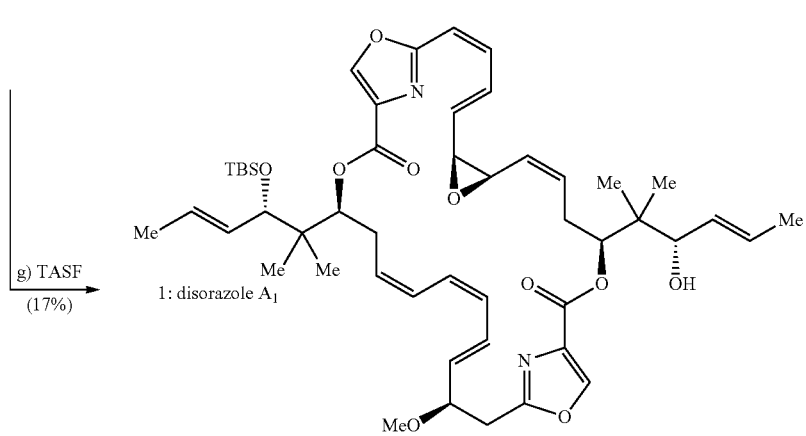
1: disorazole A₁ g) TASF
(17%)

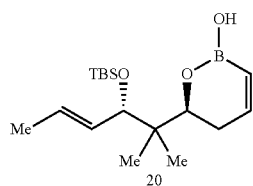
20

*Reagents and conditions: (a) 20 (1.4 equiv), Tl₂CO₃ (5.0 equiv), Pd(dppf)Cl₂ (10 mol %), THF:H₂O 3:1, 23° C., 16 h, 84%; (b) Me₃SnOH (10 equiv), DCE, 80° C., 3 h; (c) 77 (2.0 equiv), 76 (1.0 equiv), Et₃N (6.0 equiv), DMAP (8.0 equiv), TCBC (3.0 equiv), toluene, 23° C., 1.5 h, 99%; (d) Et₃N•3HF (3.0 equiv), THF, 23° C., 1 h, 99%; (e) Me₃SnOH (10 equiv), DCE, 80° C., 1.5 h; (f) TCBC (10 equiv), Et₃N (11 equiv), toluene, 23° C., 1 h; then DMAP (4.0 equiv), 23 to 40° C., 29 h, 48% from 79; (g) TASF (12 equiv), H₂O, DMF, 41° C., 72 h, 17%. DCE = dichloroethane, TCBC = 2,4,6-trichlorobenzoyl chloride.

Disorazole B$_1$ (4) was synthesized as summarized in Scheme 5. Thus, esterification of hydroxy compound 75 with carboxylic acid 77 under Yamaguchi conditions led to ester 81 in 98% yield (based on 37). Selective desilylation of the latter with Et₃N.3HF (-TMS group) furnished hydroxy methyl ester 82, whose exposure to Me₃SnOH (Nicolaou et al., 2005) afforded the corresponding hydroxy acid. Yamaguchi macrolactonization of the so obtained crude seco acid led to precursor 83 (48% overall yield), from which disorazole B$_1$ (4) was liberated through TASF-mediated desilylation (64% yield). Synthetic disorazole B$_1$ exhibited identical $^1$H— and $^{13}$C-NMR spectral data and comparable specific rotation value {$[\alpha]_D^{25}$=−59 (c=0.61, MeOH:CH₂Cl₂ 1:1, v/v); Lit.$^1$ $[\alpha]_D^{22}$=−65 (c=0.5, MeOH:CH₂Cl₂ 1:1, v/v)} to those of the natural product.

Starting with acetoxy epoxide (−)-70 (Scheme 10) and following a similar sequence disorazole B$_1$ diastereoisomer 4a was synthesized, whose spectral data were in agreement with its structure but differed from those of disorazole B$_1$ (4).

Scheme 12. Completion of the Synthesis of Disorazole B₁ (2)[a]
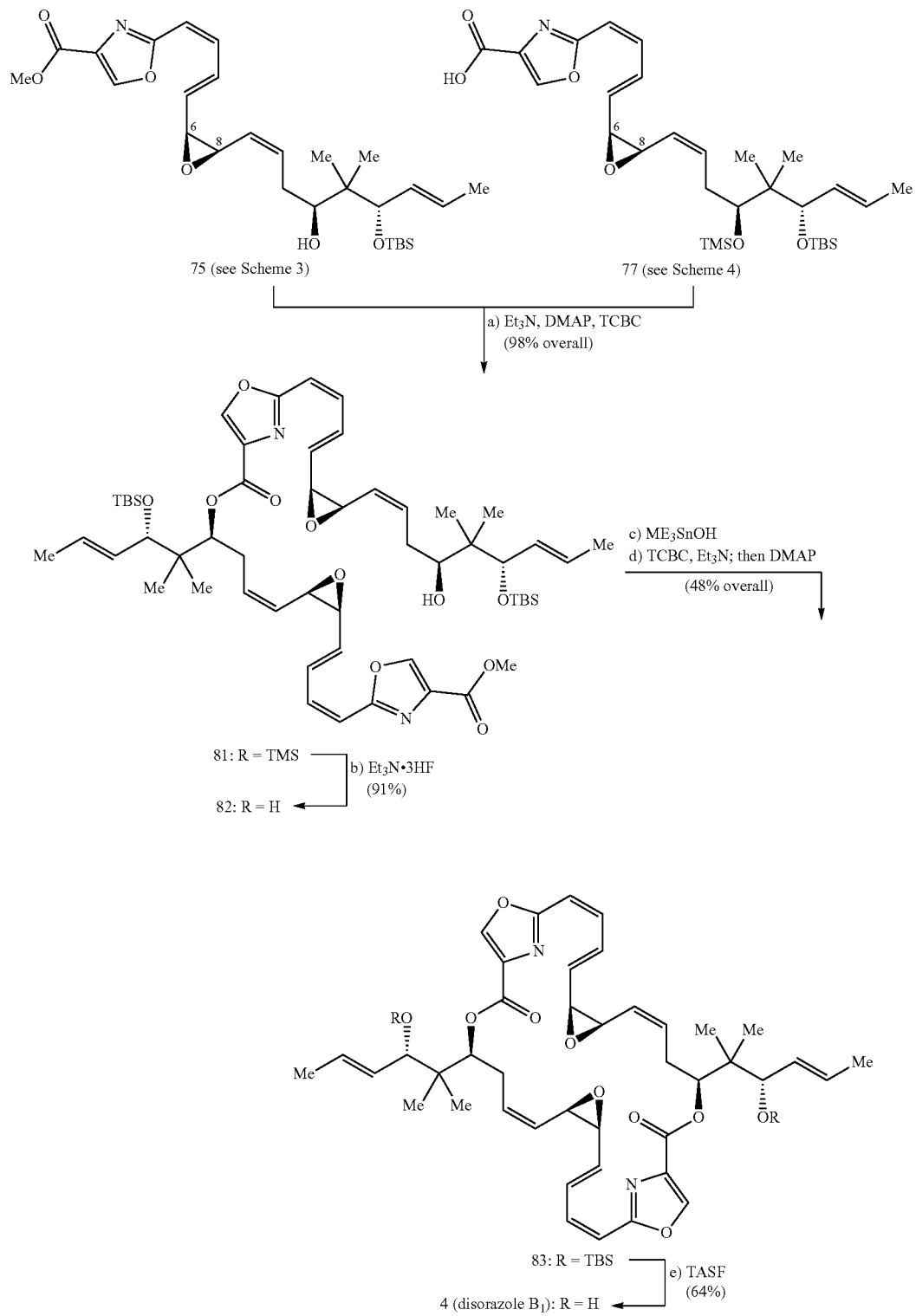
[a]Reagents and conditions:
(a) 75 (1.0 equiv), 77 (2.0 equiv), Et₃N (6.0 equiv), DMAP (8.0 equiv), TCBC (3.0 equiv), toluene, 23° C., 1 h, 98% (for 2 steps);
(b) Et₃N·3HF (3.0 equiv), THF, 23° C., 1 h, 91%;
(c) Me₃SnOH (10 equiv), DCE, 80° C., 1.5 h;
(d) TCBC (10 equiv), Et₃N (11 equiv), toluene, 23° C., 1 h; then DMAP (4.0 equiv), 23 to 40° C., 29 h, 48% (for 2 steps);
(e) TASF (11.5 equiv), H₂O, DMF, 40 to 45° C., 72 h, 64%.

Figure 3:
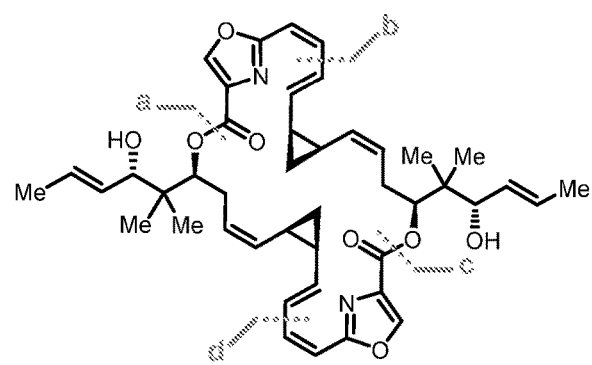
FIG. 3 shows the molecular structures of the synthesised designed cyclopropyl and thiazole analogues 84-86.
Figure 3:
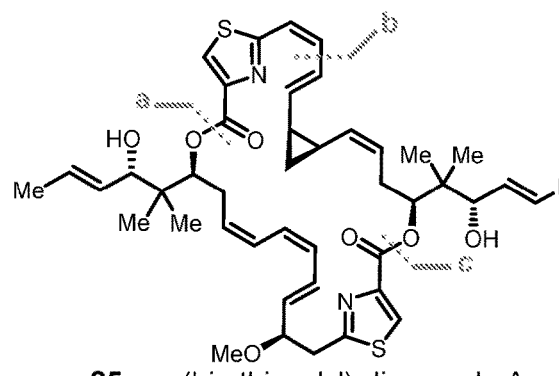
Figure 3:
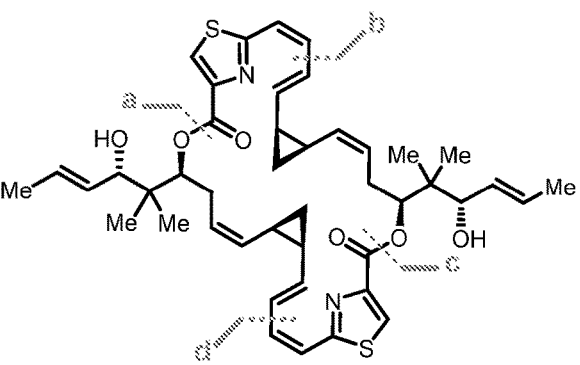

C. Synthesis of Cyclopropyl Analogues of Disorazoles $A_1$ and $B_1$ and Corresponding Thiazoles The bis-cyclopropyl disorazole $B_1$ analogue 84 (FIG. 3) was synthesized from cyclopropyl vinyl stannane 40 and building blocks 72 and 58 (see Scheme 13). Thus, 40 was coupled with vinyl bromide methyl ester 72 in the presence of CuTC (NMP) to afford hydroxy methyl ester 87 (77% yield), which reacted with carboxylic acid vinyl bromide 58 (TCBC, $Et_3N$, DMAP) to give vinyl bromide ester 88 in 68% yield. To the growing molecule was attached the second cyclopropyl domain through CuTC-facilitated coupling with vinyl stannane fragment 40 leading to hydroxy methyl ester 89 (72% yield). The latter was subjected to $Ba(OH)_2$ for methyl ester hydrolysis and the resulting hydroxy acid was subsequently treated with TCBC in the presence of $Et_3N$ and DMAP to furnish bis-TBS ether 90 (28% overall yield from 89), from which bis-cyclopropyl disorazole $B_1$ analogue 84 emerged upon exposure to TASF in 98% yield.

The synthesis of thiazole analogues 85 and 86 required the construction of thiazole building blocks 93, 95 and 100 (Scheme 14), in addition to the previously synthesized fragments 20[6] and 40 (see Schemes 1 and 3) The former were prepared from thiazole bromide 91 (Scheme 14A) and TIPS diene 46 (Scheme 14B) as depicted in Scheme 14. Thus, and as shown in Scheme 14A, bromide 91 was coupled with TIPS-acetylene [33, $Pd(PPh_3)_4$, $Et_3N$, CuI] to afford the corresponding TIPS-protected intermediate from which the TIPS group was removed (TBAF) leading to terminal acetylene 92 in 85% overall yield. Hydrobromination of the latter was achieved stereoselectively employing LiBr, LiOAC in AcOH at 90° C. to afford the desired (Z)-vinyl bromide (93, 71% yield) contaminated with 7% of the corresponding (E)-isomer, the latter removed chromatographically. The required vinyl bromide carboxylic acid (i.e., 95) was prepared from terminal carboxylic acid 94 (generated from methyl ester 92 by LiOH-induced saponification in 99% yield) through the same LiBr-LiOAc-AcOH protocol in 75% yield and >20:1 dr as summarized in Scheme 14A. Fragment 100 was prepared from TIPS-diene thioxothiazolidine 46 as shown in Scheme 14B. Thus, 46 was hydrolyzed to its carboxylic counterpart (aq. LiOH) and thence to the corresponding acid chloride [$(COCl)_2$], whose treatment with $NH_3$ led to primary amide 96 in 83% overall yield for the three steps. This amide was then converted to the corresponding thioamide (97) through the aid of the Lawesson's reagent (94% yield). The latter served well as the precursor of the desired thiazole derivative (i.e., 100) upon sequential reaction with bromoketo methyl ester 98 and pyridine/TFAA (60% overall yield for the two steps) and subsequent replacement of the TIPS group of 99 for a bromide (NBS, $Ag_2CO_3$, HFIP) to furnish the coveted building block 100 in 52% yield.

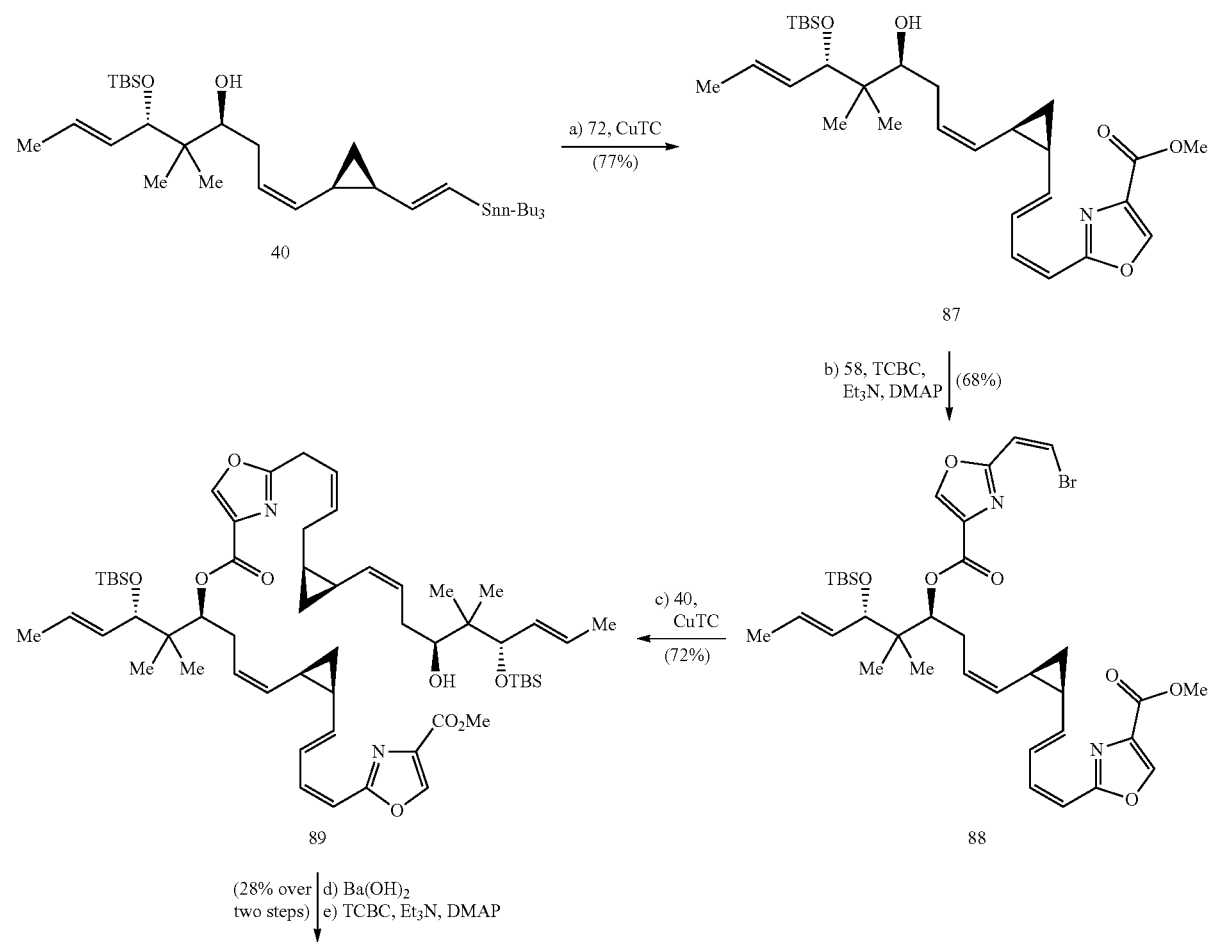

Scheme 13. Synthesis of cp-disorazole $B_1$ (84).

-continued

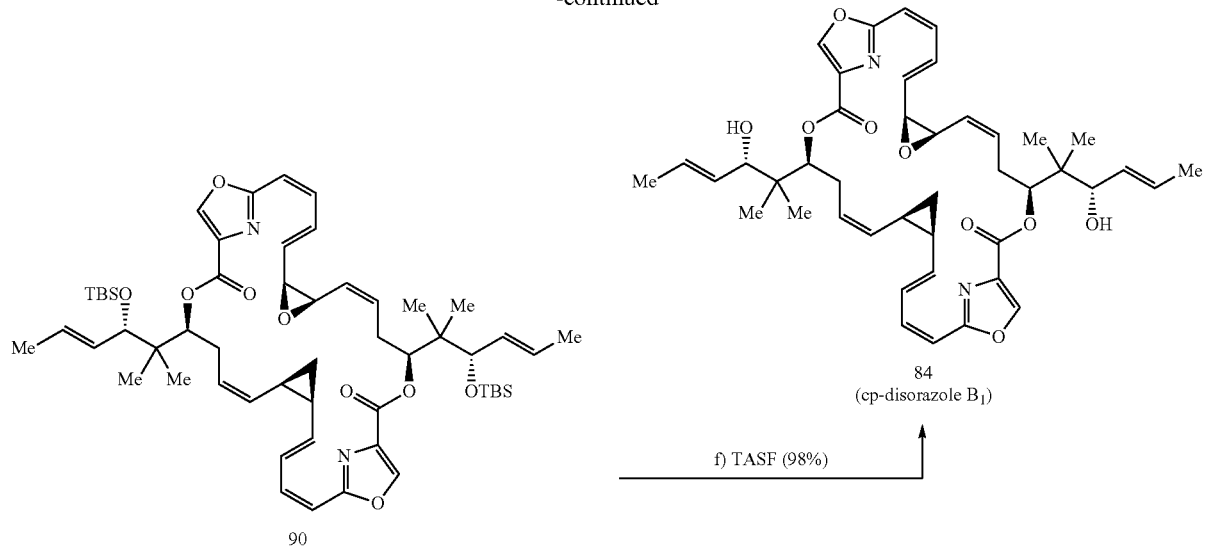

Reagents and conditions: (a) 20 (1.0 equiv), 28 (1.0 equiv), CuTC (1.5 equiv), NMP, 23° C., 1 h, 77%; (b) 29 (1.0 equiv), 30 (2.0 equiv), Et$_3$N (6.0 equiv), 23° C., 5 min; then DMAP (8.0 equiv), TCBC (6.0 equiv), 23° C., 1.5 h, 68%: (c) 20 (1.5 equiv), CuTC (1.5 equiv), NMP, 23° C., 1 h, 72%; (d) Ba(OH)$_2$•8H$_2$O (30 equiv) in MeOH:H$_2$O (3:2 v/v), THF, 23° C., 3 h; (e) TCBC (10 equiv), Et$_3$N (11 equiv), 23° C., toluene, 1 h; then dilution with toluene to 7.5 mM; DMAP (4.0 equiv), 40° C., 29 h, 28% from 32; (f) TASF (5.0 equiv), H$_2$O (14 equiv), DMF, 40° C., 48 h, 98%.

Scheme 14. Synthesis of building blocks 93, 95, and 100.

A.

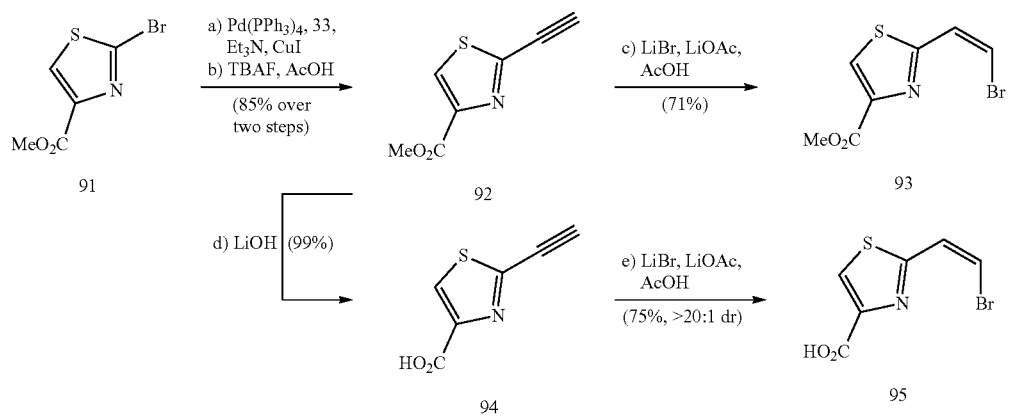

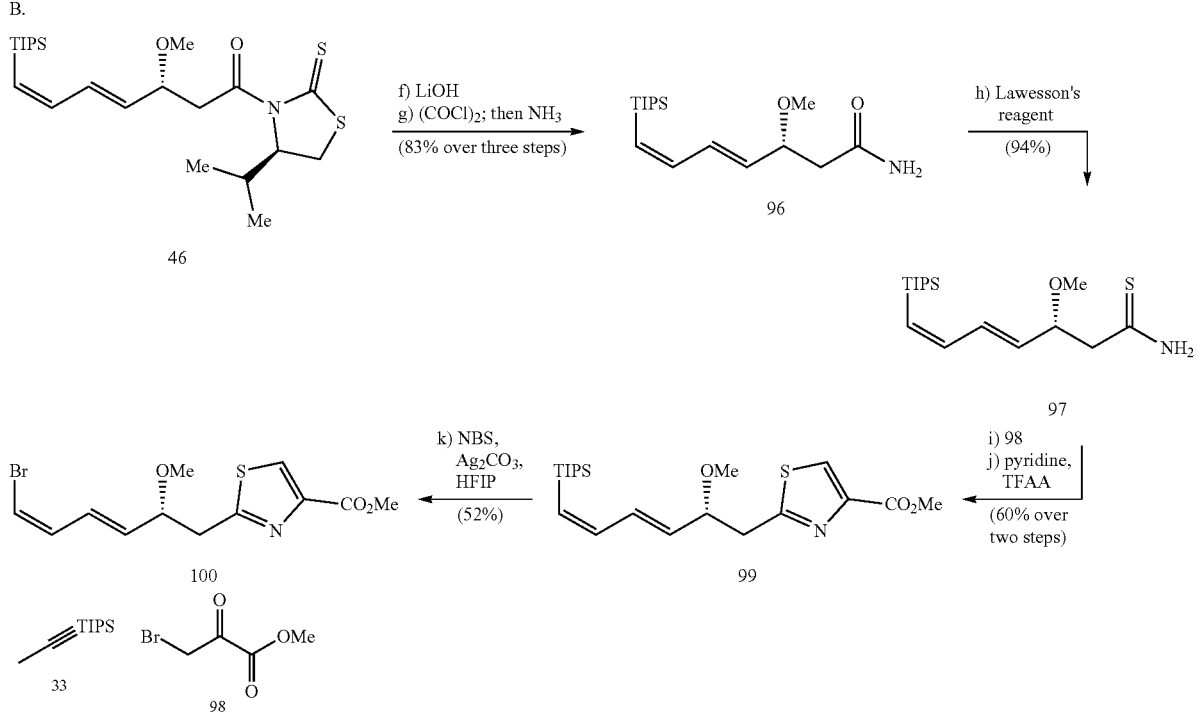

Reagents and conditions: (a) 33 (5.0 equiv), Pd(PPh₃)₄ (0.05 equiv), CuI (0.05 equiv), DMF:Et₃N (1:1 v/v), 60 °C., 16 h, 90%; (b) TBAF (2.0 equiv), AcOH (4.0 equiv), THF, 0° C., 1 h 94%; (c) LiBr (1.5 equiv), LiOAc (4.5 equiv), AcOH, 90° C., 16 h, 71% + 7% (E)-isomer; (d) LiOH·H₂O (1.5 equiv), THF:H₂O (5:4 v/v), 23° C., 1 h, 99%: (e) LiBr (1.5 equiv), LiOAc (4.5 equiv), AcOH, 100° C., 16 h, 75%, >20:1 dr; (f) LiOH·H₂O (1.5 equiv), THF:H₂O (25:6 v/v), 0 to 23° C., 16 h; (g) (COCl)₂ (3.0 equiv), DMF (cat.), Et₂O, 0 to 23° C., 1 h: then NH₃ (7M in MeOH, 8.0 equiv), DCM, 0 to 23° C., 16 h, 83% from 46; (h) Lawesson's reagent (0.70 equiv), THF, 23° C., 1 h, 94%; (i) 98 (1.4 equiv), acetone, -10° C., 2 h; (j) pyridine (2.5 equiv ), TFAA (1.28 equiv), CH₂Cl₂, -30 to 23° C., 2 h, 60% from 97; (k) Ag₂CO₃ (1.02 equiv), NBS (1.25 equiv), HFIP, 0° C., 1.5 h, 52%. Abbreviations: HFIP = 1,1,1,3,3,3-hexafluoro-2-propanol, Lawesson's reagent = 2,4-bis(4-methoxyphenyl)-1,3,2,4-dithiadiphosphetane-2,4-dithione, NBS = 1-bromo-2.5-pyrrolidinedione, TFAA = trifluoroacetic anhydride.

With building block 100 readily available, its conversion to the targeted bis-thiazole cyclopropyl disorazole A₁ analogue 85 proceeded as summarized in Scheme 15. Thus, 100 was joined with our previously synthesized boronic acid fragment 20 through a Suzuki coupling [PdCl₂(dppf), Tl₂CO₃, 59% yield] to furnish extended fragment 101, onto which was attached thiazole vinyl bromide carboxylic acid 95 through esterification (TCBC, Et₃N, DMAP) to give ester vinyl bromide 102 in 87% yield. The latter was coupled with cyclopropyl vinyl stannane 40 through a palladium-catalyzed reaction [Pd₂(dba)₃, AsPh₃, CuI] leading to intermediate 103 in 94% yield. Methyl ester hydrolysis within 103 [Ba(OH)₂] followed by Yamaguchi macrolactonization (TCBC, Et₃N, DMAP) then furnished bis-TBS protected precursor 104 (41% overall yield for the two steps) from which the targeted cyclopropyl bis-thiazole disorazole A₁ analogue 85 was generated by exposure to H₂SiF₆ (Speed et al., 2014) (43% yield).

Scheme 15. Synthesis of cp-(bis-thiazolyl)-disorazole A1 (85).

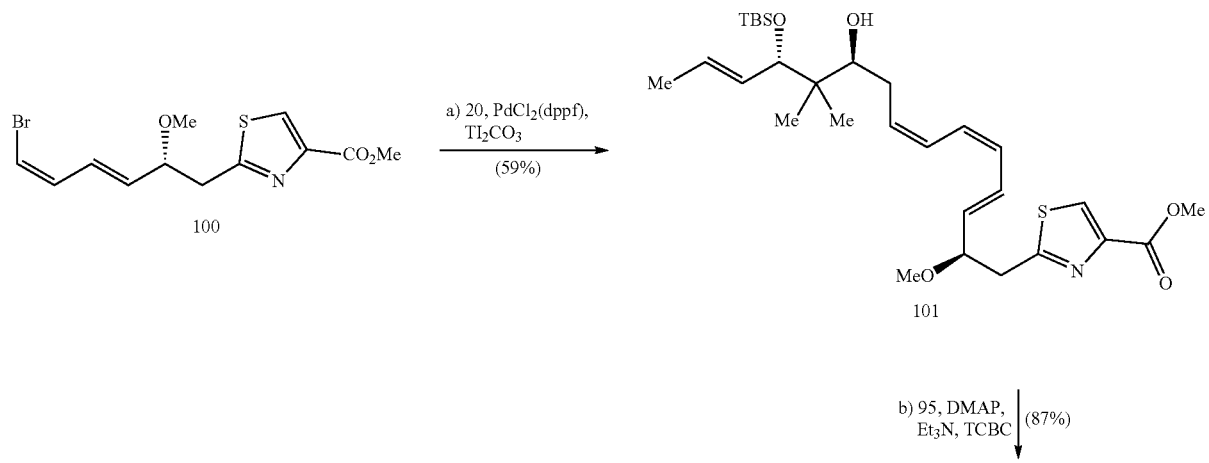

-continued
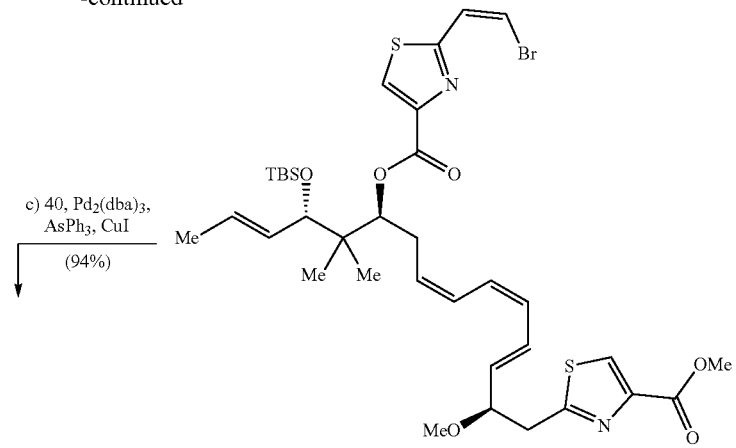
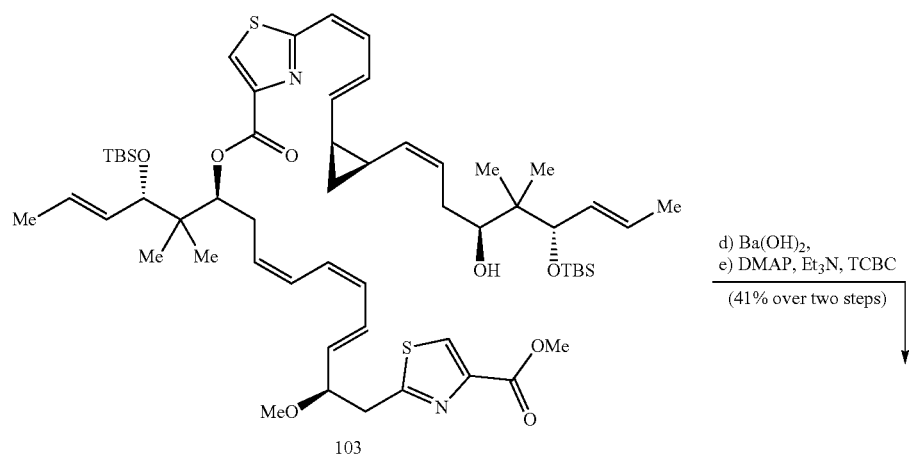
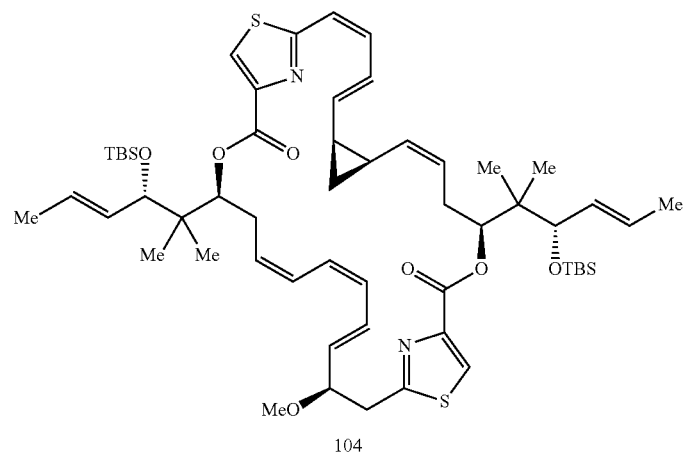

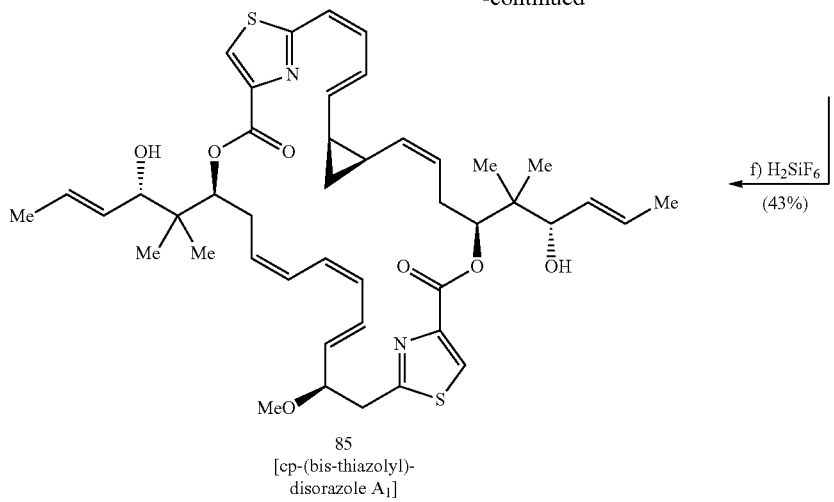

85
[cp-(bis-thiazolyl)-
disorazole A₁]

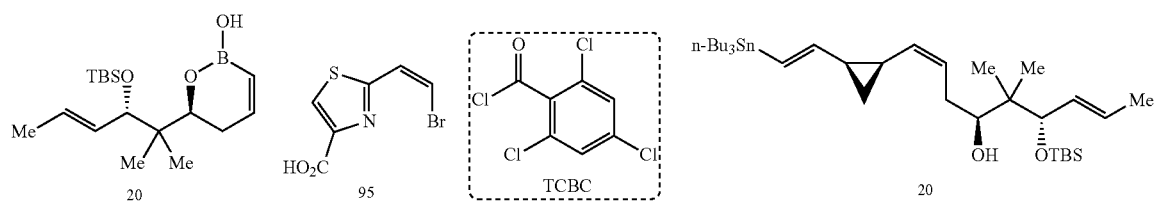

Reagents and conditions: (a) 20 (1.4 equiv), Tl₂CO₃ (5.0 equiv), Pd(dppf)Cl₂ (0.01 equiv), 25° C., THF:H₂O (3:1 v/v), 16 h, 59%; (b) 95 (1.2 equiv), Et₃N (6.0 equiv), DMAP (8.0 equiv), TCBC, toluene, 0 to 23° C., 3 h, 87%; (c) 40 (1.3 equiv), Pd₂(dba)₃ (0.5 equiv), AsPh₃ (2.0 equiv), CuI (4.25 equiv), DMF, 23° C., 3 h, 94%; (d) Ba(OH)₂ (30 equiv) in MeOH/H₂O (3:2 v/v), THF, 23° C., 3 h; (e) TCBC (10 equiv), Et₃N (11 equiv), toluene, 23° C., 1 h; then DMAP (4.0 equiv), 30° C., 19 h, 41% from 102; (f) H₂SiF₆ (75 equiv), MeOH, 0 to 23° C., 17 h; then 23° C., 24 h, 43%.

The bis-thiazole bis-cyclopropyl disorazole B₁ analogue 86 was prepared from fragment 40, 20, 93 and 95 as depicted in Scheme 16. Thus, vinyl stannane 40 and boronic acid 20 were efficiently coupled under the influence of CuTC to afford hydroxy methyl ester 105 (84% yield), which was coupled with carboxylic acid 95 (Et₃N, DMAP, 90% yield) to furnish intermediate 106, which reacted with vinyl stannane fragment 40 as facilitated by CuTC to afford advanced intermediate 107 in 92% yield. Hydrolysis of the latter [Ba(OH)₂] followed by sequential Yamaguchi macrolactonization (TCBC, Et₃N, DMAP) and TASF-induced global desilylation (46% yield) gave rise to the targeted bis-thiazole bis-cyclopropyl analogue 86 of disorazole B₁ as shown in Scheme 16.

Scheme 16. Synthesis of bis-(cp-thiazolyl)-disorazole B1 (86).

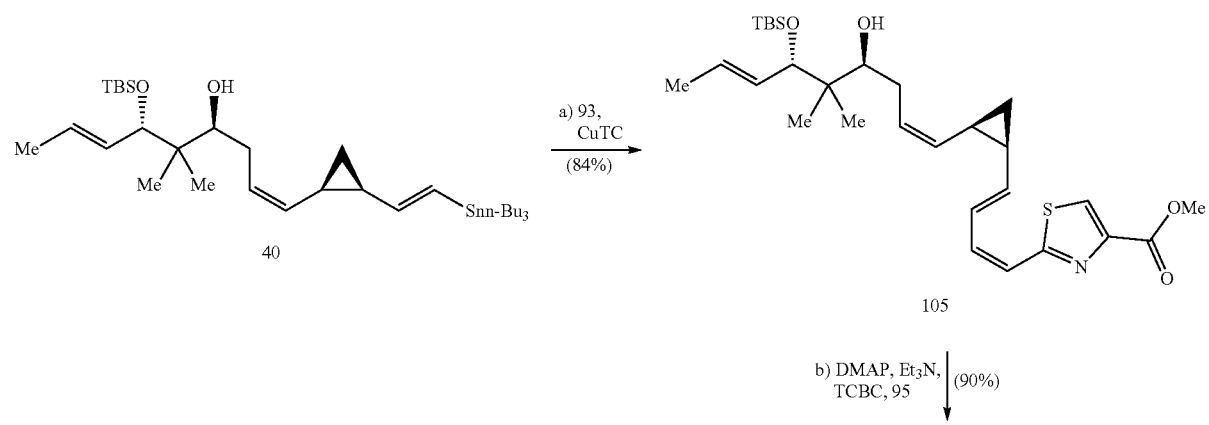

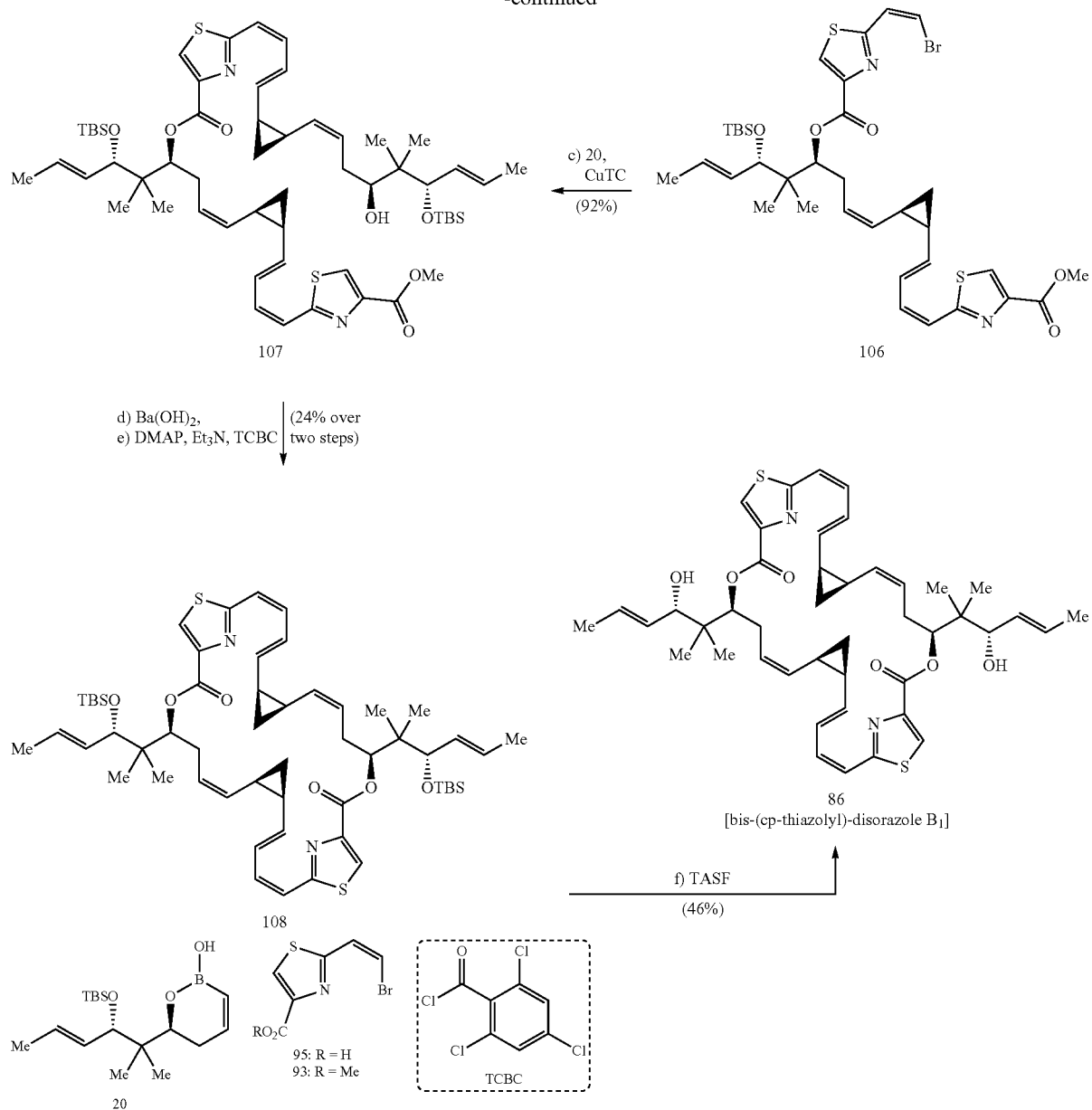

Reagents and conditions: (a) 93 (1.0 equiv), CuTC (1.5 equiv), NMP, 23° C., 1 h, 84%; (b) 95 (2.0 equiv), Et₃N (6.0 equiv), DMAP (8.0 equiv), TCBC (3.0 equiv), toluene, 23° C., 1.5 h, 90%; (c) 40 (1.0 equiv), CuTC (1.5 equiv), NMP, 23° C., 1 h, 92%; (d) Ba(OH)₂·8H₂O (30 equiv) in MeOH:H₂O (3:2 v/v), THF, 23° C., 5 h; (e) TCBC (10 equiv), Et₃N (11 equiv), 23° C., toluene, 1 h; then dilution with toluene to 7.5 mM, DMAP (4.0 equiv), 40° C., 29 h, 24% from 107; (f) TASF (5.0 equiv), H₂O (14 equiv), DMF, 40° C., 48 h, 98%.

Example 2—General Methods and Materials

All reactions were carried out under an argon atmosphere with dry solvent under anhydrous conditions, unless otherwise noted. Dry acetonitrile (MeCN), dimethylformamide (DMF), dichloromethane (CH$_2$Cl$_2$), tetrahydrofuran (THF) and toluene were obtained by passing commercially available pre-dried, oxygen-free formulations through activated alumina columns. Anhydrous benzene, acetone, chloroform (CHCl$_3$), methanol (MeOH), ethanol (EtOH) and nitromethane (MeNO$_2$) were purchased from commercial suppliers and stored under argon. Yields refer to chromatographically and spectroscopically ($^1$H NMR) homogenous material, unless otherwise stated. Reagents were purchased at the highest commercial quality and were used without further purification, unless otherwise noted. Reactions were monitored by thin-layer chromatography (TLC) carried out on S-2 0.25 mm E. Merck silica gel plates (60F-254) using UV light as visualizing agent and an ethanolic solution of phosphomolybdic acid, an aqueous solution of cerium sulfate or a basic aqueous solution of potassium permanganate as developing agents. E. Merck silica gel (60, particle size 0.040-0.063 mm) was used for flash column chromatography. NMR spectra were recorded on a Bruker DRX-600 instrument and calibrated using the signal of residual undeuterated solvent for $^1$H NMR and of the deuterated solvent for $^{13}$C NMR (CDCl$_3$, $\delta_H$=7.26 ppm, $\delta_C$=77.16 ppm; C$_6$D$_6$, $\delta_H$=7.16 ppm, $\delta_C$=128.06 ppm) as an internal reference. The following abbreviations were used to designate multiplicities: s=singlet, d=doublet, t=triplet, q=quartet, quint=quintet, m=multiplet, br=broad. Infrared (IR) spectra were recorded on a Perkin-Elmer 100 FT-IR spectrometer. High-resolution mass spectra (HR-MS) were recorded on an Agilent ESI-TOF (time of flight) mass spectrometer using MALDI (matrix-assisted laser desorption ionization) or ESI (electrospray ionization). Optical rotations were recorded on a Schmidt+Haensch POLARTRONIC M100 polarimeter at 589 nm, using 100 mm cells and the solvent and concentration indicated [in units of $10^{-1}$ (deg cm$^2$ g$^{-1}$)].

Example 3—Compound Characterization tert-Butyl((1-methoxy-2-methylprop-1-en-1-yl)oxy)dimethylsilane (13): was prepared according to a literature procedure (Schäckel et al., 2010):

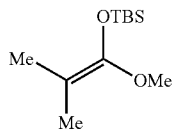

13: $^1$H NMR (600 MHz, CDCl$_3$) δ 3.51 (s, 3H), 1.57 (s, 3H), 1.53 (s, 3H), 0.96 (s, 9H), 0.15 (s, 6H) ppm; $^{13}$C NMR (151 MHz, CDCl$_3$) δ 149.90, 91.51, 57.20, 25.86, 18.22, 17.03, 16.39, −4.47 ppm.

(3S,E)-1-[(tert-Butyldimethylsilyl)oxy]-1-methoxy-2,2-dimethylhex-4-en-3-ol (14)

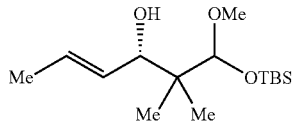

To a cooled stirred suspension (0° C.) of N-Ts-D-valine (18.0 g, 66.3 mmol, 1.10 equiv) in CH$_2$Cl$_2$ (300 mL) was added BH$_3$·THF (63.3 mL, 1 M in THF, 63.3 mmol, 1.05 equiv) dropwise. After the addition was completed, the solution was stirred an additional 30 min at 0° C. and allowed to warm to 23° C. over 1 h. The mixture was cooled to −78° C. and a precooled (−78° C.) solution of crotonaldehyde (4.99 mL, 60.3 mmol, 1.00 equiv) in CH$_2$Cl$_2$ (15 mL) was added in one portion, followed by the dropwise addition of a precooled solution of silyl vinyl ether 13 (15.0 g, 69.3 mmol, 1.15 equiv) in CH$_2$Cl$_2$ (15 mL). The reaction mixture was stirred for 3 h at −78° C. and was quenched by the addition of buffer solution (pH 7, 300 mL) at −78° C. The reaction mixture was allowed to warm up to 23° C. overnight. The phases were separated and the aqueous phase was extracted three times with CH$_2$Cl$_2$ (3×200 mL) and the combined organic extracts were dried over MgSO$_4$, filtered and concentrated under reduced pressure. n-Pentane (600 mL) was added to the crude product, whereupon a white precipitate of N-Ts-D-valine was formed that was removed by filtration. The filtrate was concentrated under reduced pressure and the crude residue was purified by flash column chromatography (SiO$_2$, hexanes:EtOAc 19:1→93:7→9:1) to yield 14 (15.5 g, 53.7 mmol, 83% yield) as a colorless oil consisting of a mixture of diastereomers. Spectral data and the procedure employed for the synthesis of this material were identical to those reported in the literature (Schäckel et al., 2010). 14: R$_f$=0.46 (hexanes:EtOAc, 8:2); $^1$H NMR (600 MHz, CDCl$_3$) δ 5.54-5.47 (m, 1H), 5.32 (ddq, J=15.1, 7.5, 1.6 Hz, 1H), 4.28 (s, 1H), 3.96 (dd, J=7.7, 2.8 Hz, 1H), 3.25 (s, 3H), 1.55 (dd, J=6.5, 1.6 Hz, 3H), 0.77 (s, 9H), 0.73 (s, 3H), 0.63 (s, 3H), 0.00 (s, 3H), −0.05 (s, 3H) ppm; $^{13}$C NMR (151 MHz, CDCl$_3$) δ 130.28, 128.08, 106.43, 76.68, 57.37, 43.35, 26.03, 21.19, 18.76, 18.38, 17.97, −3.44, −4.00 ppm.

(S,E)-3-[(tert-Butyldimethylsilyl)oxy]-2,2-dimethyl-hex-4-enal (15)

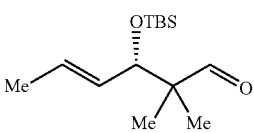

To a cooled stirred solution of alcohol 14 (27.8 g, 96.0 mmol, 1.00 equiv) in THF (480 mL) at −78° C. was added a solution of NaHMDS (96.0 mL, 1 M in THF, 96.0 mmol, 1.00 equiv) and the reaction mixture was allowed to warm to 23° C. over 1 h. Then, the reaction was quenched by the addition a saturated aqueous NH$_4$Cl solution. The phases were separated and the aqueous phase was extracted three times with CH$_2$Cl$_2$ (3×200 mL). The combined organic extracts were dried over MgSO$_4$, filtered and concentrated under reduced pressure. The crude was purified by flash column chromatography (SiO$_2$, hexanes:benzene 7:3; then hexanes:EtOAc 19:1) to yield 15 (20.2 g, 79.7 mmol, 83% yield) as a clear oil. Spectral data and procedure used to make this material were identical to those found in the literature (Schäckel et al., 2010). 15: R$_f$=0.73 (hexanes:EtOAc, 9:1); IR (film): v$_{max}$=2952, 2930, 2858, 1731, 1471, 1251, 1093, 1054, 834, 774 cm$^{-1}$; $^1$H NMR (600 MHz, CDCl$_3$) δ 9.58 (s, 1H), 5.60 (ddt, J=15.6, 6.9, 6.0 Hz, 1H), 5.38 (ddq, J=15.4, 8.2, 1.7 Hz, 1H), 4.09 (d, J=8.2 Hz, 1H), 1.71 (dd, J=6.5, 1.6 Hz, 3H), 1.02 (s, 3H), 0.96 (s, 3H), 0.85 (s, 9H), 0.02 (s, 3H), −0.02 (s, 3H) ppm; $^{13}$C NMR (151 MHz, CDCl$_3$) δ 206.81, 129.99, 129.15, 78.56, 51.00, 25.89, 19.33, 18.20, 17.79, 16.88, −3.62, −4.94 ppm.

(3S,5S,E)-5-{[tert-Butyl(dimethyl)silyl]oxy}-3-hydroxy-1-[(4R)-4-isopropyl-2-thioxo-1,3-thiazolidin-3-yl]-4,4-dimethyloct-6-en-1-one (16)

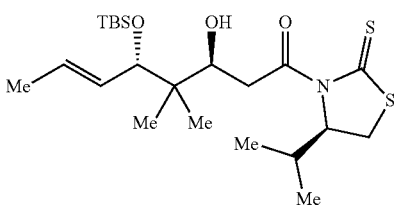

To a stirred solution of auxiliary 22 (5.09 g, 25.0 mmol, 1.00 equiv) in dry CH$_2$Cl$_2$ (200 mL) at 0° C. was added TiCl$_4$ (4.32 mL, 7.49 g, 39.0 mmol, 1.50 equiv), after 5 min at 0° C. the reaction mixture was cooled to −78° C. and a solution of i-Pr$_2$EtN (4.76 mL, 27.0 mmol, 1.10 equiv) in dry CH$_2$Cl$_2$ (10 mL) was added dropwise and the reaction mixture was stirred for 30 min at −78° C. and a further 2 h at −50° C. Upon re-cooling to −78° C., a solution of aldehyde 15 (6.45 g, 25.0 mmol, 1.00 equiv) in CH$_2$Cl$_2$ (20 mL) was added and the reaction mixture was stirred for 1 h at −78° C. The reaction was then quenched by the addition of a saturated aqueous solution of NH$_4$Cl (50 mL). extracted with CH$_2$Cl$_2$ (3×200 mL) and the combined organic extracts were washed with brine (200 mL), dried over MgSO$_4$ and concentrated under reduced pressure. Purification of the crude residue (12:1 dr) by flash column chromatography (SiO$_2$, hexanes:EtOAc, 95:5→8:2) yielded 16 (10.3 g, 22.2 mmol, 89% yield) as a yellow oil. 16: R$_f$=0.21 (hexanes: EtOAc, 9:1); $[\alpha]_D^{25}$=−239.2 (c=1.0, CHCl$_3$); IR (film): $v_{max}$=3468, 2959, 2930, 1701, 1470, 1366, 1307, 1257, 1159, 1037, 836, 776 cm$^{-1}$; $^1$H NMR (600 MHz, CDCl$_3$) δ 5.68-5.46 (m, 2H), 5.13 (ddd, J=8.0, 5.9, 1.0 Hz, 1H), 4.34 (dd, J=10.5, 1.7 Hz, 1H), 4.00-3.83 (m, 1H), 3.52 (dd, J=11.4, 8.0 Hz, 1H), 3.41 (dd, J=17.1, 10.5 Hz, 1H), 3.18 (dd, J=17.1, 1.7 Hz, 1H), 3.01 (dd, J=11.4, 1.0 Hz, 1H), 2.42 (dq, J=13.5, 6.8 Hz, 1H), 1.81-1.63 (m, 3H), 1.06 (d, J=6.8 Hz, 3H), 0.98 (d, J=7.0 Hz, 3H), 0.96 (s, 3H), 0.87 (s, 9H), 0.77 (s, 3H). 0.07 (s, 3H), 0.01 (s, 3H) ppm; $^{13}$C NMR (151 MHz, CDCl$_3$) δ 203.36, 173.09, 130.25, 129.13, 84.05, 72.64, 72.15, 41.51, 40.68, 31.12, 30.88, 25.99, 22.44, 20.22, 19.29, 18.16, 17.88, 17.87, −3.76, −4.97 ppm; HR-MS (ESI-TOF): calcd for C$_{22}$H$_{40}$NO$_3$SiS$_2$Na [M+Na]$^+$: 482.2189. Found: 482.2198.

(3S,5S,E)-5-[(tert-Butyldimethylsilyl)oxy]-1-[(R)-4-isopropyl-2-thioxothiazolidin-3-yl]-4,4-dimethyl-3-[(trimethylsilyl)oxy]oct-6-en-1-one (17)

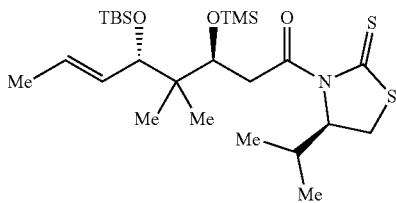

To a stirred solution of alcohol 16 (5.00 g, 10.9 mmol, 1.00 equiv) in CH$_2$Cl$_2$ (54 mL) cooled to 0° C. was added lutidine (3.80 mL, 32.6 mmol, 3.00 eq.) and sequentially TMSOTf (3.93 mL, 21.8 mmol, 2.00 equiv). The reaction was followed by TLC and after 25 min all starting material was consumed. The reaction was quenched by addition of saturated aqueous solution of NaHCO$_3$ (50 mL) and the aqueous phase was extracted three times with CH$_2$Cl$_2$ (3×20 mL). The combined organic extracts were dried over MgSO$_4$, filtered and concentrated under reduced pressure. The crude oil was used in the next reaction without further purification. A small aliquot was purified by flash column chromatography (SiO$_2$, hexanes:EtOAc, 19:1) for characterization purposes. 17: R$_f$=0.46 (hexanes:EtOAc, 9:1); $[\alpha]_D^{25}$=−249.0 (c=1.0, CHCl$_3$); IR (film): $v_{max}$=2959, 2857, 1701, 1470, 1371, 1295, 1280, 1248, 1168, 1086, 1045, 972 cm$^{-1}$; $^1$H NMR (600 MHz, CDCl$_3$) δ 5.49-5.37 (m, 2H), 5.07 (t, J=6.7 Hz, 1H), 4.19 (dd, J=9.3, 1.6 Hz, 1H), 3.83 (d, J=7.9 Hz, 1H), 3.50-3.43 (m, 2H), 3.19 (dd, J=17.9, 1.5 Hz, 1H), 3.02 (dd, J=11.5, 0.9 Hz, 1H), 2.39 (h, J=6.9 Hz, 1H), 1.68 (d, J=5.0 Hz, 2H), 1.07 (d, J=6.8 Hz, 3H), 0.98 (d, J=6.9 Hz, 3H), 0.88 (s, 9H), 0.84 (s, 3H), 0.81 (s, 3H), 0.07 (s, 9H), 0.02 (s, 3H), −0.03 (s, 3H) ppm; $^{13}$C NMR (151 MHz, CDCl$_3$) δ 202.97, 172.73, 131.74, 127.70, 78.96, 73.75, 71.66, 43.39, 42.50, 31.30, 30.88, 26.17, 20.35, 20.08, 19.26, 18.39, 18.19, 17.84, 0.78, −3.30, −4.55 ppm; HR-MS (ESI-TOF): calcd for C$_{25}$H$_{49}$NO$_3$Si$_2$S$_2$Na [M+Na]$^+$: 554.2585. Found: 554.2600.

(3S,5S,E)-5-[(tert-Butyldimethylsilyl)oxy]-4,4-dimethyl-3-[(trimethylsilyl)oxy]oct-6-enal (18)

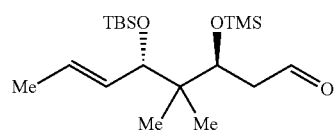

To a stirred solution of thioxothiazolidine 17 (3.47 g, 6.52 mmol, 1.00 equiv.) in Et$_2$O (33.0 mL) cooled to −78° C., was slowly added a solution of DIBAL-H (16.3 mL, 1 M in CH$_2$Cl$_2$, 16.3 mmol, 2.5 equiv). The mixture was stirred for 2 h at the same temperature until all starting material was consumed. Water (642 µL) was added slowly and the reaction flask was allowed to warm to 0° C. Then, the reaction mixture was stirred for 10 min at 0° C. and a 15% aqueous solution of NaOH (652 µL) was added dropwise and finally water was added (1.63 mL) in one portion. The resulting mixture was stirred for 30 min at 23° C. and filtered through a Celite® pad. The filtrate was concentrated under reduced pressure and the crude residue was purified by flash column chromatography (SiO$_2$, hexanes:EtOAc 19:1) to yield aldehyde 18 (1.94 g, 5.22 mmol, 80% yield) as a colorless oil. 18: R$_f$=0.66 (hexanes:EtOAc, 9:1); $[\alpha]_D^{25}$=−55.7 (c=1.0, CHCl$_3$); IR (film): $v_{max}$=2957, 2931, 2885, 2299, 1730, 1472, 1387, 1361, 1251, 1085, 1052, 663 cm$^{-1}$; $^1$H NMR (600 MHz, CDCl$_3$) δ 9.77 (t, J=2.3 Hz, 1H), 5.52-5.39 (m, 2H), 4.14 (dd, J=6.4, 5.0 Hz, 1H), 3.82 (d, J=7.9 Hz, 1H), 2.60-2.54 (m, 2H), 1.69 (d, J=5.2 Hz, 3H), 0.88 (s, 9H), 0.82 (s, 3H), 0.81 (s, 3H), 0.09 (s, 9H), 0.01 (s, 3H), −0.02 (s, 3H) ppm; $^{13}$C NMR (151 MHz, CDCl$_3$) δ 202.85, 131.67, 128.04, 79.09, 72.44, 47.94, 43.38, 26.13, 20.35, 19.81, 18.38, 17.80, 0.84, −3.14, −4.53 ppm.

(4S,6S)-4-[(Z)-3-Iodoallyl]-2,2,5,5,8,8,9,9-octamethyl-6-[(E)-prop-1-en-1-yl]-3,7-dioxa-2,8-disiladecane (19)

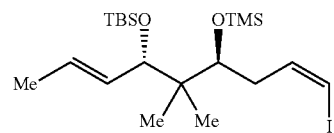

To a stirred solution of (iodomethyl)triphenylphosphonium iodide (21) (4.14 g, 7.81 mmol, 1.50 equiv) in THF (52 mL) at 0° C. was added dropwise NaHMDS (7.81 mL, 1 M in THF, 7.81 mmol, 1.50 equiv) and the mixture was allowed to warm to 25° C. for 5 min before the mixture was cooled to −78° C. Then, DMPU (4.72 mL, 39.0 mmol, 7.50 equiv) was added and the mixture was stirred at −78° C. for 15 min before a solution of aldehyde 18 (1.94 g, 5.21 mmol, 1.00 equiv) in THF (12 mL) was added. The resulting mixture was stirred for 1 h at −78° C. and before it was allowed to warm to 23° C. over 30 min before quenching by addition of saturated aqueous solution of NH₄Cl (20 mL). The aqueous phase was extracted three times with Et₂O (3×20 mL) and the combined organic extracts were dried over MgSO₄, filtered and concentrated under reduced pressure. The crude residue was purified by flash column chromatography (SiO₂, hexanes) to yield vinyl iodide 19 (1.88 g, 3.80 mmol, 73% yield) as a colorless oil. 19: $R_f$=0.80 (hexanes: EtOAc, 97:3); $[\alpha]_D^{25}$=−45.5 (c=1.0, CHCl₃); IR (film): $v_{max}$=2956, 2929, 2884, 2856, 1670, 1609, 1471, 1387, 1360, 1249, 1081, 773 cm⁻¹; ¹H NMR (600 MHz, CDCl₃) δ 6.27 (dd, J=6.8 Hz, 1H), 6.23 (d, 1H), 5.57 (dq, J=15.5, 6.4 Hz, 1H), 5.44 (ddq, J=15.4, 8.7, 1.6 Hz, 1H), 3.90 (d, J=8.6 Hz, 1H), 3.65 (dd, J=8.0, 3.8 Hz, 1H), 2.37-2.23 (m, 2H), 1.70 (dd, J=6.4, 1.6 Hz, 3H), 0.88 (s, 9H), 0.85 (s, 3H), 0.80 (s, 3H), 0.09 (s, 9H), 0.03 (s, 3H), −0.02 (s, 3H) ppm; ¹³C NMR (151 MHz, CDCl₃) δ 140.52, 131.65, 128.09, 82.85, 78.70, 76.15, 43.90, 38.42, 26.17, 20.07, 19.65, 18.40, 17.88, 1.06, −3.12, −4.46 ppm.

(S)-6-{(S,E)-3-[(tert-Butyldimethylsilyl)oxy]-2-methylhex-4-en-2-yl}-5,6-dihydro-2H-1,2-oxa-borinin-2-ol (20)

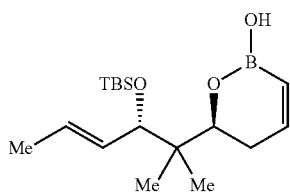

To a stirred solution of vinyl iodide 19 (1.80 g, 3.62 mmol, 1.00 equiv) in toluene:THF [24 mL, 4:1 (v/v)] and triisopropyl borate (920 μL, 3.99 mmol, 1.10 equiv) cooled to −78° C., was added n-BuLi (1.67 mL, 2.5 M in hexane, 4.17 mmol, 1.15 equiv). The resulting mixture was stirred for 30 min at the same temperature before TBAF (5.07 mL, 5.07 mmol, 1 M in THF, 1.4 equiv) was added in one portion and the reaction mixture was allowed to warm to 23° C. over 48 h. The reaction mixture was quenched by the addition of saturated aqueous solution of NH₄Cl (30 mL) and the aqueous phase was extracted three times with EtOAc. The combined organic extracts were dried over MgSO₄, filtered and concentrated under reduced pressure. The crude residue was purified by flash column chromatography (SiO₂, hexanes:benzene, 7:3; then hexanes:EtOAc 19:1→17:3) to yield boronic acid 20 (907 mg, 2.78 mmol, 77% yield) as a colorless oil. 20: $R_f$=0.22 (hexanes:EtOAc, 9:1); $[\alpha]_D^{25}$=−37.0 (c=1.0, CHCl₃); IR (film): $v_{max}$=3373, 2956, 2928, 1606, 1410, 1320, 1052, 835, 774 cm⁻¹; ¹H NMR (600 MHz, CDCl₃) δ 6.95 (ddd, J=12.1, 5.9, 2.2 Hz, 1H), 5.67 (dd, J=12.1, 2.7 Hz, 1H), 5.53 (dq, J=15.5, 6.4 Hz, 1H), 5.41 (ddq, J=15.4, 8.2, 1.6 Hz, 1H), 4.19-4.17 (m, 1H), 4.17-4.15 (m, 1H), 3.80 (s, 1H), 2.18 (ddt, J=17.6, 12.5, 2.5 Hz, 1H), 2.12 (dt, J=17.9, 4.8 Hz, 1H), 1.69 (dd, J=6.3, 1.6 Hz, 3H), 0.86 (s, 9H), 0.76 (s, 3H), 0.74 (s, 3H), 0.01 (s, 3H), −0.03 (s, 3H) ppm; ¹³C NMR (151 MHz, CDCl₃) δ 152.00, 131.62, 127.71, 76.24, 75.89, 53.56, 41.99, 29.86, 28.68, 26.07, 18.35, 18.16, 17.92, 17.67, −3.63, −4.79 ppm; HR-MS (ESI-TOF): calcd for C₁₇H₃₃O₃BSiNa [M+Na]⁺: 347.2188. Found: 347.2176.

1-[(4R)-4-Isopropyl-2-thioxo-1,3-thiazolidin-3-yl]ethanone (22) was prepared according to a literature procedure (Fürstner et al., 2006).

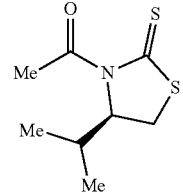

22: ¹H NMR (600 MHz, CDCl₃) 5.15 (ddd, J=7.7, 6.2, 1.2 Hz, 1H), 3.50 (dd, J=11.5, 7.8 Hz, 1H), 3.02 (dd, J=11.5, 1.2 Hz, 1H), 2.77 (s, 3H), 2.42-2.31 (m, J=6.8 Hz, 1H), 1.06 (d, J=6.8 Hz, 3H), 0.97 (d, J=6.9 Hz, 3H) ppm; ¹³C NMR (151 MHz, CDCl₃) δ 203.34, 170.85, 71.40, 30.91, 30.54, 27.07, 19.20, 17.89 ppm.

Ethyl (Z)-3-iodoacrylate (24): was prepared according to a literature procedure (De Carné-Carnavalet et al., 2011).

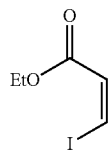

24: ¹H NMR (600 MHz, CDCl₃) δ 7.44 (d, J=8.9 Hz, 1H), 6.89 (d, J=8.9 Hz, 1H), 4.25 (q, J=7.1 Hz, 2H), 1.32 (t, J=7.1 Hz, 3H) ppm; ¹³C NMR (151 MHz, CDCl₃) δ 164.71, 130.04, 94.73, 60.92, 14.32 ppm.

(Z)-3-Iodoprop-2-en-1-ol (25)

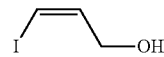

To a stirred solution of ethyl ester 24 (20.0 g, 88.0 mmol, 1.00 equiv) in Et₂O (440 mL) cooled to −78° C., was added a solution of DIBAL-H (195 mL, 1 M in hexanes, 195 mmol, 2.20 equiv) dropwise and the reaction mixture was stirred at −78° C. for 1 h and was then allowed to warm to 23° C. over 1 h. The reaction was quenched following the Fieser method: the mixture was cooled to 0° C. and water (7.80 mL) was added dropwise, after which the ice bath was removed and a 15% aqueous solution of NaOH (7.80 mL) was added dropwise followed by water (19.8 mL). The resulting mixture was stirred for 30 min and then filtered through a Celite® pad. The filtrate was concentrated under reduced pressure and the crude residue was purified by distillation under reduced pressure (73-75° C. head temperature, 1 Torr) to yield hydroxy iodide 25 (14.7 g, 79.2 mmol, 90% yield) as a pale yellow oil. Spectral data were identical to those found in the literature (Beruben et al., 1995). 25: ¹H NMR (600 MHz, CDCl₃) δ 3.93 (ddd, J=12.0, 5.1, 1.1 Hz, 1H), 3.49 (dd, J=11.9, 8.8 Hz, 1H), 2.61 (td, J=7.5, 4.9 Hz, 1H), 1.77 (br s, 1H), 1.33 (ddd, J=9.0, 7.8, 6.4 Hz, 1H), 0.98-0.91 (m, 1H), 0.67 (dt, J=7.0, 5.8 Hz, 1H) ppm; $^{13}$C NMR (151 MHz, CDCl$_3$) δ 202.58, 24.34, 16.60, −17.01 ppm.

cis-(2-Iodocyclopropyl)methanol (26)

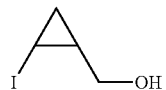

To a stirred solution of Et$_2$Zn (19.4 mL, 1 M in hexanes, 19.4 mmol, 2.00 equiv) in CH$_2$Cl$_2$ (27.6 mL) at 0° C., was added ClCH$_2$I (2.82 mL, 38.7 mmol, 4.00 equiv). After 10 min at 0° C., a solution of (Z)-3-iodoprop-2-en-1-ol (25) (1.78 g, 9.68 mmol, 1.00 equiv) in CH$_2$Cl$_2$ (2 mL) was added slowly to the reaction mixture. The reaction mixture was allowed to warm to 23° C. over 2 h before the reaction was quenched by the addition of a saturated aqueous solution of NH$_4$Cl (25 mL). The aqueous phase was extracted three times with CH$_2$Cl$_2$ (3×25 mL) and the combined organic extracts were dried over MgSO$_4$, filtered and concentrated under reduced pressure. The crude residue was purified by flash column chromatography (SiO$_2$, hexanes:EtOAc, 17:3→3:1) to yield cyclopropyl alcohol 26 (1.48 g, 7.45 mmol, 77% yield) as a colorless oil. Spectral data and the procedure employed to synthesize this material were identical to those reported in the literature (de Carné-Carnavalet, et al., 2011). 26: R$_f$=0.60 (hexanes:EtOAc, 7:3); IR (film): ν$_{max}$=3317, 1393, 1231, 1021, 821 cm$^{-1}$; $^1$H NMR (600 MHz, CDCl$_3$) δ 9.13 (d, J=5.1 Hz, 1H), 2.82 (td, J=7.7, 6.2 Hz, 1H), 1.74-1.62 (m, 2H), 1.58 (q, J=5.7 Hz, 1H) ppm; $^{13}$C NMR (151 MHz, CDCl$_3$) δ 202.58, 24.34, 16.60, −17.01 ppm.

cis-{2-[(Triisopropylsilyl)ethynyl]cyclopropyl}methanol (27)

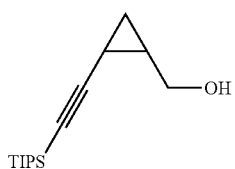

A dry round bottom flask equipped with a stir bar was charged with Cs$_2$CO$_3$ (6.05 g, 18.56 mmol, 2.50 equiv) and the solid was flame dried under reduced pressure. Once the solid was cooled back to 23° C., PdCl$_2$(MeCN)$_2$ (39.0 mg, 0.148 mmol, 2 mol %), X-Phos (0.212 g, 0.445 mmol, 0.06 equiv) and THF (37.0 mL) were added in this order. The mixture was stirred 5 min while being degassed with argon and a solution of cyclopropyl iodide 26 (1.47 g, 7.42 mmol, 1.00 equiv) in THF (2 mL) was added in one portion and degassing was continued for 5 min before the addition of TIPS-acetylene (2.49 mL, 11.1 mmol, 1.50 equiv) to the mixture. The reaction vessel was capped and heated at 60° C. for 20 h. Then, the mixture was filtered through a bed of Celite® and the pad was washed with CH$_2$Cl$_2$ (20 mL). The crude residue was purified by flash column chromatography (SiO$_2$, hexanes:EtOAc, 9:1→17:3→7:3) to yield 27 (1.78 g, 7.05 mmol, 95% yield) as a dark oil. Spectral data and the procedure employed to synthesize this material were identical to those reported in the literature (Hartung et al., 2003). 27: R$_f$=0.27 (hexanes:EtOAc, 8:2); IR (film): ν$_{max}$=3349, 2942, 2865, 2165, 1463, 1044, 883, 676 cm$^{-1}$; $^1$H NMR (600 MHz, CDCl$_3$) δ 3.93 (dd, J=11.9, 5.2 Hz, 1H), 3.62 (dd, J=11.9, 8.8 Hz, 1H), 1.74 (s, 2H), 1.54 (td, J=8.2, 5.4 Hz, 1H), 1.41 (qt, J=8.3, 5.5 Hz, 1H), 1.11-0.97 (m, 21H), 0.67 (q, J=5.4 Hz, 1H) ppm; $^{13}$C NMR (151 MHz, CDCl$_3$) δ 108.52, 78.72, 64.25, 21.19, 18.76, 13.75, 11.44, 5.57 ppm; HR-MS (ESI-TOF): calcd for C$_{15}$H$_{29}$OSi [M+H]$^+$: 253.1982. Found: 2531976.

cis-2-[(Triisopropylsilyl)ethynyl]cyclopropane-1-carbaldehyde (28)

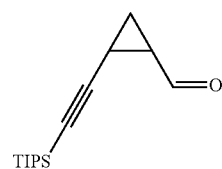

To a stirred solution of cyclopropyl alcohol 27 (0.360 g, 1.46 mmol, 1.00 equiv) in CH$_2$Cl$_2$ (7.1 mL), was added Dess-Martin periodinane (0.665 g, 1.56 mmol, 1.10 equiv) in one portion. The reaction was followed by TLC and showed full conversion after 1 h. The reaction was quenched by adding a 1:1 (v/v) mixture of saturated aqueous solution of NaHCO$_3$:saturated aqueous solution of Na$_2$S$_2$O$_3$ (20 mL). The resulting heterogenous mixture was vigorously stirred for 30 min before the phases were separated. The aqueous phase was extracted three times with CH$_2$Cl$_2$ (3×20 mL) and the combined organic extracts were dried over MgSO$_4$, filtered and concentrated under reduced pressure. The crude residue was purified by flash column chromatography (SiO$_2$, hexanes:EtOAc, 19:1) to yield 28 (0.332 g, 1.30 mmol, 92% yield) as a colorless oil. 28: R$_f$=0.25 (hexanes:EtOAc, 9:1); IR (film): ν$_{max}$=2943, 2865, 2171, 1713, 1463, 882, 782 cm$^{-1}$; $^1$H NMR (600 MHz, CDCl$_3$) δ 9.19 (d, J=6.8 Hz, 1H), 2.06 (td, J=8.2, 6.5 Hz, 1H), 1.91 (tt, J=8.1, 6.1 Hz, 1H), 1.58-1.52 (m, 1H), 1.48 (td, J=8.3, 5.1 Hz, 1H), 1.05-0.97 (m, 21H) ppm; $^{13}$C NMR (151 MHz, CDCl$_3$) δ 200.59, 104.51, 81.68, 28.39, 18.67, 15.33, 11.29, 10.02 ppm;

cis-2-[(Triisopropylsilyl)ethynyl]cyclopropane-1-carboxylic acid (29)

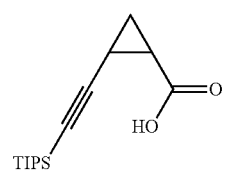

To a stirred solution of aldehyde 28 (0.500 g, 2.00 mmol, 1.00 equiv) in a 3:3:1 (v/v/v) mixture of t-BuOH:THF:H$_2$O (20 mL) was added NaH$_2$PO$_4$ (2.49 g, 16.0 mmol, 8.00 equiv), 2-methylbut-2-ene (4.70 mL, 3.11 g, 40.0 mmol, 20.0 equiv) and NaClO$_2$ (720 mg, 8.00 mmol, 4.00 equiv)

and the reaction mixture was stirred at 23° C. for 15 min. Then, the mixture was diluted with water (100 mL) and extracted with EtOAc (3×200 mL). The combined organic extracts were dried over MgSO$_4$ and concentrated under reduced pressure. Purification of the crude residue by flash column chromatography (SiO$_2$, hexanes:EtOAc 9:1→7:3) yielded carboxylic acid 29 (0.580 g, 2.10 mmol, quant. yield). 29: R$_f$=0.44 (hexanes:EtOAc, 7:3); IR (film): $v_{max}$=2942, 2865, 2170, 1698, 1462, 1234, 883, 662 cm$^{-1}$; $^1$H NMR (600 MHz, CDCl$_3$) δ 2.00-1.89 (m, 2H), 1.45 (td, J=6.6, 4.6 Hz, 1H), 1.26 (td, J=8.2, 4.6 Hz, 1H), 1.05 (d, J=5.7 Hz, 18H), 1.04-0.98 (m, 3H) ppm; $^{13}$C NMR (151 MHz, CDCl$_3$) δ 175.92, 104.45, 80.90, 29.85, 21.47, 18.68, 15.56, 11.35 ppm; HR-MS (ESI-TOF): calcd for C$_{15}$H$_{26}$O$_2$SiNa [M+Na]$^+$: 289.1594. Found: 289.1582.

2'-Hydroxy-1,1'-binaphthalen-2-yl (1S,2R)-2-[(tri-isopropylsilyl)ethynyl]cyclopropane-1-carboxylate (30)

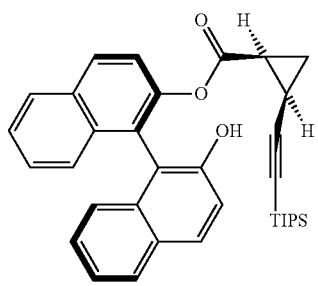

To a stirred solution of carboxylic acid 29 (1.45 g, 5.44 mmol, 1.00 equiv) in CH$_2$Cl$_2$ (54 mL) was added DMAP (0.530 g, 4.34 mmol, 0.800 equiv) and (R)-BINOL (4.61 g, 16.1 mmol, 3.00 equiv) and the reaction mixture was stirred at 23° C. for 10 min. Then, it was cooled to 0° C. and DCC (1.22 g, 5.91 mmol, 1.10 equiv) was added, after which the reaction mixture was allowed to warm up to 23° C. over 30 min and was then stirred at 23° C. for 16 h. Subsequently, the reaction mixture was cooled to 0° C., filtered through a fritted funnel and concentrated under reduced pressure. Purification of the crude residue by flash column chromatography (SiO$_2$, hexanes:EtOAc 9:1→7:3) yielded ester 30 (1.13 g, 2.11 mmol, 39% yield) as white solid. 30: R$_f$=0.56 (hexanes:EtOAc, 7:3); [α]$_D^{25}$=+93.0 (c=1.0, CHCl$_3$); IR (film): $v_{max}$=3504, 2941, 2864, 2166, 1748, 1621, 1382, 1209, 1140, 1118, 745 cm$^{-1}$; $^1$H NMR (600 MHz, CDCl$_3$) δ 8.02 (d, J=8.9 Hz, 1H), 7.97 (d, J=8.2 Hz, 1H), 7.91 (d, J=8.9 Hz, 1H), 7.86 (d, J=8.1 Hz, 1H), 7.53-7.47 (m, 1H), 7.42 (d, J=8.9 Hz, 1H), 7.36-7.31 (m, 3H), 7.27-7.25 (m, 1H) 7.24 (dd, J=9.8, 8.4 Hz, 1H), 7.05 (d, J=8.4 Hz, 1H), 1.86 (td, J=8.6, 7.0 Hz, 1H), 1.72 (td, J=8.1, 6.2 Hz, 1H), 1.33 (td, J=6.6, 4.8 Hz, 1H), 1.20-1.12 (m, 1H), 1.10-0.99 (m, 21H) ppm; $^{13}$C NMR (151 MHz, CDCl$_3$) δ 169.70, 152.10, 148.35, 133.75, 133.69, 132.39, 130.61, 130.40, 129.16, 128.38, 128.12, 127.46, 126.81, 126.34, 125.93, 124.73, 123.62, 123.14, 122.67, 118.68, 114.38, 104.39, 80.92, 21.15, 18.76, 15.24, 11.49, 11.42 ppm.

{(1S,2R)-2-[(Triisopropylsilyl)ethynyl]cyclopropyl}methanol (31)

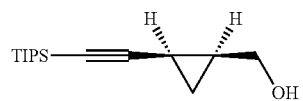

To a stirred solution of binol ester 30 (1.00 g, 1.87 mmol, 1.00 equiv) in Et$_2$O (9.4 mL) cooled to −78° C., was added DIBAL-H (5.98 mL, 1 M in hexane, 5.98 mmol, 3.20 equiv) dropwise and the reaction mixture was allowed to warm to 23° C. over 3 h. The reaction was quenched following the Fieser method: the mixture was cooled to 0° C. and water (0.24 mL) was added dropwise, after which the ice bath was removed and a 15% aqueous solution of NaOH (0.24 mL) was added dropwise followed by water (0.60 mL). The resulting mixture was stirred for 30 min and filtered through a pad of Celite®. Subsequently, the filter cake was washed with Et$_2$O (3×10 mL). The filtrate was concentrated under reduced pressure and the crude residue was purified by flash column chromatography (SiO$_2$, hexanes:EtOAc, 9:1) to yield alcohol 31 (0.450 g, 1.75 mmol, 94% yield) as a colorless oil. 31: R$_f$=0.26 (hexanes:EtOAc, 9:1); [α]$_D^{25}$=−75.3 (c=1.0, CHCl$_3$); IR (film): $v_{max}$=3349, 2942, 2865, 2165, 1463, 1044, 883, 676 cm$^{-1}$; $^1$H NMR (600 MHz, CDCl$_3$) δ 3.93 (dd, J=11.9, 5.2 Hz, 1H), 3.62 (dd, J=11.9, 8.8 Hz, 1H), 1.74 (s, 1H), 1.54 (td, J=8.2, 5.4 Hz, 1H), 1.41 (qt, J=8.3, 5.5 Hz, 1H), 1.11-0.97 (m, 22H), 0.67 (q, J=5.4 Hz, 1H) ppm; $^{13}$C NMR (151 MHz, CDCl$_3$) δ 108.52, 78.72, 64.25, 21.19, 18.76, 13.75, 11.44, 5.57 ppm; HR-MS (ESI-TOF): calcd for C$_{15}$H$_{29}$OSi [M+H]$^+$: 253.1982. Found: 2531976.

(1S,2R)-2-[(Triisopropylsilyl)ethynyl]cyclopropane-1-carbaldehyde (32): Same Procedure as for Substrate 28

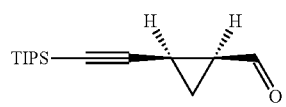

32: R$_f$=0.25 (hexanes:EtOAc, 9:1); [α]$_D^{25}$=−153.2 (c=1.0, CHCl$_3$); IR (film): $v_{max}$=2943, 2865, 2171, 1713, 1463, 882, 782 cm$^{-1}$; $^1$H NMR (600 MHz, CDCl$_3$) δ9.19 (d, J=6.8 Hz, 1H), 2.06 (td, J=8.2, 6.5 Hz, 1H), 1.91 (tt, J=8.1, 6.1 Hz, 1H), 1.58-1.52 (m, 1H), 1.48 (td, J=8.3, 5.1 Hz, 1H), 1.05-0.97 (m, 21H) ppm; $^{13}$C NMR (151 MHz, CDCl$_3$) δ 200.59, 104.51, 81.68, 28.39, 18.67, 15.33, 11.29, 10.02 ppm.

(3S,5S,E)-5-[(tert-Butyldimethylsilyl)oxy]-4,4-dimethyl-3-[(trimethylsilyl)oxy]oct-6-en-1-ol (34)

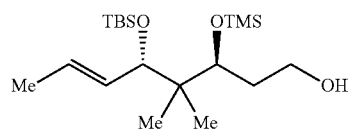

To a stirred solution of crude thiooxothiazolidin 17 (based on 5.00 g of alcohol 16) in Et$_2$O (54 mL) cooled to −78° C., was added DIBAL-H (54.3 mL, 1 M in CH$_2$Cl$_2$, 54.3 mmol, 5.00 equiv) dropwise and the reaction mixture was allowed to warm to 23° C. over 2 h. The reaction was quenched following the Fieser method: the mixture was cooled to 0° C. and water (2.17 mL) was added dropwise, after which the ice bath was removed and a 15% aqueous solution of NaOH (2.17 mL) was added dropwise followed by water (5.43 mL). The resulting mixture was stirred for 30 min and filtered through a pad of Celite®. Subsequently, the filter cake was washed with Et$_2$O (3×20 mL). The filtrate was concentrated under reduced pressure and the crude residue was purified by flash column chromatography (SiO$_2$, hexanes:EtOAc, 19:1→9:1) to yield alcohol 34 (2.91 g, 7.71 mmol, 71% yield over two steps) as a colorless oil and the alcohol was used immediately in the next step since the product was found to be highly unstable. 34: R$_f$=0.18 (hexanes:EtOAc, 9:1); IR (film): v$_{max}$=3357, 2957, 2930, 1471, 1249, 1049, 832 cm$^{-1}$; $^1$H NMR (600 MHz, CDCl$_3$) δ 5.37 (dq, J=15.4, 6.2 Hz, 1H), 5.32-5.24 (m, 1H), 3.72 (d, J=8.4 Hz, 1H), 3.61 (ddd, J=10.4, 6.8, 5.2 Hz, 1H), 3.56-3.47 (m, 2H), 1.65-1.58 (m, 1H), 1.56 (dd, J=6.4, 1.5 Hz, 3H), 1.50 (dddd, J=13.9, 9.7, 6.2, 5.2 Hz, 1H), 0.75 (s, 9H), 0.70 (s, 3H), 0.68 (s, 3H), 0.00 (s, 6H), −0.12 (s, 3H), −0.16 (s, 3H) ppm; $^{13}$C NMR (151 MHz, CDCl$_3$) δ 131.69, 127.73, 78.67, 75.05, 61.21, 43.53, 35.03, 26.12, 20.13, 19.43, 18.38, 17.82, 1.06, −3.20, −4.54.

(4S,6S)-4-(2-Iodoethyl)-2,2,5,5,8,8,9,9-octamethyl-6-[(1E)-prop-1-en-1-yl]-3,7-dioxa-2,8-disiladecane (35)

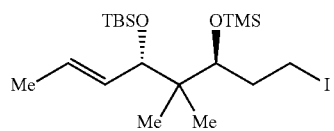

To a stirred solution of alcohol 34 (1.99 g, 5.31 mmol, 1.00 equiv) in CH$_2$Cl$_2$ (26 mL) at 23° C. was added in order imidazole (0.542 g, 7.97 mmol, 1.50 equiv), PPh$_3$ (1.67 g, 6.37 mmol, 1.20 equiv) and I$_2$ (1.82 g, 7.17 mmol, 1.35 equiv). The reaction vessel was covered in aluminium foil. The reaction was followed by TLC and showed complete conversion of the starting material after 1 h. The reaction mixture was concentrated under reduced pressure at low temperature (23° C.) and the crude residue was purified directly by flash column chromatography (SiO$_2$, hexanes:benzene 7:3; then hexanes:EtOAc, 19:1) to yield iodide 35 (2.00 g, 4.13 mmol, 77% yield) as a clear oil. 35: R$_f$=0.68 (hexanes:EtOAc, 19:1); [α]$_D^{25}$=−54.5 (c=1.0, CHCl$_3$); IR (film): v$_{max}$=2957, 2857, 1471, 1250, 1049, 834 cm$^{-1}$; $^1$H NMR (600 MHz, CDCl$_3$) δ 5.35 (dq, 1=15.5, 6.4 Hz, 1H), 5.24 (ddq, J=15.5, 8.8, 1.6 Hz, 1H), 3.63 (d, J=8.4 Hz, 1H), 3.40 (dd, J=9.7, 1.9 Hz, 1H), 3.19 (ddd, J=9.5, 6.8, 4.1 Hz, 1H), 2.94 (td, J=9.7, 6.2 Hz, 1H), 1.81 (dddd, J=14.5, 10.1, 6.9, 2.0 Hz, 1H), 1.68 (dddd, J=14.2, 10.0, 6.2, 4.1 Hz, 1H), 1.54 (dd, J=6.3, 1.5 Hz, 3H), 0.72 (s, 9H), 0.66 (s, 6H), 0.00 (s, 9H), −0.15 (s, 3H), −0.19 (s, 3H) ppm; $^{13}$C NMR (151 MHz, CDCl$_3$) δ 130.33, 127.16, 77.93, 76.54, 42.56, 34.88, 25.13, 19.35, 19.03, 17.38, 16.85, 5.03, 0.22, −4.21, −5.57 ppm.

(4S,6S)-2,2,5,5,8,8,9,9-Octamethyl-6-[(1E)-prop-1-en-1-yl]-4-[(2Z)-3-{(1R,2R)-2-[(triisopropylsilyl)ethynyl]cyclopropyl}prop-2-en-1-yl]-3,7-dioxa-2,8-disiladecane (36)

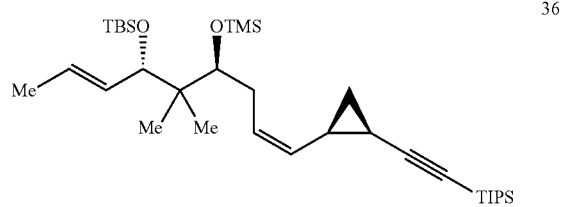

To a stirred solution of iodide 35 (2.00 g, 4.13 mmol, 1.00 equiv) in i-Pr$_2$EtN (5.03 mL, 28.9 mmol, 7.00 equiv) was added PPh$_3$ (1.89 g, 7.22 mmol, 1.75 equiv). The reaction vessel was capped and heated at 90° C. for 16 h. Subsequently, the mixture was allowed to cool to 23° C. and pentane (70 mL) was added resulting in a thick paste material that was carefully separated from the cloudy pentane solution. The paste was washed three times with pentane (3×50 mL). Then, the paste was dissolved in THF (41.0 mL) and the stirred solution was cooled to −78° C. Next, LiHMDS (4.33 mL, 1 M in THF, 4.33 mmol, 1.05 equiv) was added and the reaction mixture was stirred for 15 min before DMPU (0.299 mL, 2.48 mmol, 0.60 equiv) was added, followed by the addition of a solution of aldehyde 32 (1.14 g, 4.54 mmol, 1.10 equiv) in THF (4 mL). The reaction mixture was stirred at −78° C. for 15 min and was subsequently allowed to warm to 23° C. over 1 h. Then, the reaction was quenched by the addition of a saturated aqueous solution of NaHCO$_3$ (50 mL) and the aqueous phase was extracted three times with Et$_2$O (3×35 mL). The combined organic extracts were dried over MgSO$_4$, filtered and concentrated under reduced pressure. The crude residue was purified by flash column chromatography (SiO$_2$, hexanes:benzene 3:2→1:1→2:3; then hexanes:EtOAc 19:1→17:3) to yield cyclopropyl compound 36 (2.04 g, 3.45 mmol, 83% yield) as a colorless oil. 36: R$_f$=0.60 (hexanes:EtOAc, 19:1); [α]$_D^{25}$=−117.5 (c=1.0, CHCl$_3$); IR (film): v$_{max}$=2956, 2864, 2165, 1463, 1249, 1048, 834 cm$^{-1}$; $^1$H NMR (600 MHz, C$_6$D$_6$) δ 5.75 (ddd, J=11.0, 8.3, 6.7 Hz, 1H), 5.66 (tt, J=10.9, 1.4 Hz, 1H), 5.55-5.49 (m, 1H), 5.41 (dq, J=15.4, 6.4 Hz, 1H), 4.05 (d, J=8.6 Hz, 1H), 3.80 (dd, J=8.4, 3.2 Hz, 1H), 2.46-2.34 (m, 2H), 1.70-1.63 (m, 1H), 1.50 (dd, J=6.4, 1.5 Hz, 3H), 1.46 (td, J=8.3, 5.7 Hz, 1H), 1.19 (d, J=7.2 Hz, 21H), 1.09 (s, 3H), 1.05 (s, 3H), 1.04 (s, 9H), 0.84 (td, J=8.4, 4.2 Hz, 1H), 0.66 (td, J=5.9, 4.2 Hz, 1H), 0.26 (s, 9H), 0.14 (s, 3H), 0.10 (s, 3H) ppm; $^{13}$C NMR (151 MHz, C$_6$D$_6$) δ 132.27, 130.48, 129.94, 128.35, 109.24, 79.36, 79.29, 77.98, 44.17, 31.74, 26.31, 20.28, 19.78, 18.99, 18.58, 17.66, 17.59, 16.98, 11.79, 9.34, 1.36, −2.93, −4.31 ppm.

(1Z,4S,6S,7E)-6-{[tert-Butyl(dimethyl)silyl]oxy}-5,5-dimethyl-1-{(1R,2R)-2-[(triisopropylsilyl)-ethynyl]cyclopropyl}nona-1,7-dien-4-ol (37)

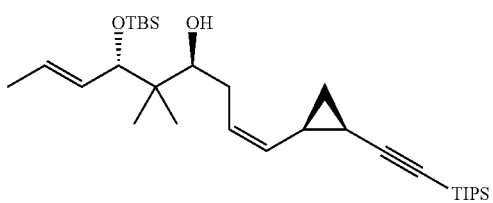

To a stirred solution tris-silane 36 (0.623 g, 1.05 mmol, 1.00 equiv) in Et$_2$O (10 mL) was added 4 N HCl (10 mL) and the biphasic solution was stirred 16 h at 23° C. The resulting mixture was quenched by the addition of a saturated aqueous solution NaHCO$_3$ (30 mL) and the aqueous phase was extracted with Et$_2$O (3×20 mL). The combined organic extracts were dried over MgSO$_4$, filtered and concentrated under reduced pressure. The crude residue was purified by flash column chromatography (SiO$_2$, hexanes: EtOAc 19:1) to yield alcohol 37 (0.543 g, 1.04 mmol, 99% yield) as a colorless oil. 37: R$_f$=0.31 (hexanes:EtOAc, 19:1); IR (film): v$_{max}$=3317, 1393, 1231, 1021, 821 cm$^{-1}$; $^1$H NMR (600 MHz, C$_6$D$_6$) δ 6.00 (dtd, J=10.9, 7.4, 1.0 Hz, 1H), 5.65 (ddt, J=10.7, 9.1, 1.6 Hz, 1H), 5.52 (ddq, J=15.2, 8.0, 1.5 Hz, 1H), 5.39 (dq, J=15.4, 6.4 Hz, 1H), 4.00 (d, J=8.1 Hz, 1H), 3.87 (ddd, J=7.6, 5.1, 2.3 Hz, 1H), 3.35 (d, J=2.1 Hz, 1H), 2.37-2.29 (m, 2H), 1.68-1.61 (m, 1H), 1.50 (dd, J=6.4, 1.6 Hz, 3H), 1.41 (td, J=8.3, 5.7 Hz, 1H), 1.18 (d, J=7.2 Hz, 18H), 1.11-1.06 (m, 2H), 1.04 (s, 3H), 0.98 (s, 9H), 0.80 (s, 3H), 0.78 (dt, J=8.3, 4.1 Hz, 1H), 0.64 (td, J=5.9, 4.3 Hz, 1H), 0.10 (s, 3H), 0.05 (s, 3H) ppm; $^{13}$C NMR (151 MHz, C$_6$D$_6$) δ 131.65, 130.89, 129.90, 128.51, 109.52, 82.62, 79.44, 75.55, 41.91, 31.25, 26.27, 21.47, 19.57, 19.14, 18.51, 17.84, 17.70, 17.33, 11.94, 9.44, -3.46, -4.74 ppm.

(1Z,4S,6S,7E)-6-{[tert-Butyl(dimethyl)silyl]oxy}-1-[(1R,2R)-2-ethynylcyclopropyl]-5,5-dimethyl-nona-1,7-dien-4-ol (38)

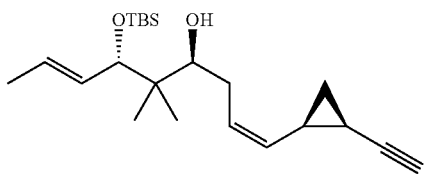

To a stirred solution of alcohol 37 (0.540 g, 1.04 mmol, 1.00 equiv) in MeOH (10 mL) was added AgF (0.172 g, 1.35 mmol, 1.30 equiv) and the reaction vessel was protected from light with aluminium foil. The reaction mixture was stirred for 30 min at 23° C. and the solution was diluted in CH$_2$C2 (50 mL) and quenched with 1 M aqueous HCl solution (20 mL). The aqueous phase was extracted three times with CH$_2$Cl$_2$ (3×30 mL) and the combined organic extracts were dried over MgSO$_4$, filtered and concentrated under reduced pressure. The crude residue was purified by flash column chromatography (SiO$_2$, hexanes:EtOAc, 97:3→19:1) to yield alcohol 38 (0.320 g, 0.880 mmol, 85% yield) as a pale black-yellow oil. 38: R$_f$=0.24 (hexanes: EtOAc, 19:1); [α]$_D^{25}$=-124.7 (c=1.0, CHCl$_3$); IR (film): v$_{max}$=3483, 3316, 2957, 2930, 2857, 2120, 1471, 1252, 1033, 834 cm$^{-1}$; $^1$H NMR (600 MHz, CDCl$_3$) δ 5.68 (dt, J=10.8, 7.2 Hz, 1H), 5.49 (dd, J=5.8, 3.6 Hz, 2H), 5.25 (ddt, J=10.8, 9.2, 1.6 Hz, 1H), 4.08 (s, 1H), 3.81 (d, J=6.5 Hz, 1H), 3.65 (dt, J=9.9, 2.3 Hz, 1H), 2.24 (ddt, J=14.4, 7.6, 1.5 Hz, 1H), 2.14 (dddd, J=14.4, 9.8, 6.9, 1.6 Hz, 1H), 1.82 (d, J=2.2 Hz, 1H), 1.80-1.72 (m, 1H), 1.65 (d, J=4.8 Hz, 3H), 1.57-1.49 (m, 1H), 1.11 (td, J=8.5, 4.5 Hz, 1H), 0.92 (s, 3H), 0.82 (s, 9H), 0.69 (s, 3H), 0.61 (td, J=5.9, 4.5 Hz, 1H), 0.00 (s, 3H), -0.05 (s, 3H) ppm; $^{13}$C NMR (151 MHz, CDCl$_3$) δ 130.47, 129.49, 129.44, 128.71, 84.41, 84.20, 76.34, 66.99, 41.15, 30.52, 26.00, 22.60, 19.71, 18.17, 17.88, 16.65, 16.18, 7.45, -3.79, -4.95 ppm; HR-MS (ESI-TOF): calcd for C22H38O2Si [M+Na]$^+$: 385.2534. Found: 385.2533.

(1Z,4S,6S,7E)-1-[(1R,2R)-2-(Bromoethynyl)cyclopropyl]-6-{[tert-butyl(dimethyl)silyl]oxy}-5,5-dimethylnona-1,7-dien-4-ol (39)

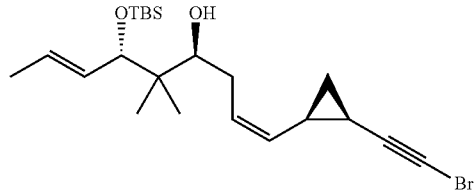

To a stirred solution of terminal alkyne 38 (0.320 g, 0.882 mmol, 1.00 equiv), in acetone (5 mL), was added NBS (0.188 g, 1.05 mmol, 1.20 equiv) and AgNO$_3$ (30.0 mg, 17.6 µmol, 0.200 equiv). The reaction flask was covered with aluminium foil and the reaction mixture was stirred for 30 min before it was concentrated under reduced pressure at low temperature (25° C.). The crude residue was purified directly by flash column chromatography (SiO$_2$, hexanes: benzene 1:1→hexanes: EtOAc 19:1) to yield alkynyl bromide 39 (0.326 g, 0.740 mmol, 84% yield) as a yellow oil. 39: R$_f$=0.59 (hexanes:EtOAc, 9:1); [α]$_D^{25}$=-146.3 (c=1.0, CHCl$_3$); IR (film): v$_{max}$=2957, 1471, 1252, 1033, 972, 836, 776 cm$^{-1}$; $^1$H NMR (600 MHz, CDCl$_3$) δ 5.74 (dt, J=10.9, 7.2 Hz, 1H), 5.62-5.51 (m, 2H), 5.28 (ddt, J=10.8, 9.2, 1.5 Hz, 1H), 4.17 (s, 1H), 3.88 (d, J=6.5 Hz, 1H), 3.72 (dd, J=9.6, 1.6 Hz, 1H), 2.29 (dd, J=14.5, 7.1 Hz, 1H), 2.21 (dddd, J=14.4, 9.9, 7.1, 1.6 Hz, 1H), 1.87-1.78 (m, 1H), 1.72 (d, J=4.7 Hz, 3H), 1.61 (apparent td, J=8.3, 5.7 Hz, 1H), 1.16 (apparent td, J=8.5, 4.5 Hz, 1H), 0.99 (s, 3H), 0.89 (s, 9H), 0.76 (s, 2H), 0.68 (apparent td, J=5.9, 4.4 Hz, 1H), 0.07 (s, 3H), 0.02 (s, 3H) ppm; $^{13}$C NMR (151 MHz, CDCl$_3$) δ 130.45, 129.61, 129.41, 128.74, 84.29, 80.25, 76.31, 41.13, 36.51, 30.53, 26.01, 22.67, 19.73, 18.18, 17.89, 16.93, 15.97, 8.75, -3.79, -4.95 ppm; HR-MS (ESI-TOF): calcd for C$_{22}$H$_{37}$O$_2$SiBrNa [M+Na]$^+$: 463.1638. Found: 463.1633.

(1Z,4S,6S,7E)-6-{[tert-Butyl(dimethyl)silyl]oxy}-5,5-dimethyl-1-{(1R,2R)-2-[(E)-2-(tributylstannyl)-vinyl]cyclopropyl}nona-1,7-dien-4-ol (40)

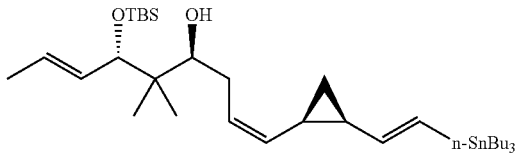

To a stirred solution of alkynyl bromide 39 (0.155 g, 0.351 mmol, 1.00 equiv) in toluene cooled to −78° C. was added PdCl$_2$(PPh$_3$)$_2$ (11.0 mg, 0.0156 mmol, 0.045 equiv) in one portion and argon was bubbled through the solution for 5 min. Then, a solution of n-Bu$_3$SnH (0.208 mL, 0.772 mmol, 2.20 equiv) in THF (1 mL) was added dropwise to the reaction mixture and it was stirred at this temperature for 10 min before the cooling bath was removed and the mixture was allowed to slowly warm to 23° C. Once the reaction mixture turned from pale yellow to pale brown the mixture was concentrated under reduced pressure and the crude residue was purified directly by flash column chromatography (deactivated SiO$_2$ with Et$_3$N, hexanes) to yield vinyl stannane 40 (0.183 g, 0.280 mmol, 80% yield) as a colorless oil. 40: R$_f$=0.31 (hexanes:EtOAc, 19:1); [α]$_D^{25}$=−82.7 (c=1.0, CHCl$_3$); IR (film): ν$_{max}$=3495, 2956, 2855, 1593, 1463, 1251, 1049, 1033, 835, 775 cm$^{-1}$; $^1$H NMR (600 MHz, CDCl$_3$) δ 6.00 (d, J=18.9 Hz, 1H), 5.69 (dd, J=18.8, 7.4 Hz, 1H), 5.63 (dt, J=10.7, 7.0 Hz, 1H), 5.56-5.54 (m, 2H), 5.19 (dd, J=10.7, 8.9 Hz, 1H), 4.10 (s, 1H), 3.86 (d, J=6.5 Hz, 1H), 3.70 (dt, J=10.0, 2.2 Hz, 1H), 2.32 (dd, J=14.6, 7.7 Hz, 1H), 2.14 (dddd, J=14.5, 9.9, 6.6, 1.6 Hz, 1H), 1.78 (dtd, J=15.8, 8.2, 5.9 Hz, 2H), 1.70 (d, J=4.4 Hz, 3H), 1.54-1.41 (m, 6H), 1.29 (dt, J=14.7, 7.4 Hz, 6H), 1.12 (td, J=8.2, 4.7 Hz, 1H), 0.97 (s, 3H), 0.91-0.85 (m, 24H), 0.75 (s, 3H), 0.60 (q, J=5.5 Hz, 1H), 0.06 (d, J=2.3 Hz, 3H), 0.00 (s, 3H) ppm; $^{13}$C NMR (151 MHz, CDCl$_3$) δ 148.15, 130.53, 129.91, 128.63, 128.38, 127.87, 84.23, 76.40, 41.16, 30.28, 29.26, 27.43, 26.01, 25.76, 22.59, 19.72, 18.17, 17.92, 17.88, 14.88, 13.87, 9.65, −3.80, −4.95 ppm; HR-MS (ESI-TOF): calcd for C$_{34}$H$_{66}$O$_2$SiSnNa [M+Na]$^+$: 677.3753. Found: 677.3765.

(Iodoethynyl)triisopropylsilane (41)

To a stirred solution of ethynyltriisopropylsilane (8.40 mL, 6.83 g, 37.4 mmol, 1.00 equiv) in anhydrous acetone (105 mL), protected from light with aluminium foil, were added sequentially NIS (10.1 g, 44.9 mmol, 1.20 equiv) and silver nitrate (0.633 g, 3.73 mmol, 0.10 equiv). After stirring at 23° C. for 10 minutes the volatiles from the reaction mixture were removed under reduced pressure and the crude residue was filtered through a plug of silica (hexanes) to afford the product as a colorless liquid (11.4 g, 37.0 mmol, 98% yield). Spectral data and the procedure employed to synthesize this material were identical to those reported in the literature (López et al., 2005) 41: R$_f$=0.72 (hexanes); IR (film): ν$_{max}$=3229, 2944, 2865, 1727, 1460, 1211, 1061, 882, 756 cm$^{-1}$; $^1$H NMR (600 MHz, CDCl$_3$) δ 1.07 (s, 21H) ppm; $^{13}$C NMR (151 MHz, CDCl$_3$) δ 101.00, 20.01, 18.65, 11.56 ppm.

(Z)-(2-Iodovinyl)triisopropylsilane(42)

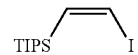

To a stirred solution of iodoalkyne 41 (11.3 g, 36.6 mmol. 1.00 equiv) in a mixture of THF:i-PrOH [126 mL, 5:2 (v/v)] protected from light with aluminium foil, freshly prepared 2-nitrobenzenesulfonyhydrazide (NBSH; 7.00 g, 32.2 mmol, 0.90 equiv) was added in one portion. The reaction mixture was stirred for 16 h at 23° C., after which the reaction was quenched by the addition of water (50 mL) and extracted with Et$_2$O (3×50 mL). The combined organic extracts were dried over MgSO$_4$, concentrated under reduced pressure and the crude residue was purified by flash column chromatography (SiO$_2$, hexanes) to yield iodoalkene 42 (6.00 g, 19.3 mmol, 53% yield, 98% brsm) as colorless oil. 42: R$_f$=0.66 (hexanes); $^1$H NMR (600 MHz, CDCl$_3$) δ 7.30 (d, J=10.0 Hz, 1H), 7.12 (d, J=10.0 Hz. 1H), 1.39 (hept, J=7.4 Hz, 3H), 1.11 (d, J=7.4 Hz, 18H) ppm; $^{13}$C NMR (151 MHz, CDCl$_3$) δ 140.31, 97.19, 18.99, 11.58 ppm.

(Z)-(5,5-Diethoxypent-1-en-3-yn-1-yl)triisopropylsilane (43)

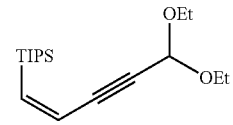

To a stirred solution of iodoalkene 42 (8.73 g. 28.1 mmol, 1.00 equiv) in degassed diisopropylamine (200 mL), Pd(PhCN)$_2$Cl$_2$ (0.539 g, 1.40 mmol, 0.05 equiv), PPh$_3$ (0.737 g, 2.81 mmol, 0.10 equiv) and CuI (0.376 g, 1.97 mmol, 0.07 equiv) were added and the reaction mixture was purged with Ar for 10 min after which 3,3-diethoxyprop-1-yne (6.05 mL, 5.41 g, 42.1 mmol, 1.50 equiv) was added and the reaction mixture was stirred for 1 h at 23° C. Then, the reaction mixture was then partitioned between Et$_2$O (300 mL) and water (100 mL) and the organic layer was washed with water (3×100 mL), dried over MgSO$_4$ and concentrated under reduced pressure. The crude residue was purified by flash column chromatography (SiO$_2$, hexanes→hexanes:benzene 3:1→hexanes:EtOAc 9:1) to yield acetal 43 (7.87 g, 25.3 mmol, 90% yield) as a colorless liquid. 43: R$_f$=0.70 (hexanes: EtOAc, 9:1); IR (film): $^1$H NMR (600 MHz, CDCl$_3$) δ 6.45 (dd, J=15.6, 1.5 Hz, 1H), 6.13 (d, J=15.6 Hz, 1H), 5.37 (d, J=1.5 Hz, 1H), 3.73 (dq, J=9.4, 7.1 Hz, 2H), 3.58 (dq, J=9.4, 7.1 Hz, 2H), 1.30 (hept, J=7.5 Hz, 3H), 1.23 (t. J=7.1 Hz, 6H), 1.08 (d, J=7.5 Hz, 18H) ppm; $^{13}$C NMR (151 MHz, CDCl$_3$) δ 142.22, 125.13, 92.05, 87.65, 85.86, 61.02, 18.91, 15.21, 11.67 ppm.

(2E,4Z)-5-(Triisopropylsilyl)penta-2,4-dien-1-ol (44)

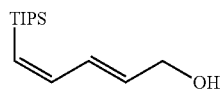

To a vigorously stirred solution of acetal 43 (4.18 g, 13.5 mmol, 1.00 equiv) in chloroform (90 mL) was added a 50% aqueous solution of TFA (10.3 mL, 135 mmol, 10.0 equiv) and the reaction mixture was stirred at 23° C. for 30 min. The reaction was then quenched by the slow addition of a saturated aqueous solution of NaHCO$_3$ (50 mL) and extracted with Et$_2$O (3×50 mL). The combined organic extracts were dried over MgSO$_4$ and concentrated under reduced pressure to afford the crude aldehyde (S, analytical data is given below), which was then dissolved in Et$_2$O (30 mL) and added to a solution of Red-Al® (8.98 mL, 60 wt. % in toluene, 27.6 mmol, 2.05 equiv) in Et$_2$O (30 mL) at 0° C. via cannula. The reaction mixture was allowed to warm to 23° C. over 2 h. Then, it was quenched by the careful addition of 1 M HCl (50 mL), extracted with Et$_2$O (3×50 mL) and the combined organic extracts were dried over MgSO$_4$ and concentrated under reduced pressure. The crude residue was purified by flash column chromatography (SiO$_2$, hexanes:EtOAc, 9:1→7:3) to yield alcohol 44 (3.23 g, 13.4 mmol, quant. yield). 44: R$_f$=0.16 (hexanes:EtOAc, 9:1); IR (film): v$_{max}$=3329, 2942, 2891, 2865, 1567, 1463, 997, 882, 665 cm$^{-1}$; $^1$H NMR (600 MHz, CDCl$_3$) δ 6.97 (ddd, J=14.4, 11.1, 0.7 Hz, 1H), 6.36 (ddq, J=15.0, 11.1, 1.4 Hz, 1H), 5.89 (dtt, J=15.0, 5.7, 0.7 Hz, 1H), 5.58 (d, J=14.4 Hz, 1H), 4.22 (dd, J=5.7, 1.5 Hz, 2H), 1.20-1.11 (m, 3H), 1.06 (d, J=7.2 Hz, 18H) ppm; $^{13}$C NMR (151 MHz, CDCl$_3$) δ 146.25, 134.77, 132.53, 128.55, 63.48, 18.99, 12.33 ppm.

(Z)-5-(Triisopropylsilyl)pent-4-en-2-ynal (S1)

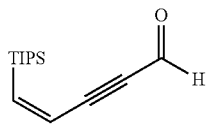

R$_f$=0.75 (hexanes: EtOAc, 9:1); IR (film): v$_{max}$=2942, 2889, 2866, 2229, 2169, 1667, 1463, 1110, 882, 715, 663 cm$^{-1}$; $^1$H NMR (600 MHz, CDCl$_3$) δ 9.32 (d, J=1.0 Hz, 1H), 6.60 (d, J=15.8 Hz, 1H), 6.56 (dd, J=15.8, 1.0 Hz, 1H), 1.33 (hept, J=7.4 Hz, 3H), 1.09 (d, J=7.4 Hz, 18H) ppm; $^{13}$C NMR (151 MHz, CDCl$_3$) δ 176.66, 151.49, 123.17, 95.29, 90.53, 18.86, 11.71 ppm; HR-MS (ESI-TOF): calcd for C$_{14}$H$_{25}$OSi [M+H]+: 237.1669. Found: 237.1663.

[(1Z,3E)-5,5-Dimethoxypenta-1,3-dien-1-yl]triiso-propylsilane (45)

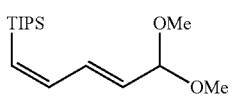

To a stirred solution of alcohol 44 (5.30 g, 22.0 mmol, 1.00 equiv) in CH$_2$Cl$_2$ (150 mL) at 0° C. was added DMP (18.7 g, 44.0 mmol, 2.00 equiv) and the reaction mixture was allowed to warm to 23° C. and stirred for additional 2 h. Then, a 1:1 (v/v) mixture of a saturated aqueous solution of Na$_2$S$_2$O$_3$ and a saturated aqueous solution of NaHCO$_3$ (100 mL) was added and the reaction mixture was stirred for further 30 min at 23° C. after which it was extracted with CH$_2$Cl$_2$ (3×50 mL), dried over MgSO$_4$ and the combined organic extracts were concentrated under reduced pressure. The crude aldehyde (S2, analytical data is given below) was then dissolved in dry MeOH (50 mL) before trimethyl orthoformate (2.41 mL, 2.34 g, 22.0 mmol, 1.00 equiv) and pTsOH hydrate (42 mg, 0.22 mmol, 0.01 equiv) were added sequentially and the reaction mixture was stirred for 1 h at 23° C. The reaction mixture was then concentrated under reduced pressure backfilled with Ar and addition of solid NaHCO$_3$ (1.00 g) and dry Et$_2$O (20 mL) gave a white suspension, which was filtered through a syringe filter. The resulting solution was then azeotroped with toluene (3×30 mL) under reduced pressure to give acetal 45 (6.20, 21.8 mmol, 99% yield), which was used in the next step without further purification. 45: R$_f$=0.71 (hexanes: EtOAc, 8:2); IR (film): v$_{max}$=2942, 2866, 1567, 1464, 1129, 1055, 882 cm$^{-1}$; $^1$H NMR (600 MHz, CDCl$_3$) δ 6.97 (dd, J=14.7, 11.0 Hz, 1H), 6.44 (ddt, J=15.5, 11.0, 1.2 Hz, 1H), 5.67 (d, J=14.7 Hz, 1H), 5.65 (dd, J=15.5, 4.8 Hz, 2H), 4.83 (dd, J=4.8, 1.2 Hz, 1H), 3.32 (s, 6H), 1.21-1.11 (m, 3H), 1.06 (d, J=7.2 Hz, 18H) ppm; $^{13}$C NMR (151 MHz, CDCl$_3$) δ 145.82, 134.95, 131.46, 130.36, 102.89, 52.87, 18.97, 12.28 ppm.

(2E,4Z)-5-(Triisopropylsilyl)penta-2,4-dienal (S2)

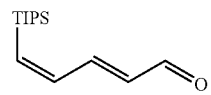

R$_f$=0.58 (hexanes: EtOAc, 9:1), 0.69 (hexanes: EtOAc, 8:2); IR (film): v$_{max}$=2942, 2891, 2866, 1685, 1463, 1264, 1239, 1125, 882, 663 cm$^{-1}$; $^1$H NMR (600 MHz, CDCl$_3$) δ 9.61 (d, J=8.0 Hz, 1H), 7.23-7.13 (m, 2H), 6.28 (dd, J=13.4, 7.3 Hz, 1H), 6.23-6.14 (m, 1H), 1.28-1.17 (m, 3H), 1.09 (d, J=7.4 Hz, 18H) ppm; $^{13}$C NMR (151 MHz, CDCl$_3$) δ 193.91, 152.11, 144.26, 142.84, 133.75, 18.89, 12.33 ppm; HR-MS (ESI-TOF): calcd for C$_{14}$H$_{27}$OSi [M+H]+: 239.1826. Found: 239.1817.

(3R,4E,6Z)-1-[(4R)-4-Isopropyl-2-thioxo-1,3-thiazo-lidin-3-yl]-3-methoxy-7-(triiso-propylsilyl)hepta-4,6-dien-1-one (46)

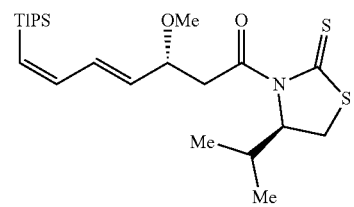

To a stirred solution of auxiliary 22 (1.07 g, 5.27 mmol, 1.00 equiv) in dry CH$_2$Cl$_2$ (50 mL) at 0° C. was added TiCl$_4$ (0.640 mL, 1.10 g, 5.80 mmol, 1.10 equiv) and after 5 min at 0° C. the reaction mixture was cooled to −78° C. Then, a solution of i-Pr$_2$EtN (1.01 mL, 0.750 g, 5.80 mmol, 1.10 equiv) in dry CH$_2$Cl$_2$ (20 mL) was added dropwise and the reaction mixture was stirred for 30 min at −78° C. and further 2 h at −50° C. Upon re-cooling to −78° C., boron trifluoride etherate (0.670 mL, 0.750 g, 5.27 mmol, 1.00 equiv) was added, immediately followed by a solution of acetal 45 (1.50 g, 5.27 mmol, 1.00 equiv) in CH$_2$Cl$_2$ (20 mL) and the reaction mixture was stirred for 1 h at −78° C. The reaction was then quenched by the addition of a saturated aqueous solution of NH$_4$Cl (20 mL) extracted with CH$_2$Cl$_2$ (3×50 mL) and the combined organic extracts were washed with brine (50 mL), dried over MgSO$_4$ and concentrated under reduced pressure. Purification of the crude residue (−3:1 dr) by flash column chromatography (SiO$_2$, hexanes:EtOAc, 9:1) yielded compound 46 (1.62 g, 3.55 mmol, 67% yield) as a yellow oil. 46: R$_f$=0.61 (hexanes:EtOAc, 8:2); $[\alpha]_D^{25}$=−151.2 (c=1.0, CHCl$_3$); IR (film): v$_{max}$=2961, 2941, 2890, 2864, 1699, 1464, 1364, 1258, 1158, 1091, 882, 665 cm$^{-1}$; $^1$H NMR (600 MHz, CDCl$_3$) δ 6.95 (dd, J=14.5, 11.1 Hz, 1H), 6.36 (dd, J=15.1, 11.1 Hz, 1H), 5.69-5.62 (m, 1H), 5.61 (d, J=14.5 Hz, 1H), 5.11 (ddd, J=7.7, 5.9, 1.5 Hz, 1H), 4.21 (td, J=7.4, 5.6 Hz, 1H), 3.65 (dd, J=16.7, 7.4 Hz, 1H), 3.53-3.41 (m, 2H), 3.28 (s, 3H), 3.01 (dd, J=11.5, 1.5 Hz, 1H), 2.44-2.30 (m, 1H), 1.22-1.12 (m, 3H), 1.06 (d, J=5.7 Hz, 18H), 1.05 (d, J=4.9 Hz, 3H), 0.97 (d, J=6.9 Hz, 3H) ppm; $^{13}$C NMR (151 MHz, CDCl$_3$) δ 202.86, 171.13, 146.00, 134.50, 134.39, 129.33, 78.16, 71.94, 56.61, 44.53, 30.88, 30.39, 19.24, 18.99, 18.96, 17.64, 12.30 ppm; HR-MS (ESI-TOF): calcd for C$_{23}$H$_{41}$NO$_2$SiS$_2$Na [M+Na]$^+$: 478.2240. Found: 478.2243.

Methyl (2S)-3-hydroxy-2-{[(3R,4E,6Z)-3-methoxy-7-(triisopropylsilyl)hepta-4,6-dienoyl]amino}-propanoate (47)

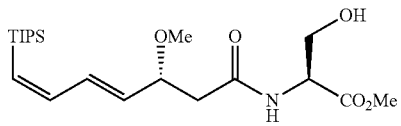

To a stirred solution of methyl serinate hydrochloride (1.08 g, 6.91 mmol, 1.50 equiv) in THF (70 mL) was added dropwise i-Pr$_2$EtN (1.61 mL, 1.19 g, 9.22 mmol, 2.00 equiv) and the reaction mixture was stirred for 10 min at 23° C. before the addition of amide 46 (2.10 g, 4.61 mmol, 1.00 equiv) in THF (20 mL). After 5 minutes, imidazole (0.938 g, 13.8 mmol, 3.00 equiv) was added and the reaction mixture was stirred for 16 h at 23° C. Then, the reaction mixture was concentrated under reduced pressure and purification of the crude residue by flash column chromatography (SiO$_2$, hexanes:EtOAc, 1:1→1:5) yielded amide 47 (1.75 g, 4.23 mmol, 92% yield) as a colorless oil. 47: R$_f$=0.21 (hexanes:EtOAc, 1:1), $[\alpha]_D^{25}$=+17.8 (c=1.0, CHCl$_3$); IR (film): v$_{max}$=3360, 2942, 2890, 2865, 1747, 1649, 1534, 1463, 1210, 1089, 882, 665 cm$^{-1}$; $^1$H NMR (600 MHz, CDCl$_3$) δ 7.32 (d, J=7.2 Hz, 1H), 6.95 (dd, J=14.5, 11.1 Hz, 1H), 6.36 (dd, J=15.1, 11.1 Hz, 1H), 5.65 (d, J=15.1, 7.7 Hz, 1H), 5.59 (dd, J=15.1, 7.7 Hz, 1H), 4.67 (dt, J=7.4, 3.8 Hz, 1H), 4.04 (td, J=8.4, 3.3 Hz, 1H), 3.99-3.90 (m, 2H), 3.80 (s, 3H), 3.33 (s, 3H), 2.54 (dd, J=15.1, 9.0 Hz, 1H), 2.45 (dd, J=15.1, 3.3 Hz, 1H), 1.21-1.10 (m, 3H), 1.05 (dd, J=7.3, 2.1 Hz, 18H) ppm; $^{13}$C NMR (151 MHz, CDCl$_3$) δ $^{13}$C NMR (151 MHz, CDCl$_3$) δ 171.24, 170.99, 145.64, 134.75, 133.53, 130.03, 78.78, 63.73, 56.58, 55.07, 52.89, 42.77, 18.94, 18.92, 12.29 ppm; HR-MS (ESI-TOF): calcd for C$_{21}$H$_{39}$NO$_5$SiNa [M+Na]$^+$: 436.2490. Found: 436.2499.

Methyl 2-[(2R,3E,5Z)-2-methoxy-6-(triisopropylsilyl)hexa-3,5-dien-1-yl]-1,3-oxazole-4-carboxylate (48)

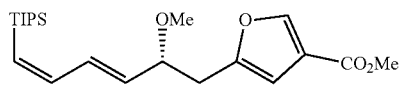

To a stirred solution of amide 47 (1.75 g, 4.23 mmol, 1.00 equiv) in dry CH$_2$Cl$_2$ (70 mL) at −20° C. was added Deoxofluor® (0.936 mL, 1.12 g, 5.08 mmol, 1.20 equiv) dropwise and the reaction mixture was stirred at −20° C. for 30 min. The reaction was then quenched by the addition of a saturated aqueous solution of NaHCO$_3$ (50 mL), extracted with CH$_2$Cl$_2$ (3×50 mL). dried over MgSO$_4$ and concentrated under reduced pressure. The crude oxazoline was then dissolved in dry CH$_2$Cl$_2$ (70 mL), the reaction flask was protected from light with aluminium foil and BrCCl$_3$ (1.66 mL, 3.35 g, 16.9 mmol, 4.00 equiv) and DBU (2.54 mL, 2.57 g, 16.9 mmol, 4.00 equiv) were added sequentially at 0° C. The reaction mixture was then allowed to warm up to 23° C. and further stirred for 16 h at 23° C. before the reaction was quenched by the addition of a saturated aqueous solution of NaHCO$_3$ (50 mL). The mixture was extracted with CH$_2$Cl$_2$ (3×50 mL), dried over MgSO$_4$ and concentrated under reduced pressure. The crude residue was purified by flash column chromatography (SiO$_2$, hexanes:EtOAc, 9:1→7:3) to yield oxazole 48 (1.52 g, 3.85 mmol, 91% yield) as a light brown oil. 48: R$_f$=0.81 (hexanes:EtOAc, 1:1); $[\alpha]_D^{25}$=−6.0 (c=1.0, CHCl$_3$); IR (film): v$_{max}$=2942, 2891, 2865, 1751, 1732, 1585, 1323, 1137, 1107, 1000, 882, 666 cm$^{-1}$; $^1$H NMR (600 MHz, CDCl$_3$) δ 8.14 (s, 1H), 6.93 (dd, J=14.4, 11.2, 1H), 6.32 (dd, J=15.2, 11.2, 1H), 5.66-5.56 (m, 2H), 4.17 (tdd, J=7.8, 6.0, 0.8 Hz, 1H), 3.91 (s, 3H), 3.25 (s, 3H), 3.12 (dd, J=14.9, 7.7 Hz, 1H), 3.00 (dd, J=14.9, 6.0 Hz, 1H), 1.17-1.08 (m, 3H), 1.02 (d, J=7.3 Hz, 18H) ppm; $^{13}$C NMR (151 MHz, CDCl$_3$) δ 162.90, 161.83, 145.64, 144.04, 135.30, 133.67, 133.48, 130.00, 79.72, 56.61, 52.26, 35.00, 18.90, 12.27 ppm; HR-MS (ESI-TOF): calcd for C$_{21}$H$_{35}$NO$_4$SiNa [M+Na]$^+$: 416.2228. Found: 416.2217.

Methyl 2-[(2R,3E,5Z)-6-bromo-2-methoxyhexa-3,5-dien-1-yl]-1,3-oxazole-4-carboxylate (49)

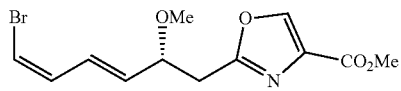

To a stirred solution of oxazole 48 (1.10 g, 2.79 mmol, 1.00 equiv) in hexafluoro-2-propanol (50 mL) at 0° C. that was protected from light with aluminium foil were sequentially added Ag$_2$CO$_3$ (0.772 g, 2.79 mmol, 1.00 equiv) and NBS (0.618 g, 3.47 mmol, 1.25 equiv) and the reaction mixture was stirred for 2 h at 0° C. The reaction was then quenched by the addition of water (20 mL) and a saturated aqueous solution of $Na_2S_2O_3$ (20 mL). The mixture was extracted with $CH_2Cl_2$ (3×50 mL), dried over $MgSO_4$ and concentrated under reduced pressure. The crude residue was purified by flash column chromatography ($SiO_2$, hexanes: EtOAc, 7:3, 1:1) to yield bromide 49 (0.800 g, 2.54 mmol, 91% yield) as a light brown oil. 49: $R_f$=0.50 (hexanes: EtOAc, 1:1); $[\alpha]_D^{25}$=+7.1 (c=1.0, $CHCl_3$); IR (film): $v_{max}$=2926, 1739, 1583, 1321, 1139, 1106, 1003, 977, 805, 687 cm$^{-1}$; $^1$H NMR (600 MHz, $CDCl_3$) δ 8.17 (s, 1H), 6.62 (dd, J=10.2, 6.9 Hz, 1H), 6.57 (dd, J=14.9, 10.2 Hz, 1H), 6.22 (d, J=6.9 Hz, 1H), 5.81 (dd, J=14.9, 7.9 Hz, 1H), 4.22 (td, J=7.6, 5.8 Hz, 2H), 3.91 (s, 3H), 3.29 (s, 3H), 3.13 (dd, J=14.9, 7.6 Hz, 1H), 3.03 (dd, J=14.9, 5.8 Hz, 1H) ppm; $^{13}$C NMR (151 MHz, $CDCl_3$) δ 162.61, 161.81, 144.16, 135.69, 133.49, 131.50, 129.24, 109.86, 79.44, 56.93, 52.28, 34.76 ppm; HR-MS (ESI-TOF): calcd for $C_{12}H_{14}NO_4BrNa$ [M+Na]$^+$: 337.9998. Found: 337.9995.

2-Nitrobenzenesulfonohydrazide (51) was prepared according to a literature procedure (Myers et al., 1997)

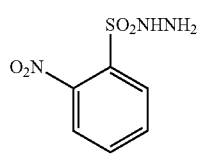

51

51: $^1$H NMR (600 MHz, $CD_3CN$) δ 8.07 (dd, J=7.3, 1.8 Hz, 1H), 7.92-7.74 (m, 3H), 6.94 (s, 1H) ppm; $^{13}$C NMR (151 MHz, $CD_3CN$) δ 149.61, 135.55, 133.49, 133.26, 131.02, 125.89 ppm;

Ethyl 2-iodooxazole-4-carboxylate (54) was prepared according to a literature procedure (de Carné-Carnavalet et al., 2011).

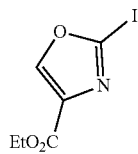

54

54: $^1$H NMR (600 MHz, $CDCl_3$) δ 8.29 (s, 1H), 4.40 (q, J=7.1 Hz, 2H), 1.38 (t, J=7.1 Hz, 3H) ppm; $^{13}$C NMR (151 MHz, $CDCl_3$) δ 159.98, 149.11, 136.72, 102.47, 61.74, 14.39 ppm.

Ethyl 2-[(triisopropylsilyl)ethynyl]oxazole-4-carboxylate (55)

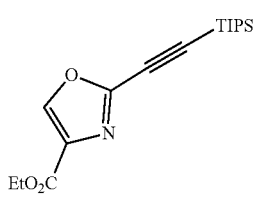

55

To a stirred solution of iodide 54 (4.14 g, 15.5 mmol, 1.00 equiv) and ethynyltriisopropylsilane (17.4 mL, 14.1 g, 77.5 mmol, 5.00 equiv) in a degassed mixture of DMF (14 mL) and $Et_3N$ (14 mL) were added $Pd(PPh_3)_4$ (0.355 g, 0.307 mmol, 0.02 equiv) and CuI (0.148 g, 0.777 mmol, 0.05 equiv) and the reaction mixture was purged with Ar for 10 minutes after which the reaction mixture was stirred for 16 h at 60° C. After the mixture was allowed to cool to 23° C. it was partitioned between $Et_2O$ (300 mL) and water (300 mL), extracted with $Et_2O$ (3×100 mL), and the combined organic layers was dried over $MgSO_4$ and concentrated under reduced pressure. The crude residue was purified by flash column chromatography ($SiO_2$, hexanes:EtOAc 95:5→8:2) to yield oxazole 55 (3.78 g, 11.6 mmol, 75% yield) as a brown oil. 55: $R_f$=0.61 (hexanes:EtOAc, 8:2); IR (film): $v_{max}$=2945, 2867, 1747, 1724, 1534, 1284, 1140, 1108, 882, 765, 678 cm$^{-1}$; $^1$H NMR (600 MHz, $CDCl_3$) δ 8.16 (s, 1H), 4.39 (q, J=7.1 Hz, 2H), 1.37 (t, J=7.1 Hz, 3H), 1.18-1.12 (m, 3H), 1.11 (d, J=6.1 Hz, 18H) ppm; $^{13}$C NMR (151 MHz, $CDCl_3$) δ 160.67, 146.79, 144.14, 134.28, 98.23, 92.09, 61.61, 18.59, 14.39, 11.15 ppm; HR-MS (ESI-TOF): calcd for $C_{17}H_{28}NO_3Si$ [M+H]$^+$: 322.1833. Found: 322.1826.

Ethyl 2-ethynyloxazole-4-carboxylate (56)

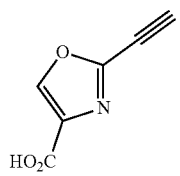

56

To a stirred solution of oxazole 55 (3.78 g, 11.8 mmol, 1.00 equiv) in THF (150 mL) at 0° C. was added glacial AcOH (2.68 mL, 2.81 g, 46.8 mmol, 4.00 equiv) and TBAF (23.5 mL, 1 M in THF, 23.5 mmol, 2.00 equiv) and the reaction mixture was stirred for 1 h at 23° C. Then, the reaction mixture was concentrated under reduced pressure and the crude residue was purified by flash column chromatography (dryload on Celite®, $SiO_2$, hexanes:EtOAc 9:1→7:3) to yield alkyne 56 (1.76 g, 10.7 mmol. 91% yield) as a white solid. Spectral data were identical to those reported in the literature (Hartung et al., 2003). 56: $R_f$=0.29 (hexanes:EtOAc, 8:2); mp=82° C. (EtOAc); IR (film): $v_{max}$=3204, 2125, 1728, 1716, 1575, 1533, 1313, 1300, 1209, 1121, 1023, 984, 744 cm$^{-1}$; $^1$H NMR (600 MHz, $CDCl_3$) δ 8.19 (s, 1H), 4.39 (q, J=7.1 Hz, 2H), 3.29 (s, 1H), 1.38 (t, J=7.1 Hz, 3H) ppm; $^3$C NMR (151 MHz, $CDCl_3$) δ 160.43, 146.08, 144.60, 134.44, 81.30, 70.50, 61.70, 14.36 ppm; HR-MS (ESI-TOF): calcd for $C_8H_7NO_3Na$ [M+Na]$^+$: 188.0318. Found: 188.0315.

2-Ethynyloxazole-4-carboxylic acid (57)

57

To a stirred solution of alkyne 56 (1.37 g, 8.30 mmol, 1.00 equiv) in a mixture of THF (33 mL) and water (25 mL) was added LiOH hydrate (523 mg, 12.5 mmol, 1.50 equiv) and the reaction mixture was stirred at 23° C. for 90 min. Then, the reaction mixture was acidified by the addition of 1 M aqueous HCl (50 mL) and extracted with EtOAc (3×50 mL). The combined organic phases were dried over MgSO$_4$ and concentrated under reduced pressure to give carboxylic acid 57 (1.09 g, 7.97 mmol, 96% yield) as a white solid. 57: R$_f$=0.07 (EtOAc with 1% formic acid); mp=170° C. (EtOAc, decomposing to brown oil); $^1$H NMR (600 MHz, CD$_3$D) δ 8.53 (s, 1H), 4.24 (s, 1H) ppm; $^{13}$C NMR (151 MHz, CD$_3$OD) δ 162.97, 147.53, 146.79, 135.35, 83.97, 71.02 ppm; HR-MS (ESI-TOF): calcd for C$_6$H2NO$_3$Na [M+Na]$^+$: 181.9825. Found: 181.9817.

(Z)-2-(2-Bromovinyl)oxazole-4-carboxylicacid (58)

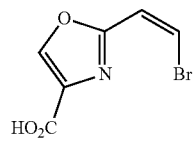

To a stirred solution of dry LiBr (132 mg, 1.50 mmol, 1.50 equiv) and dry LiOAc (298 mg, 4.50 mmol, 4.50 equiv) in glacial AcOH (4.0 mL) was added carboxylic acid 57 (138 mg, 1.00 mmol, 1.00 equiv) and the resulting mixture was heated to 70° C. for 16 h. The reaction mixture was then cooled to 23° C., diluted with water (5 mL) and extracted with EtOAc (5×15 mL). Combined organic extracts were dried over MgSO$_4$ and concentrated under reduced pressure. The resulting solid was then azeotroped with toluene (3×30 mL) under reduced pressure to afford the desired bromide (200 mg, 0.910 mmol, 91% yield), as a white amorphous solid. Procedure adapted from Wipf et al. (2005). 58: IR (film): v$_{max}$=3024, 1682, 1637, 1582, 1420, 1308, 1114, 759 cm$^{-1}$; $^1$H NMR (600 MHz, CD$_3$OD) δ 8.56 (s, 1H), 7.22 (d, J=8.6 Hz, 1H), 7.14 (d, J=8.6 Hz, 1H) ppm; $^{13}$C NMR (151 MHz, CD$_3$OD) δ 163.75, 160.85, 145.64, 135.64, 120.29, 116.68 ppm; HR-MS (ESI-TOF): calcd for C$_6$H$_5$NO$_3$Br [M+H]$^+$: 217.9447. Found: 217.9443.

Methyl 2-[(2R,3E,5Z,7Z,10S,12S,13E)-12-{[tert-butyl(dimethyl)silyl]oxy}-10-hydroxy-2-methoxy-11,11-dimethylpentadeca-3,5,7,13-tetraen-1-yl]-1,3-oxazole-4-carboxylate (59)

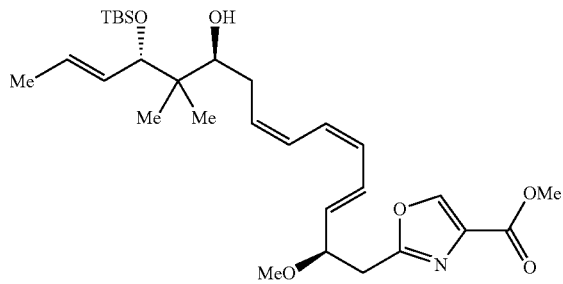

To a stirred solution of vinyl bromide 49 (0.155 g, 0.490 mmol, 1.0 equiv) and boronic acid 20 (0.22 g, 0.69 mmol, 1.4 equiv) in a 3:1 (v/v) mixture of THF:water (2.5 mL) was added thallium carbonate (1.2 g, 2.5 mmol, 5.0 equiv) and the solution was degassed for 10 min with Argon. Subsequently, Pd(dppf)Cl$_2$ (0.036 g, 0.049 mmol, 10 mol %) was added in one portion and the reaction flask was covered in aluminium foil and stirred for 16 h at 23° C. The reaction mixture was filtered through Celite® and the concentrated under reduced pressure. The crude material was purified by column flash chromatography (SiO$_2$, hexanes:EtOAc, 4:1→3:2) to yield oxazole alcohol 59 (0.20 g, 0.37 mmol, 76% yield) as an orange thick oil. 59: R$_f$=0.39 (hexanes: EtOAc, 13:7); [α]$_D^{25}$=−13.4 (c=0.5, CHCl$_3$); IR (film): v$_{max}$=3479, 2955, 2857, 1749, 1585, 1471, 1323, 1323, 1110, 836 cm$^{-1}$; $^1$H NMR (600 MHz, CDCl$_3$) δ 8.15 (s, 1H), 6.70 (dd, J=15.2, 11.3 Hz, 1H), 6.51 (dd, J=11.4, 11.4 Hz, 1H), 6.29 (dd, J=11.5, 11.5 Hz, 1H), 5.98 (dd, J=11.1, 11.1 Hz, 1H), 5.82-5.74 (m, 1H), 5.62-5.50 (m, 3H), 4.31 (s, 1H), 4.18 (td, J=7.8, 5.9 Hz, 1H), 3.91 (s, 3H), 3.85 (d, J=6.8 Hz, 1H), 3.71 (dd, J=9.3, 2.2 Hz, 1H), 3.26 (s, 3H), 3.12 (dd, J=14.9, 7.6 Hz, 1H), 3.00 (dd, J=14.9, 5.9 Hz, 1H), 2.35-2.20 (m, 2H), 1.71 (d, J=5.2 Hz, 3H), 1.00 (s, 3H), 0.88 (s, 9H), 0.75 (s, 3H), 0.07 (s, 3H), 0.01 (s, 3H) ppm; $^{13}$C NMR (151 MHz, CDCl$_3$) δ 162.89, 161.86, 144.11, 133.47, 132.40, 132.24, 130.25, 129.20, 128.91, 127.74, 126.01, 124.38, 84.69, 79.78, 76.24, 56.67, 52.24, 41.05, 35.07, 30.23, 25.99, 22.90, 19.81, 18.15, 17.89, −3.82, −4.96 ppm; HR-MS (ESI-TOF): calcd for C$_{29}$H$_{47}$NO$_6$SiNa [M+Na]$^+$: 556.3065. Found: 556.3072.

(2E,4S,6S,8Z,10Z,12E,14R)-4-{[tert-Butyl(dimethyl)silyl]oxy}-14-methoxy-15-[4-(methoxy-carbonyl)-1,3-oxazol-2-yl]-5,5-dimethylpentadeca-2,8,10,12-tetraen-6-yl 2-[(Z)-2-bromovinyl]-1,3-oxazole-4-carboxylate (60)

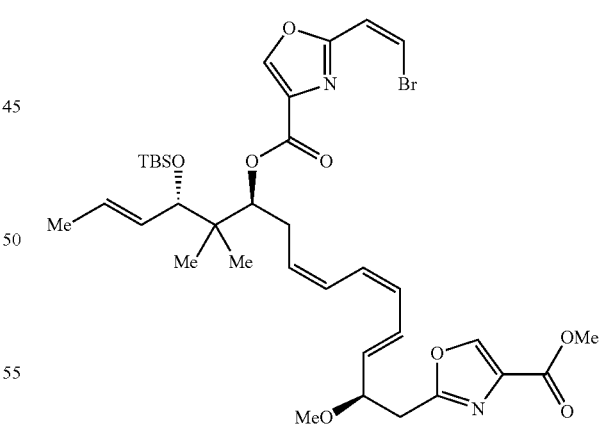

To a stirred solution of alcohol 59 (0.10 g, 0.19 mmol, 1.0 equiv) and carboxylic acid 58 (49 mg, 0.23 mmol, 1.2 equiv) in toluene (2.0 mL) was added Et$_3$N (0.16 mL, 1.1 mmol, 6.0 equiv) and DMAP (0.18 g, 1.5 mmol, 8.0 equiv). The solution was cooled to 0° C. and 2,4,6-trichlorobenzoyl chloride (64) (0.088 mL, 0.56 mmol, 3.0 equiv) was added dropwise before the reaction mixture was allowed to warm to 23° C. Upon complete consumption of the starting material (about 3 h), the reaction was quenched by the addition of a saturated aqueous solution of NaHCO₃. The aqueous phase was extracted three times with EtOAc (3×10 mL) and the combined organic extracts were dried over MgSO₄, filtered and concentrated under reduced pressure. The crude residue was purified by flash column chromatography (SiO₂, hexanes:EtOAc 4:1→3:1→7:3→1:1) to yield vinyl bromide 60 (0.12 g, 0.16 mmol, 88% yield) as a colorless oil. 60: $R_f$=0.28 (hexanes:EtOAc. 13:7); $[\alpha]_D^{25}$=−49.0 (c=1.0, CHCl₃); IR (film): $v_{max}$=2953, 2856, 1740, 1584, 1322, 1112, 834 cm⁻¹; ¹H NMR (600 MHz, CDCl₃) δ 8.15 (s, 1H), 8.14 (s, 1H), 7.16 (d, J=8.7 Hz, 1H), 6.88 (d, J=8.7 Hz, 1H), 6.60 (dd, J=15.2, 11.3 Hz, 1H), 6.45-6.36 (m, 1H), 6.24 (t, J=11.4 Hz, 1H), 5.96 (t, J=11.1 Hz, 1H), 5.60-5.43 (m, 4H), 5.23 (dd, J=9.8, 3.3 Hz, 1H), 4.14 (td, J=7.8, 5.5 Hz, 1H), 3.90 (s, 3H), 3.84 (d, J=8.1 Hz, 1H), 3.23 (s, 3H), 3.08 (dd, J=15.0, 7.8 Hz, 1H), 2.98 (dd, J=14.9, 5.6 Hz, 1H), 2.66-2.57 (m, 1H), 2.52 (dddd, J=15.2, 6.7, 3.3, 1.7 Hz, 1H), 1.68 (dd, J=6.1, 1.2 Hz, 3H), 0.96 (s, 3H), 0.92 (s, 3H), 0.87 (s, 9H), −0.02 (s, 3H), −0.05 (s, 3H) ppm; ¹³C NMR (151 MHz, CDCl₃) δ 162.87, 161.84, 160.47, 159.35, 144.10, 143.13, 134.64, 133.44, 132.71, 131.28, 129.92, 128.77, 128.56, 128.36, 125.44, 125.34, 119.84, 114.91, 79.57, 79.14, 78.12, 56.73, 52.24, 42.98, 35.00, 28.61, 26.09, 20.18, 19.48, 18.32, 17.92, −3.37, −4.80 ppm; HR-MS (ESI-TOF): calcd for C₃₅H₄₉N₂O₈SiBrNa [M+Na]⁺: 755.2334. Found: 755.2334.

Methyl 2-{(2R,3E,5Z,7Z,10S,12S,13E)-12-{[tert-butyl(dimethyl)silyl]oxy}-10-[({2-[(1Z,3E)-4-{(1S, 2R)-2-[(1Z,4S,6S,7E)-6-{[tert-butyl(dimethyl)silyl] oxy}-4-hydroxy-5,5-dimethylnona-1,7-dien-1-yl] cyclopropyl}buta-1,3-dien-1-yl]-1,3-oxazol-4-yl}carbonyl)oxy]-2-methoxy-11,11-dimethylpentadeca-3,5,7,13-tetraen-1-yl}-1,3-oxazole-4-carboxylate (61)

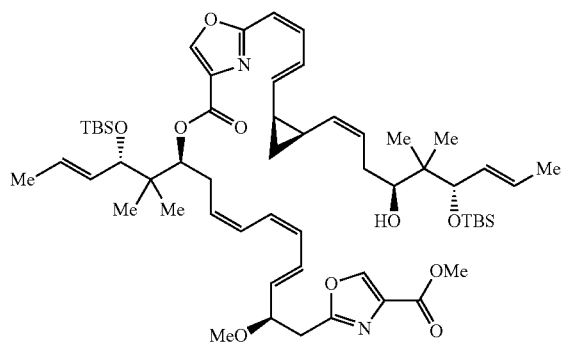

To a stirred solution of vinyl bromide 60 (0.12 g, 0.16 mmol, 1.0 equiv) and vinyl stannane 40 (0.14 g, 0.21 mmol, 1.3 equiv) in DMF (1.6 mL) purged with Ar was added CuI (0.13 g, 0.65 mmol, 4.0 equiv), AsPh₃ (0.10 g, 0.33 mmol, 2.0 equiv) and Pd₂(dba)₃ (75 mg, 0.082 mmol, 0.50 equiv). The resulting mixture was stirred at 23° C. for 3 h and the reaction mixture was filtered through Celite®, diluted with EtOAc (15 mL) and washed three times with brine (3×10 mL). The organic phase was dried over MgSO₄, filtered and concentrated under reduced pressure. The crude residue was purified by flash column chromatography (SiO₂, hexanes: EtOAc 4:1→3:1→7:3). The purified residue was dissolved in CH₂Cl₂ (10 mL) and washed with a solution of 1 N aqueous HCl (10 mL), saturated aqueous NaHCO₃ (10 mL). The organic layer was dried over MgSO₄ and concentrated under reduced pressure before the residue was purified once again by flash column chromatography (SiO₂, hexanes: EtOAc 3:1→7:3) to give hetero-dimer 61 (60 mg, 59 mmol, 36%) as a clear oil. 61: $R_f$=0.40 (hexanes:EtOAc, 13:7); $[\alpha]_D^{25}$=−23.6 (c=1.0, CHCl₃); IR (film): $v_{max}$=3481, 2955, 2856, 1740, 1463, 1321, 1252, 1113 cm⁻¹; ¹H NMR (600 MHz, CDCl₃) δ ¹H NMR (600 MHz, CDCl₃) δ 8.14 (s, 1H), 8.05 (s, 1H), 7.49 (dd, J=15.0, 11.5 Hz, 1H), 6.61 (dd, J=15.1, 11.3 Hz, 1H), 6.44 (t, J=11.7 Hz, 1H), 6.40 (t, J=11.5 Hz, 1H), 6.25 (t, J=11.3 Hz, 1H), 5.99 (d, J=11.8 Hz, 1H), 5.95 (d, J=11.1 Hz, 1H), 5.81 (dd, J=14.9, 9.4 Hz, 1H), 5.70 (dt, J=11.0, 7.1 Hz, 1H), 5.61-5.45 (m, 7H), 5.26-5.19 (m, 3H), 4.19 (s, 1H), 4.17-4.13 (m, 1H), 3.90 (d, J=6.7 Hz, 4H), 3.86 (t, J=6.8 Hz, 3H), 3.70 (dd, J=10.3, 2.6 Hz, 1H), 3.23 (s, 4H), 3.08 (dd, J=14.9, 7.8 Hz, 1H), 2.98 (dd, J=15.0, 5.5 Hz, 1H), 2.60 (dt, J=16.9, 9.0 Hz, 1H), 2.56-2.50 (m, 1H), 2.31 (dd, J=14.4, 7.7 Hz, 1H), 2.19-2.11 (m, 1H), 2.01-1.95 (m, 1H), 1.92 (ddd, J=12.1, 8.5, 4.2 Hz, 1H), 1.71 (d, J=4.7 Hz, 4H), 1.70-1.66 (m, 5H), 1.31 (td, J=8.2, 4.8 Hz, 1H), 0.98 (s, 5H), 0.97 (s, 3H), 0.93 (s, 3H), 0.88 (d, J=2.6 Hz, 26H), 0.76 (s, 4H), 0.71 (q, J=5.6 Hz, 1H), 0.06 (s, 4H), 0.01 (s, 4H), −0.01 (s, 3H), −0.05 (s, 3H) ppm.

(2Z,4E,6S,8R,9Z,12S,20R,21E,23Z,25Z,28S)-12,28-Bis[(3S,4E)-3-{[tert-butyl(dimethyl)silyl]oxy}-2-methylhex-4-en-2-yl]-20-methoxy-13,17,29,33-tetraoxa-34,35-diazatetracyclo[29.2.1.1¹⁵,¹⁸.0⁶,⁸]-pentatriaconta-1 (34),2,4,9,15,18 (35),21,23,25,31-decaene-14,30-dione (62)

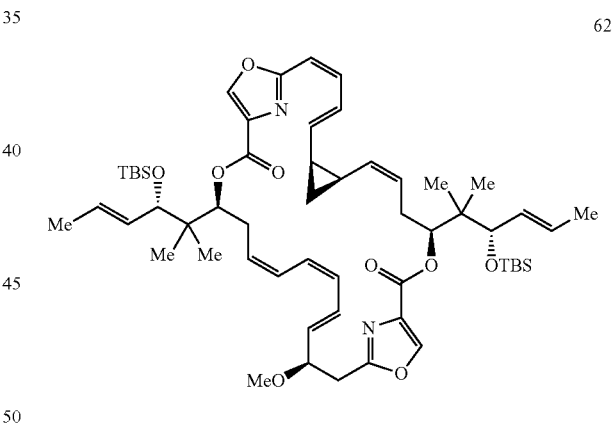

To a stirred solution of ester 61 (0.060 g, 0.059 mmol, 1.0 equiv) in THF (1.2 mL) cooled to 0° C. was added dropwise a saturated aqueous solution of barium hydroxide octohydrate [0.56 mL, MeOH:H₂O 3:2 (v/v)]. The reaction mixture was allowed to warm to 23° C. and stirred until all starting material was consumed by TLC (about 3 h). The reaction was quenched by the addition of a 1N HCl solution (3 mL) and the aqueous phase was extracted six times with EtOAc (6×10 mL). The combined organic extracts were dried over MgSO₄, filtered and concentrated under reduced pressure. The crude oil was used in the next reaction without any further purification.

To a solution of the crude carboxylic acid, stirred in toluene (2.4 mL), was added a solution of 2,4,6-trichlorobenzoyl chloride (64; 0.092 mL, 0.59 mmol, 10 equiv) in toluene (1.0 mL) and a solution of Et₃N (0.090 mL, 0.65 mmol, 11 equiv) in toluene (1.0 mL). The mixture was stirred 1 h at 23° C. and it was diluted to a concentration of 0.0075 M by the addition of toluene (4.4 mL). The latter reaction mixture was added over 5 h, via a syringe pump, to a solution of DMAP (0.029 g, 0.24 mmol, 4.0 equiv) in toluene (11 mL) heated at 40° C. After the addition was completed, stirring was continued for 24 h before the reaction was quenched by the addition of a saturated aqueous solution of NaHCO$_3$ (15 mL). The aqueous phase was extracted six times with EtOAc (6×10 mL). The combined organic extracts were dried over MgSO$_4$, filtered and concentrated under reduced pressure. The crude residue was purified by flash column chromatography (SiO$_2$, hexanes:EtOAc 3:1→7:3→13:7) to give bis-TBS protected cp-disorazole A$_1$ 62 (0.016 g, 0.016 mmol, 28% yield over two steps) as a colorless oil. 62: R$_f$=0.33 (hexanes:EtOAc, 13:7); IR (film): $v_{max}$=2957, 2928, 1740, 1716, 1464, 1142, 1114, 835 cm$^{-1}$; $^1$H NMR (600 MHz, CDCl$_3$) δ 7.97 (s, 1H), 7.89 (s, 1H), 6.96 (dd, J=14.9, 11.7 Hz, 1H), 6.42-6.35 (m, 2H), 6.25 (t, J=11.0 Hz, 1H), 6.15 (t, J=11.8 Hz, 1H), 5.97-5.94 (m, 2H), 5.69 (dd, J=15.2, 8.9 Hz, 1H), 5.59-5.42 (m, 6H), 5.39 (td, J=11.0, 4.9 Hz, 1H), 5.19 (dd, J=11.3, 2.6 Hz, 2H), 5.03 (t, J=10.7 Hz, 1H), 3.83 (ddt, J=18.9, 6.4, 3.9 Hz, 3H), 3.18 (s, 3H), 2.76 (q, J=11.9 Hz, 1H), 2.68 (q, J=11.5 Hz, 1H), 2.59 (dd, J=14.9, 3.8 Hz, 1H), 2.30-2.20 (m, 3H), 2.09 (p, J=8.0 Hz, 1H), 1.83-1.75 (m, 1H), 1.68 (t, J=5.9 Hz, 6H), 0.98 (s, 3H), 0.97 (s, 3H), 0.94 (s, 3H), 0.93 (s, 3H), 0.87 (s, 9H), 0.87 (s, 9H), 0.76-0.69 (m, 1H) 0.55 (q, J=5.6 Hz, 1H), −0.00 (m, 6H), −0.05 (m, 6H) ppm.

(2Z,4E,6S,8R,9Z,12S,20R,21E,23Z,25Z,28S)-12,28-Bis[(3S,4E)-3-hydroxy-2-methylhex-4-en-2-yl]-20-methoxy-13,17,29,33-tetraoxa-34,35-diazatetracyclo [29.2.1.1$^{15,18}$.0$^{6,8}$]pentatriaconta-1 (34),2,4,9,15,18 (35),21,23,25,31-decaene-14,30-dione (5)

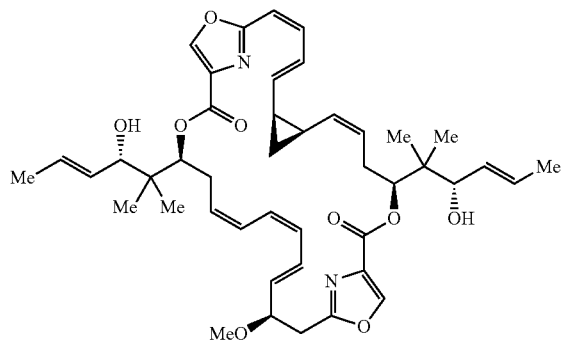

To a stirred solution of bis silyl ether 62 (10 mg, 10 µmol) in MeOH (2 mL), in an argon purged plastic Falcon™ tube, was added hexafluorosilicic acid (0.24 mL, 0.66 mmol, 33-35% in water, 65 equiv) dropwise at 23° C. and the tube was covered with aluminium foil. The resulting mixture was cooled to 4° C. and stirred for five consecutive days at the same temperature and one day at 23° C. At this point, no starting material and a minute amount of mono-deprotected intermediates could be observed by TLC. The reaction mixture was diluted with EtOAc (50 mL), followed by the addition of a saturated aqueous solution of NaHCO$_3$ (10 mL). The phases were separated and the organic phase was washed with two portions of saturated aqueous solution of NaHCO$_3$ (2×10 mL). The combined organic extracts were dried over MgSO$_4$, filtered and concentrated under reduced pressure. The crude residue was purified by flash column chromatography (SiO$_2$, hexanes:EtOAc 7:3→1:1→0:1) to yield cp-disorazole A$_1$ (5) (3.5 mg, 4.6 µmol, 45% yield). 5: R$_f$=0.13 (hexanes:EtOAc 2:3); [α]$_D^{25}$=−65.7 (c=0.14, CHCl$_3$); IR (film): $v_{max}$=3429, 2967, 2937, 1734, 1628, 1555, 1388, 1317, 1142, 1109 cm$^{-1}$; 1H NMR (600 MHz, CD$_3$OD) δ 8.37 (s, 1H), 8.28 (s, 1H), 7.02 (dd, J=14.8, 11.7 Hz, 1H), 6.52-6.44 (m, 2H), 6.36 (dd, J=11.0, 11.0 Hz, 1H), 6.30 (dd, J=11.8, 11.8 Hz, 1H), 5.99 (dd, J=11.1, 11.1 Hz, 1H), 5.89 (d, J=11.8 Hz, 1H), 5.73 (dd, J=15.1, 9.2 Hz, 1H), 5.69-5.62 (m, 3H), 5.61-5.51 (m, 2H), 5.36 (ddd, J=11.1, 11.1, 4.8 Hz, 1H), 5.30 (dd, J=11.6, 2.9 Hz, 1H), 5.29 (dd, J=11.7, 2.9 Hz, 1H), 5.15 (dd, J=10.9, 10.9 Hz, 1H), 3.96 (ddd, J=8.9, 5.3, 3.4 Hz, 1H), 3.84 (d, J=7.8 Hz, 2H), 3.21 (dd, J=14.9, 5.4 Hz, 1H), 3.16 (s, 3H), 2.88-2.74 (m, 2H), 2.56 (dd, J=14.8, 3.5 Hz, 1H), 2.35-2.29 (m, 1H), 2.28-2.23 (m, 1H), 2.23-2.17 (m, 1H), 2.21 (ddd, J=15.8, 10.8, 8.2 Hz, 1H), 1.73-1.67 (m, 6H), 1.33 (td, J=8.3, 4.4 Hz, 1H), 1.03 (s, 3H), 1.02 (s, 3H), 0.98 (s, 3H), 0.97 (s, 3H), 0.58 (dd, J=5.5, 5.5 Hz, 1H) ppm; $^{13}$C NMR (151 MHz, CD$_3$OD) δ 163.91, 163.82, 162.18, 162.00, 146.13, 145.87, 145.65, 138.90, 134.56, 134.07, 133.72, 132.80, 131.73 (2C), 130.99, 129.68, 129.55, 129.53, 129.43, 128.08, 127.29, 127.14, 126.99, 109.50, 80.16, 78.39, 78.22, 77.90 (2C), 56.63, 42.68, 42.60, 36.02, 29.24, 29.21, 24.51, 20.19, 19.46, 19.43, 19.40, 19.35, 18.03 (2C), 17.74 ppm; HR-MS (ESI-TOF): calcd for C$_{44}$H$_{56}$N$_2$O$_9$Na [M+Na]$^+$: 779.3878. Found: 779.3882.

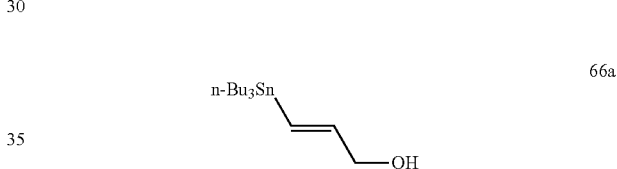

66a (2E)-3-(Tributylstannyl)prop-2-en-1-ol (66a): To a stirred mixture of propargyl alcohol (1.77 mL, 29.7 mmol, 1.0 equiv) and tributyltin hydride (10.4 mL, 38.6 mmol, 1.3 equiv) was added AIBN (0.390 g, 2.374 mmol, 0.08 equiv) at 23° C. The reaction mixture was put in an oil bath at 50° C. and heated to 80° C. over 10 min. The latter was stirred at 80° C. for 2.5 h and allowed to cool to 23° C. before directly purify the mixture by flash column chromatography (SiO$_2$, hexanes:EtOAc, 19:1) to yield alcohol 66a (5.05 g, 14.6 mmol, 49% yield) as a colorless oil. 66a: R$_f$=0.10 (hexanes:EtOAc, 19:1); IR (film): $v_{max}$=3295, 2922, 1463, 1070, 990 cm$^{-1}$; $^1$H NMR (600 MHz, CDCl$_3$) δ 6.22 (dt, J=19.1, 1.1 Hz, 1H), 6.16 (dt, J=19.1, 4.0 Hz, 1H), 4.18 (ddd, J=6.0, 4.0, 1.1 Hz, 2H), 1.53-1.47 (m, 6H), 1.37 (t, J=6.1 Hz, 1H), 1.31 (h, J=7.3 Hz, 6H), 0.92-0.87 (m, 15H) ppm; $^{13}$C NMR (151 MHz, CDCl$_3$) δ 147.18, 128.52, 66.57, 29.22, 27.43, 13.84, 9.59 ppm.

66

(2E)-3-(Tributylstannyl)acrylaldehyde (66): To a stirred solution of allylic alcohol 66a (1.23 g, 3.54 mmol, 1.0 equiv) and sodium bicarbonate (0.357 g, 4.25 mmol, 1.2 equiv) in CH$_2$C2 (18 mL), was added Dess-Martin periodinane (1.80 g, 4.25 mmol, 1.2 equiv) in one portion. The reaction was followed by TLC and showed full conversion after 1 h. The reaction was quenched by adding a 1:1 (v/v) mixture of saturated aqueous solution of NaHCO$_3$:saturated aqueous solution of Na$_2$S$_2$O$_3$ (30 mL). The resulting heterogeneous mixture was vigorously stirred for 30 min before the phases were separated. The aqueous phase was extracted three times with CH$_2$Cl$_2$ (3×30 mL) and the combined organic extracts were dried over MgSO$_4$, filtered and concentrated under reduced pressure. The crude residue was purified by flash column chromatography (SiO$_2$, hexanes:EtOAc, 19:1) to yield aldehyde 66 (1.05 g, 3.04 mmol, 86% yield) as a colorless oil. 66: R$_f$=0.75 (hexanes:EtOAc, 9:1); IR (film): v$_{max}$=2956, 2922, 1688, 1463, 1190, 1071, 665 cm$^{-1}$; $^1$H NMR (600 M Hz, CDCl$_3$) δ 9.42 (d, J=7.5 Hz, 1H), 7.79 (d, J=19.2 Hz, 1H), 6.63 (dd, J=19.2, 7.6 Hz, 1H), 1.56-1.48 (m, 6H), 1.32 (h, J=7.3 Hz, 6H), 1.06-0.99 (m, 6H), 0.90 (t, J=7.3 Hz, 9H) ppm; $^{13}$C NMR (151 M Hz, CDCl$_3$) δ 193.87, 163.44, 147.78, 29.11, 27.36, 13.78, 9.98 ppm; HR-MS (ESI-TOF): calcd for C$_{15}$H$_{31}$OSn$^+$ [M+H]$^+$: 347.1394. Found: 347.1383.

10 min. The reaction was quenched following the Fieser method: the mixture was cooled to 0° C. and water (1.04 mL) was added dropwise, after which the ice bath was removed and a 15% aqueous solution of NaOH (1.04 mL) was added dropwise followed by water (2.6 mL). The resulting mixture was stirred for 30 min and then filtered through a Celite pad. The filtrate was concentrated under reduced pressure and the crude residue was purified by flash column chromatography (SiO$_2$, hexanes:EtOAc, 9:1→4:1) to yield alcohol 69 (3.58 g, 9.56 mmol, 92% yield) as a colorless oil. 69: R$_f$=0.31 (hexanes:EtOAc, 17:3); IR (film): v$_{max}$=3293, 2922, 1604, 1463, 1070, 990 cm$^{-1}$; $^1$H NMR (600 M Hz, CDCl$_3$) δ 6.80 (ddd, J=18.5, 10.6, 1.2 Hz, 1H), 6.34 (d, J=18.5 Hz, 1H), 6.07 (ap. tq, J=10.7, 1.3 Hz, 1H), 5.54 (ap. dt, J=10.9, 7.0 Hz, 1H), 4.37 (ddd, J=7.0, 5.6, 1.5 Hz, 2H), 1.53-1.48 (m, 6H), 1.31 (m, 6H), 0.90 (m, 15H) ppm; $^{13}$C NMR (151 M Hz, CDCl$_3$) δ 141.09, 137.80, 134.00, 128.15, 59.11, 29.24, 27.41, 13.84, 9.70 ppm; HR-MS (ESI-TOF): calcd for C$_{17}$H$_{34}$OSn$^+$ [M+Na]$^+$: 397.1527. Found: 397.1531.

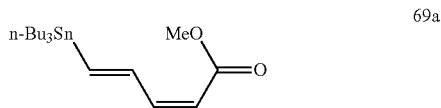

69a

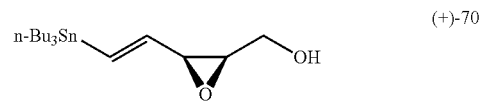

(+)-70

Methyl (2Z,4E)-5-(tributylstannyl)penta-2,4-dienoate (69a): To a stirred solution of 18-crown-6 (13.1 g, 49.6 mmol, 4.0 equiv) and methyl 2-(bis(2,2,2-trifluoroethoxy)phosphoryl)acetate (67, 3.41 mL, 16.12 mmol, 1.3 equiv) in THF (62 mL) cooled to −78° C. was added KHMDS (0.5 M in toluene, 29.6 mL, 14.8 mmol, 1.2 equiv) and the solution was stirred for 5 min at −78° C. before the introduction of aldehyde 66 (4.28 g, 12.4 mmol, 1.0 equiv) in THF (5 mL). The resulting mixture was stirred 30 min at −78° C. and quenched with an aqueous saturated solution of NH$_4$Cl. The aqueous phase was extracted three times with EtOAc (3×40 mL) and the combined organic extracts were dried over MgSO$_4$, filtered and concentrated under reduced pressure. The crude residue was purified by flash column chromatography (SiO$_2$, hexanes:EtOAc, 19:1→9:1) to yield 69a (4.59 g, 11.4 mmol, 92% yield) as a pale yellow oil. 69a: R$_f$=0.31 (hexanes:EtOAc, 19:1); IR (film): v$_{max}$=2956, 2852, 1689, 1463, 1071, 990 cm$^{-1}$; $^1$H NMR (600 MHz, CDCl$_3$) δ 7.82 (ddd, J=18.8, 10.7, 1.1 Hz, 1H), 6.76 (dd, J=18.8, 1.0 Hz, 1H), 6.51 (dd, J=11.0, 11.0 Hz, 1H), 5.59 (dt, J=11.4, 1.0 Hz, 1H), 3.74 (s, 3H), 1.55-1.48 (m, 6H), 1.32 (h, J=7.3 Hz, 6H), 0.98-0.94 (m, 6H), 0.89 (t, J=7.3 Hz, 9H) ppm; $^{13}$C NMR (151 MHz, CDCl$_3$) δ 166.85, 148.49, 147.05, 142.61, 115.51, 51.31, 29.21, 27.40, 13.83, 9.83 ppm; HR-MS (ESI-TOF): calcd for C$_{18}$H$_{35}$SO$_2$Sn$^+$ [M+H]$^+$: 403.1657. Found: 403.1649.

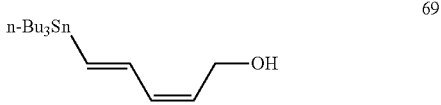

69

(2Z,4E)-5-(Tributylstannyl)penta-2,4-dien-1-ol (69): To a stirred solution of methyl ester 69a (4.59 g, 11.4 mmol, 1.0 equiv) in Et$_2$O (440 mL) cooled to −78° C., was added a solution of DIBAL-H (21.1 mL, 1 M in hexanes, 26.0 mmol, 2.5 equiv) dropwise and the reaction mixture was stirred at −78° C. for 1 h and was then allowed to warm to 23° C. over

[(2R,3S)-3-[(E)-2-(Tributylstannyl)ethenyl]oxiran-2-yl]methanol [(+)-70]: A round bottom flask equipped with a stir bar was charged with pre-dried 4Å molecular sieves and flame dried two times under reduce pressure. The round bottom flask was allowed to cool to room temperature and it was cooled to −20° C. CH$_2$Cl$_2$ (7.0 mL) was added and then Ti(Oi-Pr)$_4$ (0.393 mL, 1.34 mmol, 1.0 equiv) and (−)-DET (0.321 mL, 1.876 mmol, 1.4 equiv) were added in this order and stirred at −20° C. for 10 min. TBHP (5.5 M in decane, 0.731 mL, 4.02 mmol, 3.0 equiv) was added and the reaction mixture was stirred for another 30 min before alcohol 69 (500 mg, 1.34 mmol, 1.0 equiv) in CH$_2$Cl$_2$ (2 mL) was added dropwise to the reaction mixture. The resulting reaction mixture was capped with a plastic top and stored in a −20° C. freezer for 16 h. The reaction was then filtered through a Celite pad and the pad was washed with CH$_2$Cl$_2$ (3×10 mL) three times. A saturated aqueous solution of Na$_2$SO$_4$ (20 mL) was added and the heterogenous mixture was stirred at 23° C. for 30 min. The aqueous phase was extracted three times with EtOAc (3×20 mL) and the combined organic extracts were dried over MgSO$_4$, filtered and concentrated under reduced pressure. The crude residue was purified by flash column chromatography (SiO$_2$, hexanes:EtOAc, 9:1→4:1) to yield 70 (318 mg, 817 μmol, 61% yield, 43% ee) as a colorless oil.

To improve the enantiomeric excess glycidol 70 was kinetically resolved with a lipase. To a stirred solution of glycidol 70 (266 mg, 684 μmol, 1.0 equiv) and vinyl acetate (126 μl, 1.36 mmol, 2.0 equiv) in CH$_2$Cl$_2$ (7 mL), was added Amano lipase PS from *Burkholderia cepacian* (0.266 g, ≥30000 U/g; purchased from Sigma-Aldrich) (Lipase from *Pseudomonas cepacian* was also suitable for the enantioenrichment of glycidol 70) and the resulting mixture was stirred at 23° C. for 48 h. The resulting mixture was concentrated under reduce pressure and the crude residue was purified by flash column chromatography (SiO$_2$, hexanes:EtOAc, 9:1→4:1) to yield glycidol (+)-70 (190 mg, 697 μmol, 71% yield, >95% ee) as a colorless oil and acetate (−)-70 (72.5 mg, 168 μmol, 25% yield) as a pale yellow oil.

Enantiomeric ratio was determined by HPLC (ChiralPak IA, 25° C., flow rate: 1 mL/min, hexanes/i-PrOH: 97:3, 230 nm): 6.27 min for (+)-70; 6.67 min for (−)-70. (+)-70: $R_f$=0.45 (hexanes:EtOAc, 4:1); $[\alpha]_D^{25}$=+33.2 (c=1.0, CHCl$_3$); IR (film): $\nu_{max}$=3424, 2923, 1463, 1041, 985 cm$^{-1}$; $^1$H NMR (600 M Hz, CDCl$_3$) δ 6.55 (d, J=19.1 Hz, 1H), 5.86 (dd, J=19.2, 6.9 Hz, 1H), 3.84 (ddd, J=11.7, 7.3, 4.1 Hz, 1H), 3.71 (ddd, J=12.2, 6.8, 5.2 Hz, 1H), 3.53 (dd, J=6.9, 4.4 Hz, 1H), 3.31 (ap. dt, J=6.9, 4.2 Hz, 1H), 1.61 (dd, J=7.3, 5.3 Hz, 1H), 1.52-1.45 (m, 6H), 1.30 (h, J=7.3 Hz, 6H), 0.92-0.88 (m, 15H) ppm; $^{13}$C NMR (151 MHz, CDCl$_3$) δ 140.96, 137.66, 61.12, 59.19, 58.70, 29.18, 27.37, 13.83, 9.70 ppm; HR-MS (ESI-TOF): calcd for C$_{19}$H$_{38}$O$_2$Sn$^+$ [M+H]$^+$: 432.1922. Found: 432.1922.

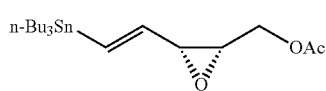

(−)-70

[(2S,3R)-3-[(E)-2-(Tributylstannyl)ethenyl]oxiran-2-yl] methyl acetate [(−)-70]: (−)-70: $R_f$=0.81 (hexanes:EtOAc, 4:1); $[\alpha]_D^{25}$=−23.7 (c=1.0, CHCl$_3$); IR (film): $\nu_{max}$=2924, 1744, 1375, 1227, 1038 cm$^{-1}$; $^1$H NMR (600 MHz, CDCl$_3$) δ 6.57 (dd, J=19.2, 0.9 Hz, 1H), 5.83 (dd, J=19.2, 6.7 Hz, 1H), 4.34 (dd, J=12.2, 3.8 Hz, 1H), 4.04 (dd, J=12.2, 7.3 Hz, 1H), 3.52 (ddd, J=6.5, 4.4, 0.9 Hz, 1H), 3.33 (dt, J=7.2, 4.1 Hz, 1H), 2.11 (s, 3H), 1.52-1.45 (m, 6H), 1.30 (h, J=7.3 Hz, 6H), 0.94-0.84 (m, 15H) ppm; $^{13}$C NMR (151 MHz, CDCl$_3$) δ 170.94, 140.33, 138.06, 63.00, 58.39, 55.75, 29.17, 27.37, 20.94, 13.82, 9.70 ppm; HR-MS (ESI-TOF): calcd for C$_{19}$H$_{36}$O$_3$SnNa$^+$ [M+Na]$^+$: 455.1582. Found: 455.1573.

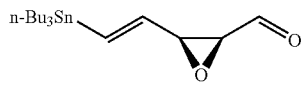

(2S,3S)-3-[(E)-2-(Tributylstannyl)ethenyl]oxirane-2-carbaldehyde [(−)-71]: To a stirred solution of alcohol (+)-70 (345 mg, 887 μmol, 1.0 equiv) in CH$_2$Cl$_2$ (5.00 mL), was added NaHCO$_3$ (97 mg, 1.15 mmol, 1.3 equiv) and Dess-Martin periodinane (0.489 g, 1.15 mmol, 1.3 equiv) in one portion. The reaction was followed by TLC and showed full conversion after 1 h. The reaction was quenched by adding a 1:1 (v/v) mixture of saturated aqueous solution of NaHCO$_3$:saturated aqueous solution of Na$_2$S$_2$O$_3$ (20 mL). The resulting heterogenous mixture was vigorously stirred for 30 min before the phases were separated. The aqueous phase was extracted three times with CH$_2$Cl$_2$ (3×20 mL) and the combined organic extracts were dried over MgSO$_4$, filtered and concentrated under reduced pressure. The crude residue was purified by flash column chromatography (SiO$_2$, hexanes:EtOAc, 19:1→9:1) to yield (−)-71 (276 mg, 715 μmol, 81% yield) as a colorless oil. (−)-71: $R_f$=0.58 (hexanes:EtOAc, 9:1); $[\alpha]_D^{25}$=−70.3 (c=1.0, CHCl$_3$); IR (film): $\nu_{max}$=2923, 1726, 1463, 983 cm$^{-1}$; $^1$H NMR (600 MHz, CDCl$_3$) δ 9.44 (d, J=5.6 Hz, 1H), 6.74 (d, J=19.1 Hz, 1H), 5.92 (dd, J=19.2, 7.4 Hz, 1H), 3.74 (dd, J=7.3, 4.7 Hz, 1H), 3.48 (dd, J=5.6, 4.7 Hz, 1H), 1.52-1.43 (m, 6H), 1.30 (h, J=7.3 Hz, 6H), 0.93-0.87 (m, 15H) ppm; $^{13}$C NMR (151 MHz, CDCl$_3$) δ 198.86, 140.55, 138.85, 60.81, 59.82, 29.14, 27.36, 13.80, 9.74 ppm; HR-MS (ESI-TOF): calcd for C$_{17}$H$_{33}$O$_2$Sn$^+$ [M+H]$^+$: 389.1500. Found: 389.1507.

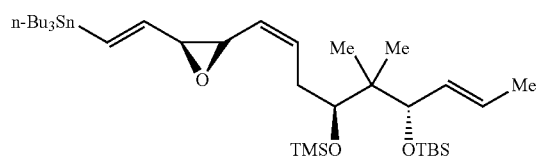

73

(4S,6S)-2,2,5,5,8,8,9,9-Octamethyl-6-[(1E)-prop-1-en-1-yl]-4-[(2Z)-3-{(2R,3S)-3-[(E)-2-(tri- butylstannyl)vinyl]oxiran-2-yl}prop-2-en-1-yl]-3,7-dioxa-2,8-disiladecane (73): To a stirred solution of iodide 5 (359 mg, 740 μmol, 1.05 equiv) in i-Pr$_2$EtN (860 μL, 4.94 mmol, 7.0 equiv) was added PPh$_3$ (324 mg, 1.23 mmol, 1.75 equiv). The reaction vessel was capped and heated at 90° C. for 16 h. Subsequently, the mixture was allowed to cool to 23° C. and pentane (20 mL) was added resulting in a thick paste-like material that was carefully separated from the cloudy pentane solution. The paste was washed three times with pentane (3×20 mL). Then, the paste was dissolved in THF (7.05 mL) and the stirred solution was cooled to −78° C. Next, LiHMDS (0.740 mL, 1 M in THF, 0.740 mmol, 1.05 equiv) was added and the reaction mixture was stirred for 15 min before DMPU (51 μL, 423 μmol, 0.60 equiv) was added, followed by the addition of a solution of aldehyde (−)-71 (0.273 g, 0.705 mmol, 1.0 equiv) in THF (2 mL). The reaction mixture was stirred at −78° C. for 15 min and was subsequently allowed to warm to 23° C. over 1 h. Then, the reaction was quenched by the addition of a saturated aqueous solution of NaHCO$_3$ (20 mL) and the aqueous phase was extracted three times with Et$_2$O (3×20 mL). The combined organic extracts were dried over MgSO$_4$, filtered and concentrated under reduced pressure. The crude residue was purified by flash column chromatography (SiO$_2$, hexanes:benzene 7:3) to yield epoxide compound 73 (408 mg, 561 μmol, 76% yield) in an inseparable mixture with residual PPh$_3$ as a colorless oil although a small pure sample was obtained for characterization purpose. 73: $R_f$=0.59 (hexanes:EtOAc, 19:1); $[\alpha]_D^{25}$=−58.0 (c=1.0, CHCl$_3$); IR (film): $\nu_{max}$=2956, 1464, 1249, 1052, 837 cm$^{-1}$; $^1$H NMR (600 MHz, CDCl$_3$) δ 6.52 (d, J=19.1 Hz, 1H), 5.86 (dd, J=19.2, 7.0 Hz, 1H), 5.82-5.75 (m, 1H), 5.49 (dq, J=15.4, 6.2 Hz, 1H), 5.42 (ddd, J=15.4, 8.5, 1.5 Hz, 1H), 5.32 (dd, J=11.0, 9.1 Hz, 1H), 3.87 (d, J=8.4 Hz, 1H), 3.77 (ddd, J=9.0, 4.3, 1.0 Hz, 1H), 3.61-3.55 (m, 2H), 2.36 (ddt, J=14.7, 6.6, 2.5 Hz, 1H), 2.34-2.28 (m, 1H), 1.69 (dd, J=6.1, 1.4 Hz, 3H), 1.52-1.46 (m, 6H), 1.30 (h, J=7.3 Hz, 6H), 0.92-0.87 (m, 24H), 0.84 (s, 3H), 0.80 (s, 3H), 0.06 (s, 9H), 0.01 (s, 3H), −0.03 (s, 3H) ppm; $^{13}$C NMR (151 MHz, CDCl$_3$) δ 142.11, 136.79, 136.64, 131.78, 127.89, 124.76, 78.95, 76.16, 60.86, 54.93, 43.84, 31.19, 29.19, 27.40, 26.13, 20.16, 19.55, 18.39, 17.83, 13.84, 9.68, 1.22, −3.15, −4.50 ppm; HR-MS (ESI-TOF): calcd for C$_{36}$H$_{72}$O$_3$Si$_2$SnNa$^+$ [M+Na]$^+$: 751.3941. Found: 751.3967.

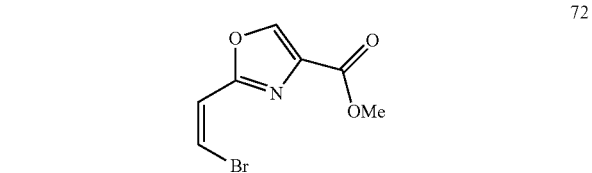 [SMILES: COC(=O)c1coc(/C=C\Br)n1]

72

Methyl 2-[(Z)-2-bromovinyl]-1,3-oxazole-4-carboxylate (72): Bromide 72 was prepared according to a literature procedure (Wipf and Graham, 2005) 72: $R_f$=0.32 (hexanes: EtOAc, 7:3); IR (film): $v_{max}$=3166, 3026, 2936, 1742, 1332, 1143, 758 cm$^{-1}$; $^1$H NMR (600 M Hz, CDCl$_3$) δ 8.29 (s, 1H), 7.17 (d, J=8.7 Hz, 1H), 6.91 (d, J=8.7 Hz, 1H), 3.94 (s, 3H) ppm; $^{13}$C NMR (151 MHz, CDCl$_3$) δ 161.52, 159.48, 143.71, 134.33, 119.68, 115.38, 52.46 ppm; HR-MS (ESI): calcd for C$_7$H6BrNO$_3$Na$^+$ [M+Na]$^+$: 253.9423. Found: 253.9416.

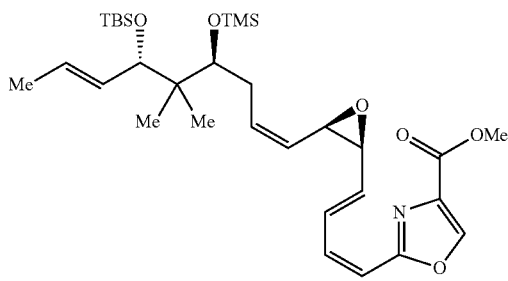

Methyl 2-[(1Z,3E)-4-(3-{(1Z,4S,6S,7E)-6-{[tert-butyl (dimethyl)silyl]oxy}-5,5-dimethyl-4-[(trimethyl- silyl)oxy] nona-1,7-dien-1-yl}oxiran-2-yl)buta-1,3-dien-1-yl]-1,3-oxazole-4-carboxylate (74): To a stirred and degassed solution of vinyl stannane 73 (942 mg, 1.29 mmol, 1.0 equiv) and oxazole 72 (0.300 mg, 1.29 mmol, 1.0 equiv) in NMP (6.5 mL) at 23° C., was added CuTc (370 mg, 1.94 mmol, 1.5 equiv). The resulting mixture was stirred for 1 h at 23° C. and was then directly purified by flash column chromatography (SiO$_2$, hexanes:EtOAc 9:1→4:1) to yield alcohol compound epoxide 74 (563 mg, 0.954 mmol, 74% yield) as a pale yellow oil. 74: $R_f$=0.64 (hexanes:EtOAc, 3:1); [α]$_D^{25}$=+8.2 (c=1.0, CHCl$_3$); IR (film): $v_{max}$=2956, 2929, 2856, 1751, 1731, 1249, 1049, 834 cm$^{-1}$; $^1$H NMR (600 M Hz, CDCl$_3$) δ 8.22 (s, 1H), 7.68 (dd, J=15.4, 11.6 Hz, 1H), 6.54 (t, J=11.7 Hz, 1H), 6.21 (d, J=11.7 Hz, 1H), 5.90 (dd, J=15.3, 7.9 Hz, 1H), 5.82 (dt, J=11.2, 7.6 Hz, 1H), 5.50 (dq, J=15.4, 6.2 Hz, 1H), 5.42 (ddd, J=15.3, 8.4, 1.5 Hz, 1H), 5.32 (ddt, J=10.4, 8.6, 1.6 Hz, 1H), 3.93 (s, 3H), 3.88-3.85 (m, 2H), 3.77 (dd, J=7.9, 4.4 Hz, 1H), 3.60 (dd, J=9.1, 2.8 Hz, 1H), 2.39 (ddt, J=14.7, 6.7, 2.4 Hz, 1H), 2.33-2.25 (m, 1H), 1.69 (dd, J=6.2, 1.4 Hz, 3H), 0.88 (s, 9H), 0.84 (s, 3H), 0.80 (s, 3H), 0.06 (s, 9H), 0.01 (s, 3H), −0.03 (s, 3H) ppm; $^{13}$C NMR (151 MHz, CDCl$_3$) δ 161.78, 161.75, 143.48, 137.53, 136.31, 136.17, 134.36, 131.79, 131.67, 127.92, 124.11, 113.28, 78.98, 76.17, 58.22, 55.61, 52.37, 43.84, 31.25, 26.13, 20.21, 19.59, 18.38, 17.84, 1.20, −3.15, −4.50 ppm; HR-MS (ESI-TOF): calcd for C$_{31}$H$_{51}$NO$_6$Si$_2$Na$^+$ [M+Na]$^+$: 612.3147. Found: 612.3137.

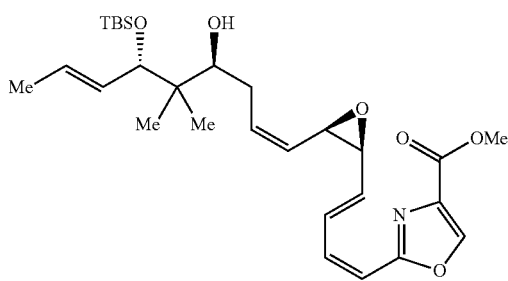

Methyl 2-[(1Z,3E)-4-{3-[(1Z,4S,6S,7E)-6-{[tert-butyl (dimethyl)silyl]oxy}-4-hydroxy-5,5-dimethyl-nona-1,7-dien-1-yl]oxiran-2-yl}buta-1,3-dien-1-yl]-1,3-oxazole-4-carboxylate (75): To a stirred solution of bis-silane 74 (0.150 g, 0.254 mmol, 1.0 equiv) in THF (1.25 mL) in a glass round bottom flask at 23° C. was added Et$_3$N·3HF (0.124 mL, 0.763 mmol, 3.0 equiv) and the solution was stirred for 1 h before all starting material was consumed by TLC. The crude was purified directly by flash column chromatography (SiO$_2$, hexanes:EtOAc 17:3→13:7) to yield alcohol 75 (100 mg, 192 μmol, 76% yield) as a pale yellow thick oil. 75: $R_f$=0.36 (hexanes:EtOAc, 7:3); [α]$_D^{25}$=−7.9 (c=0.19, CHCl$_3$); IR (film): $v_{max}$=3477, 2956, 1748, 1731, 1471, 1322, 1252, 1117, 1004, 836 cm$^{-1}$; $^1$H NMR (600 M Hz, CDCl$_3$) δ 8.22 (s, 1H), 7.67 (dd, J=15.3, 11.6 Hz, 1H), 6.53 (dd, J=11.6, 11.6 Hz, 1H), 6.20 (d, J=11.7 Hz, 1H), 6.01 (ap. dt, J=11.0, 7.2 Hz, 1H), 5.90 (dd, J=15.3, 8.0 Hz, 1H), 5.61-5.51 (m, 2H), 5.40-5.35 (m, 1H), 4.39 (s, 1H), 3.92 (s, 3H), 3.90 (dd, J=8.4, 4.4 Hz, 1H), 3.85 (d, J=7.1 Hz, 1H), 3.76 (dd, J=8.0, 4.4 Hz, 1H), 3.73-2.21 (m, 1H), 2.37-2.29 (m, 1H), 2.29-2.21 (m, 1H), 1.72 (d, J=5.5 Hz, 3H), 0.99 (s, 3H), 0.88 (s, 9H), 0.75 (s, 3H), 0.06 (s, 3H), 0.01 (s, 3H) ppm; $^{13}$C NMR (151 MHz, CDCl$_3$) δ 161.80, 161.77, 143.48, 136.57, 136.41, 136.29, 134.34, 131.66, 130.14, 129.03, 124.16, 113.20, 84.79, 75.94, 58.26, 55.71, 52.36, 40.96, 30.53, 25.98, 22.96, 19.81, 18.14, 17.90, −3.82, −4.98 ppm; HR-MS (ESI-TOF): calcd for C$_{28}$H$_{43}$NO$_6$SiNa$^+$ [M+Na]$^+$: 540.2752. Found: 540.2750.

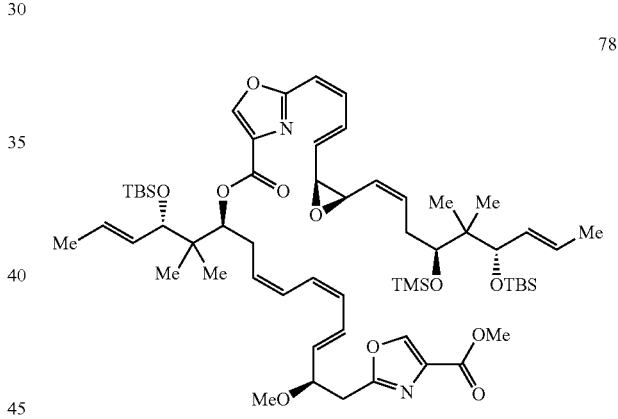

Methyl 2-[(2R,3E,5Z,7Z,10S,12S,13E)-12-{[tert-butyl (dimethyl)silyl]oxy}-10-{[(2-{(1Z,3E)-4-[(2S,3R)-3-{(1Z, 4S,6S,7E)-6-{[tert-butyl(dimethyl)silyl]oxy}-5,5-dimethyl-4-[(trimethylsilyl)oxy]-nona-1,7-dien-1-yl}oxiran-2-yl] buta-1,3-dien-1-yl}-1,3-oxazol-4-yl)carbonyl]oxy}-2-methoxy-11,11-dimethylpentadeca-3,5,7,13-tetraen-1-yl]-1,3-oxazole-4-carboxylate (78): To a stirred solution of epoxide 74 (90 mg, 153 μmol, 1.0 equiv) in DCE (1.5 mL) was added trimethyltin hydroxide (276 mg, 1.53 mmol, 10 equiv) at 23° C. and the reaction mixture was heated at 80° C. for 3 h. The resulting misty solution was cooled to 23° C., concentrated under reduced pressure and resulting residue was dissolved in EtOAc (5 mL) and extracted three times with a aqueous solution of KHSO$_4$ (0.01 N. 3×7 mL). The combined organic extracts were dried over MgSO$_4$, filtered and concentrated under reduced pressure. The crude residue was used in the next step without any further purification.

The crude acid (76) was dissolved in CH$_2$Cl$_2$ and added to a small 5 mL cylindrical vial containing alcohol 77 (41 mg, 76 μmol, 0.50 equiv) and the mixture was concentrated under reduced pressure and dried at high vacuum. The resulting thick paste was dissolved in toluene (0.764 mL) and a stir bar was added followed by the addition of Et$_3$N (64 µl, 458 µmol, 3.0 equiv) at 23° C. The resulting mixture was stirred 5 min and DMAP (75 mg, 611 µmol, 4.0 equiv) was added, followed by a slow dropwise addition of TCBC (36 µl, 229 µmol, 1.5 equiv) at 23° C. The reaction mixture was stirred for about 30 min until the reaction became a thick paste that could not be stirred anymore. At this moment, toluene (1 mL) was added and the mixture was manually shaken with force until the mixture was homogenized. The mixture was stirred further for 1 h and the crude was purified directly by flash column chromatography (SiO$_2$, hexanes:EtOAc 4:1→3:2) to yield hetero-dimer 78 (82 mg, 75 µmol, 99% yield) as a pale yellow thick paste. 78: $R_f$=0.46 (hexanes:EtOAc, 7:3); $[\alpha]_D^{25}$=−21.2 (c=1.0, CHCl$_3$); IR (film): $v_{max}$=2955, 2930, 1744, 1730, 1250, 1113, 836 cm$^{-1}$; $^1$H NMR (600 M Hz, CDCl$_3$) δ 8.14 (s, 1H), 8.08 (s, 1H), 7.76 (dd, J=15.4, 11.5 Hz, 1H), 6.61 (dd, J=15.2, 11.3 Hz, 1H), 6.51 (t, J=11.7 Hz, 1H), 6.40 (t, J=11.4 Hz, 1H), 6.25 (t, J=11.3 Hz, 1H), 6.19 (d, J=11.6 Hz, 1H), 5.95 (t, J=11.1 Hz, 1H), 5.87 (dd, J=15.4, 8.0 Hz, 1H), 5.82 (dt, J=11.4, 7.7 Hz, 1H), 5.60-5.45 (m, 5H), 5.42 (ddd, J=15.4, 8.5, 1.6 Hz, 1H), 5.31 (ddt, J=10.4, 8.6, 1.6 Hz, 1H), 5.22 (dd, J=9.6, 3.4 Hz, 1H), 4.14 (td, J=7.8, 5.5 Hz, 1H), 3.89 (s, 3H), 3.88-3.83 (m, 3H), 3.74 (dd, J=8.0, 4.3 Hz, 1H), 3.59 (dd, J=9.1, 2.7 Hz, 1H), 3.23 (s, 3H), 3.08 (dd, J=15.0, 7.8 Hz, 1H), 2.97 (dd, J=14.9, 5.6 Hz, 1H), 2.60 (dt, J=17.4, 9.0 Hz, 1H), 2.57-2.50 (m, 1H), 2.39 (ddt, J=14.8, 6.9, 2.4 Hz, 1H), 2.29 (dt, J=14.2, 8.6 Hz, 1H), 1.69 (dt, J=6.2, 1.6 Hz, 6H), 0.97 (s, 3H), 0.93 (s, 3H), 0.89-0.85 (m, 18H), 0.84 (s, 3H), 0.80 (s, 3H), 0.06 (s, 9H), 0.01 (s, 3H), −0.02 (s. 3H), −0.03 (s, 3H), −0.05 (s, 3H) ppm; $^{13}$C NMR (151 MHz, CDCl$_3$) δ 162.87, 161.84, 161.54, 160.74, 144.10, 142.84, 137.47, 136.05, 135.86, 134.70, 133.44, 132.68, 131.94, 131.79, 131.30, 130.00, 128.81, 128.55, 128.33, 127.92, 125.47, 125.27, 124.15, 113.37, 79.58, 79.16, 78.96, 78.01, 77.37, 58.25, 56.73, 55.57, 52.23, 43.84, 43.02, 35.01, 31.22, 28.63, 26.13 (3×C), 26.10 (3×C), 20.18 (2×C), 19.58, 19.49, 18.38, 18.33, 17.92, 17.83, 1.20 (3×C), −3.14, −3.37, −4.50, −4.80 ppm; HR-MS (ESI-TOF): calcd for C$_{59}$H$_{94}$N$_2$O$_{11}$Si$_3$Na$^+$ [M+Na]$^+$: 1113.6058. Found: 1113.6071.

mg, 75 µmol, 1.0 equiv) in THF (400 µL) in a glass round bottom flask at 23° C. was added Et$_3$N-3HF (37 µl, 228 µmol, 3.0 equiv) and the solution was stirred for 1 h before all starting material was consumed. The crude was purified directly by flash column chromatography (SiO$_2$, hexanes:EtOAc 4:1→3:2) to yield alcohol 79 (76 mg, 75 µmol, 99% yield) as a pale yellow thick paste. 79: $R_f$=0.52 (hexanes:EtOAc, 3:2); $[\alpha]_D^{25}$=−13.5 (c=1.0, CHCl$_3$); IR (film): $v_{max}$=3478, 2956, 2926, 1740, 1584, 1463, 1253, 1113, 836 cm$^{-1}$; $^1$H NMR (600 MHz, CDCl$_3$) δ 8.14 (s, 1H), 8.08 (s, 1H), 7.75 (dd, J=15.4, 11.5 Hz, 1H), 6.61 (dd, J=15.2, 11.3 Hz, 1H), 6.50 (t, J=11.7 Hz, J H), 6.40 (t, J=11.4 Hz, J H), 6.25 (t, J=11.3 Hz, J H), 6.18 (d, J=11.6 Hz, 1H), 6.01 (dt, J=11.3, 7.2 Hz, 1H), 5.96 (t, J=11.1 Hz, 1H), 5.88 (dd, J=15.3, 8.1 Hz, 1H), 5.61-5.50 (m, 5H), 5.51-5.44 (m, 1H), 5.41-5.34 (m, 1H), 5.22 (dd, J=9.6, 3.4 Hz, 1H), 4.39 (s, 1H), 4.14 (ddd, J=7.7, 5.5 Hz, 1H), 3.89 (s, 3H), 3.87-3.83 (m, 2H), 3.76-3.69 (m, 2H), 3.23 (s, 3H), 3.08 (dd, J=14.9, 7.7 Hz, 1H), 2.97 (dd, J=15.0, 5.6 Hz, 1H), 2.60 (dt, J=17.1, 9.0 Hz, 1H), 2.56-2.50 (m, 1H), 2.34 (dd, J=14.9, 7.4 Hz, 1H), 2.25 (dddd, J=14.6, 9.0, 7.3, 1.6 Hz, 1H), 1.72 (d, J=5.4 Hz, 3H), 1.69 (d, J=5.9 Hz, 3H), 0.99 (s, 3H), 0.97 (s, 3H), 0.93 (s, 3H), 0.88 (s, 9H), 0.87 (s, 9H), 0.75 (s, 3H), 0.06 (s, 3H), 0.01 (s, 3H), −0.02 (s, 3H), −0.05 (s, 3H) ppm; $^{13}$C NMR (151 MHz, CDCl$_3$) δ 162.87, 161.84, 161.57, 160.76, 144.11, 142.84, 136.54, 136.14, 135.98, 134.68, 133.43, 132.66, 131.92, 131.30, 130.14, 130.01, 129.01, 128.81, 128.54, 128.33, 125.47, 125.27, 124.15, 113.30, 84.77, 79.57, 79.15, 77.99, 75.96, 58.29, 56.72, 55.66, 52.23, 43.02, 40.95, 35.01, 30.50, 28.62, 26.10 (3×C), 25.98 (3×C), 22.94, 20.17, 19.80, 19.49, 18.33, 18.14, 17.92, 17.90, −3.37, −3.82, −4.79, −4.98 ppm; HR-MS (ESI-TOF): calcd for C$_{56}$H$_{86}$N$_2$O$_{11}$Si$_2$Na$^+$ [M+Na]$^+$: 1041.5685. Found: 1041.5662.

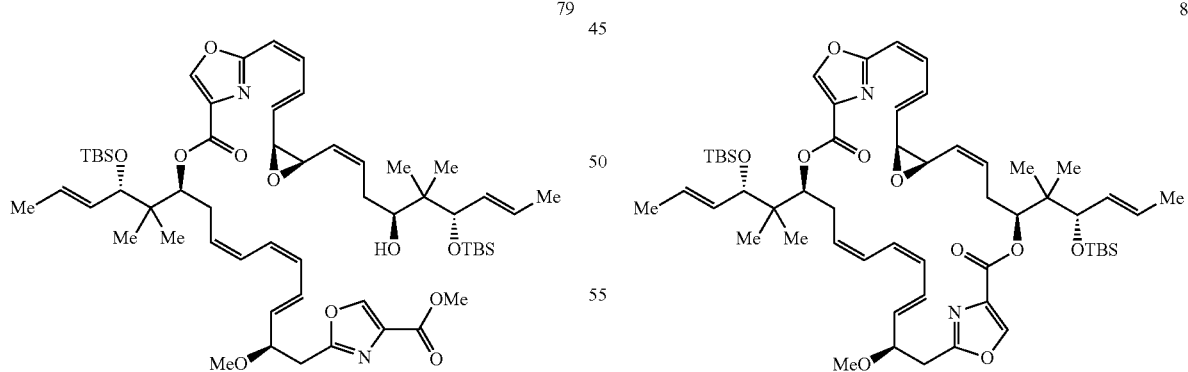

Methyl 2-{(2R,3E,5Z,7Z,10S,12S,13E)-12-{[tert-butyl(dimethyl)silyl]oxy}-10-[({2-[(1Z,3E)-4-{(2S,3R)-3-[(1Z,4S,6S,7E)-6-{[tert-butyl(dimethyl)silyl]oxy}-4-hydroxy-5,5-dimethylnona-1,7-dien-1-yl]oxiran-2-yl}buta-1,3-dien-1-yl]-1,3-oxazol-4-yl}carbonyl)oxy]-2-methoxy-11,11-dimethyl-pentadeca-3,5,7,13-tetraen-1-yl}-1,3-oxazole-4-carboxylate (79): To a stirred solution of tris-silane 78 (82

(2Z,4E,6S,8R,9Z,12S,20R,21E,23Z,25Z,28S)-12,28-Bis[(3S,4E)-3-{[tert-butyl(dimethyl)silyl]oxy}-2-methylhex-4-en-2-yl]-20-methoxy-7,13,17,29,33-pentaoxa-34,35-diazatetracyclo[29.2.1.1$^{15,18}$.0$^{6,8}$]- pentatriaconta-1 (34),2,4,9, 15,18 (35),21,23,25,31-decaene-14,30-dione (80): To a stirred solution of methyl ester 79 (50 mg, 49 µmol, 1.0 equiv) in DCE (0.49 mL) was added trimethyltin hydroxide (89 mg, 490 µmol, 10 equiv) at 23° C. and the reaction mixture was heated at 80° C. for 1.5 h. The resulting misty solution was cooled to 23° C., concentrated under reduced pressure and resulting residue was dissolved in EtOAc (20 mL) and extracted three times with a aqueous solution of KHSO$_4$ (0.01 N, 3×10 mL). The combined organic extracts were dried over MgSO$_4$, filtered and concentrated under reduced pressure. The crude residue was azeotropically dried with toluene (3×4 mL) three times and dried at high vacuum.

To a solution of the crude carboxilic acid. stirred in toluene (3.61 mL), was added 2,4,6-trichlorobenzoyl chloride (760 µl, 487 µmol, 10 equiv) and Et$_3$N (75 µl, 536 µmol, 11 equiv). The mixture was stirred 1 h at 23° C. and it was diluted to a concentration of 7.5 mM by the addition of toluene (3.61 mL). The latter reaction mixture was added over 5 h, via a syringe pump, to a solution of DMAP (24 mg, 195 µmol, 4.0 equiv) in toluene (9.02 mL) heated at 40° C. After the addition was completed, stirring was continued for 24 h before the reaction was concentrated to about 1 mL and directly subjected to flash column chromatography and purified (SiO$_2$, hexanes:EtOAc 3:1→7:3→13:7) to give bis-TBS protected disorazole A$_1$ (80, 23 mg, 23 µmol, 48% yield over two steps) as a white sticky foam. 80: R$_f$=0.32 (hexanes:EtOAc, 7:13); [α]$_D^{25}$=−57.5 (c=0.44, CHCl$_3$); IR (film): ν$_{max}$=2929, 2857, 1743, 1584, 1471, 1251, 1110, 835 cm$^{-1}$; $^1$H NMR (600 M Hz, CDCl$_3$) δ 7.98 (s, 1H), 7.91 (s, 1H), 7.21 (dd, J=15.0, 11.5 Hz, 1H), 6.43-6.34 (m, 2H), 6.33-6.23 (m, 2H), 6.19 (d, J=11.8 Hz, 1H), 6.00 (t, J=11.1 Hz, 1H), 5.82 (td, J=11.2, 5.5 Hz, 1H),5.75 (dd, J=15.1, 8.8 Hz, 1H), 5.52 (tqd, J=15.4, 8.8, 8.4, 3.4 Hz, 6H), 5.23 (ddd, J=19.0, 11.5, 2.7 Hz, 3H), 3.94 (dd, J=9.7, 4.2 Hz, 1H), 3.92-3.84 (m, 1H), 3.83 (d, J=3.6 Hz, 1H), 3.81 (d, J=3.2 Hz, 1H), 3.52 (dd, J=9.8, 4.2 Hz, 1H), 3.18 (s, 3H), 2.84-2.70 (m, 2H), 2.61 (dd, J=15.0, 4.5 Hz, 1H), 2.42-2.34 (m, 1H), 2.32-2.24 (m, 2H), 1.69 (d, J=5.7 Hz, 6H), 0.98 (s, 6H), 0.95 (s, 3H), 0.95 (s, 3H), 0.88 (s, 9H), 0.88 (s, 9H), 0.01 (s, 3H), 0.01 (s, 3H), −0.04 (s, 6H) ppm; $^{13}$C NMR (151 MHz, CDCl$_3$) δ 162.15, 161.51, 160.31, 160.25, 143.36, 143.31, 134.86, 134.79 (2×C), 133.90, 133.64, 133.50, 132.33, 131.32, 131.27, 130.47, 128.48, 128.43, 128.39, 128.00, 126.79, 126.52, 125.86, 114.04, 79.44 (2×C), 79.03, 76.85, 76.42, 58.69, 56.78, 54.95, 42.64 (2×C), 35.23, 29.18, 28.80, 26.11 (6×C), 20.56, 20.48, 19.57, 19.54, 18.35 (2×C), 18.00, 17.96, −3.36 (2×C), −4.75 (2×C) ppm; HR-MS (ESI-TOF): calcd for C$_{55}$H$_{82}$N$_2$O$_{10}$Si$_2$Na$^+$ [M+Na]$^+$: 1009.5400. Found: 1009.5416.

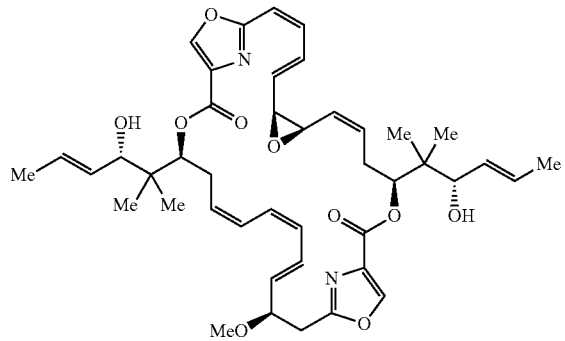

1

(2Z,4E,6S,8R,9Z,12S,20R,21E,23Z,25Z,28S)-12,28-Bis [(3S,4E)-3-hydroxy-2-methylhex-4-en-2-yl]-20-methoxy-7,13,17,29,33-pentaoxa-34,35-diazatetracyclo [29.2.1.1$^{15,18}$.0$^{6,8}$]pentatriaconta-1 (34),2,4,9,15,18 (35),21,23,25,31-decaene-14,30-dione [disorazole A$_1$ (1)]: To a stirred solution of bis-silane disorazole A$_1$ (80, 12 mg, 12 µmol, 1.0 equiv) in DMF (388 µL) and H$_2$O (2.0 µl, 120 µmol, 10 equiv) was added TASF (20 mg, 71 µmol, 6.1 equiv) and the reaction mixture was heated at 41° C. and stirred for 48 h. A second portion of TASF (20 mg, 71 µmol, 6.1 equiv) was added stirred for an extra 24 h. The resulting mixture was purified through a small silica pad (10 cm, SiO$_2$, hexanes:EtOAc 1:1→0:1). The resulting fractions containing the desired products were combined, concentrated and subjected to flash column chromatography (SiO$_2$, hexanes:EtOAc 1:1→1:4→0:1) to yield disorazole A$_1$ (1, 1.5 mg, 2.0 µmol, 17% yield) as a white film. 1: R$_f$=0.36 (hexanes:EtOAc, 1:4); [α]$_D^{25}$=−85.0 (c=0.08, MeOH); IR (film): ν$_{max}$=3419, 2925, 2853, 1734, 1635, 1555, 1370, 1322, 1146, 1109, 991, 760 cm$^{-1}$; $^1$H NMR (600 MHz, MeOH-d$_4$) δ 8.47 (s, 1H), 8.34 (s, 1H), 7.33 (dd, J=15.1, 11.7 Hz, 1H), 6.53-6.48 (m, 2H), 6.45 (t, J=11.9 Hz, 1H), 6.39 (t, J=11.0 Hz, 1H), 6.17 (d, J=11.9 Hz, 1H), 6.04 (t, J=11.0 Hz, 1H), 5.87-5.78 (m, 2H), 5.73-5.54 (m, 6H), 5.37-5.30 (m, 3H), 4.05 (dd, J=9.7, 4.3 Hz, 1H). 3.99 (dt, J=9.2, 4.6 Hz, 1H), 3.86 (d, J=7.8 Hz, 2H), 3.64 (dd, J=9.8, 4.3 Hz, 1H), 3.23 (dd, J=14.9, 5.3 Hz, 1H), 3.18 (s, 3H), 2.87 (q, J=13.7, 12.7 Hz, 2H), 2.57 (dd, J=15.0, 3.8 Hz, 1H), 2.44 (dd, J=13.5, 5.6 Hz, 1H), 2.35 (d, J=12.7 Hz, 1H), 1.73 (ddd, J=6.2, 4.8, 1.4 Hz, 6H), 1.05 (s, 6H), 1.01 (s, 3H), 1.01 (s, 3H) ppm; $^{13}$C NMR (151 MHz, MeOH-d$_4$) δ 164.04, 163.00, 161.92, 161.81, 146.14, 146.07, 137.12, 136.78, 135.16, 134.79, 134.35, 133.77, 133.49, 131.72, 131.70, 131.04, 129.72, 129.62, 129.57, 129.36, 128.42, 128.08, 126.98, 113.87, 80.01, 78.28, 77.90, 77.89, 77.67, 59.74, 56.67, 56.01, 42.67 (2×C), 36.17, 29.57, 29.25, 19.40 (4×C), 18.03 (2×C) ppm; HR-MS (ESI-TOF): calcd or C$_{43}$H$_{54}$N$_2$O$_{10}$Na$^+$ [M+Na] 781.3671, Found: 781.3689.

TABLE 1

$^1$H NMR Comparison of Synthetic and Natural Disorazole A$_1$ (1)

| Lit. (Jansen et al., 1994) 600 MHz MeOH-d$_4$ | | | This Application 600 MHz MeOH-d$_4$ | | | |
|---|---|---|---|---|---|---|
| δ [ppm] | multiplicity | J [Hz] | δ [ppm] | multiplicity | J [Hz] | Δδ |
| 8.48 | s | | 8.47 | s | | 0.01 |
| 8.35 | s | | 8.33 | s | | 0.02 |
| 7.34 | dd | 15.0, 11.9 | 7.33 | dd | 15.0, 11.8 | 0.01 |
| 6.51 | dd | 11, 11 | 6.48-6.52 | m | | — |

TABLE 1-continued

$^1$H NMR Comparison of Synthetic and Natural Disorazole A$_1$ (1)

| Lit. (Jansen et al., 1994) 600 MHz MeOH-d$_4$ | | | This Application 600 MHz MeOH-d$_4$ | | | |
|---|---|---|---|---|---|---|
| δ [ppm] | multiplicity | J [Hz] | δ [ppm] | multiplicity | J [Hz] | Δδ |
| 6.49 | dd | 15.1, 11 | 6.48-6.52 | m | | — |
| 6.46 | dd | 11.9, 11.7 | 6.45 | ap.t. | 11.8 | 0.01 |
| 6.41 | dd | 11, 11 | 6.39 | ap.t. | 11.1 | 0.02 |
| 6.18 | d | 11.7 | 6.17 | d | 11.8 | 0.01 |
| 6.05 | dd | 11, 11 | 6.04 | ap.t. | 11.1 | 0.01 |
| 5.85 | ddd | 11, 11, 5.5 | 5.79-5.86 | m | | — |
| 5.82 | dd | 15.1, 9 | 5.79-5.86 | m | | — |
| 5.71 | dqd | 15, 6, 1 | 1 | 5.66-5.73 | m | — |
| 5.71 | dqd | 15, 6, 1 | 1 | 5.66-5.73 | m | — |
| 5.69 | dd | 15, 10 | 5.66-5.73 | m | | — |
| 5.62 | ddq | 15, 7.5, 1.2 | 5.59-5.64 | m | | — |
| 5.62 | ddq | 15, 7.5, 1.2 | 5.59-5.64 | m | | — |
| 5.59 | ddd | 11, 11, 5.5 | 5.54-5.59 | m | | — |
| 5.37 | dd | 11.6, 2.5 | 5.30-5.36 | m | | — |
| 5.35 | dd | 11, 2.5 | 5.30-5.36 | m | | — |
| 5.33 | dd | 11.5, 9.7 | 5.30-5.36 | m | | — |
| 4.06 | dd | 9.7, 4.2 | 4.05 | dd | 9.76, 4.31 | 0.01 |
| 4.00 | ddd | 9, 5.4, 3.8 | 3.99 | ddd | 9.0, 4.8, 3.5 | 0.01 |
| 3.87 | d | 7.5 | 3.86 | d | 7.8 | 0.01 |
| 3.87 | d | 7.5 | 3.86 | d | 7.8 | 0.01 |
| 3.65 | ddd | 9.9, 4.2 | 3.64 | dd | 9.9, 4.3 | 0.01 |
| 3.24 | dd | 14.9, 5.4 | 3.23 | dd | 14.95, 5.43 | 0.01 |
| 3.19 | s | | 3.18 | s | | 0.01 |
| 2.89 | ddd | 13.5, 11, 11 | 2.84-2.91 | m | | — |
| 2.89 | ddd | 14, 11, 11 | 2.84-2.91 | m | | — |
| 2.57 | dd | 14.9, 3.8 | 2.57 | dd | 15.0, 3.8 | 0.00 |
| 2.47 | ddd | 13.5, 5.0, 2.5 | 2.43-2.46 | m | | — |
| 2.37 | dd | 14, 5.5 | 2.33-2.36 | m | | — |
| 1.74 | dd | 6, 1 | 1.71-1.74 | m | | — |
| 1.73 | dd | 6, 1 | 1.71-1.74 | m | | — |
| 1.07 | s | | 1.05 | s | | 0.02 |
| 1.07 | s | | 1.05 | s | | 0.02 |
| 1.03 | s | | 1.01 | s | | 0.02 |
| 1.02 | s | | 1.01 | s | | 0.01 |

TABLE 2

$^{13}$C NMR Comparison of Synthetic and Natural Disorazole A$_1$ (1)

| Lit. (Jansen et al., 1994) 150 MHz MeOH-d$_4$ δ [ppm] | HZI (From Dr. Jansen) 175 MHz MeOH-d$_4$ δ [ppm] | This Application 150 MHz MeOH-d$_4$ δ [ppm] | Δδ (last two columns) |
|---|---|---|---|
| 163.99 | 164.03 | 164.04 | −0.01 |
| 162.95 | 162.99 | 163.00 | −0.01 |
| 161.89 | 161.91 | 161.92 | −0.01 |
| 161.79 | 161.79 | 161.81 | −0.02 |
| 146.07 | 146.13 | 146.14 | −0.01 |
| 146.04 | 146.07 | 146.07 | 0.00 |
| 137.08 | 137.12 | 137.12 | 0.00 |
| 136.74 | 136.77 | 136.78 | −0.01 |
| 135.16 | 135.15 | 135.16 | −0.01 |
| 134.77 | 134.78 | 134.79 | −0.01 |
| 134.33 | 134.33 | 134.35 | −0.02 |
| 133.76 | 133.76 | 133.77 | −0.01 |
| 133.47 | 133.48 | 133.49 | −0.01 |
| 131.70 | 131.71 | 131.72 | −0.01 |
| 131.70 | 131.69 | 131.70 | −0.01 |
| 131.02 | 131.04 | 131.04 | 0.00 |
| 129.70 | 129.71 | 129.72 | −0.01 |
| 129.56 | 129.62 | 129.62 | 0.00 |
| 129.51 | 129.56 | 129.57 | −0.01 |
| 129.31 | 129.36 | 129.36 | 0.00 |
| 128.39 | 128.43 | 128.42 | 0.01 |
| 128.06 | 128.08 | 128.08 | 0.00 |
| 126.96 | 126.98 | 126.98 | 0.00 |
| 113.88 | 113.86 | 113.87 | −0.01 |
| 79.99 | 80.00 | 80.01 | −0.01 |
| 78.28 | 78.26 | 78.28 | −0.02 |
| 77.86 | 77.89 | 77.90 | −0.01 |
| 77.86 | 77.87 | 77.89 | −0.02 |
| 77.68 | 77.65 | 77.67 | −0.02 |
| 59.71 | 59.73 | 59.74 | −0.01 |
| 56.68 | 56.68 | 56.67 | 0.01 |
| 56.00 | 56.00 | 56.01 | −0.01 |
| 42.67 | 42.67 | 42.67 | 0.00 |
| 42.67 | 42.67 | 42.67 | 0.00 |
| 36.15 | 36.16 | 36.17 | −0.01 |
| 29.58 | 29.56 | 29.57 | −0.01 |
| 29.26 | 29.25 | 29.25 | 0.00 |
| 19.42 | 19.42 | 19.40 | 0.02 |
| 19.42 | 19.42 | 19.40 | 0.02 |
| 19.42 | 19.42 | 19.40 | 0.02 |
| 19.42 | 19.42 | 19.40 | 0.02 |
| 18.04 | 18.04 | 18.03 | 0.01 |
| 18.04 | 18.04 | 18.03 | 0.01 |

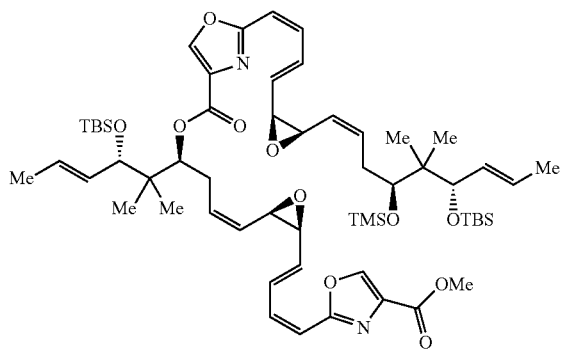

81

Methyl 2-[(1Z,3E)-4-{(2S,3R)-3-[(1Z,4S,6S,7E)-6-{[tert-butyl(dimethyl)silyl]oxy}-4-{[(2-{(1Z,3E)-4-[(2S,3R)-3-{(1Z,4S,6S,7E)-6-{[tert-butyl(dimethyl)silyl]oxy}-5,5-dimethyl-4-[(trimethylsilyl)oxy]-nona-1,7-dien-1-yl}oxiran-2-yl]buta-1,3-dien-1-yl}-1,3-oxazol-4-yl)carbonyl]oxy}-5,5-dimethylnona-1,7-dien-1-yl]oxiran-2-yl}buta-1,3-dien-1-yl]-1,3-oxazole-4-carboxylate (81): To a stirred solution of epoxide alcohol 74 (225 mg, 381 μmol, 1.0 equiv) in DCE (3.80 mL) was added trimethyltin hydroxide (690 mg, 3.81 mmol, 10 equiv) at 23° C. and the reaction mixture was heated at 80° C. for 3 h. The resulting misty solution was cooled to 23° C., concentrated under reduced pressure and the resulting residue was dissolved in EtOAc (20 mL) and extracted three times with an aqueous solution of KHSO₄ (0.01 N, 3×15 mL). The combined organic extracts were dried over MgSO₄, filtered and concentrated under reduced pressure. The crude residue was used in the next step without any further purification.

The crude acid (77) was dissolved in CH₂Cl₂ and added to a 25 mL cylindrical vial containing alcohol 75 (100 mg, 193 μmol, 0.50 equiv) and the mixture was azeotropically dried with toluene twice and thereafter dried at high vacuum. The resulting thick paste was dissolved in toluene (1.93 mL) and a stir bar was added followed by the addition of Et₃N (162 μl, 1.16 mmol, 3.0 equiv) at 23° C. The resulting mixture was stirred 5 min and DMAP (189 mg, 1.55 mmol, 4.0 equiv) was added, followed by a slow dropwise addition of TCBC (91 μl, 580 μmol, 1.5 equiv) at 23° C. The reaction mixture was allowed to stir for 1 h at 23° C. and the crude was purified directly by flash column chromatography (SiO₂, hexanes:EtOAc 4:1→3:2) to yield homo-dimer 81 (204 mg, 189 μmol, 98% yield) as a pale yellow sticky foam. 81: $R_f$=0.31 (hexanes:EtOAc, 4:1); $[\alpha]_D^{25}$=+17.2 (c=1.0, CHCl₃); IR (film): $v_{max}$=2956, 2857, 1745, 1729, 1249, 116, 1053, 836 cm⁻¹; ¹H NMR (600 M Hz, CDCl₃) δ 8.21 (s, 1H), 8.07 (s, 1H), 7.69 (dd, J=15.4, 11.5 Hz, 1H), 7.52 (dd, J=15.3, 11.6 Hz, 1H), 6.44 (t, J=11.7 Hz, 1H), 6.40 (t, J=11.7 Hz, 1H), 6.14 (d, J=11.7 Hz, 1H), 6.10 (d, J=11.6 Hz, 1H), 5.88-5.78 (m, 3H), 5.68 (dd, J=15.3, 8.4 Hz, 1H), 5.57-5.38 (m, 4H), 5.34-5.26 (m, 2H), 5.23 (dd, J=10.0, 3.0 Hz, 1H), 3.94 (s, 3H), 3.89-3.82 (m, 4H), 3.70 (dd, J=7.9, 4.3 Hz, 1H), 3.63-3.58 (m, 2H), 2.65 (dt, J=14.9, 9.6 Hz, 1H), 2.56 (dt, J=12.1, 4.4 Hz, 1H), 2.39 (ddt, J=14.6, 7.0, 2.3 Hz, 1H), 2.34-2.25 (m, 1H), 1.69 (d, J=1.8 Hz, 3H), 1.68 (s, 3H), 0.97 (s, 3H), 0.94 (s, 3H), 0.87 (s, 9H), 0.87 (s, 9H), 0.84 (s, 3H), 0.80 (s, 3H), 0.06 (s, 9H), 0.01 (s, 3H), −0.02 (s, 3H), −0.03 (s, 3H), −0.05 (s, 3H) ppm; ¹³C NMR (151 M Hz, CDCl₃) δ 161.77, 161.67, 161.54, 160.65, 143.45, 142.75, 137.52, 136.14, 136.06, 135.88, 135.66, 134.72, 134.35, 134.22, 131.88, 131.78, 131.74, 131.28, 128.59, 127.93, 125.86, 124.12, 113.27, 113.21, 79.17, 78.96, 77.52, 77.37, 58.18, 58.16, 55.59, 55.37, 52.35, 43.84, 42.87, 31.21, 29.15, 26.13 (3×C), 26.10 (3×C), 20.18 (2×C), 19.57, 19.47, 18.38, 18.33, 17.92, 17.84, 1.19 (3×C), −3.14, −3.35, −4.49, −4.80 ppm; HR-MS (ESI-TOF): calcd for $C_{58}H_{90}N_2O_{11}SiNa^+$ [M+Na]⁺: 1097.5745. Found: 1097.5733.

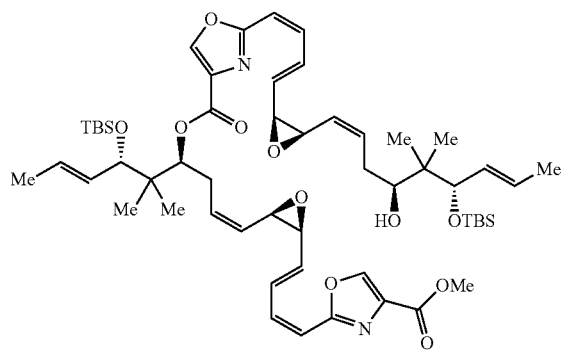

82

Methyl 2-{(1Z,3E)-4-[(2S,3R)-3-{(1Z,4S,6S,7E)-6-{[tert-butyl(dimethyl)silyl]oxy}-4-[({2-[(1Z,3E)-4-{(2S,3R)-3-[(1Z,4S,6S,7E)-6-{[tert-butyl(dimethyl)silyl]oxy}-4-hydroxy-5,5-dimethylnona-1,7-dien-1-yl]oxiran-2-yl}buta-1,3-dien-1-yl]-1,3-oxazol-4-yl}carbonyl)oxy]-5,5-dimethylnona-1,7-dien-1-yl}oxiran-2-yl]buta-1,3-dien-1-yl}-1,3-oxazole-4-carboxylate (82): To a stirred solution of tris-silane 81 (195 mg, 181 μmol, 1.0 equiv) in THF (1.0 mL) in a glass round bottom flask at 23° C. was added Et₃N-3HF (89 μl, 544 μmol, 3.0 equiv) and the solution was stirred for 1 h. The crude was purified directly by flash column chromatography (SiO₂, hexanes:EtOAc 3:1→3:2) to yield alcohol 82 (166 mg, 165 μmol, 91% yield) as a pale yellow thick paste. 82: $R_f$=0.34 (hexanes:EtOAc, 7:3); $[\alpha]_D^{25}$=+21.3 (c=1.0, CHCl₃); IR (film): $v_{max}$=3485, 2956, 2929, 2856, 1743, 1252, 1117, 836 cm⁻¹; ¹H NMR (600 MHz, CDCl₃) δ 8.23 (s, 1H), 8.07 (s, 1H), 7.66 (dd, J=15.4, 11.6 Hz, 1H), 7.52 (dd, J=15.3, 11.5 Hz, 1H), 6.43 (t, J=11.8 Hz, 1H), 6.38 (t, J=11.8 Hz, 1H), 6.12 (d, J=11.7 Hz, 1H), 6.08 (d, J=11.6 Hz, 1H), 6.01 (dt, J=11.4, 7.3 Hz, 1H), 5.88-5.79 (m, 2H), 5.66 (dd, J=15.2, 8.5 Hz, 1H), 5.62-5.44 (m, 4H), 5.36 (tt, J=10.2, 1.7 Hz, 1H), 5.32-5.26 (m, 1H), 5.22 (dd, J=10.2, 3.0 Hz, 1H), 4.40 (s, 1H), 3.93 (s, 3H), 3.91-3.82 (m, 4H), 3.73 (dt, J=10.2, 2.2 Hz, 1H), 3.68 (dd, J=8.0, 4.4 Hz, 1H), 3.61 (dd, J=8.5, 4.3 Hz, 1H), 2.65 (dt, J=14.7, 9.7 Hz, 1H), 2.57-2.50 (m, 1H), 2.37-2.31 (m, 1H), 2.27 (dddd, J=14.6, 9.1, 7.4, 1.6 Hz, 1H), 1.72 (d, J=5.4 Hz, 3H), 1.70-1.65 (m, 3H), 1.00 (s, 3H), 0.97 (s, 3H), 0.93 (s, 3H), 0.87 (s, 9H), 0.87 (s, 9H), 0.75 (s, 3H), 0.06 (s, 3H), 0.01 (s, 3H), −0.03 (s, 3H), −0.05 (s, 3H). ppm; ¹³C NMR (151 MHz, CDCl₃) δ 161.78, 161.64, 161.57, 160.63, 143.55, 142.74, 136.65, 136.09, 136.08, 135.96, 135.59, 134.67, 134.31, 134.21, 131.94, 131.74, 131.27, 130.14, 129.02, 128.58, 125.91, 124.14, 113.27, 113.18, 84.75, 79.15, 77.45, 75.95, 58.24, 58.18, 55.67, 55.36, 52.34, 42.86, 40.96, 30.50, 29.17, 26.10 (3×C), 25.96 (3×C), 22.94, 20.18, 19.78, 19.46, 18.32, 18.13, 17.92, 17.89, −3.36, −3.82, −4.80, −4.99 ppm; HR-MS (ESI-TOF): calcd for $C_{55}H_{82}N_2O_{11}Si_2Na^+$ [M+Na]⁺: 1025.5349. Found: 1025.5365.

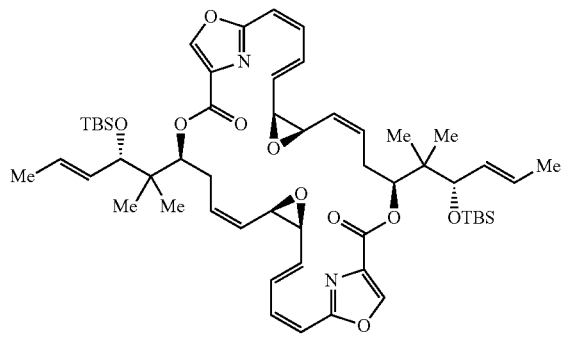

(2Z,4E,6S,8R,9Z,12S,19Z,21E,23S,25R,26Z,29S)-12,29-bis[(3S,4E)-3-{[tert-butyl(dimethyl)-silyl]oxy}-2-methylhex-4-en-2-yl]-7,13,17,24,30,34-hexaoxa-35,36-diazapentacyclo-[30.2.1.1$^{15,18}$.0$^{6,8}$.0$^{23,25}$]hexatriaconta-1 (35),2,4,9,15,18 (36),19,21,26,32-decaene-14,31-dione (83): To a stirred solution of methyl ester 82 (50 mg, 49 µmol, 1.0 equiv) in DCE (0.49 mL) was added trimethyltin hydroxide (89 mg, 490 µmol, 10 equiv) at 23° C. and the reaction mixture was heated at 80° C. for 1.5 h. The resulting misty solution was cooled to 23° C., concentrated under reduced pressure and resulting residue was dissolved in EtOAc (20 mL) and extracted three times with an aqueous solution of KHSO$_4$ (0.01 N, 3×10 mL). The combined organic extracts were dried over MgSO$_4$, filtered and concentrated under reduced pressure. The crude residue was azeotropically dried with toluene (3×4 mL) three times and dried at high vacuum.

To a solution of the crude carboxylic acid, stirred in toluene (3.61 mL), was added 2,4,6-trichlorobenzoyl chloride (760 µl, 487 µmol, 10 equiv) and Et$_3$N (75 µl, 536 µmol, 11 equiv). The mixture was stirred 1 h at 23° C. and it was diluted to a concentration of 7.5 mM by the addition of toluene (3.61 mL). The latter reaction mixture was added over 5 h, via a syringe pump, to a solution of DMAP (24 mg, 195 µmol, 4.0 equiv) in toluene (9.02 mL) heated at 40° C. After the addition was completed, stirring was continued for 24 h before the reaction was concentrated to about 1 mL and directly subjected to flash column chromatography and purified (SiO$_2$, hexanes:EtOAc 3:1→7:3→13:7) to give bis-TBS protected disorazole B$_1$ (83, 23 mg, 23 µmol, 48% yield over two steps) as a white sticky foam. 83: R$_f$=0.47 (hexanes:EtOAc, 13:7); [α]$_D^{25}$=−58.1 (c=1.0, CHCl$_3$); IR (film): v$_{max}$=2957, 2930, 1740, 1472, 1146, 1059, 834 cm$^{-1}$; $^1$H NMR (600 MHz, CDCl$_3$) δ 8.01 (s, 2H), 7.13 (dd, J=15.0, 11.6 Hz, 2H), 6.21 (t, J=11.7 Hz, 2H), 6.07 (d, J=11.8 Hz, 2H), 5.86 (td, J=11.4, 5.5 Hz, 2H), 5.58-5.40 (m, 6H), 5.30-5.21 (m, 4H), 3.92 (dd, J=9.2, 4.2 Hz, 2H), 3.81 (d, J=8.2 Hz, 2H), 3.48 (dd, J=9.9, 4.2 Hz, 2H), 2.71 (q, J=12.2 Hz, 2H), 2.40 (dd, J=13.3, 5.4 Hz, 2H), 1.69 (d, J=5.8 Hz, 6H), 0.98 (s, 6H), 0.94 (s, 6H), 0.88 (s, 18H), −0.01 (s, 6H), −0.05 (s, 6H) ppm; $^{13}$C NMR (151 M Hz, CDCl$_3$) δ 162.16, 159.72, 142.01, 134.61, 134.26, 134.23, 134.21, 132.54, 131.25, 128.52, 127.21, 114.31, 79.35, 76.52, 58.76, 55.04, 42.64, 29.33, 26.11, 20.49, 19.59, 18.34, 18.00, −3.34, −4.77 ppm; HR-MS (ESI-TOF): calcd for C$_{54}$H$_{78}$N$_2$O$_{10}$Si$_2$Na$^+$ [M+Na]$^+$: 993.5087. Found: 993.5056.

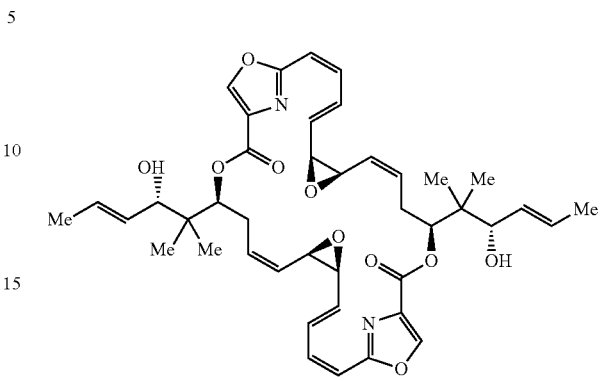

(2Z,4E,6S,8R,9Z,12S,19Z,21E,23S,25R,26Z,29S)-12,29-Bis[(3S,4E)-3-hydroxy-2-methylhex-4-en-2-yl]-7,13,17,24,30,34-hexaoxa-35,36-diazapentacyclo[30.2.1.1$^{15,18}$.0$^{6,8}$.0$^{23,25}$]hexatriaconta-1 (35),2,4,9,15,18 (36),19,21,26,32-decaene-14,31-dione [disorazole B$_1$ (4)]: To a stirred solution of bis-silane disorazole B1 (24 mg, 25 µmol, 1.0 equiv) in DMF (750 µL) and H$_2$O (10 µl, 568 µmol, 23 equiv) was added TASF (41 mg, 148 µmol, 6.0 equiv) and the reaction mixture was heated at 40° C. and stirred for 48 h. A second portion of TASF (37 mg, 136 µmol, 5.5 equiv) was added and the temperature was increased to 45° C. and stirred for 24 h. The resulting mixture was filtered through a small silica pad (10 cm, SiO$_2$, hexanes:EtOAc 1:1→0:1). The resulting fractions containing the desired products were combined, concentrated and purified by flash column chromatography (SiO$_2$, hexanes:EtOAc 1:1→1:4→0:1) to yield disorazole B$_1$ (4, 11.1 mg, 16 µmol, 64% yield) as a white foam. 4: R$_f$=0.30 (hexanes:EtOAc, 1:4); [α]$_D^{25}$=−59.3 (c=0.61, MeOH:CH$_2$Cl$_2$ 1:1); IR (film): v$_{max}$=3456, 2972, 2937, 1732, 1666, 1639, 1325, 1151, 991, 768 cm$^{-1}$; $^1$H NMR (600 MHz, CDCl$_3$) δ 8.05 (s, 2H), 7.15 (dd, J=14.9, 11.9 Hz, 2H), 6.21 (t, J=11.7 Hz, 2H), 6.07 (d, J=11.8 Hz, 2H), 5.88 (td, J=11.4, 5.3 Hz, 2H), 5.70-5.61 (m, 2H), 5.54 (dd, J=15.0, 7.5 Hz, 2H), 5.45 (dd, J=15.0, 9.9 Hz, 2H), 5.36 (d, J=11.4 Hz, 2H), 5.29 (t, J=10.2 Hz, 2H), 3.94 (dd, J=9.2, 4.2 Hz, 2H), 3.84 (d, J=7.5 Hz, 2H), 3.50 (dd, J=9.9, 3.8 Hz, 2H), 2.72 (q, J=12.2 Hz, 2H), 2.42 (dd, J=12.6, 4.7 Hz, 2H), 1.93 (s, 2H), 1.70 (d, J=6.2 Hz, 6H), 0.99 (d, J=2.0 Hz, 6H), 0.95 (d, J=1.8 Hz, 6H) ppm; $^1$H NMR (600 M Hz, DMSO-d$_6$) δ 8.72 (s, 2H), 7.09 (dd, J=14.9, 11.6 Hz, 2H), 6.28 (t, J=11.8 Hz, 2H), 6.03 (d, J=11.7 Hz, 2H), 5.74 (td, J=11.2, 7.7 Hz, 2H), 5.61 (dd, J=15.0, 10.1 Hz, 2H), 5.58-5.47 (m, 4H), 5.30 (t, J=10.3 Hz, 2H), 5.15 (dd, J=11.7, 2.4 Hz, 2H), 4.65 (d, J=4.6 Hz, 2H), 3.98 (dd, J=9.5, 4.3 Hz, 2H), 3.69 (dd, J=6.9, 4.7 Hz, 2H), 3.59 (dd, J=10.2, 4.3 Hz, 2H), 2.73 (q, J=12.2 Hz, 2H), 2.35 (dd, J=11.8, 4.3 Hz, 2H), 1.64 (d, J=5.6 Hz, 6H), 0.93 (s, 6H), 0.87 (s, 6H); $^{13}$C NMR (151 MHz, CDCl$_3$) δ 162.23, 160.21, 142.35, 134.81, 134.39, 133.91, 133.72, 132.52, 129.73, 129.71, 127.63, 114.10, 76.87, 76.76, 58.71, 54.96, 41.64, 28.83, 19.50, 18.84, 18.04 ppm; $^{13}$C NMR (151 MHz, DMSO-d$_6$) δ 161.05, 159.32, 144.74, 134.84, 134.14, 133.51, 132.95, 131.78, 131.61, 127.53, 126.50, 113.33, 75.24 (2×C), 58.15, 54.40, 41.32, 28.03, 18.84 (2×C), 17.65 ppm; HR-MS (ESI-TOF): calcd for C$_{42}$H$_{50}$N$_2$O$_{10}$Na$^+$[M+Na]$^+$: 765.3358. Found: 765.3350.

TABLE 3

<sup>1</sup>H NMR Comparison of Synthetic and Natural Disorazole B₁ (4)

| HZI (From Dr. Jansen) 700 MHz DMSO-d₆ | | | This Application 600 MHz DMSO-d₆ | | | |
|---|---|---|---|---|---|---|
| δ [ppm] | multiplicity | J [Hz] | δ [ppm] | multiplicity | J [Hz] | Δδ |
| 8.72 | s | | 8.72 | s | | 0 |
| 7.09 | dd | 14.9, 11.6 | 7.09 | dd | 14.9, 11.6 | 0 |
| 6.28 | ap. t | 11.9 | 6.28 | ap. t | 11.8 | 0 |
| 6.03 | d | 11.7 | 6.03 | d | 11.7 | 0 |
| 5.74 | ap. td | 10.83, 5.6 | 5.74 | ap.td | 11.2, 7.7 | 0 |
| 5.61 | dd | 14.9, 10.1 | 5.61 | dd | 15.0, 10.1 | 0 |
| 5.49-5.57 | malt. | | 5.58-5.47 | mult. | | — |
| 5.3 | dd | 11.3, 9.8 | 5.3 | ap.t | 10.3 | 0 |
| 5.15 | dd | 11.3, 2.5 | 5.15 | dd | 11.7, 2.4 | 0 |
| 4.65 | d | 4.7 | 4.65 | d | 4.6 | 0 |
| 3.98 | dd | 9.5, 4.0 | 3.98 | dd | 9.5, 4.3 | 0 |
| 3.68-3.70 | m | | 3.69 | dd | 6.9, 4.7 | — |
| 3.59 | dd | 10.1, 4.4 | 3.59 | dd | 10.2, 4.3 | 0 |
| 2.73 | ap. q | 12.1 | 2.73 | q | 12.2 | 0 |
| 2.34-2.37 | m | | 2.35 | dd | 11.8, 4.3 | — |
| 1.64 | d | 6.18, 1.3 | 1.64 | d | 5.6 | 0 |
| 0.93 | s | | 0.93 | s | | 0 |
| 0.87 | s | | 0.87 | s | | 0 |

TABLE 4

<sup>13</sup>C NMR comparison of synthetic and natural disorazole B₁ (4)

| HZI (From Dr. Jansen) 175 MHz DMSO-d₆ δ [ppm] | This Application 150 MHz DMSO-d₆ δ [ppm] | Δδ |
|---|---|---|
| 161.07 | 161.05 | 0.02 |
| 159.33 | 159.32 | 0.01 |
| 144.76 | 144.74 | 0.02 |
| 134.86 | 134.84 | 0.02 |
| 134.15 | 134.14 | 0.01 |
| 133.53 | 133.51 | 0.02 |
| 132.95 | 132.95 | 0 |
| 131.80 | 131.78 | 0.02 |
| 131.62 | 131.61 | 0.01 |
| 127.55 | 127.53 | 0.02 |
| 126.52 | 126.50 | 0.02 |
| 113.34 | 113.33 | 0.01 |
| 75.26 | 75.24 | 0.02 |
| 75.24 | 75.24 | 0 |
| 58.16 | 58.15 | 0.01 |
| 54.41 | 54.40 | 0.01 |
| 41.33 | 41.32 | 0.01 |
| 28.03 | 28.03 | 0 |
| 18.85 | 18.84 | 0.01 |
| 17.66 | 17.65 | 0.01 |

Methyl 2-[(1Z,3E)-4-{(1S,2R)-2-[(1Z,4S,6S,7E)-6-{[tert-butyl(dimethyl)silyl]oxy}-4-hydroxy-5,5-dimethylnona-1,7-dien-1-yl]cyclopropyl}buta-1,3-dien-1-yl]-1,3-oxazole-4-carboxylate (87)

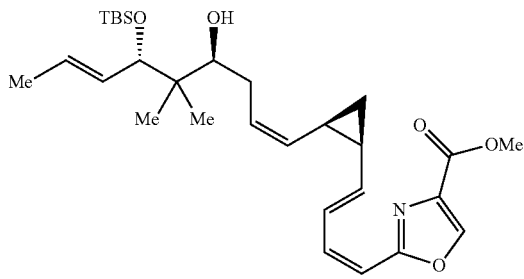 [SMILES: C/C=C/[C@H](O[Si](C)(C)C(C)(C)C)C(C)(C)[C@@H](O)C/C=C\[C@H]1C[C@H]1/C=C/C=C\c1nc(C(=O)OC)co1]

To a stirred and degassed solution of vinyl stannane 40 (330 mg, 0.505 mmol, 1.0 equiv) and oxazole methyl ester 72 (117 mg, 0.505 mmol, 1.0 equiv) in NMP (2.5 mL) at 23° C., was added CuTc (144 mg, 0.757 mmol, 1.5 equiv). The resulting mixture was stirred for 1 h at 23° C. and was then directly purified by flash column chromatography (SiO₂, hexanes:EtOAc 9:1→4:1) to yield the title compound 87 (202 mg, 0.392 mmol, 77% yield) as a pale yellow oil. 87: R$_f$=0.28 (hexanes:EtOAc, 17:3); [α]$_D^{25}$=+55.3 (c=1.0, CHCl₃); IR (film): v$_{max}$=3486, 2956, 2930, 2857, 1749, 1732, 1630, 1464, 1322, 1116, 1005, 836 cm$^{-1}$; <sup>1</sup>H NMR (600 MHz, CDCl₃) δ 8.19 (s, 1H), 7.41 (dd, J=15.0, 11.6 Hz, 1H), 6.47 (t, J=11.6 Hz, 1H), 6.01 (d, J=11.6 Hz. 1H), 5.82 (dd, J=15.0, 9.4 Hz, 1H), 5.70 (dt, J=10.9, 7.1 Hz, 1H), 5.60-5.51 (m, 2H), 5.23 (dd, J=10.7, 8.7 Hz, 1H), 4.19 (s, 1H), 3.92 (s, 3H), 3.86 (d, J=6.8 Hz, 1H), 3.70 (d, J=9.5 Hz, 1H), 2.31 (dd, J=14.6, 7.5 Hz, 1H), 2.15 (dddd, J=14.7, 10.1, 6.7, 1.6 Hz, 1H), 1.96 (ddt, J=26.4, 14.3, 8.3 Hz, 2H), 1.71 (d, J=4.8 Hz, 3H), 1.33 (td, J=8.2, 4.8 Hz, 1H), 0.97 (s, 3H), 0.88 (s, 9H), 0.76 (s, 3H), 0.72 (q, J=5.7 Hz, 1H), 0.06 (s, 3H), 0.00 (s, 3H) ppm; $^{13}$C NMR (151 MHz, CDCl$_3$) δ 162.51, 162.00, 144.59, 143.03, 138.22, 134.14, 130.41, 129.85, 129.12, 128.75, 127.20, 109.47, 84.39, 76.41, 52.26, 41.08, 30.27, 25.98, 22.86, 22.70, 19.78, 19.43, 18.15, 17.87, 16.96, −3.81, −4.96 ppm; HR-MS (ESI-TOF): calcd for C$_{29}$H$_{45}$O$_5$NSiNa [M+Na]$^+$: 538.2959. Found: 538.2977.

(1Z,4S,6S,7E)-6-{[tert-Butyl(dimethyl)silyl]oxy}-1-[(1R,2S)-2-{(1E,3Z)-4-[4-(methoxycarbonyl)-1,3-oxazol-2-yl]buta-1,3-dien-1-yl}cyclopropyl]-5,5-dimethylnona-1,7-di-en-4-yl 2-[(Z)-2-bromoethenyl]-1,3-oxazole-4-carboxylate (88)

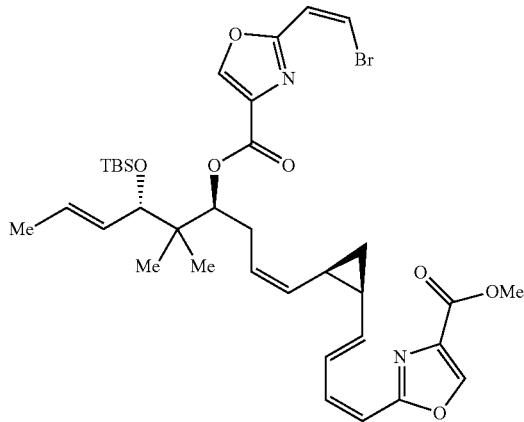 [SMILES: C/C=C/[C@H](O[Si](C)(C)C(C)(C)C)C(C)(C)[C@H](C/C=C\[C@H]1C[C@H]1/C=C/C=C\c1nc(C(=O)OC)co1)OC(=O)c1coc(/C=C\Br)n1]

A solution of hydroxy compound 87 (40 mg, 0.078 mmol, 1.0 equiv) in CH$_2$Cl$_2$ (1.0 mL) was added a solution carboxylic acid 58 (34 mg, 0.155 mmol, 2.0 equiv) in CH$_2$Cl$_2$ (1.0 mL) and the mixture was concentrated under reduced pressure and dried at high vacuum. Then, the resulting thick paste was dissolved in toluene (0.78 mL) and to the resulting stirred solution were subsequently added at 23° C. Et$_3$N (65 μL, 47 mg, 0.470 mmol, 6.0 equiv), and after 5 min DMAP (76 mg, 0.620 mmol. 8.0 equiv), and then dropwise TCBC (36 μL, 57 mg, 0.470 mmol, 6.0 equiv). After the reaction mixture was stirred at 23° C. for 0.5 h additional toluene was added (1.0 mL) and the mixture was stirred for an additional 1 h at 23° C. and was then directly purified by flash column chromatography (SiO$_2$, hexanes:EtOAc 4:1→3:2) to yield title compound 88 (38 mg, 0.053 mmol, 68% yield) as a pale yellow oil. 88: R$_f$=0.37 (hexanes:EtOAc, 3:1); [α]$_D^{25}$+31.3 (c=0.8, CHCl$_3$); IR (film): ν$_{max}$=3162, 2954, 2856, 1743, 1630, 1573, 1323, 1116, 835, 758 cm$^{-1}$; $^1$H NMR (600 MHz, CDCl$_3$) δ 8.19 (s, 1H), 8.14 (s, 1H), 7.25 (dd, J=15.1, 11.5 Hz, 1H), 7.08 (d, J=8.6 Hz, 1H), 6.79 (d, J=8.7 Hz, 1H), 6.33 (t, J=11.7 Hz, 1H), 5.95 (d, J=11.6 Hz, 1H), 5.64 (dd, J=14.9, 9.9 Hz, 1H), 5.56-5.42 (m, 3H), 5.23 (dd, J=10.1, 3.1 Hz, 1H), 5.13-5.08 (m, 1H), 3.93 (s, 3H), 3.84 (d, J=7.9 Hz, 1H), 2.62-2.52 (m, 1H), 2.49-2.42 (m, 1H), 2.04-1.95 (m, 1H), 1.90-1.81 (m, 1H), 1.67 (d, J=5.6 Hz, 3H), 1.31 (td, J=8.2, 4.9 Hz, 1H), 0.97 (s, 3H), 0.92 (s, 3H), 0.87 (s, 9H), 0.67 (q, J=5.6 Hz, 1H), −0.02 (s, 3H), −0.05 (s, 3H) ppm; $^{13}$C NMR (151 MHz, CDCl$_3$) δ 162.44, 161.98, 160.48, 159.28, 144.03, 143.06, 143.04, 137.99, 134.73, 134.16, 131.38, 130.58, 128.41, 127.52, 126.98, 119.77, 114.71, 109.49, 79.15, 78.21, 52.29, 42.88, 28.62, 26.10, 22.99, 20.22, 19.43, 19.22, 18.33, 17.91, 17.07, −3.36, −4.80 ppm; HR-MS (ESI-TOF): calcd for C$_{35}$H$_{47}$O$_7$N$_2$SiBrNa [M+Na]$^+$: 737.2228. Found: 737.2238.

Methyl 2-{(1Z,3E)-4-[(1S,2R)-2-{(1Z,4S,6S,7E)-6-{[tert-butyl(dimethyl)silyl]oxy}-4-[({2-[(2Z)-4-{(1S,2R)-2-[(1Z,4S,6S,7E)-6-{[tert-butyl(dimethyl)silyl]oxy}-4-hydroxy-5,5-dimethylnona-1,7-dien-1-yl]cyclopropyl}but-2-en-1-yl]-1,3-oxazol-4-yl}carbonyl)oxy]-5,5-dimethylnona-1,7-dien-1-yl}cyclopropyl]buta-1,3-dien-1-yl}-1,3-oxazole-4-carboxylate (89)

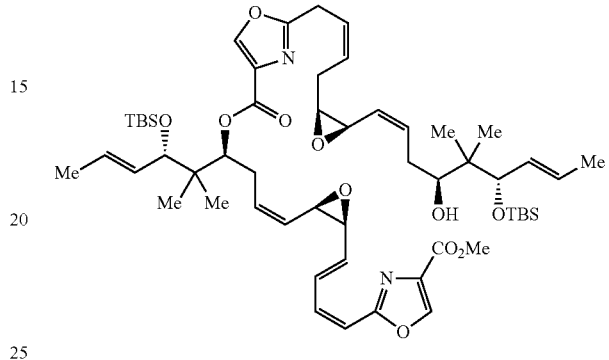

To a stirred and degassed solution of vinyl stannane 40 (32 mg, 0.048 mmol, 1.5 equiv) and vinyl bromide 88 (23 mg, 0.032 mmol, 1.0 equiv) in NMP (160 μL) at 23° C., was added CuTc (9.2 mg, 0.048 mmol, 1.5 equiv). The resulting mixture was stirred for 1 h at 23° C. and was then directly purified by flash column chromatography (SiO$_2$, hexanes:EtOAc 9:1→4:1) to yield the title compound 89 (23 mg, 0.023 mmol, 72% yield) as a pale yellow oil. 89: R$_f$=0.32 (hexanes:EtOAc, 3:1); [α]$_D^{25}$=+40.0 (c=1.0, CHCl$_3$); IR (film): ν$_{max}$=3477, 2956, 2929, 2856, 1743, 1630, 1471, 1115, 835, 775 cm$^{-1}$; $^1$H NMR (600 MHz, CDCl$_3$) δ 8.20 (s, 1H), 8.03 (s, 1H), 7.41 (dd, J=15.0, 11.5 Hz, 1H), 7.26 (s, 1H), 6.37 (t, J=11.6 Hz, 1H), 6.32 (t, J=11.7 Hz, 1H), 5.94 (d, J=11.6 Hz, 1H), 5.90 (d, J=11.6 Hz, 1H), 5.77 (dd, J=15.0, 9.6 Hz, 1H), 5.69 (dt, J=11.0, 7.1 Hz, 1H), 5.64 (dd, J=15.0, 9.8 Hz, 1H), 5.58-5.44 (m, 5H), 5.25-5.19 (m, 2H), 5.14-5.08 (m, 1H), 4.21 (s, 1H), 3.93 (s, 3H), 3.85 (dd, J=10.0, 7.2 Hz, 2H), 3.70 (dt, J=9.8, 2.2 Hz, 1H), 2.56 (dt, J=15.1, 9.2 Hz, 1H), 2.50-2.43 (m, 1H), 2.31 (dd, J=14.7, 7.5 Hz, 1H), 2.16 (dddd, J=14.6, 10.1, 6.6, 1.6 Hz, 1H), 1.98 (dp, J=16.2, 8.4 Hz, 2H), 1.91-1.82 (m, 2H), 1.71 (d, J=4.7 Hz, 3H), 1.67 (d, J=5.5 Hz, 3H), 1.31 (td, J=8.3, 4.8 Hz, 2H), 0.98 (s, 3H), 0.97 (s, 3H), 0.92 (s, 3H), 0.87 (s, 18H), 0.76 (s, 3H), 0.70 (q, J=5.7 Hz, 1H), 0.68-0.65 (m, 1H), 0.05 (s, 3H), 0.00 (s, 3H), −0.01 (s, 3H), −0.05 (s, 3H) ppm; $^{13}$C NMR (151 MHz, CDCl$_3$) δ 162.46, 162.20, 162.03, 160.97, 144.02, 143.94, 143.18, 142.39, 137.97, 137.74, 134.56, 134.07, 131.46, 130.50, 130.42, 129.70, 129.21, 128.75, 128.31, 127.64, 127.41, 127.06, 109.63, 109.49, 84.41, 79.18, 77.96, 76.42, 52.25, 42.93, 41.08, 30.26, 28.64, 26.11, 25.98, 22.99, 22.80, 22.71, 20.24, 19.77, 19.46, 19.36, 19.24, 18.34, 18.15, 17.91, 17.88, 17.02, 16.84, −3.37, −3.80, −4.79, −4.97 ppm; HR-MS (ESI-TOF): calcd for C$_{57}$H$_{86}$O$_9$N$_2$Si$_2$Na [M+Na]$^+$: 1021.5764. Found: 1021.5792.

(2Z,4E,6R,8R,9Z,12S,19Z,21E,23R,25R,26Z,29S)-12,29-Bis[(3R,4E)-3-{[tert-butyl(di-methyl)silyl]oxy}-2-methylhex-4-en-2-yl]-13,17,30,34-tetraoxa-35,36-diazapentacyclo[30.2.1.1$^{15,18}$.0$^{6,8}$.0$^{23,25}$]hexatriaconta-1 (35),2,4,9,15,18 (36),19,21,26,32-deca-ene-14,31-dione (90)

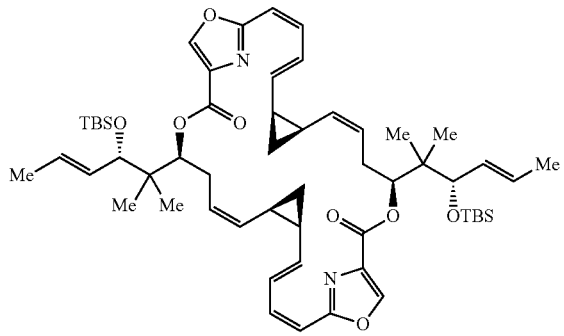 [SMILES: C/C=C/[C@H](O[Si](C)(C)C(C)(C)C)C(C)(C)[C@@H]1C/C=C\[C@H]2C[C@H]2/C=C/C=C\c2nc(co2)C(=O)O[C@H](C(C)(C)[C@H](/C=C/C)O[Si](C)(C)C(C)(C)C)C/C=C\[C@H]2C[C@H]2/C=C/C=C\c2nc(co2)C(=O)O1]

To a stirred solution of methyl ester 89 (14.5 mg, 0.015 mmol, 1.0 equiv) in THF (290 μL) was added a saturated solution of Ba(OH)$_2$.8 H$_2$O (137 mg in MeOH:H$_2$O, 3:2 v/v) at 23° C. and the reaction mixture was stirred for 3 h. Then, the resulting mixture was quenched by the addition of satd. aq. NH$_4$Cl solution (5 mL). After separation of the phases, the aqueous layer was extracted with EtOAc (4×10 mL) and the combined organic layers were dried over MgSO$_4$, filtered and concentrated under reduced pressure. The obtained residue was used in the next step without further purification.

To a stirred solution of the crude carboxylic acid in toluene (1.0 mL), was added a solution of 2,4,6-trichlorobenzoyl chloride (22 μL, 35 mg, 0.142 mmol, 10 equiv) and Et$_3$N (22 μL, 16 mg, 0.156 mmol, 11.0 equiv) in toluene (1.0 mL). The mixture was stirred for 1 h at 23° C. and it was diluted to reach a final concentration of 7.5 mM by the addition of toluene (4.4 mL). The latter reaction mixture was added over 5 h, via a syringe pump, to a solution of DMAP (6.9 mg, 57 μmol, 4.0 equiv) in toluene (2.6 mL) that was heated to 40° C. After the addition was completed, stirring was continued for 24 h before the reaction was quenched by the addition of saturated aq. NaHCO$_3$ solution (15 mL). Then, the aqueous layer was extracted with EtOAc (6×10 mL) and the combined organic extracts were dried over MgSO$_4$, filtered and concentrated under reduced pressure. The crude residue was purified by flash column chromatography (SiO$_2$, hexanes:EtOAc 3:1→7:3→13:7) to give titled compound 90 (1.5 mg, 4.2 μmol, 28% yield over two steps) as a colorless oil. 90: R$_f$=0.18 (hexanes:EtOAc, 3:1); [α]$_D^{25}$=−160.0 (c=0.15, CHCl$_3$); IR (film): ν$_{max}$=2956, 2928, 2855, 1740, 1630, 1142, 1060, 834, 774 cm$^{-1}$; $^1$H NMR (600 MHz, CDCl$_3$) δ 7.99 (s, 2H), 6.85 (dd, J=14.8, 11.6 Hz, 2H), 6.11 (t, J=11.7 Hz, 2H), 5.86 (d, J=11.8 Hz, 2H), 5.58-5.37 (m, 8H), 5.20 (dd, J=11.5, 2.2 Hz, 2H), 5.06 (t, J=10.8 Hz, 2H), 3.82 (d, J=7.9 Hz, 2H), 2.70 (q, J=12.2 Hz, 2H), 2.28-2.20 (m, 2H), 2.06 (ddd, J=14.0, 11.1, 6.8 Hz, 2H), 1.77-1.70 (m, 2H), 1.68 (d, J=5.7 Hz, 6H), 1.30-1.24 (m, 2H), 0.98 (s, 6H), 0.92 (s, 6H), 0.88 (s, 18H), 0.56 (q, J=5.5 Hz, 2H), −0.00 (s, 6H), −0.05 (s, 6H) ppm; $^{13}$C NMR (151 MHz, CDCl$_3$) δ 162.85, 160.27, 142.26, 141.98, 136.31, 133.98, 131.38 (2×), 128.27, 127.10, 126.23, 110.49, 79.31, 77.37, 42.64, 28.77, 26.12, 23.45, 20.52, 19.42, 18.60, 18.36, 18.01, 17.24, −3.37, −4.76 ppm; HR-MS (ESI-TOF): calcd for C$_{56}$H$_{82}$O$_8$N$_2$Si$_2$Na [M+Na]$^+$: 989.5502. Found: 989.5528.

(2Z,4E,6S,8R,9Z,12S,19Z,21E,23S,25R,26Z,29S)-12,29-Bis[(3S,4E)-3-hydroxy-2-methylhex-4-en-2-yl]-13,17,30,34-tetraoxa-35,36-diazapentacyclo[30.2.1.1$^{15,18}$.0$^{6,8}$.0$^{23,25}$]hexatriaconta-1 (35),2,4,9,15,18 (36),19,21,26,32-decaene-14,31-dione (84)

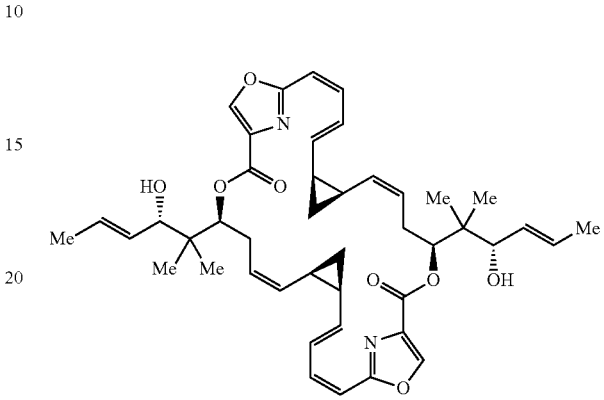

To a stirred solution of bis-silane 90 (2.0 mg, 2.1 μmol, 1.0 equiv) in DMF (70 μL) and H$_2$O (0.5 μL, 29 μmol, 14 equiv) was added TASF (2.9 mg, 10 μmol, 5.0 equiv) and the reaction mixture was heated at 40° C. and stirred for 48 h. The resulting mixture was purified through a small silica pad (10 cm, SiO$_2$, hexanes:EtOAc 1:1→0:1). The resulting fractions containing the desired products were combined, concentrated and purified again by flash column chromatography (SiO$_2$, hexanes:EtOAc 1:1→1:4→0:1) to yield the titled compound (1.5 mg, 2.0 μmol, 98% yield) as colorless oil. 84: R$_f$=0.23 (hexanes:EtOAc, 2:3); [α]$_D^{25}$=−74.7 (c=0.15, CHCl$_3$); IR (film): ν$_{max}$ 3428, 2924, 2854, 1736, 1629, 1556, 1323, 1145, 993, 757 cm$^{-1}$; $^1$H NMR (600 MHz, CDCl$_3$) δ 8.03 (s, 2H), 6.89 (dd, J=14.9, 11.6 Hz, 2H), 6.13 (t, J=11.7 Hz, 2H), 5.86 (d, J=11.7 Hz, 2H), 5.64 (dq, J=15.0, 6.3 Hz, 2H), 5.54 (ddd, J=15.1, 7.5, 1.6 Hz, 2H), 5.49 (td, J=11.4, 4.9 Hz, 2H), 5.43 (dd, J=14.8, 10.5 Hz, 2H), 5.33 (dd, J=11.5, 2.0 Hz, 2H), 5.10 (t, J=10.8 Hz, 2H), 3.85 (d, J=7.4 Hz, 2H), 3.35 (s, 2H), 2.73 (q, J=11.9 Hz, 2H), 2.31-2.24 (m, 2H), 2.13-2.07 (m, 2H), 1.82-1.74 (m, 2H), 1.70 (d, J=6.4 Hz, 6H), 1.30 (td, J=8.4, 4.9 Hz, 2H), 0.99 (s, 6H), 0.93 (s, 6H), 0.60 (q, J=5.5 Hz, 2H) ppm; $^{13}$C NMR (151 MHz, CDCl$_3$) δ 162.99, 160.92, 142.41, 142.38, 136.62, 133.47, 131.90, 129.71, 129.44, 126.62, 126.35, 110.28, 77.58, 76.78, 41.62, 28.22, 23.49, 19.57, 18.84, 18.62, 18.06, 17.31 ppm; HR-MS (ESI-TOF): calcd for C$_{44}$H$_{54}$O$_8$N$_2$Na [M+Na]$^+$: 761.3772. Found: 761.3778.

Methyl 2-[(tripropan-2-ylsilyl)ethynyl]-1,3-thiazole-4-carboxylate (91a)

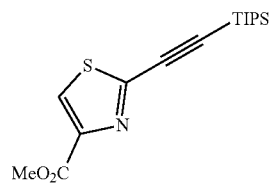

To a stirred degassed solution of bromide 91 (1.00 g, 4.50 mmol, 1.0 equiv) and ethynyltriisopropylsilane (4.96 mL, 4.03 g, 22.1 mmol, 5.0 equiv) in a 1:1 v/v mixture of DMF and Et$_3$N (10 mL) were added Pd(PPh$_3$)$_4$ (102 mg, 0.221 mmol, 0.05 equiv) and CuI (42 mg, 0.221 mmol, 0.05 equiv), the reaction mixture was degassed by bubbling Ar, sealed and heated to 60° C. for 16 h. Then, the resulting mixture was cooled to 23° C., partitioned between Et$_2$O (50 mL) and H$_2$O (50 mL). Extraction with Et$_2$O (2×50 mL) followed by drying over MgSO$_4$, filtration and concentration under reduced pressure gave the crude residue which was purified by flash column chromatography (SiO$_2$, hexanes:EtOAc, 9:1→8:1) gave thiazole 91a (1.31 g, 4.05 mmol, 90% yield) as a colorless liquid. 91a: R$_f$=0.55 (hexanes:EtOAc, 8:2), IR (film): v$_{max}$=2944, 2923, 2893, 2865, 1725, 1448, 1242, 1214, 1151, 1086, 994, 881, 779, 750, 677, 661 cm$^{-1}$; $^1$H NMR (600 MHz, CDCl$_3$) δ 8.16 (s, 1H), 3.96 (s, 3H), 1.17-1.12 (m, 3H), 1.13 (d, J=5.5 Hz, 18H) ppm; $^{13}$C NMR (151 MHz, CDCl$_3$) δ 161.50, 149.48, 147.14, 128.73, 100.28, 97.62, 52.79, 18.70, 11.29 ppm; HR-MS (ESI): calcd for C$_{16}$H$_{25}$NO$_2$SSiNa$^+$ [M+Na]$^+$: 364.1267. Found: 364.1273.

Methyl 2-ethynyl-1,3-thiazole-4-carboxylate (92)

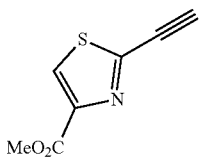

To a stirred solution of thiazole 91a (8.59 g, 26.6 mmol, 1.0 equiv) in THF (300 mL) at 0° C. was added AcOH (6.08 mL, 6.38 g, 106 mmol, 4.0 equiv) followed by TBAF (1 M in THF, 53.3 mL, 53.3 mmol, 2.0 equiv) and the reaction mixture was stirred at 0° C. for 1 h. Then, the resulting mixture was quenched with by addition of satd. aq. NH$_4$Cl (200 mL) extracted with Et$_2$O (3×250 mL), dried over MgSO$_4$, filtered and concentrated under reduced pressure. The crude residue was purified by flash column chromatography (SiO$_2$, hexanes:EtOAc, 17:3→1:1) gave thiazole 92 (4.18 g, 25.0 mmol, 94% yield) as a white amorphous solid. 92: R$_f$=0.21 (hexanes:EtOAc, 8:2), IR (film): v$_{max}$=3237, 3104, 2111, 1708, 1489, 1442, 1319, 1250, 1139, 988, 764 cm$^{-1}$; $^1$H NMR (600 MHz, CDCl$_3$) δ 8.20 (s, 1H), 3.97 (s, 3H), 3.51 (s, 1H) ppm; $^{13}$C NMR (151 MHz, CDCl$_3$) δ 161.31, 148.36, 147.42, 129.06, 83.56, 75.73, 52.82 ppm; HR-MS (ESI): calcd for C$_7$H$_5$NO$_2$SNa$^+$ [M+Na]$^+$: 189.9933. Found: 189.9933.

Methyl 2-[(Z)-2-bromoethenyl]-1,3-thiazole-4-carboxylate (93)

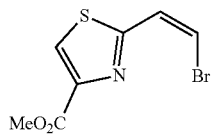

A dry round bottom flask equipped with a stir bar was charged with LiBr (16 mg, 0.18 mmol, 1.5 equiv) and LiOAc (36 mg, 0.54 mmol, 4.5 equiv) and the solids were dried by stirring at 70° C. under high vacuum for 1 h. Once the solids were cooled back to 25° C., AcOH (1 mL), and thiazole 92 (20 mg, 0.12 mmol, 1.0 equiv) were added and the sealed reaction was heated to 90° C. for 16 h. After cooling back to 23° C., the reaction was diluted with EtOAc (20 mL), washed with 1 M NaOH (2×10 mL), Na$_2$S$_2$O$_3$ (10 mL), brine (10 mL) and then dried over MgSO$_4$, filtered and concentrated under reduced pressure. The crude residue was purified by flash column chromatography (SiO$_2$, hexanes:EtOAc, 8:2→6:4) to give thiazole 93 (21 mg, 0.085 mmol, 71% yield) and the corresponding (E)-isomer (2 mg, 8.06 μmol, 7% yield) as white amorphous solids, respectively. 93: R$_f$=0.35 (hexanes:EtOAc, 7:3), IR (film): v$_{max}$=3118, 1722, 1614, 1496, 1437, 1298, 1260, 1243, 1135, 987, 726 cm$^{-1}$; $^1$H NMR (600 MHz, CDCl$_3$) δ 8.27 (s, 1H), 7.69 (d, J=8.1 Hz, 1H), 6.91 (d, J=8.1 Hz, 1H), 3.98 (s, 3H) ppm; $^{13}$C NMR (151 MHz, CDCl$_3$) δ 163.37, 161.99, 146.42, 127.96, 127.88, 112.93, 52.76 ppm; HR-MS (ESI): calcd for C$_7$H6BrNO$_2$SNa$^+$ [M+Na]$^+$: 269.9195. Found: 261.9197. Methyl 2-[(E)-2-bromoethenyl]-1,3-thiazole-4-carboxylate [(E)-isomer]: R$_f$=0.46 (hexanes:EtOAc, 7:3), IR (film): v$_{max}$=2953, 2924, 1724, 1596, 1498, 1457, 1343, 1324, 1245, 1217, 1094, 929 cm$^{-1}$; $^1$H NMR (600 MHz, CDCl$_3$) δ 8.12 (s, 1H), 7.37 (d, J=14.1 Hz, 1H), 7.32 (dd, J=14.1, 0.6 Hz, 1H), 3.96 (s, 3H) ppm; $^{13}$C NMR (151 MHz, CDCl$_3$) δ 164.55, 161.71, 147.65, 129.92, 127.27, 115.62, 52.76 ppm; HR-MS (ESI): calcd for C$_7$H$_6$BrNO$_2$SNa$^+$ [M+Na]$^+$: 269.9195. Found: 269.9200.

2-Ethynyl-1,3-thiazole-4-carboxylic acid (94)

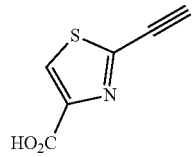

To a stirred solution of 35 (2.72 g, 16.3 mmol, 1.0 equiv) in THF:H$_2$O mixture (55:44 mL) at 23° C. was added LiOH hydrate (945 mg, 24.5 mmol, 1.5 equiv) and the reaction mixture was stirred for 1 h at 23° C. Then, aq. HCl (1 M, 40 mL) was added dropwise until the pH was <2 and the reaction mixture was extracted with EtOAc (5×75 mL), dried over MgSO$_4$, filtered and concentrated under reduced pressure to give the titered product (2.47 g, 16.1 mmol, 99% yield) as a white amorphous solid. 94: R$_f$=0.07 (hexanes:EtOAc, 1:1), IR (film): v$_{max}$=3287, 3094, 1675, 1455, 1245, 1098, 881, 848, 776, 666 cm$^{-1}$; $^1$H NMR (600 MHz, MeOD) δ 8.41 (s, 1H), 4.33 (s, 1H) ppm; $^{13}$C NMR (151 MHz, MeOD) δ 163.18, 149.91, 148.90, 130.89, 85.91, 76.24 ppm; HR-MS (CI): calcd for C$_6$H$_3$NO$_2$S$^+$ [M+H]$^+$: 152.9885. Found: 152.9884.

2-[(Z)-2-Bromoethenyl]-1,3-thiazole-4-carboxylic acid (95)

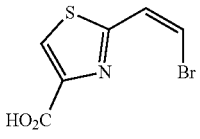 [SMILES: O=C(O)c1csc(/C=C\Br)n1]

A dry round bottom flask equipped with a stir bar was charged with LiBr (2.15 g, 24.2 mmol, 1.5 equiv) and LiOAc (4.85 g, 72.6 mmol, 4.5 equiv) and the solids were dried while stirring at 80° C. under high vacuum for 3 h. Once the solids were cooled back to 23° C., AcOH (66 mL), and thiazole 94 (2.47 g, 16.1 mmol, 1.0 equiv) were added and the sealed reaction was heated to 100° C. for 16 h. After cooling back to 23° C., the reaction was diluted with EtOAc (300 mL), washed with aq. NaOH (1 M, 2×100 mL), Na$_2$S$_2$O$_3$ (100 mL), brine (100 mL) and then dried over MgSO$_4$, filtered and concentrated under reduced pressure to give the thiazole 95 (2.86 mg, 12.2 mmol, 75% yield, >20:1 dr) as a white amorphous solid. 95: R$_f$=0.21 (EtOAc with 1% HCO$_2$H), IR (film): $v_{max}$=3104, 1673, 1482, 1438, 1375, 1300, 1269, 1236, 1101, 733 cm$^{-1}$; $^1$H NMR (600 MHz, MeOD) δ 8.44 (s, 1H), 7.65 (d, J=8.1 Hz, 1H), 7.16 (d, J=8.1 Hz, 1H) ppm; $^{13}$C NMR (151 MHz, MeOD) δ 164.77, 164.09, 148.20, 129.10, 128.30, 114.33 ppm; HR-MS (ESI): calcd for C$_6$H$_4$BrNO$_2$S$^+$ [M+H]$^+$: 233.9219. Found: 233.9215.

(3R,4E,6Z)-3-Methoxy-7-(tripropan-2-ylsilyl)hepta-4,6-dienoicacid (46a)

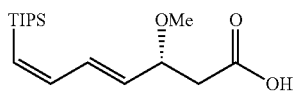

To a stirred solution of 46 (4.40 g, 9.65 mmol, 1.0 equiv) in THF:H$_2$O mixture (50:12 mL) at 0° C. was added LiOH hydrate (630 mg, 14.5 mmol, 1.5 equiv) and the reaction was allowed to warm up to 23° C. and stirred for 16 h. Then, aq. HCl (1 M, 15 mL) was added dropwise until the pH was <3 and the reaction mixture was extracted with EtOAc (5×75 mL), dried over MgSO$_4$, filtered and concentrated under reduced pressure. The residue was then filtered through a plug of silica (SiO$_2$, hexanes:EtOAc, 7:3 with 1% HCOOH→1:1 with 1% HCOOH) to give the crude product (4.16 g, contaminated with the auxiliary), which was used in the next step without further purification. A small aliquot was purified by preparative TLC for analytical purposes of 46a. 46a: colorless oil; R$_f$=0.75 (hexanes:EtOAc, 1:1), [α]$_D^{25}$=−12.0 (c=0.5, CHCl$_3$); IR (film): $v_{max}$=2941, 2892, 2865, 1714, 1566, 1464, 1301, 1079, 1000, 882, 666 cm$^{-1}$; $^1$H NMR (600 MHz, CDCl$_3$) δ 6.95 (dd, J=14.5, 11.1 Hz, 1H), 6.38 (dd, J=15.1, 11.1 Hz, 1H), 5.66 (d, J=14.4 Hz. 1H), 5.59 (dd, J=15.1, 7.8 Hz, 1H), 4.09 (td, J=8.1, 4.8 Hz, 1H), 3.30 (s, 3H), 2.65 (dd, J=15.6, 8.4 Hz, 1H), 2.55 (dd, J=15.6, 4.8 Hz, 1H), 1.16 (h, J=7.2 Hz, 3H), 1.06 (d, J=7.2 Hz, 18H) ppm; $^{13}$C NMR (151 MHz, CDCl$_3$) δ 174.98, 145.62, 135.18, 133.17, 130.16, 78.16, 56.64, 40.84, 18.92, 12.29 ppm; HR-MS (ESI): calcd for C$_7$H$_{32}$O$_3$SiNa$^+$ [M+Na]$^+$: 335.2013. Found: 335.2017.

(3R,4E,6Z)-3-Methoxy-7-(tripropan-2-ylsilyl)hepta-4,6-dienamide (96)

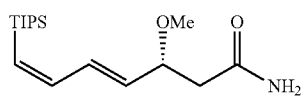

To a solution of the crude acid 46a (4.16 g) in Et$_2$O (140 mL) was added (COCl)$_2$ (2.53 mL, 3.74 g, 29.5 mmol, 3.0 equiv) followed by 2 drops of DMF at 0° C. after which the reaction mixture was allowed to warm to 23° C. and stirred for 1 h. Then, the volatiles were removed under reduced pressure and the residue was redissolved in DCM (100 mL) at 0° C. and then NH$_3$ (7 M in MeOH, 11 mL, 77 mmol, 8.0 equiv) was added. The reaction was then allowed to warm to 23° C. and stirred for 16 h before being diluted with brine (100 mL), extracted with CH$_2$Cl$_2$ (3×100 mL), dried over MgSO$_4$, filtered and concentrated under reduced pressure. The crude residue was purified by flash column chromatography (SiO$_2$, hexanes:EtOAc, 1:1→0:1) gave amide 96 (2.49 g, 7.99 mmol, 83% yield over three steps) as a colorless oil. 96: R$_f$=0.18 (hexanes:EtOAc, 1:1), [α]$_D^{25}$=+10.3 (c=1.0, CHCl$_3$); IR (film): $v_{max}$=3341, 3200, 2941, 2890, 2865, 1668, 1618, 1566, 1463, 1401, 1096, 1074, 999, 882, 665 cm$^{-1}$; $^1$H NMR (600 MHz, CDCl$_3$) δ 6.95 (dd, J=14.5, 11.1 Hz, 1H), 6.36 (dd, J=15.1, 11.1 Hz, 1H), 6.23 (s, 1H), 5.64 (d, J=14.5 Hz, 1H), 5.59 (dd, J=15.1, 7.7 Hz, 1H), 5.50 (s, 1H), 4.04 (td, J=7.8, 4.1 Hz, 1H), 3.30 (s, 3H), 2.50-2.37 (m, 2H), 1.15 (h, J=7.2, 6.8 Hz, 3H), 1.05 (d, J=7.3 Hz, 18H) ppm; $^{13}$C NMR (151 MHz, CDCl$_3$) δ 173.00, 145.69, 134.70, 133.56, 129.84, 78.62, 56.58, 42.57, 18.92, 12.28 ppm; HR-MS (ESI): calcd for C$_{17}$H$_{33}$NO$_2$SiNa$^+$ [M+Na]$^+$: 334.2173. Found: 334.2176.

(3R,4E,6Z)-3-Methoxy-7-(tripropan-2-ylsilyl)hepta-4,6-dienethioamide (97)

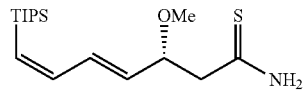

To a stirred solution of 96 (2.00 g, 6.42 mmol, 1.0 equiv) in THF (50 mL) at 23° C. was added Lawesson's reagent (1.81 g, 4.47 mmol, 0.7 equiv) and the reaction was stirred for 1 h. Then, the resulting mixture was diluted with brine (50 mL) extracted with Et$_2$O (3×50 mL), dried over MgSO$_4$, filtered and concentrated under reduced pressure. The crude residue was purified by flash column chromatography (SiO$_2$, hexanes:EtOAc, 8:2→6:4) to give thioamide 97 (1.97 g, 6.01 mmol, 94% yield) as a yellow oil. 97: R$_f$=0.44 (hexanes:EtOAc, 7:3), [α]$_D^{25}$=+44.4 (c=0.5, CHCl$_3$); IR (film): $v_{max}$=3306, 3177, 2941, 2891, 2865 1620, 1566, 1462, 1410, 1308, 1230, 1088, 998, 957, 882, 711, 665 cm$^{-1}$; $^1$H NMR (600 MHz, CDCl$_3$) δ 8.00 (br s, 1H), 7.47 (br s, 1H), 6.95 (dd, J=14.5, 11.1 Hz, 1H), 6.37 (dd, J=15.1, 11.2 Hz, 1H), 5.66 (d, J=14.4 Hz, 1H), 5.57 (dd, J=15.1, 7.5 Hz, 1H), 4.07 (td, J=8.0, 3.2 Hz, 1H), 3.31 (s, 3H), 3.01 (dd, J=15.3, 3.0 Hz, 1H), 2.90 (dd, J=15.3, 8.4 Hz, 1H), 1.21-1.11 (m, 3H), 1.06 (d, J=7.2 Hz, 18H) ppm; $^{13}$C NMR (151 MHz, CDCl$_3$) δ 13C NMR (151 MHz, CDCl$_3$) δ 207.00, 145.57, 135.01, 132.66, 130.23, 80.40, 56.64, 50.78, 18.96, 12.30 ppm; HR-MS (ESI): calcd for C$_7$H$_{33}$NOSSiNa$^+$ [M+Na]$^+$: 350.1944. Found: 350.1946.

Methyl 2-[(2R,3E,5Z)-2-methoxy-6-(tripropan-2-ylsilyl)hexa-3,5-dien-1-yl]-1,3-thiazole-4-carboxylate (99)

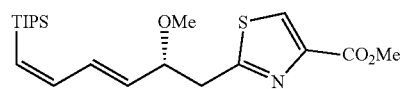

To a stirred solution of thioamide 97 (1.95 g, 5.95 mmol, 1.0 equiv) in acetone (30 mL) at −10° C. was added methylbromopyruvate (0.894 mL, 1.52 g, 8.40 mmol, 1.4 equiv) and the mixture was stirred for 2 h at −10° C. Then, the reaction mixture was quenched by addition of satd. aq. NaHCO$_3$ solution (50 mL), diluted with CHCl$_3$ (50 mL) and extracted with CH$_2$C2 (3×50 mL) followed by drying with MgSO$_4$ and concentrating under reduced pressure.

The crude residue was then dissolved in CH$_2$Cl$_2$ (50 mL) at −30° C. and pyridine (1.21 mL, 1.19 g, 15.0 mmol, 2.5 equiv) and TFAA (1.06 mL, 1.60 g, 7.63 mmol, 1.28 equiv) were added sequentially and the reaction mixture was allowed to warm to 23° C. over 2 h. Then, the resulting mixture was quenched by addition of satd. aq. NaHCO$_3$ solution (50 mL), extracted with CH$_2$Cl$_2$ (3×50 mL) followed by drying with MgSO$_4$ and concentrating under reduced pressure. The crude residue was purified by flash column chromatography (SiO$_2$, hexanes:EtOAc, 8:2→6:4) gave thiazole 99 (1.47 g, 3.59 mmol, 60% yield over two steps) as a light brown oil. 99: R$_f$=0.42 (hexanes:EtOAc, 7:3), [α]$_D^{25}$=+14.8 (c=1.0, CHCl$_3$); IR (film): ν$_{max}$=2941, 2890, 2864, 1740, 1721, 1483, 1463, 1238, 1208, 1093, 997, 882, 666 cm$^{-1}$; $^1$H NMR (600 MHz, CDCl$_3$) δ 8.09 (s, 1H), 6.94 (ddd, J=14.4, 11.2, 0.8 Hz, 1H), 6.33 (ddt, J=15.1, 11.1, 1.0 Hz, 1H), 5.63 (d, J=14.5 Hz, 1H), 5.61 (dd, J=15.1, 7.6 Hz, 2H), 4.03-3.96 (m, 1H), 3.95 (s, 3H), 3.31 (dd, J=10.2, 4.8 Hz, 1H), 3.29 (s, 3H), 3.25 (dd, J=15.0, 8.4 Hz, 1H), 1.12 (ddt, J=13.7, 8.5, 6.6 Hz, 3H), 1.03 (ap. t, J=6.8 Hz, 18H) ppm; $^{13}$C NMR (151 MHz, CDCl$_3$) δ 168.01, 162.13, 146.06, 145.73, 135.16, 133.65, 129.87, 128.39, 80.62, 56.57, 52.55, 39.89, 18.92, 12.28 ppm; HR-MS (ESI): calcd for C$_{21}$H$_{35}$NO$_3$SSiNa$^+$ [M+Na]$^+$: 432.1999. Found: 432.2006.

Methyl 2-[(2R,3E,5Z)-6-bromo-2-methoxyhexa-3,5-dien-1-yl]-1,3-thiazole-4-carboxylate (100)

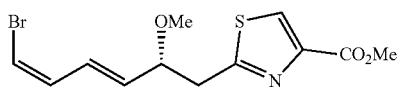

To a stirred solution of thiazole 99 (1.46 g, 3.56 mmol, 1.0 equiv) in HFIP (60 mL) at 0° C. that was protected from light with aluminium foil were sequentially added Ag$_2$CO$_3$ (998 mg, 3.62 mmol, 1.02 equiv) and NBS (803 mg, 4.51 mmol, 1.25 equiv) and the reaction mixture was stirred for 1.5 h at 0° C. in the dark. Then, the reaction mixture was quenched by the addition of water (200 mL) and satd. aq. Na$_2$S$_2$O$_3$ (50 mL), extracted with CH$_2$Cl$_2$ (3×150 mL), dried over MgSO$_4$, filtered and concentrated under reduced pressure. The crude residue was purified by flash column chromatography (SiO$_2$, hexanes:EtOAc, 7:3→3:7) to yield bromide 100 (0.620 g, 1.87 mmol, 52% yield) as a light brown oil. 100: R$_f$=0.34 (hexanes:EtOAc, 7:3), [α]$_D^{25}$=+56.0 (c=0.2, CHCl$_3$); IR (film): ν$_{max}$=2947, 2864, 2826, 1718, 1483, 1435, 1342, 1320, 1239, 1211, 1092, 980, 778, 755 cm$^{-1}$; $^1$H NMR (600 MHz, CDCl$_3$) δ 8.12 (s, 1H), 6.67-6.56 (m, 2H), 6.25-6.18 (m, 1H), 5.86-5.69 (m, 1H), 4.06 (td, J=8.0, 4.0 Hz, 1H), 3.95 (s, 3H), 3.37-3.28 (m, 4H), 3.26 (dd, J=15.0, 8.4 Hz, 1H) ppm; $^{13}$C NMR (151 MHz, CDCl$_3$) δ 167.75, 162.09, 146.05, 135.61, 131.54, 129.15, 128.49, 109.81, 80.48, 56.95, 52.58, 39.75 ppm; HR-MS (ESI): calcd for C$_{12}$H$_{14}$BrNO$_3$SNa$^+$ [M+Na]$^+$: 353.9770. Found: 353.9774.

Methyl 2-[(2R,3E,5Z,7Z,10S,12S,13E)-12-{[tert-butyl(dimethyl)silyl]oxy}-10-hydroxy-2-methoxy-11,11-dimethylpentadeca-3,5,7,13-tetraen-1-yl]-1,3-thiazole-4-carboxylate (101)

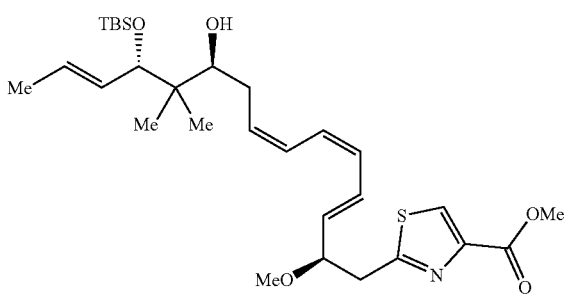 [SMILES: C/C=C/[C@H](O[Si](C)(C)C(C)(C)C)C(C)(C)[C@@H](O)C\C=C/C=C\C=C\[C@@H](Cc1nc(C(=O)OC)cs1)OC]

To a stirred solution of bromide 100 (100 mg, 0.301 mmol, 1.0 equiv) and boronic acid 20 (137 mg, 0.421 mmol, 1.4 equiv) in a 3:1 (v/v) mixture of THF:water (1.60 mL) was added thallium carbonate (706 mg, 1.51 mmol, 5.0 equiv) and the solution was degassed for 10 min by bubbling Ar through the mixture. Subsequently, Pd(dppf)Cl$_2$ (22 mg, 0.030 mmol, 0.01 equiv) was added and the reaction flask was stirred at 23° C. for 16 h shielded from light by aluminum foil. The reaction mixture was then filtered through a pad of Celite and the filtrate was concentrated under reduced pressure. The crude residue was purified by flash column chromatography (SiO$_2$, hexanes:EtOAc, 7:3) to yield compound 101 (100 mg, 0.182 mmol, 59% yield) as a colorless oil. 101: R$_f$=0.44 (hexanes:EtOAc, 7:3), [α]$_D^{25}$=+5.5 (c=1.0, CHCl$_3$); IR (film): ν$_{max}$=3463, 2955, 2929, 2856, 1725, 1471, 1249, 1214, 1093, 1051, 1002, 972, 836, 776 cm$^{-1}$; $^1$H NMR (600 MHz, CDCl$_3$) 8.10 (s, 1H), 6.72 (dd, J=15.2, 11.3 Hz, 1H), 6.52 (t, J=11.2 Hz, 1H), 6.30 (t, J=11.4 Hz, 1H), 5.99 (t, J=11.1 Hz, 1H), 5.77 (dt, J=10.6, 7.5 Hz, 1H), 5.62-5.48 (m, 3H), 4.32 (br. s, 1H), 4.01 (td, J=8.0, 4.4 Hz, 1H), 3.94 (s, 3H), 3.85 (d, J=6.9 Hz, 1H), 3.71 (dd, J=9.7, 3.0 Hz, 1H), 3.34-3.29 (m, 1H), 3.30 (s, 3H), 3.25 (dd, J=15.1, 8.3 Hz, 1H), 2.38-2.19 (m, 2H), 1.71 (d, J=5.2 Hz, 3H), 1.00 (s, 3H), 0.88 (s, 9H), 0.75 (s, 3H), 0.07 (s, 3H), 0.01 (s, 3H) ppm; $^{13}$C NMR (151 MHz, CDCl$_3$) δ 168.08, 162.13, 146.01, 132.36, 132.16, 130.25, 129.06, 128.89, 128.42, 127.77, 125.95, 124.39, 84.67, 80.79, 76.25, 56.68, 52.53, 41.05, 40.06, 30.23, 25.98, 22.88, 19.81, 18.15, 17.88, −3.82, −4.96 ppm; HR-MS (ESI): calcd for C$_{29}$H$_{47}$NO$_5$SSiNa$^+$ [M+Na]$^+$: 572.2836. Found: 572.2834.

175

(2E,4R,6S,8Z,10Z,12E,14R)-4-{[tert-Butyl(dimethyl)silyl]oxy}-14-methoxy-15-[4-(methoxy-carbonyl)-1,3-thiazol-2-yl]-5,5-dimethylpentadeca-2,8,10,12-tetraen-6-yl 2-[(Z)-2-bromoethenyl]-1,3-thiazole-4-carboxylate (102)

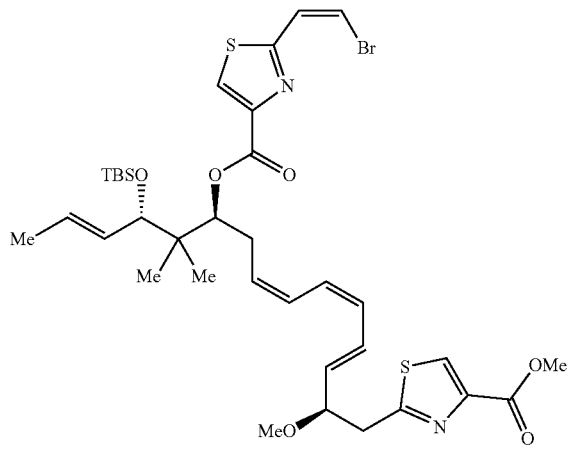 [SMILES: C/C=C/[C@H](O[Si](C)(C)C(C)(C)C)C(C)(C)[C@H](C\C=C/C=C\C=C\[C@@H](Cc1nc(C(=O)OC)cs1)OC)OC(=O)c1csc(/C=C\Br)n1]

To a stirred solution of compound 101 (90 mg, 0.164 mmol, 1.0 equiv) and acid 38 (46 mg, 0.197 mmol, 1.2 equiv) in toluene (5 mL) at 23° C. was added Et$_3$N (0.14 mL, 0.102 g, 1.00 mmol, 6.0 equiv) and DMAP (0.157 g, 1.29 mmol, 8.0 equiv) and the solution was cooled to 0° C. before 2,4,6-trichlorobenzoyl chloride (77 µL, 120 mg, 0.493 mmol, 3.0 equiv) was added dropwise. Then, the reaction mixture was allowed to warm to 23° C. and stirred for 3 h before being quenched by the addition of satd. aq. NaHCO$_3$ (10 mL). The aqueous layer was extracted with EtOAc (3×20 mL) and the combined organic extracts were dried over MgSO$_4$, filtered and concentrated under reduced pressure. The crude residue was purified by flash column chromatography (SiO$_2$, hexanes:EtOAc 7:3) to yield bromide 102 (109 mg, 0.142 mmol, 87% yield) as a colorless oil. 102: R$_f$=0.27 (hexanes:EtOAc, 7:3), [α]$_D^{25}$=−59.4 (c=0.5, CHCl$_3$); IR (film): ν$_{max}$=2954, 2928, 2885, 1733, 1471, 1303, 1240, 1210, 1093, 1056, 973, 858, 836, 776, 748 cm$^{-1}$; $^1$H NMR (600 MHz, CDCl$_3$) δ 8.09 (s, 1H), 8.08 (s, 1H), 7.68 (d, J=8.2 Hz, 1H), 6.87 (d, J=8.2 Hz, 1H), 6.59 (dd, J=15.2, 11.3 Hz, 1H), 6.39 (t, J=11.4 Hz, 1H), 6.26 (t, J=11.3 Hz, 1H), 5.95 (t, J=11.1 Hz, 1H), 5.58-5.50 (m, 3H), 5.26 (dd, J=9.8, 3.3 Hz, 1H), 3.97 (dd, J=8.0, 4.1 Hz, 1H), 3.94 (s, 3H), 3.86 (d, J=7.4 Hz, 1H), 3.33-3.27 (m, 1H), 3.26 (s, 3H), 3.21 (dd, J=15.1, 8.3 Hz, 1H), 2.66 (dt, J=15.4, 9.2 Hz, 1H), 2.60-2.47 (m, 1H), 1.67 (d, J=5.0 Hz, 3H), 0.99 (s, 3H), 0.96 (s, 3H), 0.87 (s, 9H), −0.02 (s, 3H), −0.05 (s, 3H) ppm; $^{13}$C NMR (151 MHz, CDCl$_3$) δ 168.01, 162.98, 162.14, 160.73, 147.00, 146.00, 132.56, 131.39, 130.00, 128.72, 128.44, 128.33, 128.16, 126.97, 125.45, 125.36, 112.44, 80.64, 79.35, 78.27, 56.74, 52.53, 43.04, 40.02, 28.73, 26.11, 20.44, 19.61, 18.34, 17.92, −3.38, −4.77 ppm; HR-MS (ESI): calcd for C$_{35}$H$_{49}$BrN$_2$O$_6$S$_2$Si$^+$ [M+H]$^+$: 765.2057. Found: 765.2060.

176

Methyl 2-{(2R,3E,5Z,7Z,10S,12R,13E)-12-{[tert-butyl(dimethyl)silyl]oxy}-10-[({2-[(1Z,3E)-4-{(1S,2R)-2-[(1Z,4S,6R,7E)-6-{[tert-butyl(dimethyl)silyl]oxy}-4-hydroxy-5,5-dimethylnona-1,7-dien-1-yl]cyclopropyl}buta-1,3-dien-1-yl]-1,3-thiazol-4-yl}carbonyl)oxy]-2-methoxy-11,11-dimethylpentadeca-3,5,7,13-tetraen-1-yl}-1,3-thiazole-4-carboxylate (103)

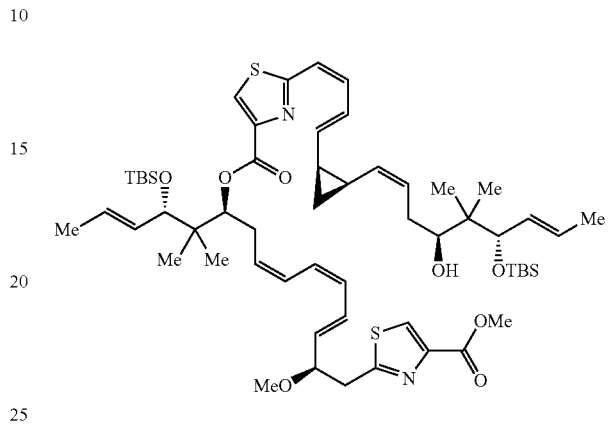

A stirred solution of bromide 102 (100 mg, 0.131 mmol, 1.0 equiv), stannane 20 (112 mg, 0.171 mmol, 1.3 equiv), CuI (106 mg, 0.557 mmol, 4.25 equiv), AsPh$_3$ (81 mg, 0.264 mmol, 2.0 equiv) and Pd$_2$(dba)$_3$ (61 mg, 0.067 mmol, 0.5 equiv) in DMF (1.3 mL) degassed three times with Ar by the freeze-pump-thaw method was stirred at 23° C. for 3 h after which the reaction mixture was filtered through a pad of Celite, diluted with EtOAc (15 mL), washed three times with brine (3×10 mL) and then the combined aqueous layers were reextracted with EtOAc (2×20 mL). The combined organic layers were dried over MgSO$_4$, filtered and concentrated under reduced pressure. The crude residue was purified by flash column chromatography (SiO$_2$, hexanes:EtOAc 17:3→7:3) to give compound 103 (129 mg, 0.123 mmol, 94% yield) as a light brown oil. 103: R$_f$=0.41 (hexanes:EtOAc, 7:3), [α]$_D^{25}$=−16.5 (c=0.2, CHCl$_3$); IR (film): ν$_{max}$=3480, 2956, 2929, 2856, 1721, 1627, 1471, 1246, 1209, 1093, 1055, 1003, 972, 857, 836, 776 cm$^{-1}$; $^1$H NMR (600 MHz, CD$_3$CN) δ 8.07 (s, 1H), 8.06 (s. 1H), 7.57 (dd, J=15.1, 11.4 Hz, 1H), 6.60 (dd, J=15.2, 11.4 Hz, 1H), 6.43-6.34 (m, 2H), 6.31-6.23 (m, 2H), 5.94-5.82 (m, 2H), 5.57-5.43 (m, 6H), 5.18-5.07 (m, 2H), 3.96 (ap. t, J=7.6 Hz, 2H), 3.91 (d, J=8.4 Hz, 1H), 3.79 (s, 3H), 3.54-3.43 (m, 2H), 3.16 (s, 3H), 3.15-3.12 (m, 1H), 2.63-2.54 (m, 1H), 2.54-2.47 (m, 1H), 2.27 (dd, J=14.6, 7.4 Hz, 2H), 2.10-1.92 (m, 2H), 1.88-1.80 (m, 1H), 1.65-1.58 (m, 6H), 1.25 (td, J=8.2, 4.5 Hz, 1H), 0.94 (s, 3H), 0.91 (s, 3H), 0.81 (s, 9H), 0.81 (s, 9H), 0.69 (ap. p, J=5.9 Hz, 1H), 0.00 (s, 3H), −0.06 (s, 3H), −0.08 (s, 3H), −0.10 (s, 3H) ppm; $^{13}$C NMR (151 MHz, CD$_3$CN) δ168.71, 166.20, 162.66, 161.63, 148.69, 146.72, 144.83, 135.75, 134.09, 132.15, 131.66, 130.97, 130.65, 130.03, 129.56, 129.50, 129.44, 129.33, 129.31, 128.46, 128.07, 126.22, 126.13, 117.36, 82.80, 81.22, 79.74, 78.42, 76.85, 56.71, 52.61, 43.70, 42.20, 40.18, 30.91, 29.27, 26.38, 26.25, 23.69, 21.52, 20.31, 20.29, 19.79, 19.54, 18.82, 18.68, 17.88, 17.86, 17.22, −3.21, −3.52, −4.67, −4.76 ppm; HR-MS (ESI): calcd for C$_{57}$H$_{88}$N$_2$O$_8$S$_2$Si$_2^+$ [M+H]+: 1049.5593. Found: 1049.5603.

(2Z,4E,6S,8R,9Z,12S,20R,21E,23Z,25Z,28S)-12-
[(3R,4E)-3-{[tert-Butyl(dimethyl)silyl]oxy}-2-methylhex-4-en-2-yl]-28-[(3S,4E)-3-{[tert-butyl(dimethyl)silyl]oxy}-2-methylhex-4-en-2-yl]-20-
methoxy-13,29-dioxa-17,33-dithia-34,35-
diazatetracyclo[29.2.1.1$^{15,18}$.0$^{6,8}$]penta-triaconta-1
(34),2,4,9,15,18 (35),21,23,25,31-decaene-14,30-
dione (104)

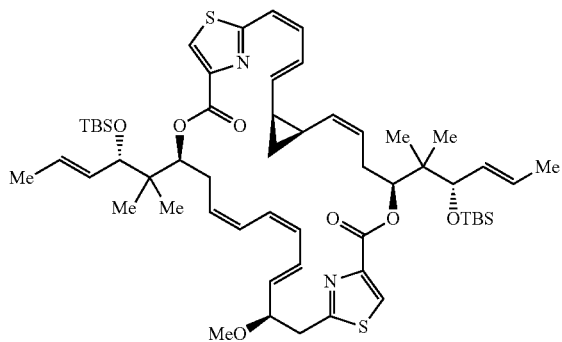 [SMILES: C/C=C/[C@H](O[Si](C)(C)C(C)(C)C)C(C)(C)[C@@H]1C\C=C/C=C\C=C\[C@H](OC)Cc2nc(cs2)C(=O)O[C@H](C(C)(C)[C@H](/C=C/C)O[Si](C)(C)C(C)(C)C)C/C=C\[C@H]2C[C@H]2/C=C/C=C\c2nc(cs2)C(=O)O1]

To a stirred solution of 103 (60 mg, 57.2 μmol, 1.0 equiv) in THF (2 mL) at 23° C. was added dropwise satd. solution of barium hydroxide octahydrate [0.56 mL, MeOH:H$_2$O 3:2 (v/v)]. The reaction mixture was stirred for 3 h before being quenched by the addition of satd. aq. NH$_4$Cl (10 mL) and the aqueous phase was extracted EtOAc (4×20 mL). The combined organic extracts were dried over MgSO$_4$, filtered and concentrated under reduced pressure. The residue was used crude in the next reaction. To a stirred solution of the crude carboxylic acid in toluene (2.4 mL), was added a solution of 2,4,6-trichlorobenzoyl chloride (92 μL, 144 mg, 0.590 mmol, 10.0 equiv) in toluene (1.0 mL) and a solution of Et$_3$N (90 μL, 0.65 mmol, 11.0 equiv) in toluene (1.0 mL). The mixture was stirred 1 h at 23° C. and then the resulting mixture was diluted by the addition of toluene (5.0 mL) and added over 3 h, via a syringe pump, to a solution of DMAP (30 mg, 0.24 mmol, 4.0 equiv) in toluene (10 mL) heated at 30° C. After the addition was completed, stirring was continued for 16 h before the reaction was quenched by the addition of satd. aq. NaHCO$_3$ (20 mL). The aqueous layer was extracted with EtOAc (4×20 mL), the combined organic extracts were dried over MgSO$_4$, filtered and concentrated under reduced pressure. The crude residue was purified by flash column chromatography (SiO$_2$, hexanes:EtOAc 17:3→7:3) to give compound 104 (24 mg, 23.6 μmol, 41% yield over two steps) as a colorless oil. 104: R$_f$=0.40 (hexanes:EtOAc, 7:3), [α]$_D^{25}$=−65.3 (c=1.0, CHCl$_3$; IR (film): ν$_{max}$=2956, 2928, 2856, 1732, 1627, 1471, 1386, 1361, 1248, 1199, 1094, 1055, 996, 972, 858, 836, 775 cm$^{-1}$; $^1$H NMR (600 MHz, CDCl$_3$) δ 7.92 (s, 1H), 7.83 (s, 1H), 6.74-6.66 (m, 1H), 6.47 (d, J=11.8 Hz, 1H). 6.42-6.33 (m, 2H), 6.31-6.23 (m, 1H), 6.22-6.14 (m, 1H), 5.89 (t, J=11.0 Hz, 1H), 5.61 (dd, J=15.2, 8.2 Hz, 1H), 5.57-5.49 (m, 4H), 5.43 (td, J=10.8, 4.8 Hz, 1H), 5.23 (ddd, J=16.2, 11.1, 2.6 Hz, 2H), 5.06 (t, J=10.7 Hz, 1H), 3.86-3.84 (m, 2H), 3.41 (dd, J=15.2, 4.8 Hz, 1H), 3.19 (s, 3H), 2.99 (dd, J=15.2, 5.7 Hz, 1H), 2.84-2.68 (m, 2H), 2.36-2.26 (m, 2H), 2.13-2.06 (m, 1H), 1.75 (dtd, J=10.3, 8.3, 5.6 Hz, 1H), 1.70-1.65 (m, 6H), 1.67-1.60 (m, 1H), 1.43 (d, J=5.7 Hz, 1H), 1.39-1.31 (m, 1H), 1.32-1.26 (m, 1H), 1.01 (s, 3H), 1.00 (s, 3H), 0.99 (s, 3H), 0.95 (s, 3H), 0.88 (s, 9H) 0.87 (s, 9H), 0.59 (ap. q, J=5.6 Hz, 1H), 0.01 (s, 3H), 0.00 (s, 3H), −0.04 (s, 3H), −0.05 (s, 3H) ppm; $^{13}$C NMR (151 MHz, CDCl$_3$) δ 166.60, 164.31, 160.96, 160.32, 146.89, 146.67, 143.11, 134.20, 132.99, 131.44, 130.54, 130.40, 128.54, 128.24, 127.42, 126.98, 126.59, 126.26, 125.75, 125.37, 118.97, 80.30, 79.61, 79.38, 77.65, 56.82, 42.74, 42.71, 40.60, 29.86, 28.92, 28.90, 28.00, 27.00, 26.12, 23.35, 20.79, 20.49, 19.67, 19.49, 19.41, 18.36, 17.98, 17.93, 17.68, 17.29, 13.76, −3.37, −3.38, −4.73, −4.75 ppm; HR-MS (ESI): calcd for C$_{56}$H$_{84}$N$_2$O$_7$S$_2$Si$_2$Na$^+$ [M+Na]$^+$: 1039.5151. Found: 1039.5164.

(2Z,4E,6S,8R,9Z,12S,20R,21E,23Z,25Z,28S)-12,28-
Bis[(3S,4E)-3-hydroxy-2-methylhex-4-en-2-yl]-20-
methoxy-13,29-dioxa-17,33-dithia-34,35-diazatetra-
cyclo[29.2.1.1$^{15,18}$.0$^{6,8}$]penta-triaconta-1 (34),2,4,9,
15,18 (35),21,23,25,31-decaene-14,30-dione (85)

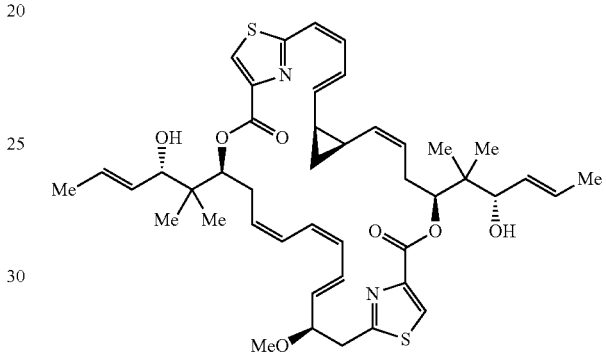

To a stirred solution of compound 104 (24 mg, 23.6 mol, 1.0 equiv) in degassed MeOH (5 mL), in a plastic Falcon™ tube, was added hexafluorosilicic acid (33.5-35%, 0.60 mL, 1.80 mmol, 33-35% in water, 75 equiv) dropwise at 0° C. and the tube was covered with aluminium foil. The resulting mixture was allowed to warm to 23° C. over 1 h and then stirred for 16 h. The resulting mixture was then diluted with EtOAc (30 mL), followed by the addition of a satd. aq. NaHCO$_3$ (30 mL). The aqueous layer was extracted with EtOAc (3×10 mL) and the combined organic extracts were dried over MgSO$_4$, filtered and concentrated under reduced pressure. The crude residue was purified by flash column chromatography (SiO$_2$, hexanes:EtOAc 1:1→0:1) to yield compound 85 (8.0 mg, 10.1 μmol, 43% yield) as a white amorphous solid. 85: R$_f$=0.48 (hexanes:EtOAc, 3:7), [α]$_D^{25}$=−106.8 (c=0.25, MeOH); IR (film): ν$_{max}$=3419, 2926, 2854, 1722, 1626, 1464, 1381, 1209, 1094, 971, 744 cm$^{-1}$; $^1$H NMR (600 MHz, CDCl$_3$) δ 7.98 (s, 1H), 7.91 (s, 1H), 6.75 (dd, J=14.4, 12.0 Hz, 1H). 6.49 (d, J=11.7 Hz, 1H), 6.47-6.39 (m, 2H), 6.34 (t, J=11.1 Hz, 1H), 6.26 (t, J=11.9 Hz, 1H), 5.96 (t, J=11.0 Hz, 1H), 5.71-5.62 (m, 2H), 5.64-5.55 (m, 2H), 5.57-5.49 (m, 1H), 5.46 (td, J=10.7, 4.8 Hz, 1H), 5.35 (dd, J=11.3, 2.3 Hz, 1H), 5.28 (dd, J=10.9, 2.4 Hz, 1H), 5.17-5.10 (m, 1H), 3.94 (d, J=7.3 Hz, 1H), 3.91-3.84 (m, 2H), 3.37-3.30 (m, 1H), 3.20 (s, 3H), 3.11 (dd, J=15.2, 6.3 Hz, 1H), 2.89-2.77 (m, 2H), 2.53 (d, J=40 Hz, 1H), 2.38-2.29 (m, 1H), 2.20-2.11 (m, 1H), 1.83-1.74 (m, 1H), 1.71 (dd, J=6.3, 1.5 Hz, 3H), 1.69 (dd, J=6.4, 1.5 Hz, 3H), 1.35 (dt, J=8.4, 4.2 Hz, 1H), 1.01 (s, 3H), 0.98 (s, 3H), 0.98 (s, 3H), 0.95 (s, 3H), 0.88 (t, J=6.9 Hz, 1H), 0.64 (ap. q, J=5.6 Hz, 1H) ppm; $^{13}$C NMR (151 MHz, CDCl$_3$) δ 167.20, 164.67, 161.81, 161.28, 146.14, 145.96, 143.50, 134.51, 133.20, 131.15, 129.85, 129.59, 129.55, 129.38, 129.05, 128.87, 128.55, 128.02, 127.14, 126.87, 126.86, 125.73, 125.43, 118.95, 80.67, 79.33, 77.94, 76.48, 76.35, 56.87, 41.82, 41.74, 40.51, 29.86, 28.30, 23.39, 20.05, 19.59, 19.37, 19.09, 18.69, 18.08, 18.05, 17.36 ppm; $^1$H NMR (600 MHz, CD$_3$CN) δ 8.15 (s, 1H), 8.12 (s, 1H), 6.88-6.71 (m, 1H), 6.52-6.41 (m, 2H), 6.39 (d, J=11.4 Hz, 2H), 6.30-6.22 (m, 1H), 5.95 (t, J=10.8 Hz, 1H), 5.74-5.55 (m, 5H), 5.42 (td, J=10.8, 4.7 Hz, 1H), 5.27 (ddd, J=18.3, 11.3, 2.4 Hz, 2H), 5.16 (t, J=10.8 Hz, 1H), 3.96 (dt, J=9.1, 4.9 Hz, 1H), 3.87-3.84 (m, 2H), 3.36 (dd, J=14.9, 4.8 Hz, 1H), 3.14 (s, 3H), 2.94-2.86 (m, 2H), 2.84-2.79 (m, 2H), 2.38-2.30 (m, 1H), 1.86 (dtd, J=10.9, 8.4, 5.8 Hz, 1H), 1.72-1.70 (m, 3H), 1.70-1.68 (m, 3H), 1.02 (s, 3H), 0.99 (s, 3H), 0.99 (s, 3H), 0.96 (s, 3H), 0.67-0.54 (m, 1H) ppm; $^{13}$C NMR (151 MHz, CD$_3$CN) 167.58, 164.81, 161.83, 161.21, 147.02, 146.81, 144.46, 134.72, 134.34, 132.04, 131.71, 131.62, 131.00, 129.36, 129.34, 129.30, 129.07, 128.85, 128.79, 127.49, 127.47, 126.60, 126.08, 119.37, 80.69, 78.30, 77.66, 77.04, 76.96, 56.69, 42.45, 42.41, 41.42, 29.02, 28.97, 24.09, 20.21, 19.53, 19.35, 19.23, 19.20, 18.00, 17.99 ppm; HR-MS (ESI): calcd for C$_{44}$H$_{56}$N$_2$O$_7$S$_2$Na$^+$ [M+Na]$^+$: 811.3421. Found: 811.3444.

Methyl 2-[(1Z,3E)-4-{(1S,2R)-2-[(1Z,4S,6S,7E)-6-{[tert-butyl(dimethyl)silyl]oxy}-4-hydroxy-5,5-dimethylnona-1,7-dien-1-yl]cyclopropyl}buta-1,3-dien-1-yl]1,3-thiazole-4-carboxylate (105)

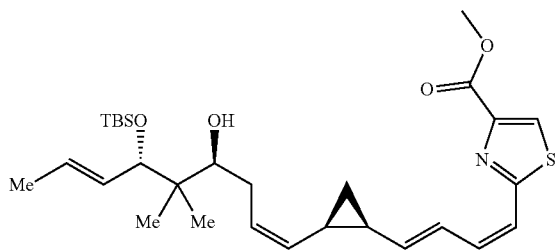 [SMILES: C/C=C/[C@H](O[Si](C)(C)C(C)(C)C)C(C)(C)[C@@H](O)C/C=C\[C@H]1C[C@H]1/C=C/C=C\c1nc(C(=O)OC)cs1]

To a stirred and degassed solution of vinyl stannane 40 (100 mg, 0.153 mmol, 1.0 equiv) and oxazole 36 (38 mg, 0.153 mmol, 1.0 equiv) in NMP (0.77 mL) at 23° C., was added CuTc (44 mg, 0.229 mmol, 1.5 equiv). The resulting mixture was stirred for 1 h at 23° C. and was directly purified by flash column chromatography (SiO$_2$, hexanes:EtOAc 9:1→4:1) to yield alcohol 105 (68 mg, 0.128 mmol, 84% yield) as a pale yellow oil. 105: R$_f$=0.52 (hexanes:EtOAc, 3:1); [α]$_D^{25}$=+44.5 (c=1.0, CHCl$_3$); IR (film): ν$_{max}$=3480, 2956, 2930, 2857, 1741, 1722, 1626, 1471, 1245, 1211, 1069, 836, 776 cm$^{-1}$; $^1$H NMR (600 MHz, CDCl$_3$) δ 8.11 (s, 1H), 7.32-7.20 (m, 1H), 6.49-6.38 (m, 2H), 5.86 (dd, J=14.8, 9.4 Hz, 1H), 5.70 (dt, J=11.3, 7.2 Hz, 1H), 5.61-5.49 (m, 2H), 5.23 (t, J=9.9 Hz, 1H), 4.19 (s, 1H), 3.95 (s, 3H), 3.86 (d, J=6.2 Hz, 1H), 3.74-3.66 (m, 1H), 2.31 (dd, J=14.8, 7.4 Hz, 1H), 2.16 (ddd, J=15.3, 9.4, 6.7 Hz, 1H), 1.99 (p, J=8.2 Hz, 1H), 1.95-1.88 (m, 1H), 1.71 (d, J=4.5 Hz, 3H), 1.33 (td, J=8.2, 4.9 Hz, 1H), 0.97 (s, 3H), 0.87 (d, J=1.7 Hz, 9H), 0.75 (s, 3H), 0.73 (q, J=5.7 Hz, 1H), 0.05 (s, 3H), 0.00 (s, 3H) ppm; $^{13}$C NMR (151 MHz, CDCl$_3$) δ 165.69, 162.16, 146.99, 143.96, 135.42, 130.41, 129.84, 129.10, 128.75, 126.95, 126.66, 117.71, 84.39, 76.40, 52.56, 41.08, 30.29, 25.98, 22.91, 22.70, 19.78, 19.46, 18.14, 17.87, 16.87, -3.81, -4.96 ppm; HR-MS (ESI-TOF): calcd for C$_{29}$H$_{45}$O$_4$NSSiNa$^+$ [M+Na]$^+$: 554.2731. Found: 554.2733.

(1Z,4S,6R,7E)-6-{[tert-Butyl(dimethyl)silyl]oxy}-1-[(1R,2S)-2-{(1E,3Z)-4-[4-(methoxycarbonyl)-1,3-thiazol-2-yl]buta-1,3-dien-1-yl}cyclopropyl]-5,5-dimethylnona-1,7-dien-4-yl 2-[(Z)-2-bromoethenyl]-1,3-thiazole-4-carboxylate (106)

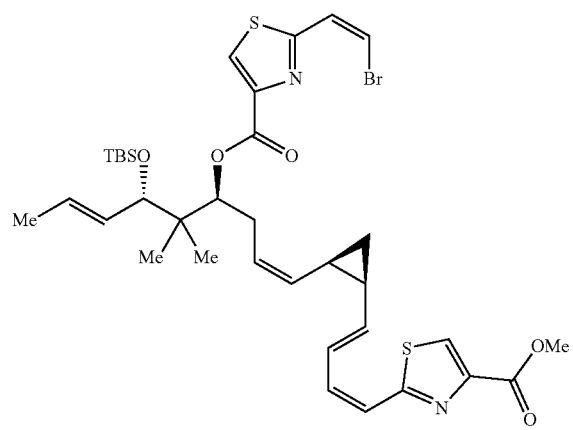 [SMILES: C/C=C/[C@H](O[Si](C)(C)C(C)(C)C)C(C)(C)[C@H](C/C=C\[C@H]1C[C@H]1/C=C/C=C\c1nc(C(=O)OC)cs1)OC(=O)c1csc(/C=C\Br)n1]

To a stirred solution of alcohol 105 (0.060 g, 0.113 mmol, 1.0 equiv) and carboxylic acid 38 (53 mg, 0.226 mmol, 2.0 equiv) in toluene (1.13 mL) was added Et$_3$N (0.094 mL, 0.677 mmol, 6.0 equiv) and DMAP (0.110 g, 0.903 mmol, 8.0 equiv). The solution was cooled to 0° C. and 2,4,6-trichlorobenzoyl chloride (0.088 mL, 0.56 mmol, 3.0 equiv) was added dropwise before the reaction mixture was allowed to warm to 23° C. Upon complete consumption of the starting material (about 1 h), the reaction was purified by flash column chromatography directly (SiO$_2$, hexanes:EtOAc 4:1→7:3) to yield vinyl bromide 106 (76 mg, 0.102 mmol, 90% yield) as a white film. 106: R$_f$=0.26 (hexanes:EtOAc, 3:1); [α]$_D^{25}$=+52.3 (c=1.0, CHCl$_3$); IR (film): ν$_{max}$=2953, 2855, 1734, 1626, 1471, 1432, 1303, 1242, 1211, 1092, 1057, 972, 836, 775, 743 cm$^{-1}$; $^1$H NMR (600 MHz, CDCl$_3$) δ 8.11 (s, 1H), 8.08 (s, 1H), 7.62 (d, J=8.1 Hz, 1H), 7.07 (dd, J=14.7, 11.4 Hz, 1H), 6.78 (d, J=8.1 Hz, 1H), 6.35 (d, J=11.7 Hz, 1H), 6.28 (t, J=11.6 Hz, 1H), 5.65 (dd, J=14.7, 9.7 Hz, 1H), 5.54-5.45 (m, 3H), 5.25 (dd, J=10.1, 3.1 Hz, 1H), 5.11 (t, J=10.2 Hz, 1H), 3.96 (s, 3H), 3.85 (d, J=7.0 Hz, 1H), 2.61 (dt, J=15.0, 9.4 Hz, 1H), 2.54-2.45 (m, 1H), 2.01 (p, J=8.7 Hz, 1H), 1.81 (qd, J=8.5, 5.6 Hz, 1H), 1.65 (d, J=4.5 Hz, 3H), 1.30 (td, J=8.2, 4.8 Hz, 1H), 0.99 (s, 3H), 0.95 (s, 3H), 0.86 (s, 9H), 0.67 (q, J=5.6 Hz, 1H), -0.03 (s, 3H), -0.06 (s, 3H) ppm; $^3$C NMR (151 MHz, CDCl$_3$) δ 165.61, 162.94, 162.14, 160.71, 147.15, 147.02, 143.36, 135.25, 131.47, 130.47, 128.28, 128.07, 127.55, 126.96, 126.78, 126.48, 117.71, 112.29, 79.33, 78.36, 52.57, 42.95, 28.70, 26.09, 23.02, 20.43, 19.54, 19.27, 18.33, 17.90, 16.93, -3.39, -4.79 ppm; HR-MS (ESI-TOF): calcd for C$_{35}$H$_{47}$O$_5$N$_2$BrS$_2$Si [M+Na]$^+$: 769.1771. Found: 169.1777.

181

Methyl 2-{(1Z,3E)-4-[(1S,2R)-2-{(1Z,4S,6R,7E)-6-{[tert-butyl(dimethyl)silyl]oxy}-4-[({2-[(1Z,3E)-4-{(1S,2R)-2-[(1Z,4S,6R,7E)-6-{[tert-butyl(dimethyl)silyl]oxy}-4-hydroxy-5,5-dimethylnona-1,7-dien-1-yl]cyclopropyl}buta-1,3-dien-1-yl]-1,3-thiazol-4-yl}carbonyl)oxy]-5,5-dimethylnona-1,7-dien-1-yl}cyclopropyl]buta-1,3-dien-1-yl}-1,3-thiazole-4-carboxylate (107)

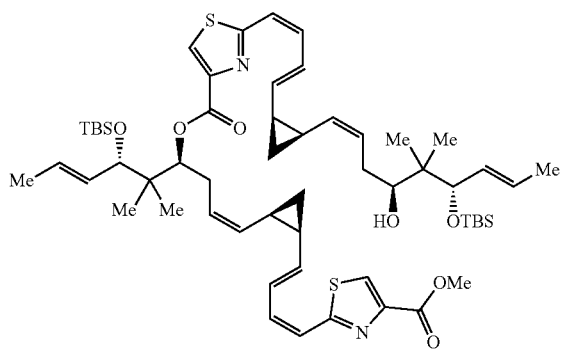 [SMILES: C/C=C/[C@H](O[Si](C)(C)C(C)(C)C)C(C)(C)[C@H](C/C=C\[C@H]1C[C@H]1/C=C/C=C\c1nc(C(=O)OC)cs1)OC(=O)c1csc(/C=C\C=C\[C@@H]2C[C@@H]2/C=C\C[C@H](O)C(C)(C)[C@H](/C=C/C)O[Si](C)(C)C(C)(C)C)n1]

To a stirred and degassed solution of vinyl stannane 40 (80 mg, 0.122 mmol, 1.2 equiv) and oxazole 106 (76 mg, 1.02 mmol, 1.0 equiv) in NMP (0.51 mL) at 23° C., was added CuTC (29 mg, 0.152 mmol, 1.5 equiv). The resulting mixture was stirred for 1 h at 23° C. and was then directly purified by flash column chromatography (SiO$_2$, hexanes:EtOAc 17:3→4:1) to yield uncyclized dimer 107 (97 mg, 0.094 mmol, 92% yield) as a pale yellow oil. 107: R$_f$=0.36 (hexanes:EtOAc, 3:1); [α]$_D^{25}$=+87.2 (c=1.0, CHCl$_3$); IR (film): v$_{max}$=3482, 2956, 2930, 2883, 2856, 1737, 1719, 1626, 1471, 1243, 1067, 836, 775 cm$^{-1}$; $^1$H NMR (600 MHz, CDCl$_3$) 8.12 (s, 1H), 7.94 (s, 1H), 7.43 (dd, J=14.8, 11.3 Hz, 1H), 7.06 (dd, J=14.7, 11.4 Hz, 1H), 6.37-6.24 (m, 4H), 5.79 (dd, J=14.8, 9.5 Hz, 1H), 5.74-5.66 (m, 1H), 5.65 (dd, J=14.7, 9.8 Hz, 1H), 5.60-5.46 (m, 5H), 5.27-5.19 (m, 2H), 5.11 (t, J=10.2 Hz, 1H), 4.20 (s, 1H), 3.96 (s, 3H), 3.90-3.85 (m, 2H), 3.71 (d, J=10.0 Hz, 1H), 2.60 (dt, J=14.9, 9.3 Hz, 1H), 2.52-2.46 (m, 1H), 2.32 (dd, J=14.7, 7.5 Hz, 1H), 2.21-2.12 (m, 1H), 2.03 (dt, J=15.1, 8.3 Hz, 1H), 1.96 (p, J=8.3 Hz, 1H), 1.87 (qd, J=8.6, 5.6 Hz, 1H), 1.79 (qd, J=8.6, 5.6 Hz, 1H), 1.71 (d, J=4.5 Hz, 3H), 1.65 (d, J=4.8 Hz, 3H), 1.33-1.26 (m, 2H), 1.00 (s, 3H), 0.98 (s, 3H), 0.96 (s, 3H), 0.87 (s, 9H), 0.87 (s, 9H), 0.76 (s, 3H), 0.71 (q, J=5.6 Hz, 1H), 0.67 (q, J=5.7 Hz, 1H), 0.06 (s, 3H), 0.00 (s, 3H), −0.03 (s, 3H), −0.06 (s, 3H) ppm; $^{13}$C NMR (151 MHz, CDCl$_3$) δ 165.68, 165.23, 162.17, 160.98, 147.97, 146.95, 143.44, 143.34, 135.36, 135.01, 131.51, 130.48, 130.42, 129.66, 129.21, 128.75, 128.26, 127.54, 127.44, 127.05, 126.49, 125.99, 117.59, 117.32, 84.42, 79.23, 78.13, 76.40, 52.54, 43.02, 41.09, 30.27, 28.69, 26.11, 25.99, 23.00, 22.85, 22.72, 20.29, 19.78, 19.44, 19.34 (2×C), 18.33, 18.15, 17.88 (2×C), 16.86, 16.79, −3.38, −3.80, −4.81, −4.96 ppm; HR-MS (ESI-TOF): calcd for C$_{57}$H$_{86}$O$_7$N$_2$S$_2$Si$_2$Na$^+$ [M+Na]$^+$: 1053.5307. Found: 1053.5329.

182

(2Z,4E,6S,8R,9Z,12S,19Z,21E,23S,25R,26Z,29S)-12,29-Bis[(3S,4E)-3-{[tert-butyl(dimethyl)- silyl]oxy}-2-methylhex-4-en-2-yl]-13,30-dioxa-17,34-dithia-35,36-diazapentacyclo-[30.2.1.1$^{15,18}$.0$^{6,8}$.0$^{23,25}$]hexatriaconta-1 (35),2,4,9,15,18 (36),19,21,26,32-decaene-14,31-dione (108)

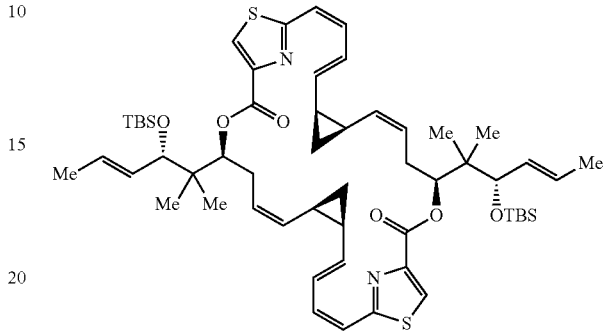

To a stirred solution of ester 107 (0.096 g, 0.093 mmol, 1.0 equiv) in THF (1.86 mL) cooled to 0° C. was added dropwise a saturated aqueous solution of barium hydroxide octahydrate [0.88 mL, MeOH:H$_2$O 3:2 (v/v)]. The reaction mixture was allowed to warm to 23° C. and stirred until all starting material was consumed by TLC (about 5 h). The reaction was quenched by the addition of a 0.01 N KHSO$_4$ solution (5 mL) and the aqueous phase was extracted six times with EtOAc (6×10 mL). The combined organic extracts were dried over MgSO$_4$, filtered and concentrated under reduced pressure. The crude oil was used in the next reaction without any further purification.

To a solution of the crude carboxylic acid, stirred in toluene (6.9 mL), was added 2,4,6-trichlorobenzoyl chloride (0.146 mL, 0.934 mmol, 10 equiv) and Et$_3$N (0.143 mL, 1.07 mmol, 11 equiv). The mixture was stirred 1 h at 23° C. and it was diluted to a concentration of 0.0075 M by the addition of toluene (6.9 mL). The latter reaction mixture was added over 5 h. via a syringe pump, to a solution of DMAP (0.046 g, 0.373 mmol, 4.0 equiv) in toluene (17 mL) heated at 40° C. After the addition was completed, stirring was continued for 24 h before the reaction was concentrated under reduced pressure. The crude residue was purified by flash column chromatography (SiO$_2$, hexanes:EtOAc 3:1→7:3→13:7) to give bis-TBS protected cp-disorazole A$_1$ 108 (0.022 g, 0.022 mmol, 24% yield over two steps) as a white film. 108: R$_f$=0.22 (hexanes:EtOAc, 3:1); [α]$_D^{25}$=−53.6 (c=0.88, CHCl$_3$); IR (film): v$_{max}$=2956, 2929, 2856, 1732, 1629, 1471, 1201, 1094, 836 cm$^{-1}$; $^1$H NMR (600 MHz, CDCl$_3$) δ 7.90 (s, 2H), 6.47-6.35 (m, 4H), 6.11 (t, J=11.9 Hz, 2H), 5.57-5.40 (m, 8H), 5.20 (d, J=11.5 Hz, 2H), 5.06 (t, J=10.9 Hz, 2H), 3.84 (d, J=6.8 Hz, 2H), 2.72 (q, J=12.2 Hz, 2H), 2.28 (dd, J=13.5, 4.8 Hz, 2H), 2.07 (dq, J=14.4, 7.8 Hz, 2H), 1.65 (d, J=4.6 Hz, 6H), 1.63-1.59 (m, 2H), 1.29-1.23 (m, 2H), 1.01 (s. 6H), 0.97 (s, 6H), 0.87 (s, 18H), 0.55 (q, J=5.5 Hz, 2H), −0.01 (s, 6H), −0.06 (s, 6H) ppm; $^{13}$C NMR (151 MHz, CDCl$_3$) δ 164.79, 160.03, 146.98, 141.77, 133.90, 131.48, 131.21, 128.16, 127.03, 124.89, 124.82, 119.47, 79.57, 77.37, 42.73, 28.77, 26.12, 23.43, 20.82, 19.51, 18.85, 18.36, 17.95, 17.34, −3.40, −4.75 ppm; HR-MS (ESI-TOF): calcd for C$_{56}$H$_{82}$O$_6$N$_2$S$_2$Si$_2$Na$^+$ [M+Na]$^+$: 1021.5045. found: 1021.5073.

(2Z,4E,6S,8R,9Z,12S,19Z,21E,23S,25R,26Z,29S)-12,29-Bis[(3S,4E)-3-hydroxy-2-methylhex-4-en-2-yl]-13,30-dioxa-17,34-dithia-35,36-diazapentacyclo[30.2.1.1$^{15,18}$.0$^{6,8}$.0$^{23,25}$]hexatriaconta-1 (35),2,4,9,15,18 (36),19,21,26,32-decaene-14,31-dione (86)

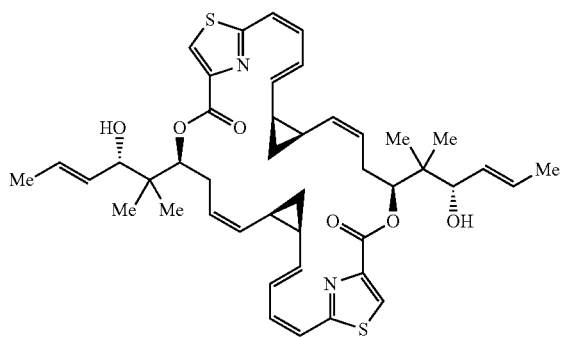 [SMILES: C/C=C/[C@H](O)C(C)(C)[C@@H]1C/C=C\[C@H]2C[C@H]2/C=C/C=C\c2nc(cs2)C(=O)O[C@H](C(C)(C)[C@@H](O)/C=C/C)C/C=C\[C@H]2C[C@H]2/C=C/C=C\c2nc(cs2)C(=O)O1]

To a stirred solution of compound 108 (9.0 mg, 9.0 µmol, 1.0 equiv) in DMF (300 µL) and H$_2$O (2.3 µl, 130 µmol, 14 equiv) was added TASF (12 mg, 45 µmol, 5.0 equiv) and the reaction mixture was heated at 40° C. and stirred for 48 h. The resulting mixture was filtered through a small silica pad (10 cm, SiO2, hexanes:EtOAc 1:1→0:1). The resulting fractions containing the desired products were combined, concentrated and purified by flash column chromatography (SiO2, hexanes:EtOAc 1:1→1:4→0:1) to yield bis-(cp-thiazolyl)-disorazole B1 (7, 3.0 mg, 4.2 µmol, 46% yield) as a white foam. The product was insoluble in most pure solvents: e.g., MeOH, DMSO, DCM, CHCl$_3$, MeCN, etc. The product was found to be soluble in a small aliquot of DMSO when DCM would be added until all product was dissolved and then most of the DCM was removed under reduce pressure leaving a cloudy solution of the desired product in DMSO with DCM. 86: R$_f$=0.15 (hexanes:EtOAc, 2:3); IR (film): v$_{max}$=3439, 2922, 2852, 1714, 1629, 1212, 1104, 964 cm$^{-1}$; $^1$H NMR (600 MHz, DMSO-d$_6$ with DCM) δ 8.37 (s, 2H), 6.45-6.37 (m, 2H), 6.21 (d, J=11.9 Hz, 2H), 6.15 (t, J=11.8 Hz, 2H), 5.66 (dd, J=14.1, 11.0 Hz, 2H), 5.60-5.49 (m, 4H), 5.39-5.31 (m, 2H), 5.23-5.11 (m, 4H), 4.64 (d, J=4.6 Hz, 2H), 3.73 (t, J=5.3 Hz, 2H), 2.70 (q, J=12.0 Hz, 2H), 2.29-2.22 (m, 2H), 2.22-2.13 (m, 2H), 1.82-1.73 (m, 2H), 1.64 (d, J=4.9 Hz, 6H), 0.96 (s, 6H), 0.88 (s, 6H), 0.60 (dd, J=10.4, 4.9 Hz, 4H) ppm; $^{13}$C NMR (151 MHz, DMSO-d$_6$ with DCM) δ 163.45, 159.37, 145.61, 142.90, 133.36, 131.70, 131.53, 127.55, 126.37, 125.78, 123.99, 118.18, 76.27, 75.30, 41.33, 27.65, 23.24, 19.05, 19.03, 18.95, 17.63, 16.64. ppm; HR-MS (ESI-TOF): calcd for C$_{44}$H$_{54}$O$_6$N$_2$S$_2$Na$^+$ [M+Na]$^+$: 793.3316. Found: 793.3322.

Example 4—Biological Activity

TABLE 5

Cytotoxic activity of 5 and MMAE in cancer cell lines.

| cell line | IC$_{50}$ (nM) | |
|---|---|---|
| | 5 | MMAE |
| MES SA | 0.11 | 0.51 |
| MES DX | 0.47 | 106 |
| 293T | 0.06 | 0.15 |

MMAE = monomethyl auristatin E,
MES SA = uterine sarcoma cell line;
MES SA DX = MES SA cell line with marked multidrug resistance;
HEK 293T = immortalized human embryonic kidney cell line Biological testing revealed cp-disorazole A$_1$ (5) to be a superior cytotoxic agent than monomethyl auristatin E (MMAE), the current payload of the approved ADC, Adcetris®, against highly resistant strains of cancer cells (see Table 1). Against MES-SA (human uterine sarcoma), MES-SA DX (human uterine sarcoma with multidrug resistance) and HEK 293T (immortalized human embryonic kidney cell line), 5 exhibits IC$_{50}$ values of 0.11, 0.47 and 0.06 nM, respectively, while MMAE has IC$_{50}$ values of 0.51, 106 and 0.15 nM, respectively (Table 5).

Figure 4A:
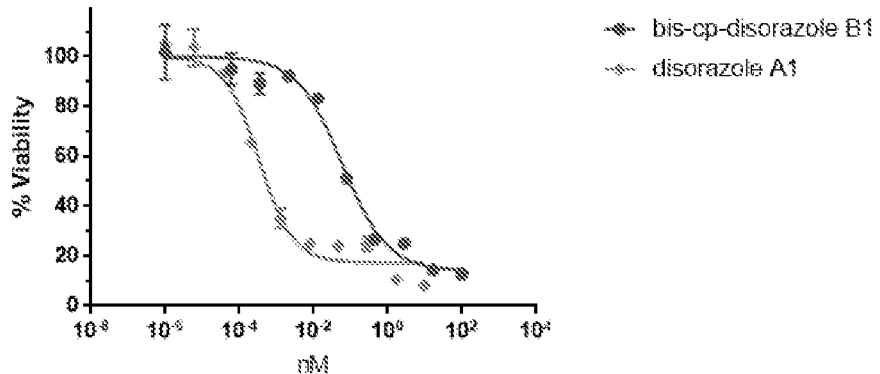
FIGS. 4A-4C shows cytotoxicity assay data for bis-cp-disorazole $B_1$ (85) against MES-SA (human uterine sarcoma) cells (FIG. 4A), MES SA/DX (human uterine sarcoma with multidrug resistance) cells (FIG. 4B), and HEK 293T (immortalized human embryonic kidney cell line) cells (FIG. 4C).
Figure 4B:
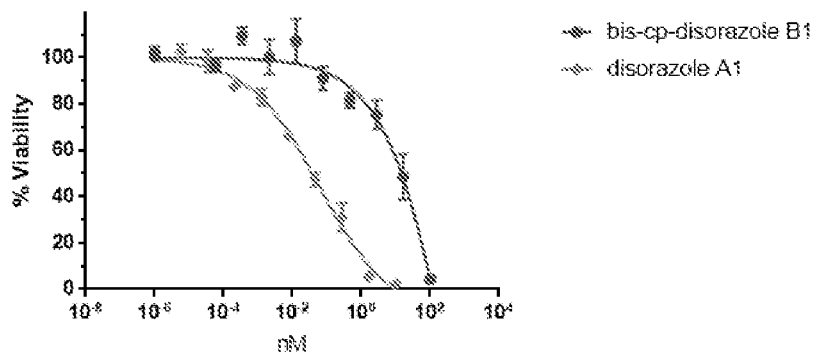
Figure 4C:
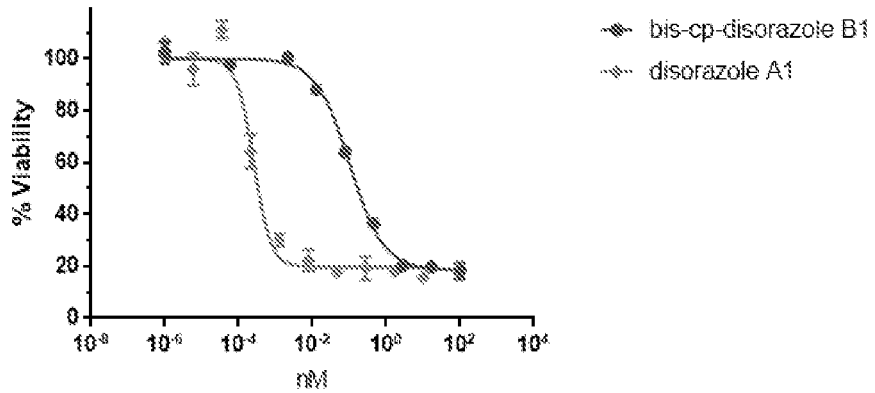

Cytotoxicity assay data is disclosed herein for bis-cp-disorazole B$_1$ (85) against MES-SA (human uterine sarcoma, FIG. 4A), MES SA/DX (human uterine sarcoma with multidrug resistance, FIG. 4B), and HEK 293T (immortalized human embryonic kidney cell line, FIG. 4C).

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

V. REFERENCES

The following references, to the extent that they provide exemplary procedural or other details supplementary to those set forth herein, are specifically incorporated herein by reference:
WO 2008/028934
Allred and Liebeskind, *J. Am. Chem. Soc.*, 118:2748-2749, 1996.
Altmann et al., *Progress in the Chemistry of Organic Natural Products*, 90; 2009.
Cosp et al., *Tetrahedron Letters*, 51:2391-2393, 2001.
Chari et al., *Angew. Chem. Int. Ed.*, 53:3796-3827, 2014.
de Carné-Carnavalet et al., *Org. Lett.*, 13:956-959, 2011.
Dosio et al., *Recent Pat. Anti Canc.*, 9:35-65, 2014.
Elnakady et al., *Biochem. Pharmacol.*, 67:927-935, 2004.
Fürstner et al., *Angew. Chem. Int. Ed.*, 45:5510-5515, 2006.
Gerber et al., *Nat. Prod. Rep.*, 30:625-639, 2013.
Ghanem and Aboul-Enein, *Chirality*, 17:1-15, 2005.
Hartung et al., *Synthesis*, 12:1844-1850, 2003.
Höfle, In Wissenschaftlicher Ergebnisbericht, Druckerei und Verlag GmbH: Braunschweig-Stöckheim, Germany, p 101-104, 1999/2000.
Hopkins & Wipf, *Nat. Prod. Rep.*, 26:585-601, 2009.
Hopkins et al., *Org. Lett.*, 13:4088-4091, 2011.
Irschik et al., *J. Antibiot.*, 48 31-35, 1995.
Jansen et al., *Liebigs Ann. Chem.*, 759-773, 1994.
López et al., *J. Org. Chem.*, 70:6346-6352, 2005.
Myers et al., *J. Org. Chem.*, 62:7507-7507, 1998.
Nagao et al., *J. Org. Chem.*, 51:2391-2393, 1986.
Nicolaou, *Chem. Biol.*, 21:1031-1045, 2014.
Nicolaou et al., *Angew. Chem. Int. Ed.*, 44:1378-1382, 2005.
Phillips et al., *Org. Lett.*, 2:1165-1168, 2000.
Pulukuri et al., *Org. Lett.*, 16:2284-2287, 2014.
Sapra & Shor, *Pharmacol. Ther.*, 138:452-469, 2013.

Schäckel et al., *Angew. Chem., Int. Ed.*, 49:1619-1622, 2010.
Scheidt et al., *J. Org. Chem.*, 63:6436-6437, 1998.
Sievers & Senter, *Annu. Rev. Med.*, 64:15-29, 2013.
Speed et al., *J. Am. Chem. Soc.*, 136:16136-16139, 2014.
Wang and Lin, *Organometallic*, 29:3077-3084, 2010.
Wipf & Graham, *Org. Biomol. Chem.*, 3:31-35, 2005.
Wu et al., *Oncotarget*, 6:40866-40879, 2015.

What is claimed is:

1. A compound of the formula:

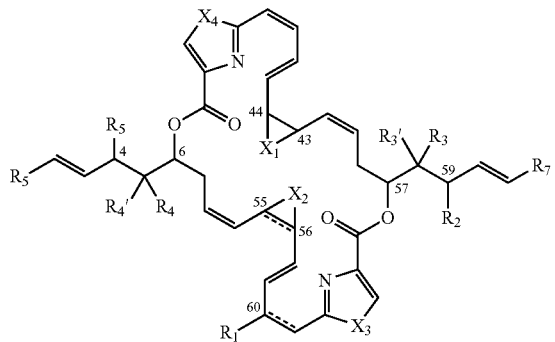

(I)

wherein:
X$_1$ is —O—, —S—, —NR$_a$—, or —CR$_b$R$_c$—;
  wherein:
    R$_a$ is hydrogen, alkyl$_{(C\leq 8)}$, substituted alkyl$_{(C\leq 8)}$, acyl$_{(C\leq 8)}$, substituted acyl$_{(C\leq 8)}$, or a monovalent amino protecting group, or —C(O)R$_a$', wherein:
      R$_a$' is amino, hydroxy, alkoxy$_{(C\leq 8)}$, substituted alkoxy$_{(C\leq 8)}$, alkylamino$_{(C\leq 8)}$, substituted alkylamino$_{(C\leq 8)}$, dialkylamino$_{(C\leq 8)}$, or substituted dialkylamino$_{(C\leq 8)}$; and
    R$_b$ and R$_c$ are each independently hydrogen, amino, cyano, halo, hydroxy, or mercapto, or alkyl$_{(C\leq 8)}$, substituted alkyl$_{(C\leq 8)}$, cycloalkyl$_{(C\leq 8)}$, substituted cycloalkyl$_{(C\leq 8)}$, alkenyl$_{(C\leq 8)}$, substituted alkenyl$_{(C\leq 8)}$, alkynyl$_{(C\leq 8)}$, substituted alkynyl$_{(C\leq 8)}$, aryl$_{(C\leq 8)}$, substituted aryl$_{(C\leq 8)}$, aralkyl$_{(C\leq 8)}$, substituted aralkyl$_{(C\leq 8)}$, heteroaryl$_{(C\leq 8)}$, substituted heteroaryl$_{(C\leq 8)}$, heterocycloalkyl$_{(C\leq 8)}$, substituted heterocycloalkyl$_{(C\leq 8)}$, acyl$_{(C\leq 8)}$, substituted acyl$_{(C\leq 8)}$, amido$_{(C\leq 8)}$, substituted amido$_{(C\leq 8)}$, alkoxy$_{(C\leq 8)}$, substituted alkoxy$_{(C\leq 8)}$, acyloxy$_{(C\leq 8)}$, substituted acyloxy$_{(C\leq 8)}$, alkylamino$_{(C\leq 8)}$, substituted alkylamino$_{(C\leq 8)}$, dialkylamino$_{(C\leq 8)}$, or substituted dialkylamino$_{(C\leq 8)}$;
X$_2$ is absent, —O—, —S—, —NR$_d$—, or —CR$_e$R$_f$—;
  wherein:
    R$_d$ is hydrogen, alkyl$_{(C\leq 8)}$, substituted alkyl$_{(C\leq 8)}$, acyl$_{(C\leq 8)}$, substituted acyl$_{(C\leq 8)}$, or a monovalent amino protecting group, or —C(O)R$_d$', wherein:
      R$_d$' is amino, hydroxy, alkoxy$_{(C\leq 8)}$, substituted alkoxy$_{(C\leq 8)}$, alkylamino$_{(C\leq 8)}$, substituted alkylamino$_{(C\leq 8)}$, dialkylamino$_{(C\leq 8)}$, or substituted dialkylamino$_{(C\leq 8)}$; and
    R$_e$ and R$_f$ are each independently hydrogen, amino, cyano, halo, hydroxy, or mercapto, or alkyl$_{(C\leq 8)}$, substituted alkyl$_{(C\leq 8)}$, cycloalkyl$_{(C\leq 8)}$, substituted cycloalkyl$_{(C\leq 8)}$, alkenyl$_{(C\leq 8)}$, substituted alkenyl$_{(C\leq 8)}$, alkynyl$_{(C\leq 8)}$, substituted alkynyl$_{(C\leq 8)}$, aryl$_{(C\leq 8)}$, substituted aryl$_{(C\leq 8)}$, aralkyl$_{(C\leq 8)}$, substituted aralkyl$_{(C\leq 8)}$, heteroaryl$_{(C\leq 8)}$, substituted heteroaryl$_{(C\leq 8)}$, heterocycloalkyl$_{(C\leq 8)}$, substituted heterocycloalkyl$_{(C\leq 8)}$, acyl$_{(C\leq 8)}$, substituted acyl$_{(C\leq 8)}$, amido$_{(C\leq 8)}$, substituted amido$_{(C\leq 8)}$, alkoxy$_{(C\leq 8)}$, substituted alkoxy$_{(C\leq 8)}$, acyloxy$_{(C\leq 8)}$, substituted acyloxy$_{(C\leq 8)}$, alkylamino$_{(C\leq 8)}$, substituted alkylamino$_{(C\leq 8)}$, dialkylamino$_{(C\leq 8)}$, or substituted dialkylamino$_{(C\leq 8)}$; and
  provided that when X$_2$ is absent, then the bond between carbon atoms 55 and 56 is a double bond;
X$_3$ and X$_4$ are each independently O, NR$_h$, or S;
  wherein:
    R$_h$ is hydrogen, alkyl$_{(C\leq 8)}$, substituted alkyl$_{(C\leq 8)}$, or a monovalent amino protecting group;
R$_1$ is hydrogen, hydroxy, alkoxy$_{(C\leq 8)}$, substituted alkoxy$_{(C\leq 8)}$, acyloxy$_{(C\leq 8)}$, substituted acyloxy$_{(C\leq 8)}$, or —OR$_g$, wherein R$_g$ is a hydroxy protecting group;
R$_2$ and R$_5$ are hydroxy, oxo, alkoxy$_{(C\leq 8)}$, or substituted alkoxy$_{(C\leq 8)}$;
R$_3$, R$_3$', R$_4$, and R$_4$' are each independently alkyl$_{(C\leq 8)}$, acyl$_{(C\leq 8)}$, or a substituted version of either group; and
R$_6$ and R$_7$ are each independently alkyl$_{(C\leq 8)}$ or substituted alkyl$_{(C\leq 8)}$;
  provided that X$_1$ is not —O—, when X$_2$ is absent, the bond between carbon atom 55 and carbon atom 56 is a double bond, X$_3$ and X$_4$ are both —O—, R$_1$ is hydrogen or methoxy, R$_2$ and R$_5$ is hydroxy, and R$_3$, R$_3$', R$_4$, R$_4$', R$_6$, and R$_7$ are all methyl, or provided that X$_1$ and X$_2$ are not both —O—, when X$_3$ and X$_4$ are both —O—, R$_1$ is hydrogen or methoxy, R$_2$ and R$_5$ is hydroxy, and R$_3$, R$_3$', R$_4$, R$_4$', R$_6$, and R$_7$ are all methyl;
wherein the term "substituted" is used with a chemical group, then one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$;
or a pharmaceutically acceptable salt thereof.

2. The compound of claim 1 further defined as:

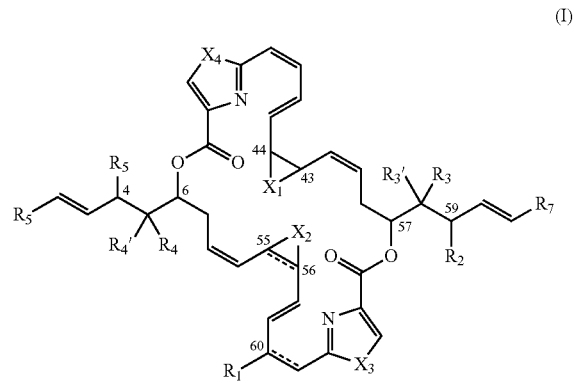

(I)

wherein:
X$_1$ is —O—, —S—, —NR$_a$—, or —CR$_b$R$_c$—;
  wherein:
    R$_a$ is hydrogen, alkyl$_{(C\leq 8)}$, substituted alkyl$_{(C\leq 8)}$, or a monovalent amino protecting group; and $R_b$ and $R_c$ are each independently hydrogen, amino, cyano, halo, hydroxy, or mercapto, or alkyl$_{(C\leq 8)}$, substituted alkyl$_{(C\leq 8)}$, cycloalkyl$_{(C\leq 8)}$, substituted cycloalkyl$_{(C\leq 8)}$, alkenyl$_{(C\leq 8)}$, substituted alkenyl$_{(C\leq 8)}$, alkynyl$_{(C\leq 8)}$, substituted alkynyl$_{(C\leq 8)}$, aryl$_{(C\leq 8)}$, substituted aryl$_{(C\leq 8)}$, aralkyl$_{(C\leq 8)}$, substituted aralkyl$_{(C\leq 8)}$, heteroaryl$_{(C\leq 8)}$, substituted heteroaryl$_{(C\leq 8)}$, heterocycloalkyl$_{(C\leq 8)}$, substituted heterocycloalkyl$_{(C\leq 8)}$, acyl$_{(C\leq 8)}$, substituted acyl$_{(C\leq 8)}$, amido$_{(C\leq 8)}$, substituted amido$_{(C\leq 8)}$, alkoxy$_{(C\leq 8)}$, substituted alkoxy$_{(C\leq 8)}$, acyloxy$_{(C\leq 8)}$, substituted acyloxy$_{(C\leq 8)}$, alkylamino$_{(C\leq 8)}$, substituted alkylamino$_{(C\leq 8)}$, dialkylamino$_{(C\leq 8)}$, or substituted dialkylamino$_{(C\leq 8)}$;

$X_2$ is absent, —S—, —NR$_d$—, or —CR$_e$R$_f$—; wherein:

$R_d$ is hydrogen, alkyl$_{(C\leq 8)}$, substituted alkyl$_{(C\leq 8)}$, or a monovalent amino protecting group;

$R_e$ and $R_f$ are each independently hydrogen, amino, cyano, halo, hydroxy, or mercapto, or alkyl$_{(C\leq 8)}$, substituted alkyl$_{(C\leq 8)}$, cycloalkyl$_{(C\leq 8)}$, substituted cycloalkyl$_{(C\leq 8)}$, alkenyl$_{(C\leq 8)}$, substituted alkenyl$_{(C\leq 8)}$, alkynyl$_{(C\leq 8)}$, substituted alkynyl$_{(C\leq 8)}$, aryl$_{(C\leq 8)}$, substituted aryl$_{(C\leq 8)}$, aralkyl$_{(C\leq 8)}$, substituted aralkyl$_{(C\leq 8)}$, heteroaryl$_{(C\leq 8)}$, substituted heteroaryl$_{(C\leq 8)}$, heterocycloalkyl$_{(C\leq 8)}$, substituted heterocycloalkyl$_{(C\leq 8)}$, acyl$_{(C\leq 8)}$, substituted acyl$_{(C\leq 8)}$, amido$_{(C\leq 8)}$, substituted amido$_{(C\leq 8)}$, alkoxy$_{(C\leq 8)}$, substituted alkoxy$_{(C\leq 8)}$, acyloxy$_{(C\leq 8)}$, substituted acyloxy$_{(C\leq 8)}$, alkylamino$_{(C\leq 8)}$, substituted alkylamino$_{(C\leq 8)}$, dialkylamino$_{(C\leq 8)}$, or substituted dialkylamino$_{(C\leq 8)}$; and provided that when $X_2$ is absent, then the bond between carbon atoms 55 and 56 is a double bond;

$X_3$ and $X_4$ are each independently O, NR$_h$, or S; wherein:

$R_h$ is hydrogen, alkyl$_{(C\leq 8)}$, substituted alkyl$_{(C\leq 8)}$, or a monovalent amino protecting group;

$R_1$ is hydrogen, hydroxy, alkoxy$_{(C\leq 8)}$, substituted alkoxy$_{(C\leq 8)}$, acyloxy$_{(C\leq 8)}$, substituted acyloxy$_{(C\leq 8)}$, or —OR$_g$, wherein R$_g$ is a hydroxy protecting group;

$R_2$ and $R_5$ are hydroxy, oxo, alkoxy$_{(C\leq 8)}$, or substituted alkoxy$_{(C\leq 8)}$;

$R_3$, $R_3'$, $R_4$, and $R_4'$ are each independently alkyl$_{(C\leq 8)}$, acyl$_{(C\leq 8)}$, or a substituted version of either group; and $R_6$ and $R_7$ are each independently alkyl$_{(C\leq 8)}$ or substituted alkyl$_{(C\leq 8)}$;

provided that $X_1$ is not —O—, when $X_2$ is absent, the bond between carbon atom 55 and carbon atom 56 is a double bond, $X_3$ and $X_4$ are both —O—, $R_1$ is hydrogen or methoxy, $R_2$ and $R_5$ is hydroxy, and $R_3$, $R_3'$, $R_4$, $R_4'$, $R_6$, and $R_7$ are all methyl;

or a pharmaceutically acceptable salt thereof.

3. The compound of claim 1 further defined:

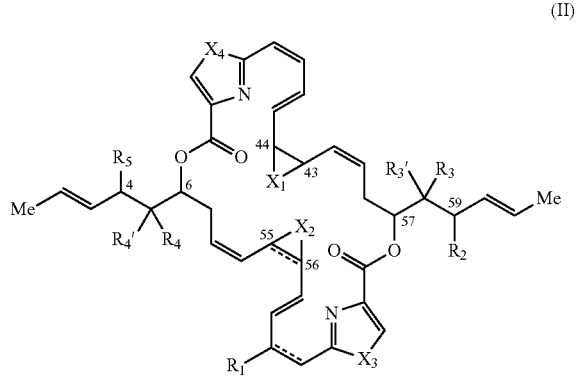

(II)

wherein:

$X_1$ is —O—, —S—, —NR$_a$—, or —CR$_b$R$_c$—; wherein:

$R_a$ is hydrogen, alkyl$_{(C\leq 8)}$, substituted alkyl$_{(C\leq 8)}$, or a monovalent amino protecting group; and $R_b$ and $R_c$ are each independently hydrogen, amino, cyano, halo, hydroxy, or mercapto, or alkyl$_{(C\leq 8)}$, substituted alkyl$_{(C\leq 8)}$, cycloalkyl$_{(C\leq 8)}$, substituted cycloalkyl$_{(C\leq 8)}$, alkenyl$_{(C\leq 8)}$, substituted alkenyl$_{(C\leq 8)}$, alkynyl$_{(C\leq 8)}$, substituted alkynyl$_{(C\leq 8)}$, aryl$_{(C\leq 8)}$, substituted aryl$_{(C\leq 8)}$, aralkyl$_{(C\leq 8)}$, substituted aralkyl$_{(C\leq 8)}$, heteroaryl$_{(C\leq 8)}$, substituted heteroaryl$_{(C\leq 8)}$, heterocycloalkyl$_{(C\leq 8)}$, substituted heterocycloalkyl$_{(C\leq 8)}$, acyl$_{(C\leq 8)}$, substituted acyl$_{(C\leq 8)}$, amido$_{(C\leq 8)}$, substituted amido$_{(C\leq 8)}$, alkoxy$_{(C\leq 8)}$, substituted alkoxy$_{(C\leq 8)}$, acyloxy$_{(C\leq 8)}$, substituted acyloxy$_{(C\leq 8)}$, alkylamino$_{(C\leq 8)}$, substituted alkylamino$_{(C\leq 8)}$, dialkylamino$_{(C\leq 8)}$, or substituted dialkylamino$_{(C\leq 8)}$;

$X_2$ is absent, —NR$_d$—, or —CR$_e$R$_f$—; wherein:

$R_d$ is hydrogen, alkyl$_{(C\leq 8)}$, substituted alkyl$_{(C\leq 8)}$, or a monovalent amino protecting group;

$R_e$ and $R_f$ are each independently hydrogen, amino, cyano, halo, hydroxy, or mercapto, or alkyl$_{(C\leq 8)}$, substituted alkyl$_{(C\leq 8)}$, cycloalkyl$_{(C\leq 8)}$, substituted cycloalkyl$_{(C\leq 8)}$, alkenyl$_{(C\leq 8)}$, substituted alkenyl$_{(C\leq 8)}$, alkynyl$_{(C\leq 8)}$, substituted alkynyl$_{(C\leq 8)}$, aryl$_{(C\leq 8)}$, substituted aryl$_{(C\leq 8)}$, aralkyl$_{(C\leq 8)}$, substituted aralkyl$_{(C\leq 8)}$, heteroaryl$_{(C\leq 8)}$, substituted heteroaryl$_{(C\leq 8)}$, heterocycloalkyl$_{(C\leq 8)}$, substituted heterocycloalkyl$_{(C\leq 8)}$, acyl$_{(C\leq 8)}$, substituted acyl$_{(C\leq 8)}$, amido$_{(C\leq 8)}$, substituted amido$_{(C\leq 8)}$, alkoxy$_{(C\leq 8)}$, substituted alkoxy$_{(C\leq 8)}$, acyloxy$_{(C\leq 8)}$, substituted acyloxy$_{(C\leq 8)}$, alkylamino$_{(C\leq 8)}$, substituted alkylamino$_{(C\leq 8)}$, dialkylamino$_{(C\leq 8)}$, or substituted dialkylamino$_{(C\leq 8)}$; and provided that when $X_2$ is absent, then the bond between carbon atoms 55 and 56 is a double bond;

$X_3$ and $X_4$ are each independently O, NR$_h$, or S; wherein:

$R_h$ is hydrogen, alkyl$_{(C\leq 8)}$, substituted alkyl$_{(C\leq 8)}$, or a monovalent amino protecting group;

$R_1$ is hydrogen, hydroxy, alkoxy$_{(C\leq 8)}$, substituted alkoxy$_{(C\leq 8)}$, acyloxy$_{(C\leq 8)}$, substituted acyloxy$_{(C\leq 8)}$, or —OR$_g$, wherein R$_g$ is a hydroxy protecting group;

$R_2$ and $R_5$ are hydroxy, oxo, alkoxy$_{(C\leq 8)}$, or substituted alkoxy$_{(C\leq 8)}$; and

189

R₃, R₃', R₄, and R₄' are each independently alkyl$_{(C\leq 8)}$, acyl$_{(C\leq 8)}$, or a substituted version of either group;
or a pharmaceutically acceptable salt thereof.

4. The compound of claim 1 further defined as:

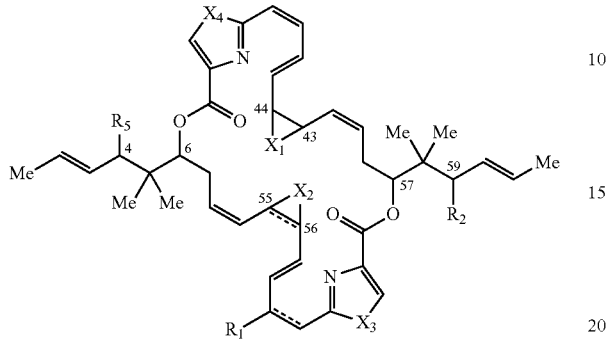

(III)

wherein:
X₁ is —O—, —S—, —NR$_a$—, or —CR$_b$R$_c$—; wherein:
R$_a$ is hydrogen, alkyl$_{(C\leq 8)}$, substituted alkyl$_{(C\leq 8)}$, or a monovalent amino protecting group; and
R$_b$ and R$_c$ are each independently hydrogen, amino, cyano, halo, hydroxy, or mercapto, or alkyl$_{(C\leq 8)}$, substituted alkyl$_{(C\leq 8)}$, cycloalkyl$_{(C\leq 8)}$, substituted cycloalkyl$_{(C\leq 8)}$, alkenyl$_{(C\leq 8)}$, substituted alkenyl$_{(C\leq 8)}$, alkynyl$_{(C\leq 8)}$, substituted alkynyl$_{(C\leq 8)}$, aryl$_{(C\leq 8)}$, substituted aryl$_{(C\leq 8)}$, aralkyl$_{(C\leq 8)}$, substituted aralkyl$_{(C\leq 8)}$, heteroaryl$_{(C\leq 8)}$, substituted heteroaryl$_{(C\leq 8)}$, heterocycloalkyl$_{(C\leq 8)}$, substituted heterocycloalkyl$_{(C\leq 8)}$, acyl$_{(C\leq 8)}$, substituted acyl$_{(C\leq 8)}$, amido$_{(C\leq 8)}$, substituted amido$_{(C\leq 8)}$, alkoxy$_{(C\leq 8)}$, substituted alkoxy$_{(C\leq 8)}$, acyloxy$_{(C\leq 8)}$, substituted acyloxy$_{(C\leq 8)}$, alkylamino$_{(C\leq 8)}$, substituted alkylamino$_{(C\leq 8)}$, dialkylamino$_{(C\leq 8)}$, or substituted dialkylamino$_{(C\leq 8)}$;

X₂ is absent, —NR$_d$—, or —CR$_e$R$_f$—; wherein:
R$_d$ is hydrogen, alkyl$_{(C\leq 8)}$, substituted alkyl$_{(C\leq 8)}$, or a monovalent amino protecting group;
R$_e$ and R$_f$ are each independently hydrogen, amino, cyano, halo, hydroxy, or mercapto, or alkyl$_{(C\leq 8)}$, substituted alkyl$_{(C\leq 8)}$, cycloalkyl$_{(C\leq 8)}$, substituted cycloalkyl$_{(C\leq 8)}$, alkenyl$_{(C\leq 8)}$, substituted alkenyl$_{(C\leq 8)}$, alkynyl$_{(C\leq 8)}$, substituted alkynyl$_{(C\leq 8)}$, aryl$_{(C\leq 8)}$, substituted aryl$_{(C\leq 8)}$, aralkyl$_{(C\leq 8)}$, substituted aralkyl$_{(C\leq 8)}$, heteroaryl$_{(C\leq 8)}$, substituted heteroaryl$_{(C\leq 8)}$, heterocycloalkyl$_{(C\leq 8)}$, substituted heterocycloalkyl$_{(C\leq 8)}$, acyl$_{(C\leq 8)}$, substituted acyl$_{(C\leq 8)}$, amido$_{(C\leq 8)}$, substituted amido$_{(C\leq 8)}$, alkoxy$_{(C\leq 8)}$, substituted alkoxy$_{(C\leq 8)}$, acyloxy$_{(C\leq 8)}$, substituted acyloxy$_{(C\leq 8)}$, alkylamino$_{(C\leq 8)}$, substituted alkylamino$_{(C\leq 8)}$, dialkylamino$_{(C\leq 8)}$, or substituted dialkylamino$_{(C\leq 8)}$; and
provided that when X₂ is absent, then the bond between carbon atoms 55 and 56 is a double bond;

X₃ and X₄ are each independently O, NR$_h$, or S; wherein:
Rh is hydrogen, alkyl$_{(C\leq 8)}$, substituted alkyl$_{(C\leq 8)}$, or a monovalent amino protecting group;
R₁ is hydrogen, hydroxy, alkoxy$_{(C\leq 8)}$, substituted alkoxy$_{(C\leq 8)}$, acyloxy$_{(C\leq 8)}$, substituted acyloxy$_{(C\leq 8)}$, or —OR$_g$, wherein R$_g$ is a hydroxy protecting group; and

190

R₂ and R₅ are hydroxy, oxo, alkoxy$_{(C\leq 8)}$, or substituted alkoxy$_{(C\leq 8)}$;
or a pharmaceutically acceptable salt thereof.

5. The compound of claim 1 further defined as:

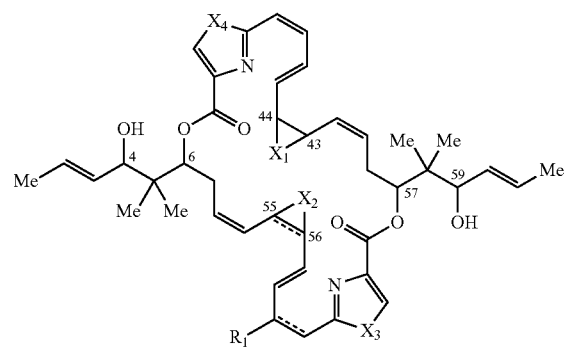

(IV)

wherein:
X₁ is —O—, —S—, —NR$_a$—, or —CR$_b$R$_c$—; wherein:
R$_a$ is hydrogen, alkyl$_{(C\leq 8)}$, substituted alkyl$_{(C\leq 8)}$, or a monovalent amino protecting group; and
R$_b$ and R$_c$, are each independently hydrogen, amino, cyano, halo, hydroxy, or mercapto, or alkyl$_{(C\leq 8)}$, substituted alkyl$_{(C\leq 8)}$, cycloalkyl$_{(C\leq 8)}$, substituted cycloalkyl$_{(C\leq 8)}$, alkenyl$_{(C\leq 8)}$, substituted alkenyl$_{(C\leq 8)}$, alkynyl$_{(C\leq 8)}$, substituted alkynyl$_{(C\leq 8)}$, aryl$_{(C\leq 8)}$, substituted aryl$_{(C\leq 8)}$, aralkyl$_{(C\leq 8)}$, substituted aralkyl$_{(C\leq 8)}$, heteroaryl$_{(C\leq 8)}$, substituted heteroaryl$_{(C\leq 8)}$, heterocycloalkyl$_{(C\leq 8)}$, substituted heterocycloalkyl$_{(C\leq 8)}$, acyl$_{(C\leq 8)}$, substituted acyl$_{(C\leq 8)}$, amido$_{(C\leq 8)}$, substituted amido$_{(C\leq 8)}$, alkoxy$_{(C\leq 8)}$, substituted alkoxy$_{(C\leq 8)}$, acyloxy$_{(C\leq 8)}$, substituted acyloxy$_{(C\leq 8)}$, alkylamino$_{(C\leq 8)}$, substituted alkylamino$_{(C\leq 8)}$, dialkylamino$_{(C\leq 8)}$, or substituted dialkylamino$_{(C\leq 8)}$;

X₂ is absent, —NR$_d$—, or —CR$_e$R$_f$—; wherein:
R$_d$ is hydrogen, alkyl$_{(C\leq 8)}$, substituted alkyl$_{(C\leq 8)}$, or a monovalent amino protecting group;
R$_e$ and R$_f$ are each independently hydrogen, amino, cyano, halo, hydroxy, or mercapto, or alkyl$_{(C\leq 8)}$, substituted alkyl$_{(C\leq 8)}$, cycloalkyl$_{(C\leq 8)}$, substituted cycloalkyl$_{(C\leq 8)}$, alkenyl$_{(C\leq 8)}$, substituted alkenyl$_{(C\leq 8)}$, alkynyl$_{(C\leq 8)}$, substituted alkynyl$_{(C\leq 8)}$, aryl$_{(C\leq 8)}$, substituted aryl$_{(C\leq 8)}$, aralkyl$_{(C\leq 8)}$, substituted aralkyl$_{(C\leq 8)}$, heteroaryl$_{(C\leq 8)}$, substituted heteroaryl$_{(C\leq 8)}$, heterocycloalkyl$_{(C\leq 8)}$, substituted heterocycloalkyl$_{(C\leq 8)}$, acyl$_{(C\leq 8)}$, substituted acyl$_{(C\leq 8)}$, amido$_{(C\leq 8)}$, substituted amido$_{(C\leq 8)}$, alkoxy$_{(C\leq 8)}$, substituted alkoxy$_{(C\leq 8)}$, acyloxy$_{(C\leq 8)}$, substituted acyloxy$_{(C\leq 8)}$, alkylamino$_{(C\leq 8)}$, substituted alkylamino$_{(C\leq 8)}$, dialkylamino$_{(C\leq 8)}$, or substituted dialkylamino$_{(C\leq 8)}$; and
provided that when X₂ is absent, then the bond between carbon atoms 55 and 56 is a double bond;

X₃ and X₄ are each independently O, NR$_h$, or S; wherein:
R$_h$ is hydrogen, alkyl$_{(C\leq 8)}$, substituted alkyl$_{(C\leq 8)}$, or a monovalent amino protecting group; and
R₁ is hydrogen, hydroxy, alkoxy$_{(C\leq 8)}$, substituted alkoxy$_{(C\leq 8)}$, acyloxy$_{(C\leq 8)}$, substituted acyloxy$_{(C\leq 8)}$, or —OR$_g$, wherein R$_g$ is a hydroxy protecting group;
or a pharmaceutically acceptable salt thereof.

6. The compound of claim 1, wherein $R_3$, $R_3'$, $R_4$, and $R_4'$ are alkyl$_{(C\leq 8)}$.

7. The compound of claim 1, wherein $R_2$ and $R_5$ is hydroxy.

8. The compound of claim 1, wherein $X_1$ is —$CR_bR_c$—; wherein:

$R_b$ and $R_c$ are each independently hydrogen, amino, cyano, halo, hydroxy, or mercapto, or alkyl$_{(C\leq 8)}$, substituted alkyl$_{(C\leq 8)}$, cycloalkyl$_{(C\leq 8)}$, substituted cycloalkyl$_{(C\leq 8)}$, alkenyl$_{(C\leq 8)}$, substituted alkenyl$_{(C\leq 8)}$, alkynyl$_{(C\leq 8)}$, substituted alkynyl$_{(C\leq 8)}$, aryl$_{(C\leq 8)}$, substituted aryl$_{(C\leq 8)}$, aralkyl$_{(C\leq 8)}$, substituted aralkyl$_{(C\leq 8)}$, heteroaryl$_{(C\leq 8)}$, substituted heteroaryl$_{(C\leq 8)}$, heterocycloalkyl$_{(C\leq 8)}$, substituted heterocycloalkyl$_{(C\leq 8)}$, acyl$_{(C\leq 8)}$, substituted acyl$_{(C\leq 8)}$, amido$_{(C\leq 8)}$, substituted amido$_{(C\leq 8)}$, alkoxy$_{(C\leq 8)}$, substituted alkoxy$_{(C\leq 8)}$, acyloxy$_{(C\leq 8)}$, substituted acyloxy$_{(C\leq 8)}$, alkylamino$_{(C\leq 8)}$, substituted alkylamino$_{(C\leq 8)}$, dialkylamino$_{(C\leq 8)}$, or substituted dialkylamino$_{(C\leq 8)}$.

9. The compound of claim 1, wherein $X_1$ is —$NR_a$—, wherein:

$R_a$ is hydrogen, alkyl$_{(C\leq 8)}$, substituted alkyl$_{(C\leq 8)}$, or a monovalent amino protecting group.

10. The compound of claim 9, wherein $R_a$ is hydrogen.

11. The compound of claim 1, wherein $X_2$ is absent.

12. The compound of claim 1, wherein $X_2$ is —$CR_eR_f$—; wherein:

$R_e$ and $R_f$ are each independently hydrogen, amino, cyano, halo, hydroxy, or mercapto, or alkyl$_{(C\leq 8)}$, substituted alkyl$_{(C\leq 8)}$, cycloalkyl$_{(C\leq 8)}$, substituted cycloalkyl$_{(C\leq 8)}$, alkenyl$_{(C\leq 8)}$, substituted alkenyl$_{(C\leq 8)}$, alkynyl$_{(C\leq 8)}$, substituted alkynyl$_{(C\leq 8)}$, aryl$_{(C\leq 8)}$, substituted aryl$_{(C\leq 8)}$, aralkyl$_{(C\leq 8)}$, substituted aralkyl$_{(C\leq 8)}$, heteroaryl$_{(C\leq 8)}$, substituted heteroaryl$_{(C\leq 8)}$, heterocycloalkyl$_{(C\leq 8)}$, substituted heterocycloalkyl$_{(C\leq 8)}$, acyl$_{(C\leq 8)}$, substituted acyl$_{(C\leq 8)}$, amido$_{(C\leq 8)}$, substituted amido$_{(C\leq 8)}$, alkoxy$_{(C\leq 8)}$, substituted alkoxy$_{(C\leq 8)}$, acyloxy$_{(C\leq 8)}$, substituted acyloxy$_{(C\leq 8)}$, alkylamino$_{(C\leq 8)}$, substituted alkylamino$_{(C\leq 8)}$, dialkylamino$_{(C\leq 8)}$, or substituted dialkylamino$_{(C\leq 8)}$.

13. The compound of claim 1, wherein $X_2$ is —$NR_d$—; wherein:

Rd is hydrogen, alkyl$_{(C\leq 8)}$, substituted alkyl$_{(C\leq 8)}$, or a monovalent amino protecting group.

14. The compound of claim 1, wherein $X_3$ is O or S.

15. The compound of claim 1, wherein $X_4$ is O or S.

16. The compound of claim 1, wherein the compound is further defined as:

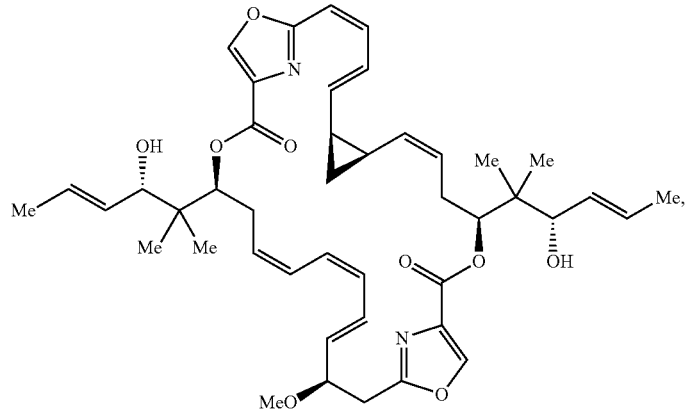

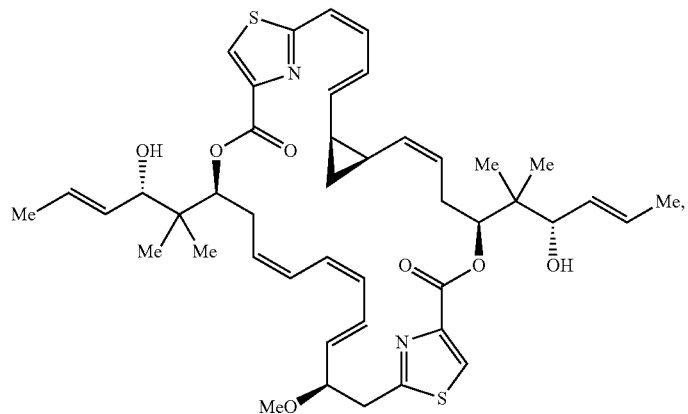

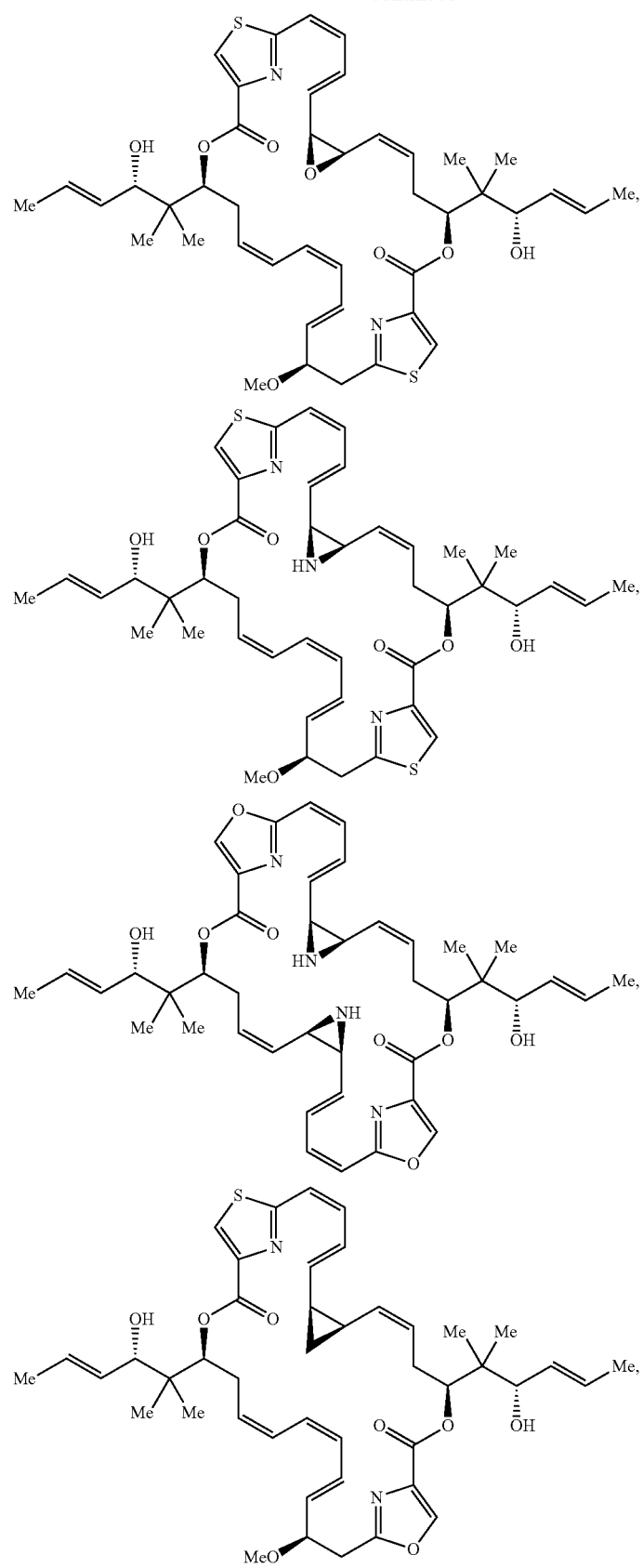

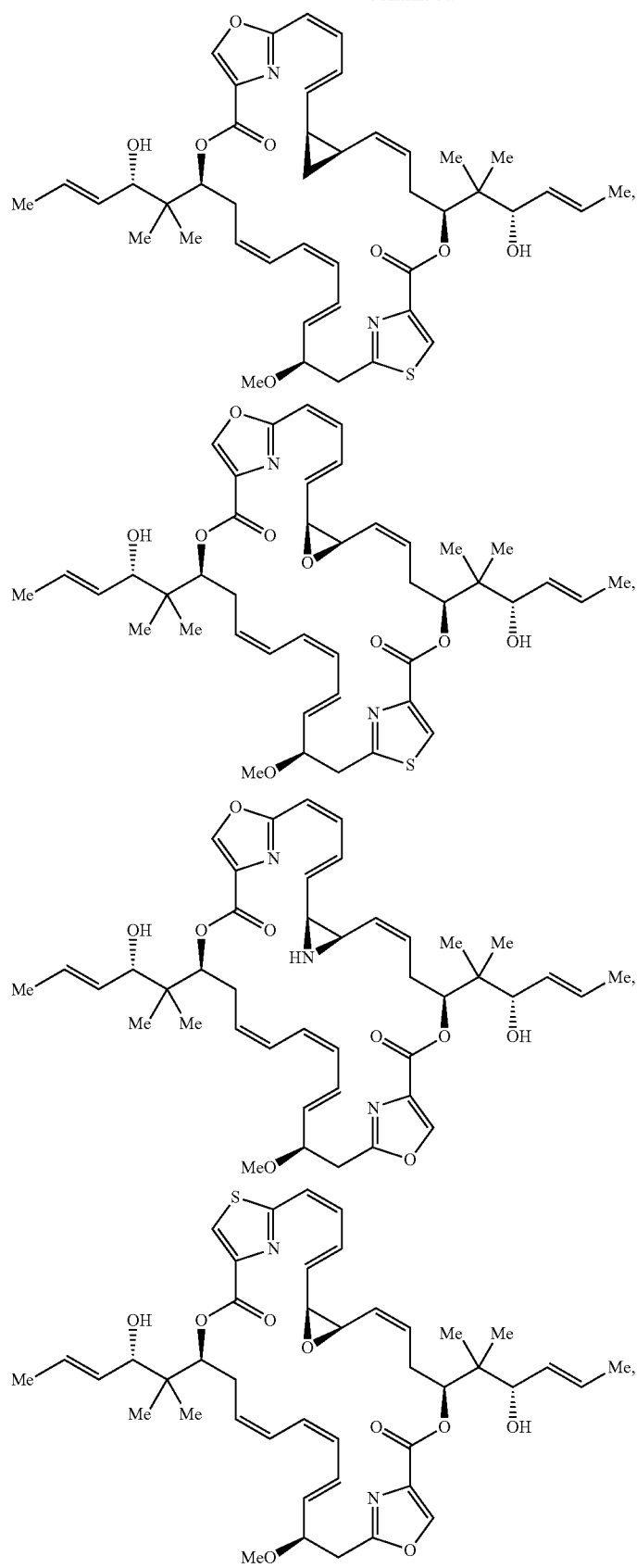

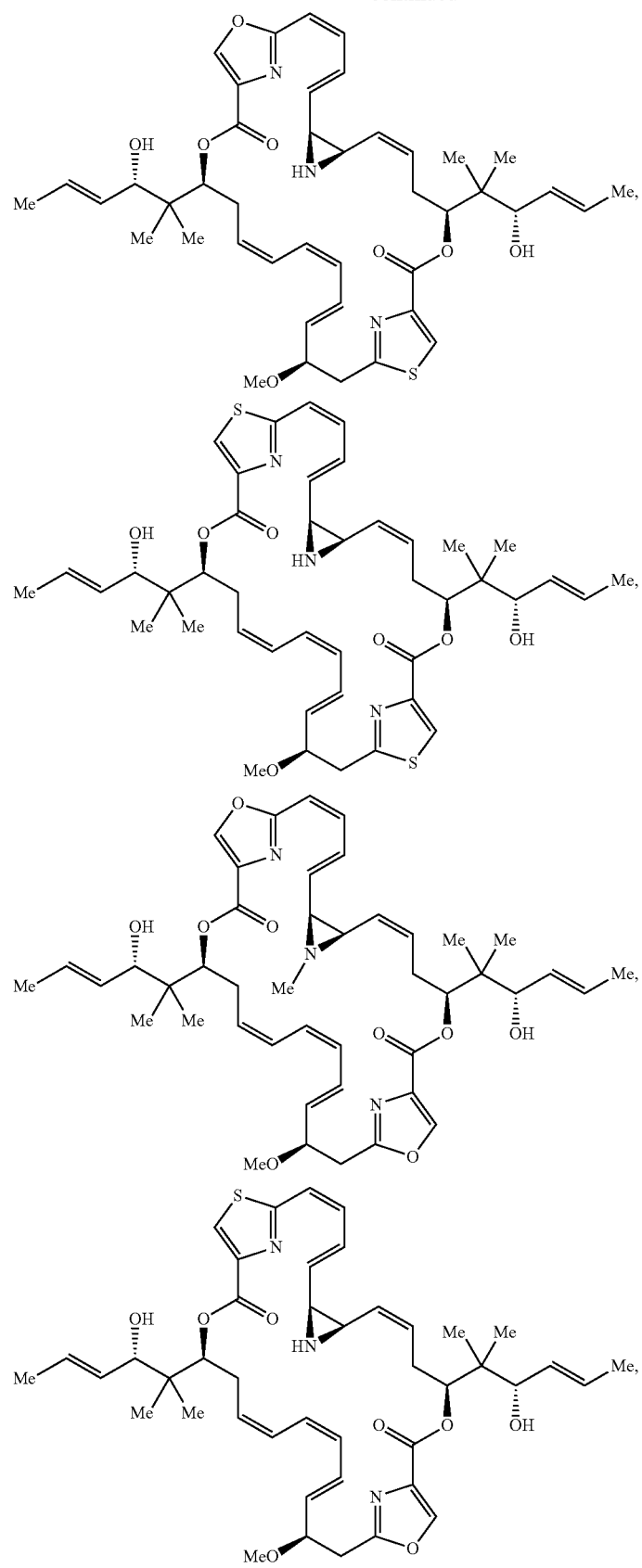

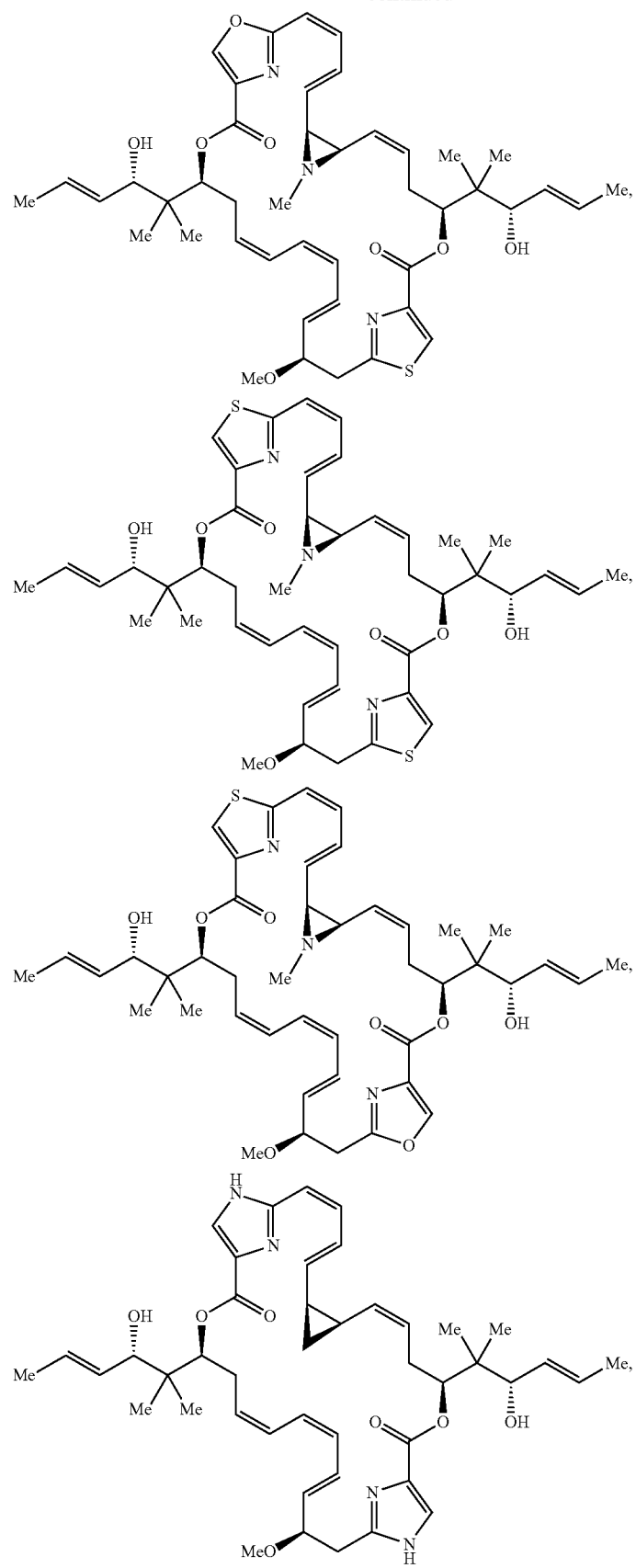

-continued
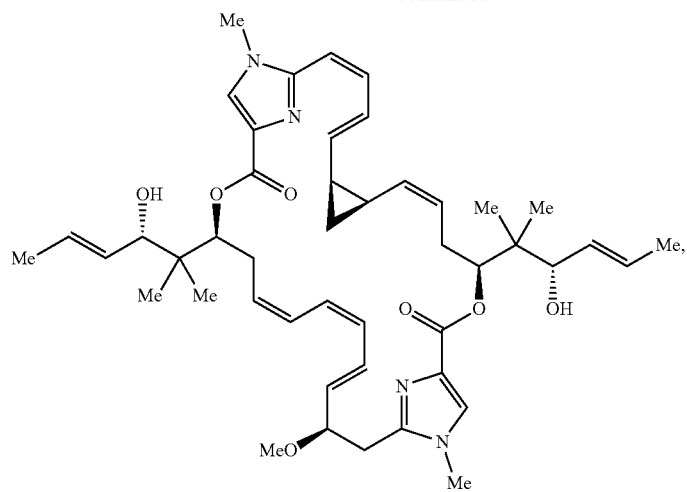
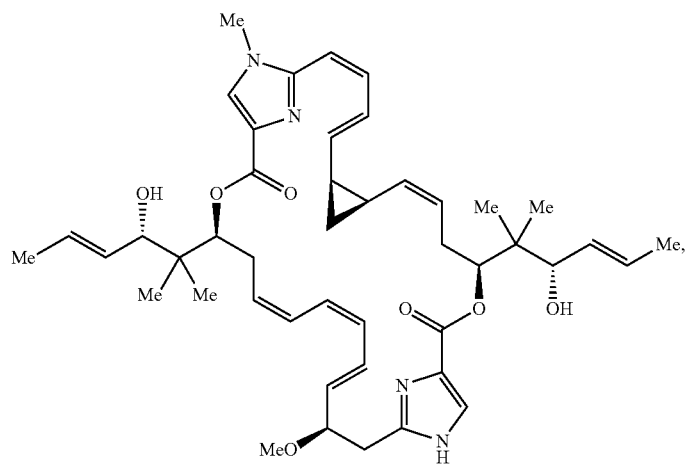
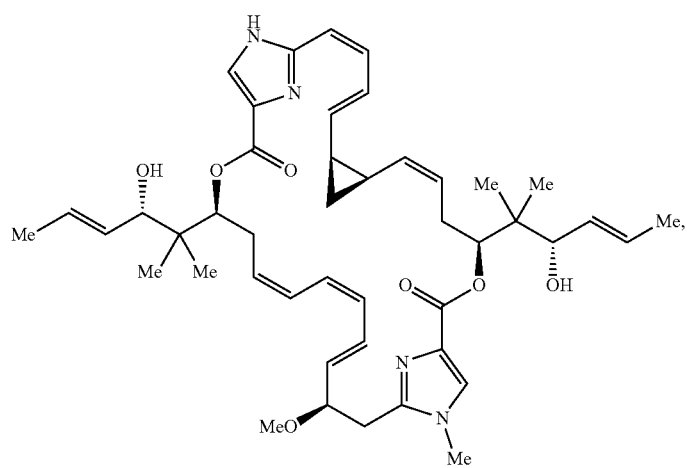

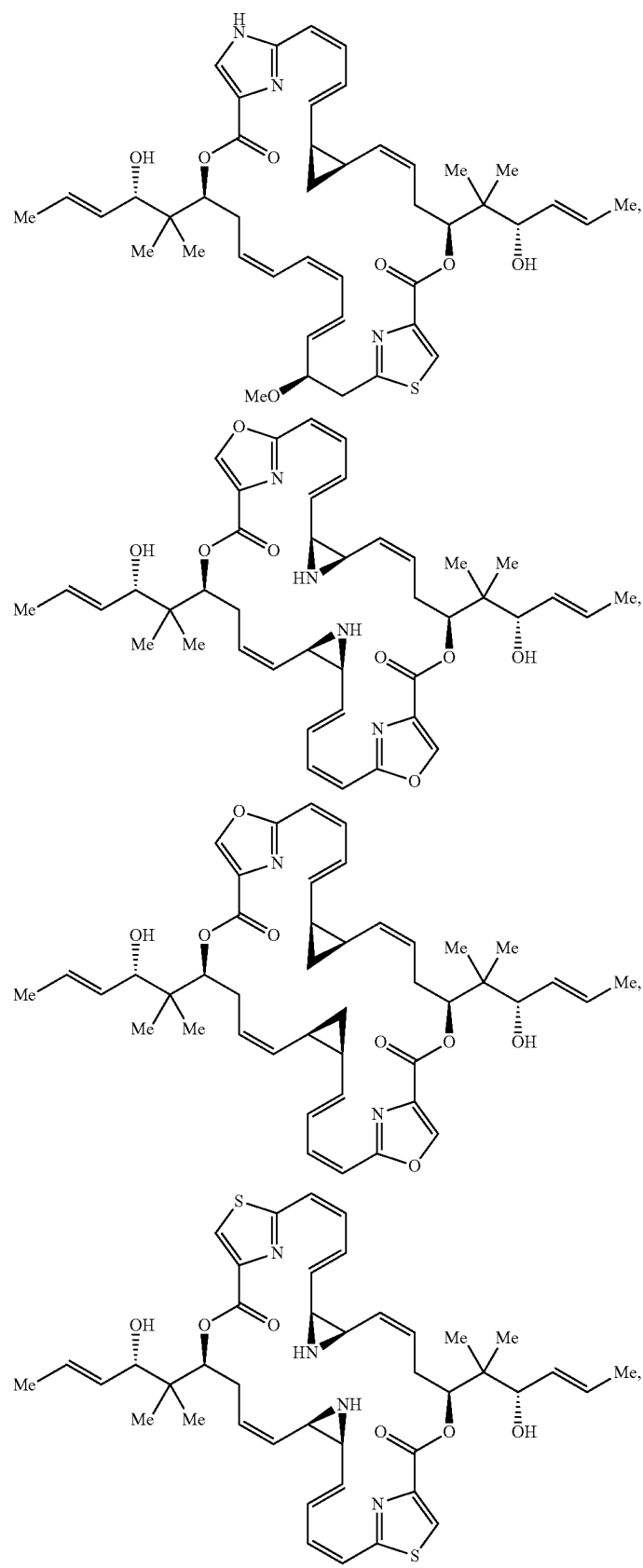

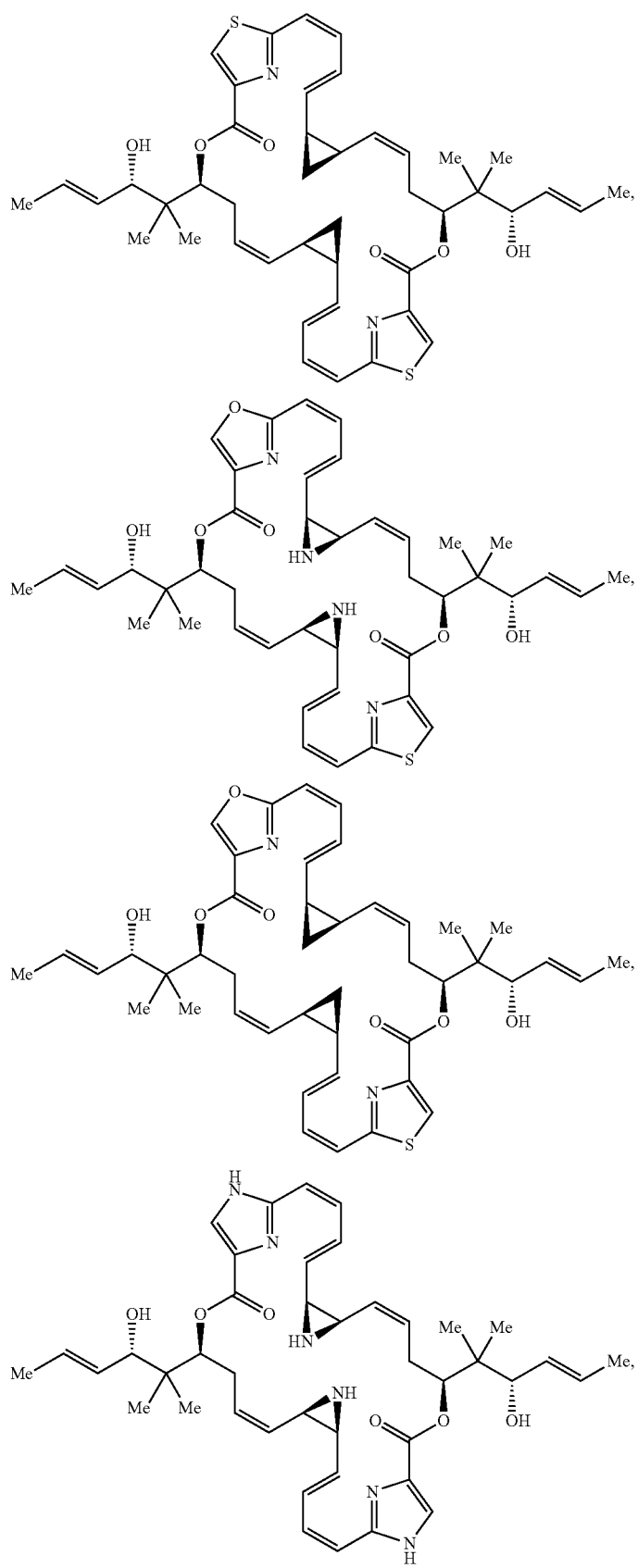

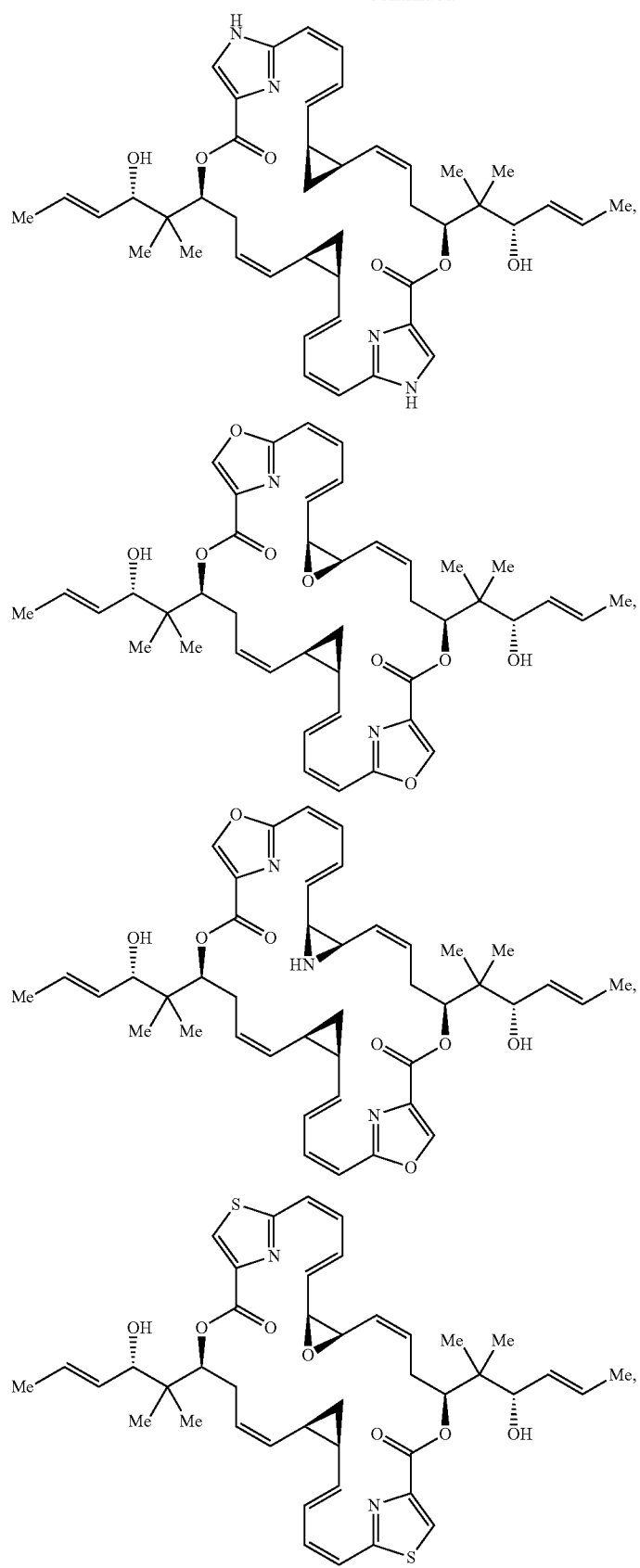

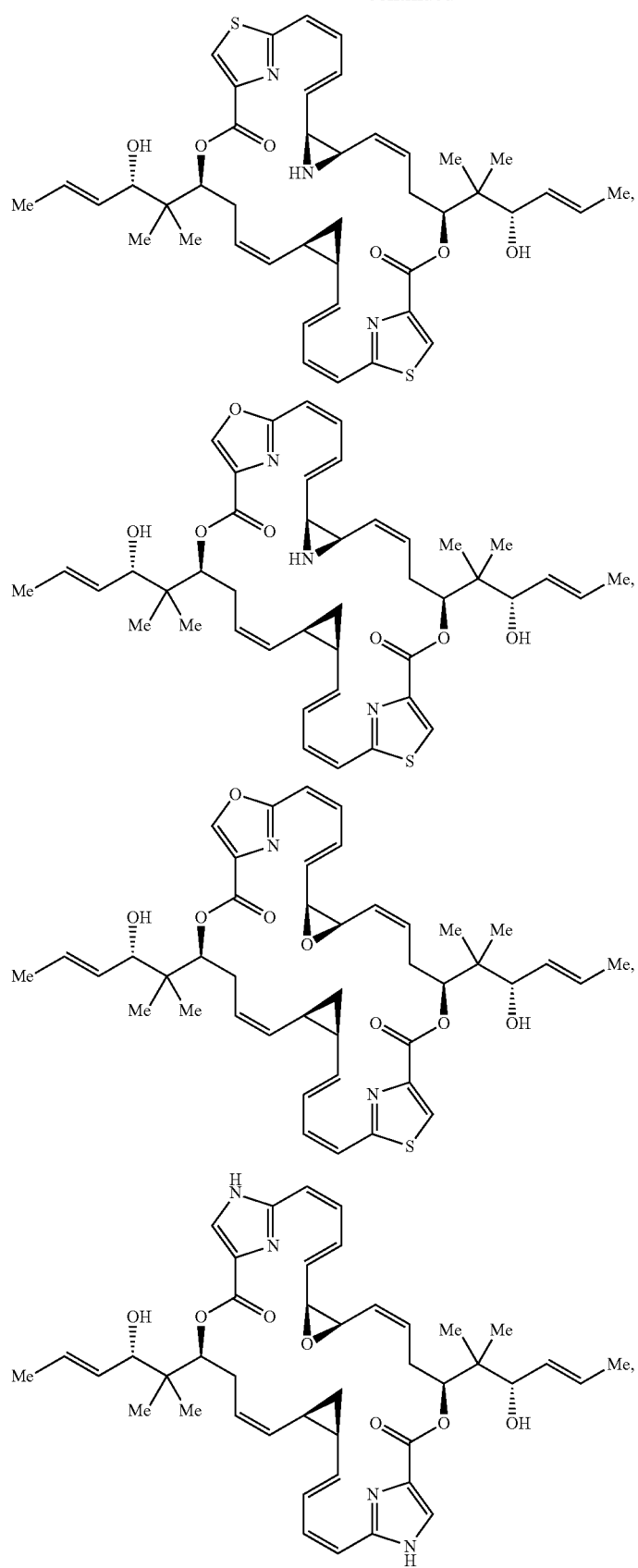

-continued
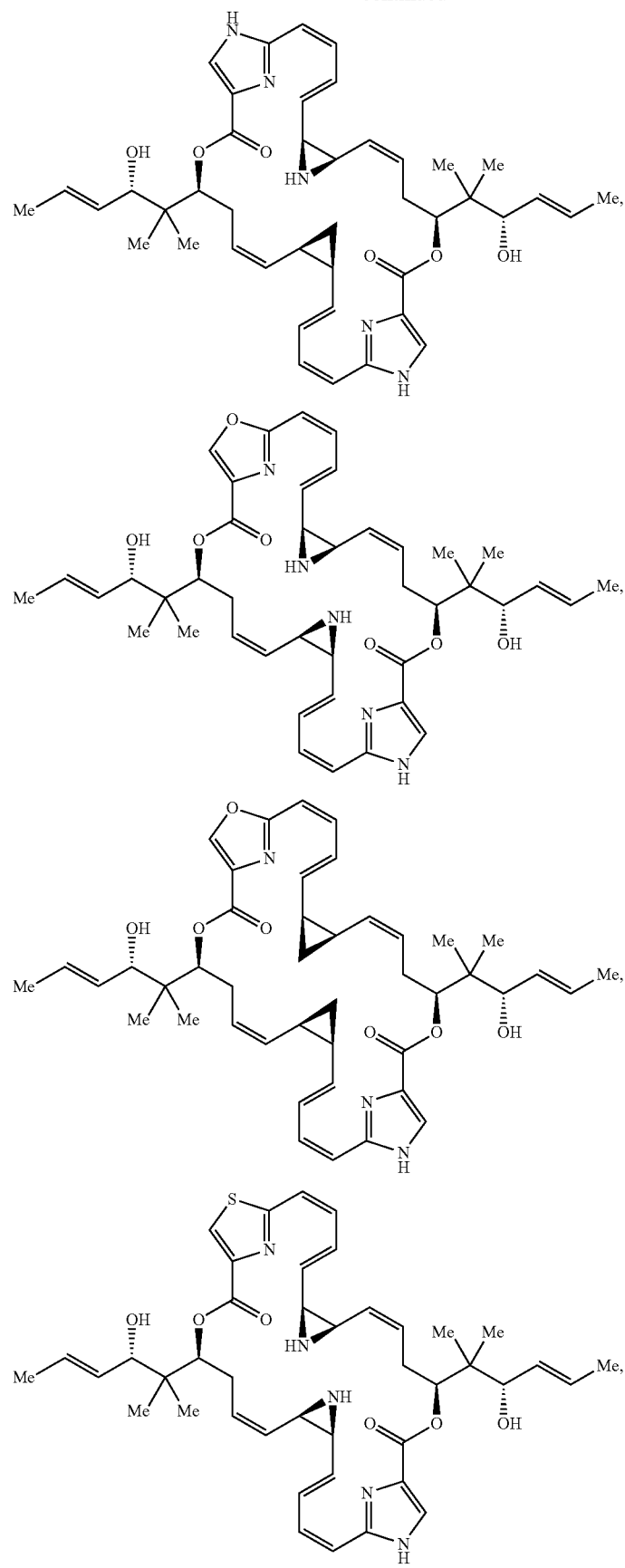

-continued
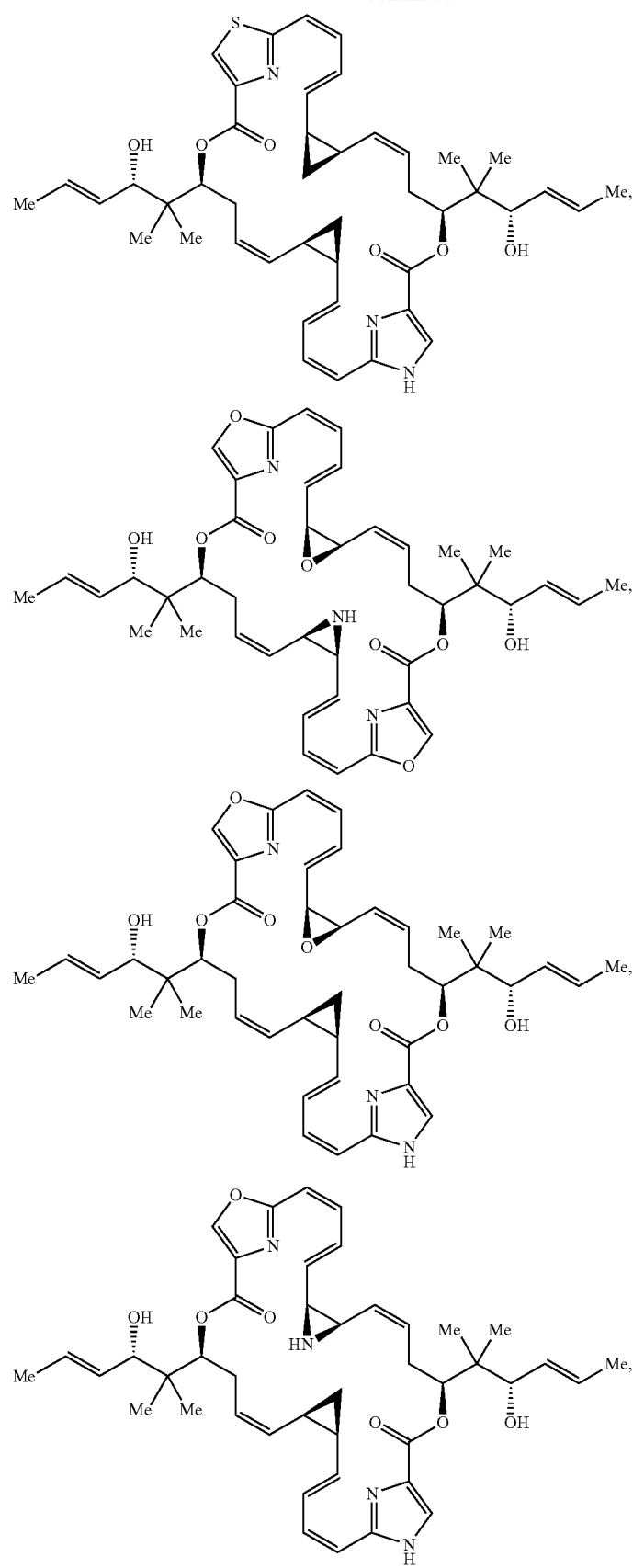

-continued
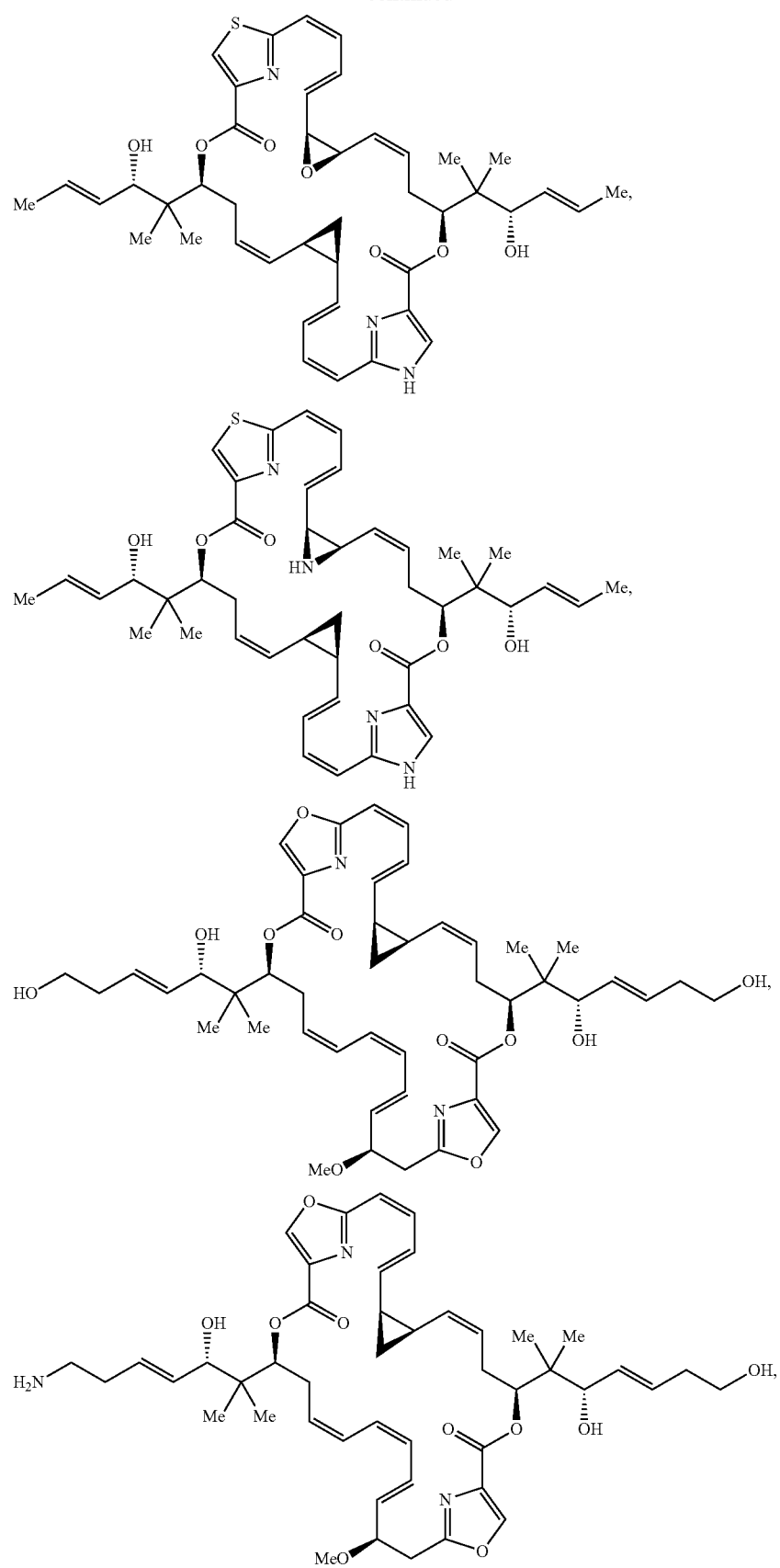

-continued
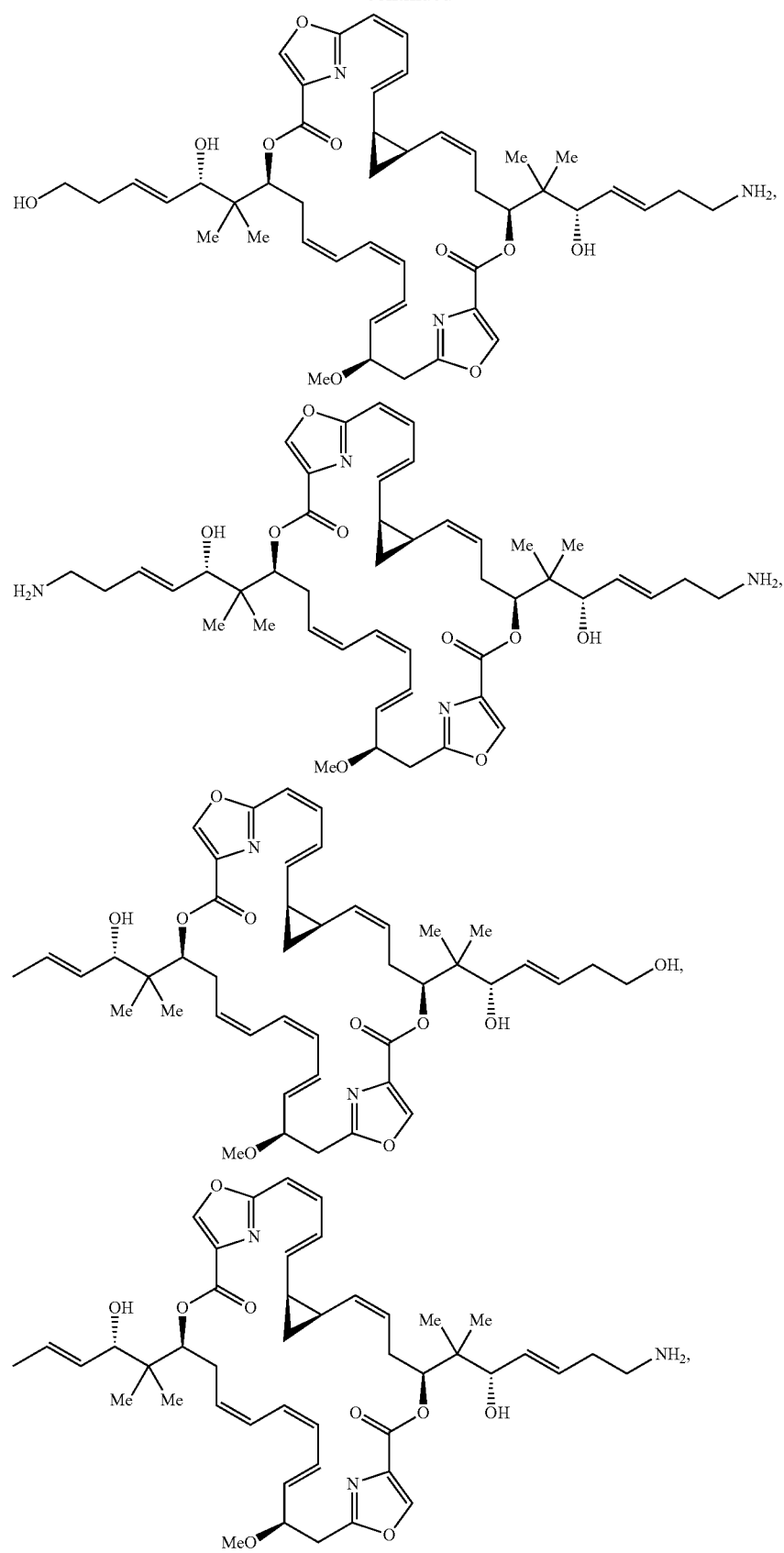

-continued
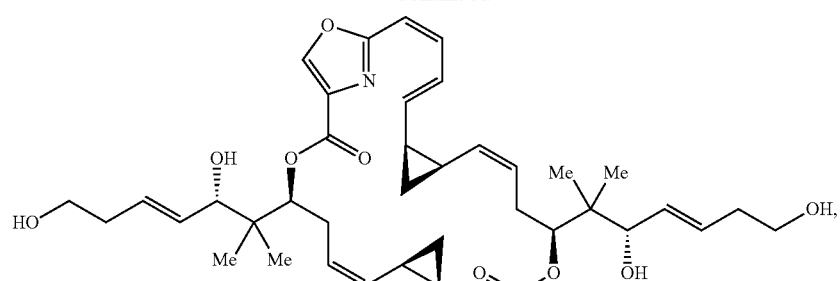
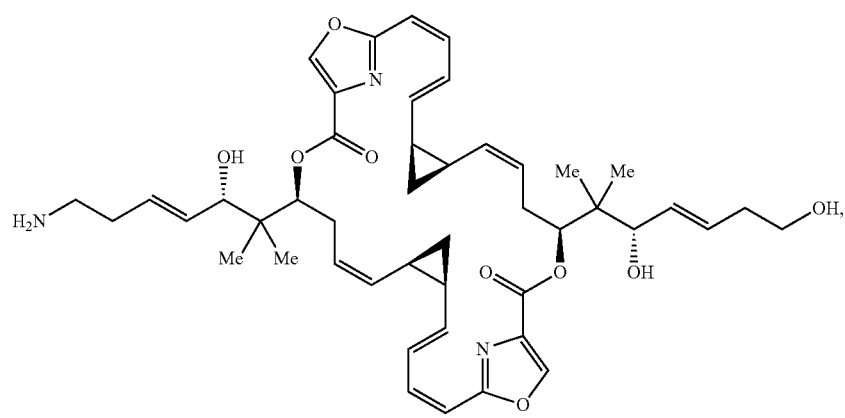
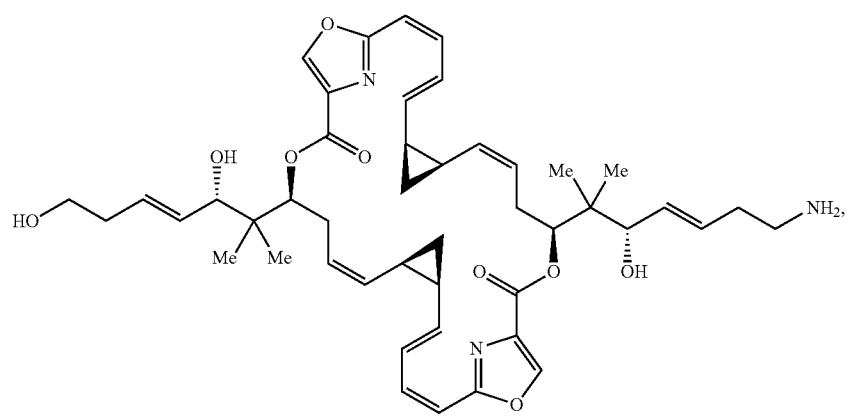
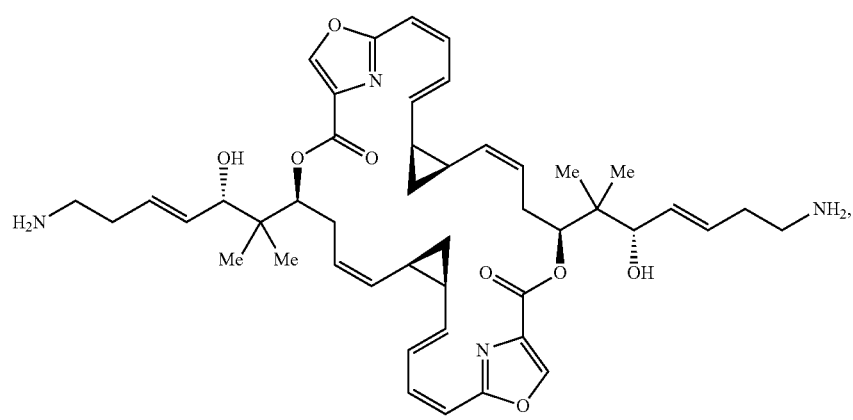

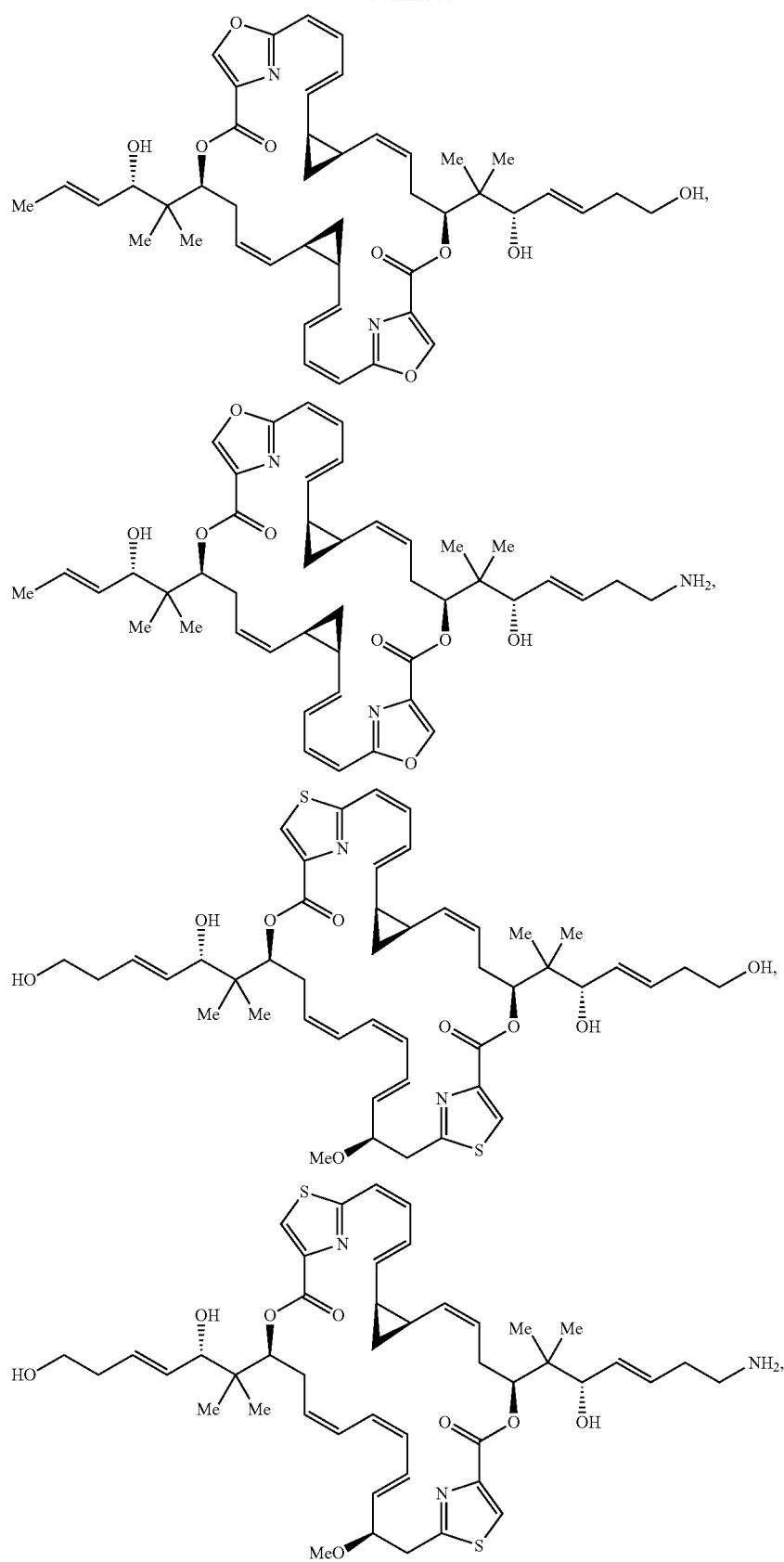

-continued
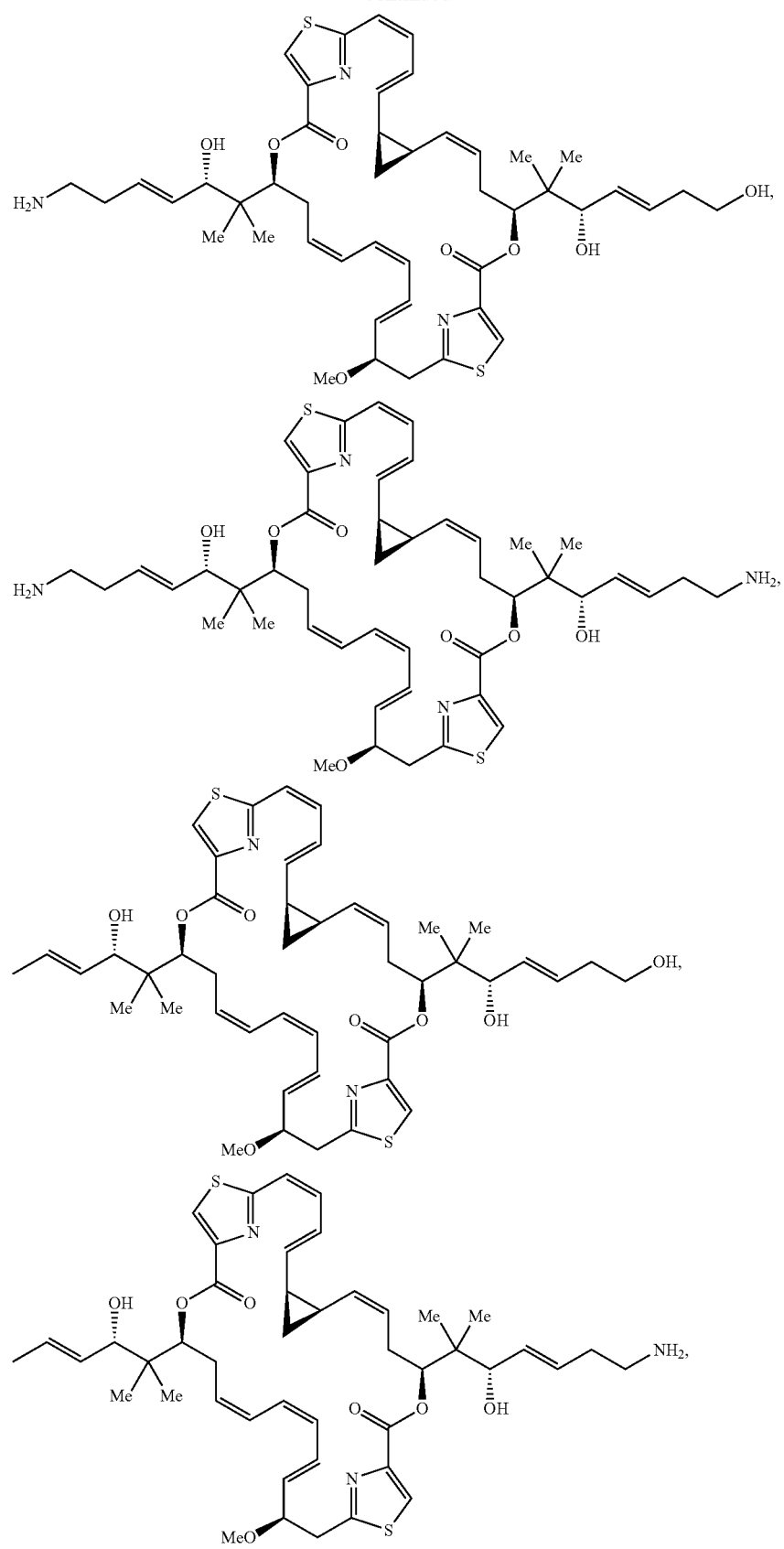

-continued
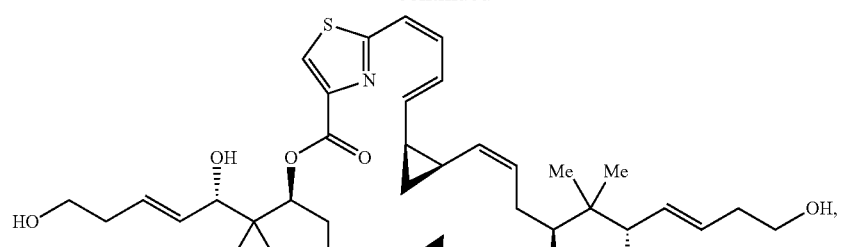
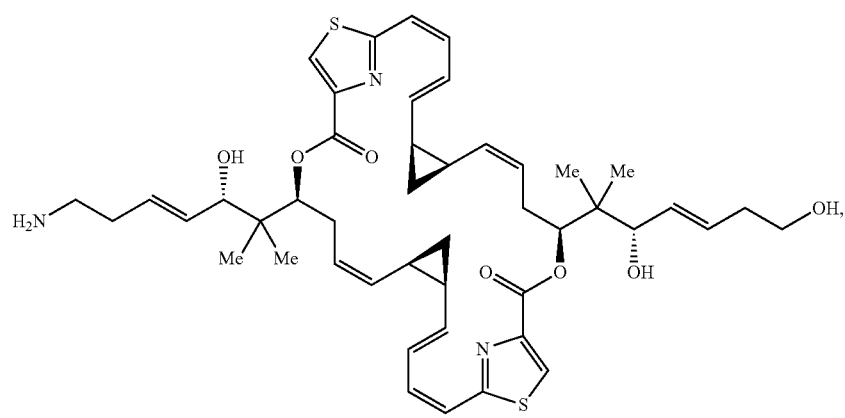
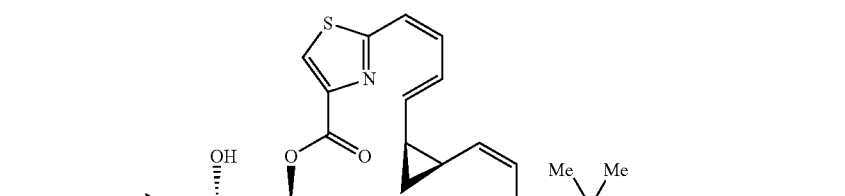
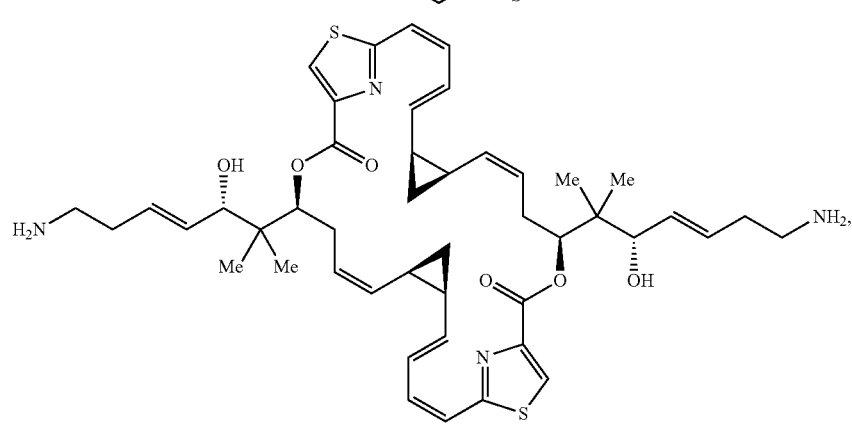

-continued

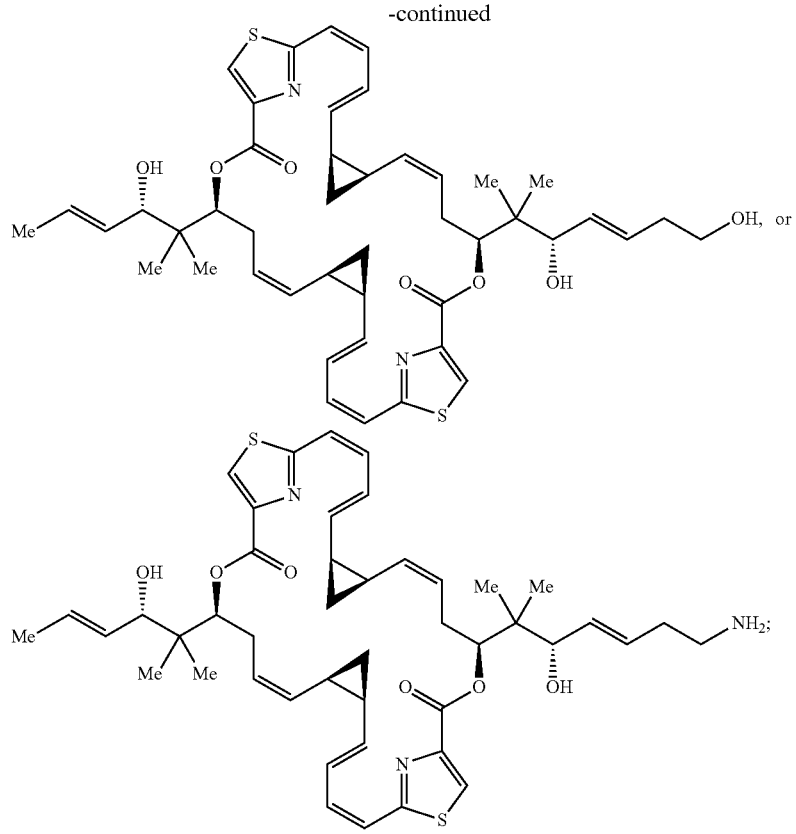

or a pharmaceutically acceptable salt thereof.

17. A pharmaceutical composition comprising:
(A) a compound of claim 1; and
(B) an excipient.

18. A method of treating cancer of the uterus in a patient comprising administering to the patient in need thereof a therapeutically effective amount of a compound of claim 1.

19. A method of preparing a compound of the formula:

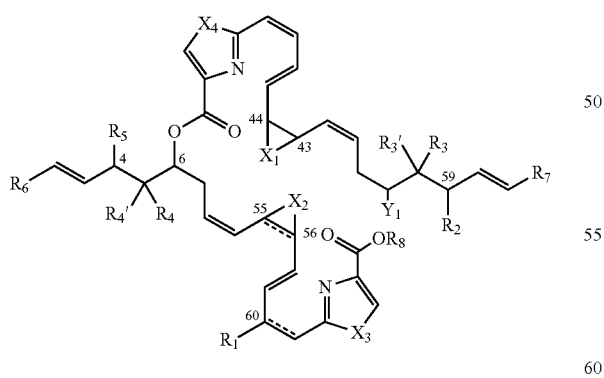

(VI)

wherein:
$X_1$ is —O—, —S—, —$NR_a$—, or —$CR_bR_c$—;
wherein:
$R_a$ is hydrogen, $alkyl_{(C\leq 8)}$, substituted $alkyl_{(C\leq 8)}$, $acyl_{(C\leq 8)}$, substituted $acyl_{(C\leq 8)}$, or a monovalent amino protecting group, or —C(O)$R_a'$, wherein:

$R_a'$ is amino, hydroxy, $alkoxy_{(C\leq 8)}$, substituted $alkoxy_{(C\leq 8)}$, $alkylamino_{(C\leq 8)}$, substituted $alkylamino_{(C\leq 8)}$, $dialkylamino_{(C\leq 8)}$, or substituted $dialkylamino_{(C\leq 8)}$; and $R_b$ and $R_c$ are each independently hydrogen, amino, cyano, halo, hydroxy, or mercapto, or $alkyl_{(C\leq 8)}$, substituted $alkyl_{(C\leq 8)}$, $cycloalkyl_{(C\leq 8)}$, substituted $cycloalkyl_{(C\leq 8)}$, $alkenyl_{(C\leq 8)}$, substituted $alkenyl_{(C\leq 8)}$, $alkynyl_{(C\leq 8)}$, substituted $alkynyl_{(C\leq 8)}$, $aryl_{(C\leq 8)}$, substituted $aryl_{(C\leq 8)}$, $aralkyl_{(C\leq 8)}$, substituted $aralkyl_{(C\leq 8)}$, $heteroaryl_{(C\leq 8)}$, substituted $heteroaryl_{(C\leq 8)}$, $heterocycloalkyl_{(C\leq 8)}$, substituted $heterocycloalkyl_{(C\leq 8)}$, $acyl_{(C\leq 8)}$, substituted $acyl_{(C\leq 8)}$, $amido_{(C\leq 8)}$, substituted $amido_{(C\leq 8)}$, $alkoxy_{(C\leq 8)}$, substituted $alkoxy_{(C\leq 8)}$, $acyloxy_{(C\leq 8)}$, substituted $acyloxy_{(C\leq 8)}$, $alkylamino_{(C\leq 8)}$, substituted $alkylamino_{(C\leq 8)}$, $dialkylamino_{(C\leq 8)}$, or substituted $dialkylamino_{(C\leq 8)}$;

$X_2$ is absent, —O—, —S—, —$NR_d$—, or —$CR_eR_f$—;
wherein:
$R_d$ is hydrogen, $alkyl_{(C\leq 8)}$, substituted $alkyl_{(C\leq 8)}$, $acyl_{(C\leq 8)}$, substituted $acyl_{(C\leq 8)}$, or a monovalent amino protecting group, or —C(O)$R_d'$, wherein:
$R_d'$ is amino, hydroxy, $alkoxy_{(C\leq 8)}$, substituted $alkoxy_{(C\leq 8)}$, $alkylamino_{(C\leq 8)}$, substituted $alkylamino_{(C\leq 8)}$, $dialkylamino_{(C\leq 8)}$, or substituted $dialkylamino_{(C\leq 8)}$; and $R_e$ and $R_f$ are each independently hydrogen, amino, cyano, halo, hydroxy, or mercapto, or $alkyl_{(C\leq 8)}$, substituted $alkyl_{(C\leq 8)}$, $cycloalkyl_{(C\leq 8)}$, substituted $cycloalkyl_{(C\leq 8)}$, $alkenyl_{(C\leq 8)}$, substituted $alkenyl_{(C\leq 8)}$, $alkynyl_{(C\leq 8)}$, substituted $alkynyl_{(C\leq 8)}$, $aryl_{(C\leq 8)}$, substituted $aryl_{(C\leq 8)}$, aralkyl$_{(C≤8)}$, substituted aralkyl$_{(C≤8)}$, heteroaryl$_{(C≤8)}$, substituted heteroaryl$_{(C≤8)}$, heterocycloalkyl$_{(C≤8)}$, substituted heterocycloalkyl$_{(C≤8)}$, acyl$_{(C≤8)}$, substituted acyl$_{(C≤8)}$, amido$_{(C≤8)}$, substituted amido$_{(C≤8)}$, alkoxy$_{(C≤8)}$, substituted alkoxy$_{(C≤8)}$, acyloxy$_{(C≤8)}$, substituted acyloxy$_{(C≤8)}$, alkylamino$_{(C≤8)}$, substituted alkylamino$_{(C≤8)}$, dialkylamino$_{(C≤8)}$, or substituted dialkylamino$_{(C≤8)}$; and provided that when $X_2$ is absent, then the bond between carbon atoms 55 and 56 is a double bond;

$X_3$ and $X_4$ are each independently O, NR$_h$, or S; wherein:

$R_h$ is hydrogen, alkyl$_{(C≤8)}$, substituted alkyl$_{(C≤8)}$, or a monovalent amino protecting group; and $R_1$ is hydrogen, hydroxy, alkoxy$_{(C≤8)}$, substituted alkoxy$_{(C≤8)}$, acyloxy$_{(C≤8)}$, substituted acyloxy$_{(C≤8)}$, or —OR$_g$, wherein R$_g$ is a hydroxy protecting group;

$R_2$ and $R_5$ are hydroxy, oxo, alkoxy$_{(C≤8)}$, substituted alkoxy$_{(C≤8)}$, or —OR$_h$, wherein R$_h$ is a hydroxy protecting group;

$R_3$, $R_3'$, $R_4$, and $R_4'$ are each independently alkyl$_{(C≤8)}$, acyl$_{(C≤8)}$, or a substituted version of either group;

$R_6$ and $R_7$ are each independently alkyl$_{(C≤8)}$ or substituted alkyl$_{(C≤8)}$; and comprising reacting a compound of the formula:

(IX)

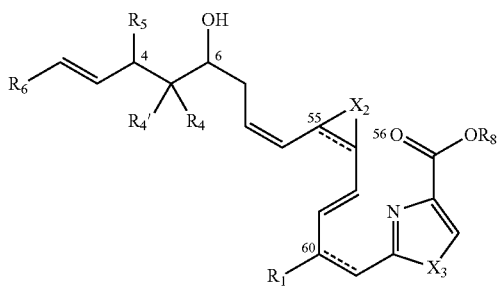

wherein:

$X_2$, $X_3$, $R_1$, $R_4$, $R_4'$, $R_5$, $R_6$, and $R_8$ are as defined above; with a compound of the formula:

(X)

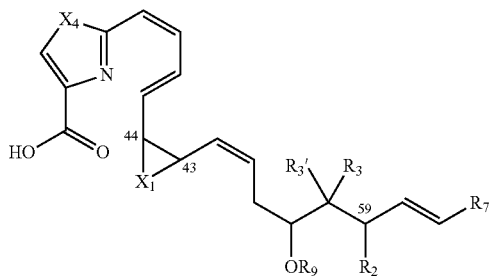

wherein:

$R_9$ is hydrogen or a hydroxy protecting group; and $X_1$, $X_4$, $R_1$, $R_2$, $R_3$, $R_3'$, and $R_7$ are as defined above;

in the presence of an carboxylic acid activating agent and a base.

* * * * *

UNITED STATES PATENT AND TRADEMARK OFFICE
CERTIFICATE OF CORRECTION

PATENT NO. : 11,465,997 B2  
APPLICATION NO. : 16/625667  
DATED : October 11, 2022  
INVENTOR(S) : Kyriacos C. Nicolaou et al.

Page 1 of 1

It is certified that error appears in the above-identified patent and that said Letters Patent is hereby corrected as shown below:

In the Claims

In Claim 1, Column 185, Line 20, delete the formula:

"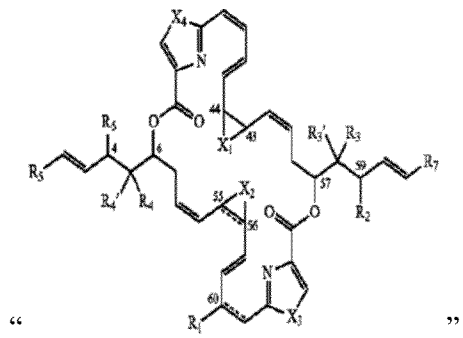"

And replace with the formula:

--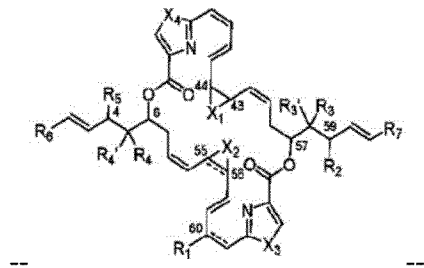--

Signed and Sealed this  
Sixth Day of June, 2023

Katherine Kelly Vidal  
*Director of the United States Patent and Trademark Office*